US011504390B2

United States Patent

(12) United States Patent
Shuldiner et al.

(10) Patent No.: US 11,504,390 B2
(45) Date of Patent: Nov. 22, 2022

(54) TREATMENT OF INCREASED LIPID LEVELS WITH STEROL REGULATORY ELEMENT BINDING TRANSCRIPTION FACTOR 1 (SREBF1) INHIBITORS

(71) Applicants: Regeneron Pharmaceuticals, Inc., Tarrytown, NY (US); University of Maryland, Baltimore, Baltimore, MD (US)

(72) Inventors: Alan Shuldiner, Tarrytown, NY (US); Nehal Gosalia, Tarrytown, NY (US); Cristopher Van Hout, Tarrytown, NY (US); Da-Wei Gong, Baltimore, MD (US); James A. Perry, Baltimore, MD (US)

(73) Assignees: Regeneron Pharmaceuticals, Inc., Tarrytown, NY (US); University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 16/823,634

(22) Filed: Mar. 19, 2020

(65) Prior Publication Data

US 2020/0297752 A1 Sep. 24, 2020

Related U.S. Application Data

(60) Provisional application No. 62/820,893, filed on Mar. 20, 2019, provisional application No. 62/879,138, filed on Jul. 26, 2019.

(51) Int. Cl.

| | |
|---|---|
| ***C07H 21/04*** | (2006.01) |
| ***A61K 31/7105*** | (2006.01) |
| ***C12N 9/22*** | (2006.01) |
| ***C12Q 1/6827*** | (2018.01) |
| ***C12Q 1/6853*** | (2018.01) |

(52) U.S. Cl.

CPC ............ *A61K 31/7105* (2013.01); *C12N 9/22* (2013.01); *C12Q 1/6827* (2013.01); *C12Q 1/6853* (2013.01); *C12N 2310/11* (2013.01); *C12N 2310/14* (2013.01); *C12N 2310/20* (2017.05); *C12N 2310/531* (2013.01)

(58) Field of Classification Search

None

See application file for complete search history.

(56) References Cited

U.S. PATENT DOCUMENTS

| | | | |
|---|---|---|---|
| 6,602,710 | B1 | 8/2003 | Chang et al. |
| 6,673,555 | B1 | 1/2004 | Grand-Perret et al. |
| 7,919,613 | B2 | 4/2011 | Soutschek et al. |
| 8,383,805 | B2 | 2/2013 | Soutschek et al. |
| 9,102,940 | B2 | 8/2015 | Soutschek et al. |
| 2003/0224347 | A1 | 12/2003 | Grand-Perret et al. |
| 2003/0224348 | A1 | 12/2003 | Grand-Perret et al. |
| 2005/0014177 | A1 | 1/2005 | Ranade et al. |
| 2013/0184324 | A1 | 7/2013 | Fitzgerald et al. |
| 2016/0068840 | A1 | 3/2016 | Soutschek et al. |
| 2016/0312216 | A1 | 10/2016 | Fitzgerald et al. |
| 2017/0002421 | A1 | 1/2017 | Sgroi et al. |
| 2021/0095277 | A1* | 4/2021 | Lindholm ............ C12N 15/113 |

FOREIGN PATENT DOCUMENTS

| | | |
|---|---|---|
| WO | 2003008625 | 1/2003 |
| WO | 2008011467 | 1/2008 |
| WO | 2008036638 | 3/2008 |
| WO | 2017191165 | 5/2017 |
| WO | 2017100542 | 6/2017 |
| WO | 2017107545 | 6/2017 |
| WO | 2019148125 | 8/2019 |
| WO | 2019186558 | 10/2019 |

OTHER PUBLICATIONS

Horie, T., Nishino, T., Baba, O. et al. MicroRNA-33b knock-in mice for an intron of sterol regulatory element-binding factor 1 (Srebf1) exhibit reduced HDL-C in vivo. Sci Rep 4, 5312 (2014).*

Enjoji, Munechika, et al. "Nutrition and nonalcoholic fatty liver disease: the significance of cholesterol." International journal of hepatology 2012 (2012).*

Lee et al. (The cellular function of SCAP in metabolic signaling. Exp Mol Med 52, 724-729 (2020).*

Talebi, Ali, et al. "Sustained SREBP-1-dependent lipogenesis as a key mediator of resistance to BRAF-targeted therapy." Nature communications 9.1 (2018): 1-11.*

Liu, Chang, et al. ("Delivery strategies of the CRISPR-Cas9 gene-editing system for therapeutic applications." Journal of controlled release 266 (2017): 17-26).*

Eberle et al., "SREBF-1 Gene Polymorphisms are Associated With Obesity and Type 2 Diabetes in French Obese and Diabetic Cohorts", Diabetes, 2004, 53(8), pp. 2153-2157.

Jensen et al., "Dose-dependent effects of siRNA-mediated inhibition of SCAP on PCSK9, LDLR, and plasma lipids in mouse and rhesus monkey", Journal of Lipid Research, 2016, 57(12), pp. 2150-2162.

Laaksonen et al., "Genetic variant of the SREBF-1 gene is significantly related to cholesterol synthesis in man", Atherosclerosis, 2006, 185(1), pp. 206-209.

(Continued)

*Primary Examiner* — Kimberly Chong

(74) *Attorney, Agent, or Firm* — Armstrong Teasdale LLP

(57) ABSTRACT

The present disclosure provides methods of treating subjects having increased lipid levels, methods of identifying subjects having an increased risk of developing an increased lipid level, methods of detecting human Sterol Regulatory Element Binding Transcription Factor 1 (SREBF1) variant nucleic acid molecules and variant polypeptides, and SREBF1 variant nucleic acid molecules and variant polypeptides.

20 Claims, 6 Drawing Sheets

Specification includes a Sequence Listing.

(56) References Cited

OTHER PUBLICATIONS

Li et al., "SCAP knockdown in vascular smooth muscle cells alleviates atherosclerosis plaque formation via up-regulating autophagy in ApoE −/− mice", The FASEB Journal, 2019, 33(3), pp. 3437-3450.

Moon et al., "The Scap/SREBP Pathway is Essential for Developing Diabetic Fatty Liver and Carbohydrate-Induced Hypertriglyceridemia in Animals", Cell Metabolism, 2011, 15(2), pp. 240-246.

Murphy et al., "siRNA-mediated inhibition of SREBP cleavage-activating protein reduces dyslipidemia in spontaneously dysmetabolic rhesus monkeys", Metabolism Clinical and Experimental, 2017, 71, pp. 202-212.

Salek et al., "Effects of SREBF-1 a and SCAP polymorphisms of plasma levels of lipids, severity, progression and regression of coronary atherosclerosis and response to therapy with fluvastatin", Journal of Molecular Medicine, 2002, 80(11) pp. 737-744.

Snpdev, "Referecne SNP (refSNP) Cluster Report: rs746678809", 2018, http://www.ncbi.nlm.nih.gov/projects/SNP/snp_ref.cgi?do_not_redirect&rs=rs746678809.

Sun et al., "SCAP gene polymorphisms decrease the risk of non-alcoholic fatty liver disease in females with metabolic syndrome", Journal of Genetics, 2013, 92, pp. 565-570.

Yahagi et al., "Absence of sterol regulatory element-binding protein-1 (SREBP-1) ameliorates fatty livers but not obesity of insulin resistance in Lep(ob)/Lep(ob) mice", The Journal of Biological Chemistry, 2002, 277(22), pp. 19353-19357.

International Search Report and Written Opinion for PCT Application PCT/US2020/023532.

International Search Report and Written Opinion for PCT Application PCT/US2020/023564.

Non-Final Office Action dated Aug. 12, 2021 in related U.S. Appl. No. 16/823,832.

Notice of Allowance dated Jan. 18, 2022 in related U.S. Appl. No. 16/823,832.

* cited by examiner

A)

B)

C)

SEQUENCE LISTING

<160> NUMBER OF SEQ ID NOS: 41

<210> SEQ ID NO 1
<211> LENGTH: 24930
<212> TYPE: DNA
<213> ORGANISM: homo sapien

<400> SEQUENCE: 1

```
gcggccgggg gaacccagtt tccgaggaac ttttcgccgg cgccgggccg cctctgaggc      60
cagggcagga cacgaacgcg cggagcggcg gcggcgactg agagccgggg ccgcggcggc     120
gctccctagg aagggccgta cgaggcggcg ggcccggcgg gcctcccgga ggaggcggct     180
gcgccatgga cgagccaccc ttcagcgagg cggctttgga gcaggcgctg ggcgagccgt     240
gcgatctgga cgcggcgctg ctgaccgaca tcgaaggtgc gtcagggcgg gcagggcttg     300
aagctgcgcc gggtggcgcg agtagggggc gcgcaggtgt ctccctggcc tttgtctccc     360
ccacgggcgc cagctccgtg ctgtgctcgc gcgggacttc ccggtgtctc tgagctcggt     420
gtcccgagcc tcaccgagcc tccctggttc ccgcgctagc gtctcgggcc gcgcgcttgt     480
gggtgagggc tcctgggccg ggccggggtc ccttggcggc tccgggccgg gacacgtgcg     540
cctctacgcg tcccaggccg ggtgccgccc gaccggtgac tctccagccc tgtgatggcc     600
acggctgaag ctggggaccc aggcgtcgcc gaagctccgc cccagcccca gccgtgacgt     660
aattgcgagg ttactcacgg tcattccctc cggcccgaga gttcagctcg gcgtcggagc     720
tcttgcgcat gcgcatgggc gctgcctcgc gcccttcccc cgcctcgtgt cgggttctcc     780
cggtctgcga cgggcacagc ctccgcactc attcactgac atccaccgaa tgccaggccc     840
cgtcttaggc accgagggtt tacagacaga cctgggtacc ccctctttta gggaacacaa     900
aaatctcccg ggaaaccaaa cggtatttta gttgtacctt gggtggagcg aggctggggg     960
agggcaggga tgtggctact ttgggtagag cggtcaggga cttctaagct gagacctgag    1020
ggtcaccccc aggaccagca aggaaagatg ttttccaggc cacggcaagg gaagggcaaa    1080
ggcctcgagg cagggcctaa gtgtgaggag ttagaggctt gcaaaggagt gaggtcaggg    1140
aggaggagga cgcaaaccga cttggtcggc cagggaaagg gcggagcaga acagtggcac    1200
cggcttccat ctttggagca tcaccctggc tgtgatgaga aggggtttgg ggccaatggt    1260
ggcaccaagt gccaattagg aggcccgttg cttccatttt gtagatagag caaacggaag    1320
cccctagcaa attgcctgca tggtttctgt gcaggagttt tagcagcact agctaagttg    1380
cacttggttg atgaggaaac tgaggccaag gtcgcaggaa caagatgcct agactcacag    1440
cctgaatgga catgtccatg gaacccgtgg ccaccctggg gttggcaaaa cagatatatc    1500
tatgccacca ccactcctgc cctactgcag ccttgcagat gagcccagct ggttgccagc    1560
cccagaagct tcccagccct ccctccttcc ccctggggct gggctagggg aggaccccag    1620
aggagaggcc ctgattgtga ggcttttcca aaacagcctc ccctatccct ggcacgaggg    1680
gttgtccttc actgccctct ggagtgatga accctgaaat cccaagccct agggagatct    1740
gggcctgact caactaccag ttccacatca ctgggcccag tgagtgtagt cccaagaggc    1800
aacgtgacca agccaggagg acatgcgctt tggggtcaga acttgaacct ggacactcct    1860
cacttccttt gtcatcctgc tcaagccctc tcaccctcta aaccttagtt tccacctcca    1920
gaaaaatgat gcaaaccctc ccttcatggg caagttggac aacagaaccc gttctgggcc    1980
acaggtctga tacagacctt tgtttgtttg tttgtttgtt ttctgcagtg gcgcaatttt    2040
ggctcactgc aagctcctcc tcctgggttc acgccattct cctgccttag tctcccaagt    2100
```

agctgggact acaggcgcca gccaccacgc ctggctaatt ttttgtattt ttagtagaga 2160
cggggtttca ctgtgctagc caggatggtc tcgatctcct gaccttgtga tccgcccgcc 2220
tcagcctccc aaagtgctgg gattacaggt gtgagccacc gctcccagcc cagacctttc 2280
ttactgacag aatctggtct gggccagagg tctgatacag acctttctta ctgactcatg 2340
gataaaaaca ttgtctctcc agaaccaaag gccaggcatg ggcagccatg tggcccaagg 2400
tctagtctat gagagagtgg gggcagtccc agccccttga agactggggg cagccccttc 2460
tcactaggca gggctcagct ttacccactt cagtagagga tttttcagtt tttattcaaa 2520
cttcctgttt ttcttcccaa ttacacacat ctttttcat tgtagaaaac ttagaaaatg 2580
caagtgagca aaaagaagaa aataaaatct ttagacctgg ggtggtggct cacacctata 2640
atcccagcac ttgggaggtc gaagcaagag gatgacttgt gtccaggagt ttgagaccag 2700
cctgggcaac atgacaaaat cctgtctcta caaaaataaa aaattagctg ggtgtgggtg 2760
acatgtgcct gtagtctcag ctactctgga ggctgaagtg ggaggattgc ttgagcctgg 2820
acttagaggc tgcagtgagc tataaccatg ccgttgcact cagcctggat gacagagtga 2880
gattctgttt caaaaaaaac tttaaaccta ccacccagag ataagccctg ctaattatgt 2940
gaaagagctt ttcttctctc tctctctctc tctctgtgtg tttatatgtg tttggggatg 3000
ggtgcacact cttcataaac tttttttttt ttgagacagg gtctcgctct tttgcccatg 3060
ctgtagtcca gtggcatgat ctcagctcac tgcaaactct gcctctcagg ttcaagagat 3120
tctccagctc ccaagtagct gggattacag tcatgcaccg ccacgcctgg ttaaattttg 3180
tatttttagt agagatggcc atgttggcca ggctggtctc gaactcctga gctcaggtga 3240
tctgcccacc tcagcctctc aaaagtgctg ggattacagg gcatgaacca ccatgcccgg 3300
ccttcatcaa tttttaaaa acgactttat tgaggtatac tttatgtatc acaaaattta 3360
cccattttta gtatatcatt caatgatttt tagttaactt tttgagttgt gtgacaatta 3420
ctagctgtcg aacattttta tcacacagtg agatccctta tacttcttta gtcagttcct 3480
gttcctgctc ccagccccgg gcagctgtgg atctgtatgt gtgtgtgtat atatatatat 3540
atatatatat attttttttt tttttttttt tttttttttt ttgagacgga gtcttgctct 3600
gtcgcccagg ctggagtgca gtggtgcgat cttggctcac tgcaagctcc gcctcccagg 3660
ttcaaacagt tctgcctcag cctcccgagt agctgggatt acaggcacct gccaccacgc 3720
ccggctaatt tttttgtatt tttagtagag atggggtttc accatgttag ccaggatggt 3780
ctcgatctcc tgaccttgtg atctgcccac ctcggcctcc caacgttctg gaattacagg 3840
cgtgagccac cgcgcccggc tggatctgta tttttataaa ttaaaatagg gtccattggt 3900
tcacagctga ttggaatctg cttggttcca tgtcaacagc cagacgacag taaggtttcc 3960
tcttattacc cacctgattc cctgtcgatg gacacctagg ttgttttatc tttataaact 4020
gctgcagtgg acactgaggc cggttttttt ctttgttttt tttttttgt ttgtttgttt 4080
ttgagacaga gtcttgctct gtcacccagg ctggagtgca gtggcgcgat ctcggctcac 4140
tgcaaactcc gcctcccggg ttcacaccat tctcctgcct cagcctcccg agtagcttgg 4200
gactataggt gcgtgccacc atgcctggct aattttttgt atttttagta gagacggggt 4260
ttcaccgtgt tagccaggat ggtctcgatc tcctgacctc atgatctgcc cgcctcggcc 4320
tcccaaagtg ctgggattac aggcgtgagc cactgtgcct ggccactgag gccagtcttt 4380
gcccggatcc tcactgtgtt cctaggatga ggttctggga ggggaattgc tggtcagagg 4440

-continued

```
tcgagcctgc ttttgaagct tcttctacca ggagtggagc tgagcaggtt tgataaggtc   4500
tgaagatttg gggtggaaa tgccaggtcc cttgagagac atgagggata agaggggcc   4560
aggctggcct tgagtgccag agtgcagagc tgggctagat gtgaggacag tcgggggtca   4620
gagcaggggc acaccgagct tcagttccct ctggctgctt ggatggagga tcgtaatgtg   4680
aacagaaaac actaattgag tacttactgt gtttcagaca gtgtgttgat aatcccactt   4740
aatcccctga caaccccaag taggtagaca tatgatgaag atgacggcct tgaggaccag   4800
agaggttaag tgatttgcct gagatcacac agccagatga tggcaaagcc agaattcaaa   4860
cccaggctgt gggctccaga gcctagctct taagctctta agcactgggc tcctaagaat   4920
ggggatgagg ggttgaggga ggctcctcca caggggctac tctgggggcc tggaagtggg   4980
tcacagaggg gtcagaggct atgtggctac ctccccatcc cagtccagag cagtgtttga   5040
gtcattagac tgggaaccag ccctggtgag ccagccaagg gccttgggcc ccatccggtc   5100
ctgctgcctg ccacagccaa actcttgtca tgtgaatgga tttggggatg gagctgcctc   5160
catgagtcct tgcatctgtg ggtgaaggca ctgccctggc tatagtgtcc ctgggtttga   5220
gtcctgcatc tgcaccaaga cctcaggtga gcctgtctcc ttctgggcct cagagtacct   5280
tgcagctgtc gggggaggat ggatcaggag atggccctgt acctgtgttg gggattattg   5340
ttaagcccgt ggcagtcttc acctccctgc tgaggattaa tttatccaat tttgcacaag   5400
cttatgagtg cagaagaggc agacggaaac agagttctgg ccaagagcct ggaacagggc   5460
ctcggggtct ctttcctatg cctggacccc gtcatgtctg ctctttgtct gtcggacccc   5520
agatgtctgc caagccccgt cagaggctgc ttcccagaaa gcccttctgg gtgtcacctt   5580
gccccgagca gtgcgttctc agagttctcc cgccctgatg tccctcccag catgcccagc   5640
ccagccacaa cagggccttg cttctagtca tgtgtctggc tgtttgctgg gtccaggcca   5700
gccctggtag ggcacaatgg gggcccgctc tgccacccca tacctctccc caggatatct   5760
catgccccag ttctctccct agttccacca agcactggca ctccttagaa aacacagctc   5820
tagactagtt actgccctag cttacagcac agaactcccc tggtctccaa ccattcatgg   5880
ctccctagtg ctccaagata aagttccctt gtctcagccg ggttgggagt taccttctgc   5940
ccaacattca cctagctgga cacaaacatc ctgagtgacc cggtcagctc caggcaggag   6000
tcactgccag cagaggcctg ggatctggac tttgcctgct gacaggtgga gcccaggccg   6060
gccagaggaa gtgcctctga ccttgtctcc tagcagccac gggccatgtg gacatgcctt   6120
ttgaccctgg gcactgacag tgtgtgacag cctgcaccat gtgctccaca ggggcggctg   6180
tgtgtgtcgg gggtgaggtg gggaaagcct taactggctc aggggtgaga ggtcagggag   6240
ccattgagac tggctccagg tgtgggtccc ctgctgggtt ggggcttgtg ggaggtggga   6300
cggggctggg ggtccatccc cctaggggga atttgtggcc taccccgaac cctgtttgag   6360
ctcctttcct aactgactcc ccgtccctgc acctgtctcc cagcaggcct tgcctctgca   6420
tgctgcccct gccaggctct ggggtccctg tgctccctgc agctagaagg ctgggatcag   6480
gggtcttaac aagcagccct actgtatgac cttggacaag tccaagaacc ttcaggttct   6540
taacaatgta aagggagcag tactaaaagc agcttcttgg aattgtgggg atccgatgag   6600
tgaaggctta agcagtgcat ggcacatagt aggccctgaa ccaatgccag ttagtgttat   6660
tattatcacc atttagccag atgcagtggc tcacgcctat aatcttattg actttagagg   6720
ctgaggttgg aggattgctt gagaccagga gttcaagacc agcctgggca acatagcaag   6780
gccctgtttg ttttagagaa aacaaacaaa tcaccattta gagcacctaa ccagtacctg   6840
```

-continued

```
gcacgcgata ggtttagctc aacaaatgtt agcagcaatt acccaaggag cctgtgctgg   6900
aagtttctag gatgtaccag gctatggttc caagttctga gcatctacca tgtggtggtc   6960
tggagttggt gagagacagg atggggctga ctaggccagt ggggagcacc ccccgccatg   7020
gggaacaagc accctatcct tggcttccat ggaagataat tgatgctggg cacagtggct   7080
cacgcctgta atcccagcac tttgggaggc tgaggcaggg ggatcgcttg agtctgggag   7140
ttcaagacca gcctgggcaa cattgtgaga cccaaactaa aaaaattagc ttggcatggt   7200
ggagtgtgcc tgtcgtccca gctactcagg aggctgaggc taaagctgga ggattgcttg   7260
agcccaggag gttgaggctg cagtgagcca tgatcatacc actacactcc agcctgggca   7320
acatagtgag gccctgtctc aaaacaaaca aacaaaaaga acctgctgag gaagcagtgt   7380
ttctggctgg gggaggacgg gcagagtggc catctggcca cagatggcgg tttctgtgca   7440
aaacacatca aggcagcctt ggaaatgtga gtgaaagcac cttcaaagtt ctggtcacag   7500
ccttgggact aagcaaagcc accaaaagta cataaaagac aatgaccatc acccagtgcc   7560
ggtgatgcta gaaggaaagg gaatacgttg tagggaaggt tgtaaagggc tttatctttt   7620
ccagactgga gcctggcagc tcgaaaacat cttgctgcct tcatatgagc tttaaaacaa   7680
gctgcagaga aacaactcaa gagggagaaa tatatatata tatgtgtgtg tgtgtgtatg   7740
tgtgagtgtg tgtgtgtgtg tgtatacata tatatatata tatatatata tatatatttt   7800
tttttttttt taagatggag tctcgttctg tcaccaggct ggagtgcagt ggtacaatct   7860
cggctcactg caacctccgc ctcctgggtt caaatgattc tcctgcgtca gcctcccaag   7920
cagctgggac tataggcaca taccaccacg cccagctaat ttttgtattt ttagtagagg   7980
ctggatttca ccatgttggc caggatggtt ttgatctcct gacctcgtga tctgcctgcc   8040
ttagcctccc aaagtgttgg gattacaggc gtgagccagt ttgtttttag agacggggtc   8100
ttgctctgtc acccaggctg gaataccatg gcacaatcac agctcgctgc aatgttgaac   8160
tcccgggttc aagggatcct cccacctcag cctccagagt aatggagact acaggctcat   8220
gccaccatgc ccagctattt ttaaaacttt gtagagatgg ggccttgcta cattgcccag   8280
gctggtcttg aactcctggg ctcaagtgat ctgcctgcct ttgcctccca aagtgctgtt   8340
attacaggtg tgagcccctg cgcctaacct tagcactgcc attttgactg aaaacaggtg   8400
cccagcagca ggggctactc ccagaattgc cactgcatca ggcccgtggg ttgttttcag   8460
ctgccagtga taagtatgtg ccctgggcca cctctcggac aaggtgtctg aattggtgcc   8520
gaccagcatc acatgtaatt gccatctcgc aggtgctgct gagggtaatt ccgcacacct   8580
gtagctccgg gaagagccta gtggggagga ggaaacgtgg ctctgaggtt tatagggtca   8640
gacggtcagt atgttgggag ctggcatgtg gaggggcaca gacaagggaa gaatgggagg   8700
tggcatcaga gcaagttttg atggaggaat aggaattcac caggtggaaa gggcattcct   8760
ggtggaggga acagcctggc cttcaatagc ttgtggtgtt cagaaagcag gcagggaaag   8820
ggaggcccag ggagacacca gttaggggat gggggtggag gcagacgagg gtggaggaag   8880
ccatggctgg agtctgcacg gcctctgact ggggtccctg ctgtggtcag ccctgtgctg   8940
ggtgaggctg gggtcacagc tggttcaggc cctgacagga ggggccccca gctgaggccc   9000
agcctctaat ttggcagggc aggtggatag gtctgggggg gtggtggtta ggaagcctcc   9060
aggaggaggc agtgccggag ctgagcctta aagagcttcg tgttgtcctc tctgtctttg   9120
cactctgcac acactcactg aactgcgaca aatgaggata gctggtcagg gcagaggcag   9180
```

gccggagttg gggctcactg ctgtccccca caggctgggg ctgaagggca ggctctgggg 9240
ccgcagaatg gggtttgtgt accagattct tcatatggca gctgtgggac tttgggcacg 9300
aggcctccgt ctgagcctta gtttcctcaa gaggacctgc gcccaggtgc acctggggct 9360
ccagccatgg gtgcgtccca ttccgggaag agctggcaca cacttgtgcc cccggggcag 9420
ccatgagtgc acaaagggca gcctgtgcca ctgctggata cacgaccagc tgagaacacg 9480
aggaccgccg actccagtta ggaggatcaa ggaagtgcct ggtgggagca gaacagcagg 9540
tggggtgcag cccagctccc tggagggatg gtgggcaccc atcctcaccc tgctgcctcc 9600
attagcaggc cgagagggtg tgctctggaa tcccatgagc acctgtgcca catcctcccc 9660
tgtggctgac ccttcttcac agttggtgca gctttgtggt ctgtagtgca gggatcaatt 9720
ggcaaatccc tttcccaccc attccctgga gaattggggt ccttggctca gatgacagac 9780
caacctgagt tggaatccca gctccttggt ggccgtcctg gcctccaccc cctcactgcc 9840
tccgctcctc ctatcctgcc cacgcccact gcagggcctt tgcacacact gtttcttctg 9900
ccctcccttc cggcccactc cctcatatca ttcagtcctc ctttcagatg tcacctccta 9960
agatgggctg ccctgaccac ctcatctata atggccccag tgcctggcac aggattggca 10020
cacagtagat attgtcagag atggatctgg gttctgtgga caaggctgtg ggggcaggtg 10080
aagagctccc tcttccagga ggttgtttgg ggttcaaggc cttgtttggg ttgtaggctt 10140
ctgtgctggt cagcgttggg ccctacaagc gcatgccatg aggcctgccc aggatttccc 10200
tcatggcctc acagaataca tcggccagag tcattaaagg gcgcctgcat ctgccttcag 10260
agagaggttt gaaggtagaa ctggggaggg atgccaggtg ggggttcagg tttcctgttg 10320
ggtcctgata gaatcagggc aggagaggaa gaagaagagg gaagaggagg aacccaggct 10380
tggggagggg tggcagggct tcacaagcct ggggaaggtg aactagggag cagttggggc 10440
caccatggcc cagagtctat gcctcctctt ccttcctgtg ttcagagtgt gtgtgggaac 10500
cacaagggcc ttctcagtgt tcatagggaa gcccggttca cccatgggtg ggccgcaatt 10560
tgggtgccac agtgagcccc tagagaccag ctctcccagc ttccaggaca gggactaggg 10620
gaggcaagag aggctcttcc ttaaattgtg cacccaaggt gcctcagctg ccttactcta 10680
gactggcccc gttaactccc cttaaaaaaa aaaaaaaaaa gactcagtcg aatggtaatg 10740
gagctccaac gtgaatactg caagtatcag gcaactcact acctgacttt ccagttctaa 10800
accattctaa ttgctgtaga gagaactaac ctttgttgag actgttgagt gatggatgtt 10860
ttacacactt gctttcccag aattcccacc tctggagatc gtaggtgtgg gagctcagag 10920
ggtggggagt ggactgtccc catcacacag caagggaggg gctaaaggaa gagcagggcc 10980
tggcatgcag ccccagatag cccacttggg tgtgtctctg agggaggctg cagggctggc 11040
tctagagttt cctttttcag tcttaacctg gtgaccagct tccacagaaa ttggcacggt 11100
gactcatgcc tgtaatcgca acacattggg aggccgaggt gggaggatca cctgaggtca 11160
ggagttcgag accagcctgg ccaacgtggt gaaaccctgt ctctactaaa aatacaaaaa 11220
ttacatttca ttacaggtgt ggtggcgcac acctgtaatc ccagctactc aggaggctga 11280
ggcaggagag tcacttgaac ccgggaggta gaggttgcag tgagctgaga tcgtgtcact 11340
gcactccagc ctgggtgaca gagccagact ctgtctcaaa aaaaaaaaaa aaaaaaaaag 11400
aaattggcca gtagatcagc cccaggggag agtgagccag ggtttggcca ggccttgagt 11460
ttcagaggct ggccatggcc agtggcaccc aggcccttcc cccttcctcg gggcatctta 11520
gcttagtctg tgccctctgc ccaagggcca gccctctgtt cccaggtcac accccctcct 11580

```
cttggaaggc cccccccgcc ccacccccat cagagtcttt aatgactctg ctgcccctgg  11640
ggctcagaga gcaaccgccc tctcccatcg cgcttcctca gtgggatggg agggggttag  11700
agcaggaaga tgagacaaat aaagacacaa taagaggcag gaatatgtgg taaagccaag  11760
atgggtaagg ggaggggaca ggcttgactg ttcacagtgg ccctggccct gctgtctcag  11820
gctagtatct gcttgttggt ctcaccacat tctaggctca gaaactgggg agcaaagtaa  11880
tgaaagaacc aggctgggag gccatgggga actcatgcct ggagttcagc tctcagtgtg  11940
cttttgggtc aaggacgctt ccctgtctta agtcactcat gtcagagcct ttgccaagag  12000
caatgctgtg ttttgttttg ggggtgaggg aacacccgcg ggctgagggg agggttgggc  12060
catgctagag aggccgtctg ttgtccttga acctcccaaa gctgggaaat aagggcctgg  12120
gctggacggc ggtggcgagg acaggttgcg agagagacat ggctgggttt tcttgcttag  12180
ggtcctgaat agagagcaag gttgaggccg cagggacccc agcccccaat ggactgctga  12240
gtcgctgggt ctgcccaggg ttcaggcacc ctctcaggtt gcagccaact ggggtgtgga  12300
ccaggcagag gcgctggcct gcagtttggg gcagaggcag gctttgctgg tggtctactt  12360
ggctgcaaaa tcaactggcc aggctctgat cactttgtgt gtgtgtgtgt gtgtaacttt  12420
tacctttgac aaaagaggga agacaggccc aggcacctcc tcaaaagaac cctagagcct  12480
gtcacccctt ccttacccat cttctgtcct agggactgca gcccttcctg gcttcccagg  12540
gccctacaat gaatagtggg tcgggactca cttggtgact gctgggttgt gaggccttga  12600
gggggagggg cagacttcac ccatctggca gagggacatc ggtgctggca gtcaggaaac  12660
ccttatttcc aggcctcagt ttcccggaag tgacctgttt tcaggagtgg cctcatccca  12720
gaccatcagc cccgctgtgg tgaggggtgg cccccttcctg gggctgccct agaaggggga  12780
ggtccctgca cccaccgcag ctgccactcg gcagcccttg gccttaatta aacgcttctt  12840
gcgtactaag tgctgcaccc atattatctc ccttctacca ttcgacgcca gggagataat  12900
gactgtcctg ttttctggag gagtaaacgg agggttggag cggttaaggc tcgctcaggg  12960
tgccagcgaa ccagtgattt cgaacacaga gttctggtgt gttgggccag gacttctctg  13020
ctttgaccct ttaacgaagg gggcgggagc tgagggccag tgaccgccag taaccccggc  13080
agacgctggc accgagcggg ttaaaggcgg acgtccgcta gtaaccccaa ccccattcag  13140
cgccgcgggg tgaaactcga gcccccgccg ccgtggggag gtggggcggg ggccggggcc  13200
gggccctagc gaggcggcag cgcggccgct gattggccgc gcgcgctcac cccatgcccg  13260
gcccgcagcc ccgaagggcg gggcggggcg ggacctgcag gcggggcggg gctggggcgg  13320
ggctgggggc ggggcggggc ggggcgggcg cgccgcagcg ctcaacggct tcaaaaatcc  13380
gccgcgcctt gacaggtgaa gtcggcgcgg ggaggggtag ggccaacggc ctggacgccc  13440
caagggcggg cgcagatcgc ggagccatgg attgcacttt cgaaggtatt tttggaggcc  13500
tccccaccag ccctttatac aatgcctccg tctcctgcag gttctcctgg ggtgggcggg  13560
catgcgggct acgcaacttg agcaggaaag agccccttcc cgagggagaa ggtgtgacag  13620
ttaccagctc gctggggaag tggagggcta cctccaacca aattagtgtc ccctgcaact  13680
caagggggaa gggtttgctt agagacccaa aagcagcatc ccgacctaag agggtttgga  13740
gggagagggt ggtcttctct acattctctg cacccgcttt gggacaggac caggaggaag  13800
cagggaggag ggcccgttgt ccctctgcca cagcgtctgc cctattcagc acccctgcct  13860
attgtgggca tcttagactt ttcaggaaga cagtgggagc cctagattgt caaaattgtc  13920
```

-continued

```
agtttttctt tcaggcctca gtttccccca tctatcgaag aggctcacac ggactggggt  13980
aaagggatgg gaaaccctgc agttgaaagt ccattatgac ttgatgactt gtgacctggg  14040
gggtccacaa accaggagag tttctacttg agaagccagg aagactgggg ctgccacccc  14100
atcctgttct gccaactgct ctaggaaatt cccctcctgc agtagcttcc ctgcctgggt  14160
acctgtcagt aggcaatgtt gggtctccac tcggtgccag ctgcctgcca agcaaagcct  14220
cgggcagccg taccaaaagg ggtttagtct tttctgttgt acagatgagg aaactggggc  14280
cagtgagagg aggctgttgg tccaggctcc acttcaagct ggtggtgggc agggctggga  14340
gctcaggctg gggatcctga gagcactgga ggcccccatg ggtcctgtag agcattctga  14400
cccagtgggt gccaccacga gtgggttaga gggccctggg ctgagccaga taggctgcta  14460
gtcaccagct gggggagagg gcccttggcc aggtggggct gaggtgggag tgtgtcccag  14520
tctgtatgag gaggaaggag tcaggacaga cagcacttgc ttttacagag atgaaatcaa  14580
agccctgagt ggccaggcct gggtcttgag gctacttggc tgcaggcaaa gcctggactt  14640
gagcccagaa ctctacacag agacacactg gttggccatg tggccagcag ctggcttggc  14700
cctaagcctt ggtctgttcc actgagtaat gggttggtga tggcagcctg gctcttggct  14760
tcttagtggg gcaagaaaag gcagagagac aatagatttg ggattttgta gacctgggtt  14820
tgaaccccac tgcatgctct tgggctgctt gtggtcctcc ctgagcctca gtgtcttttc  14880
ttgtctccaa gatgaggtga gctaatcttt tgaggtagtc tagggtagtg gccagtggtt  14940
ggggcattgg agtcaaaata gggtctggac tcagttgagt ctctgactct ataagaactt  15000
aggccagtaa gtcacctctc tacagctcag tttcttcacg tgtagaatgg ggccaatgat  15060
cacatcaccc tctcagctgt gggtgaggat taggggtcta gcctggcccc atcaatgtgg  15120
gtagccccac agcgggcctg gcttttggac cagacccacc cttctgacat gggcccccac  15180
ccttagagtc cttctagtgt ggatgaggac cctgctctga tctggggtcc tcttggggga  15240
cttccctgtc tgccattctc tttggggatc ctgcgctgcc ctaggaagag tgggcccagg  15300
ctgcacagtt ggtccttggt cacagaggat cccaccactt cttcagggcc tcaaggcaat  15360
cctgcctctc tctgcacccc tcttcccccct gtaaactgag gggaggggaa aatcacccac  15420
tcctcagcag tttctaagtt gctttgtcaa attcagtgcc cagaggatcc tgctgggggt  15480
gcgttttagg atgagaccag gagtggccaa tggtggggtg tggggcccat cgctcctata  15540
tgaagacccc ctctgcccta gactgctcct ccctccccat ccccatctcc atcccaaaga  15600
ctggagctgc tggatctgtg gatggaggcg tgccccccgt ttcacacatt gagaaacagg  15660
ccccaagtgg agccagggaa ggctgcacct gggcctctgg attccttttg ttctgtgtgg  15720
ggttgggggt gatggactgt ggagagggca ggagagctgt ctggaagggt tggtcacctc  15780
atgggcaaat gcttggaagc tggtctgagt ccacggtgca gtgtgtatgt gtgtgtgtgt  15840
gtgtgtgtgt atgtgtgtgg actcagaggt ggatgtcttg tagaatgcat gccccatgaa  15900
gacaggagta aaagtttacc accatccaca tcaagctaca ggacactccc agctccccag  15960
aaagttgctt agttctaggc agggatttcc cttattcaca gccgggagca gtgcctggca  16020
tagtgtgggc actcagcact cagcacatgc tcactggatg agtgaatgaa tgtgagcctg  16080
ctgtttgctg tggactaagg atgtttctag atgtttgggc aaataccgga tggtgggaag  16140
agctcaggct ctgaagtctg cagtcttggg cccgaccctg ggctcagccc cagcctagct  16200
gtggggcaag attgtgagcc ttgtggtgcc caccttgtcc aggtattgtg atgcactcgc  16260
agcagcaggc attgctttag acagcacagg tgctcgcaaa atggctgtat gtccgggaac  16320
```

-continued

```
accagctcct gtgggtggct ttctgtcctg gtggcattgc ccacacatac agctgtgtgc  16380
caacaagggt tgtgcaaata aggttgtgtt tggatgtgtg tgatgccctg tttgggggtc  16440
agtctctgcc tcactcacgc accctcttct ccttttcaca gacatgcttc agcttatcaa  16500
caaccaagac agtgacttcc ctggcctatt tgacccaccc tatgctggga gtggggcagg  16560
gggcacagac cctgccagcc ccgataccag ctccccaggc agcttgtctc cacctcctgc  16620
cacattgagc tcctctcttg aagccttcct gagcgggccg caggcagcgc cctcacccct  16680
gtcccctccc cagcctgcac ccactccatt gaagatgtac ccgtccatgc ccgctttctc  16740
ccctgggcct ggtatcaagg aagagtcagt gccactgagc atcctgcaga cccccacccc  16800
acagcccctg ccaggggccc tcctgccaca gagcttccca gccccagccc caccgcagtt  16860
cagctccacc cctgtgttag gctaccccag ccctccggga ggcttctcta caggtaaggg  16920
ggatgtgtgg cgggagggga cacccggggt ggggcttcca ggagcacagg aagaagcttc  16980
tgctgtgatg tgagtagagg tctgtgcagg ctttagaaac tggggctcca ctcggctgct  17040
tgagatgccc tgttactagc agtcctggtg tgcttgttgc cggggtaggc gcaacctcgc  17100
actggaggcc tggcttgaag ccagtgcatt tgcatcagag cccaggcagg gactgtccat  17160
aggaagccac atggggcaat gactcatcca aggccagtcg gtgatagaga cctgaagagc  17220
aggttgaaag tgggagaggg aggtctgtgt ctgcagcccc atgctttatt tctgcaggaa  17280
gccctcccgg gaacacccag cagccgctgc ctggcctgcc actggcttcc ccgccagggg  17340
tcccgcccgt ctccttgcac acccaggtcc agagtgtggt cccccagcag ctactgacag  17400
tcacagctgc ccccacggca gcccctgtaa cgaccactgt gacctcgcag atccagcagg  17460
tcccggtgag ggggtctggc caggggttgg ggaggggggca gccccagccc agacacacag  17520
cttacagcca agcctctccc accctcaggt cctgctgcag ccccacttca tcaaggcaga  17580
ctcgctgctt ctgacagcca tgaagacaga cggagccact gtgaaggcgg caggtctcag  17640
tcccctggtc tctggcacca ctgtgcagac agggcctttg ccggtgggtg acgtgggcag  17700
ggcataaggg agtggggtct acacacacac acacatgccc acctggtaac atgtgcctgg  17760
ccctgcagac cctggtgagt ggcggaacca tcttggcaac agtcccactg gtcgtagatg  17820
cggagaagct gcctatcaac cggctcgcag ctggcagcaa ggccccggcc tctgcccaga  17880
gccgtggaga gaagcgcaca gcccacaacg ccattgagaa gcgctaccgc tcctccatca  17940
atgacaaaat cattgagctc aaggatctgg tggtgggcac tgaggcaaag gtgtggagag  18000
gcctgcaggg gcacagaccg gggtgtccct aggaaggaac agatcagggg caactggaag  18060
gaagagaggg agtgagactg agcctggaca agcagggaat tggaattcag cctccccagg  18120
cctggccagc ctcgtttatt tagttaaact ggtttgcagg cctcttcaat aaaggtgggg  18180
ctgtgctagg cattggggat gcagcaatga acaagacaga caaaaattgt ccctcaaaga  18240
agagccgacc ttctggtggg ggagatggac agtaggcagg atgaataagt gctcgagacc  18300
accacgtttg gctcgttgca gagaaagcag gaagaggatg gtgagggtcc cctggtggta  18360
gccagggaag gcctccctga gatggcggca ggcacagcag cagctagcca gaccctgctg  18420
tctgcatctt acattctaac cctatgcccg gcctgggagg tgggtgctac taggcgagga  18480
acggttcagg tagaaggaac aagtgcaaag gtcctgaggc agtaatgttg caaagcagct  18540
ccgcaccccc ttgctagggc tctccaaccc cacaaccccc gacctgacag gccacctgtg  18600
cgctccccct ccctcccaca ccgtgcagct gaataaatct gctgtcttgc gcaaggccat  18660
```

-continued

```
cgactacatt cgctttctgc aacacagcaa ccagaaactc aagcaggaga acctaagtct  18720
gcgcactgct gtccacaaaa gcagtgagtc ctggctttat tgagctccag tctggcctct  18780
tctctagcct tgctccacct cccggcccca ccccatccct agccccaccc caccccttggt  18840
tctggcccac cctctgccct gcccacctca cccttggctg tagccctgca ttcagctcta  18900
gtcccttggt tacctctggt cctgaaagag acctggtgcc tccctttggc cctaacccag  18960
ccccatcaaa gcgtcctggg ctagctttag gagctacagt agtccctagg cctccaaggg  19020
cctaggctct gatttggggt cacatatcca gcctttactc ctggctctgt tcctttcggc  19080
ccacagaatc tctgaaggat ctggtgtcgg cctgtggcag tggagggaac acagacgtgc  19140
tcatggaggg cgtgaagact gaggtggagg acacactgac cccacccccc tcggatgctg  19200
gctcaccttt ccagagcagc cccttgtccc ttggcagcag gggcagtggc agcggtggca  19260
gtggcagtga ctcggagcct gacagcccag tctttgagga cagcaaggtt gggccctgcc  19320
acggtgcccc cttccccact cccagccata tcctctgagc ctcatgacag ggccgggaag  19380
accctaacag atcctacctc ccatttcata gacagaataa ctgaggcctg gagccacgtg  19440
gggtcccaca gtaaggtggg cagaatcctg acccccccct tcccagcccc atgctctctg  19500
gggtccctcc gattctgccc tcaccaccct gcccaacccc accaggcaaa gccagagcag  19560
cggccgtctc tgcacagccg gggcatgctg gaccgctccc gcctggccct gtgcacgctc  19620
gtcttcctct gcctgtcctg caacccccttg gcctccttgc tgggggcccg ggggcttccc  19680
agcccctcag ataccaccag cgtctaccat agccctgggc gcaacgtgct gggcaccgag  19740
agcagaggtg ggaccggcca gcctgggcat ctttgggagg gacactcggg gtgagccccc  19800
aggcttgtga acttggggct ctggatttcc tgggagctgt gtccccagct ttccctctgt  19860
ccatagatgg ccctggctgg gcccagtggc tgctgccccc agtggtctgg ctgctcaatg  19920
ggctgttggt gctcgtctcc ttggtgcttc tctttgtcta cggtgagcca gtcacacggc  19980
cccactcagg ccccgccgtg tacttctgga ggcatcgcaa gcaggctgac ctggacctgg  20040
cccgggtaag gggctggccc cggcagagtg ggcagggcag ggaccccagg ctgtgaaggt  20100
gctgggtgtc aacccttgtt cctgctccct gtgcacacca tgaatctgtc ccgtcctccc  20160
tgtgcctagc cacgcatccg cagaccccca ccacccctcc agagcctgct gtggacggct  20220
cttctgagct ttggggcagc tgctctgacc tcacttttct cacctggaaa accctcatcc  20280
acagggagac tttgcccagg ctgcccagca gctgtggctg gccctgcggg cactgggccg  20340
gcccctgccc acctcccacc tggacctggc ttgtagcctc ctctggaacc tcatccgtca  20400
cctgctgcag cgtctctggg tgggccgctg gctggcaggc cgggcagggg gcctgcagca  20460
ggactgtgct ctgcgagtgg atgctagcgc cagcgcccga gacgcagccc tggtctacca  20520
taagctgcac cagctgcaca ccatgggtag gactgagcgt ggggcgggct ccgaggtgct  20580
ccctgctgcc tgtgctccac ccacagcctc atgcctgctt gccttccagg gaagcacaca  20640
ggcgggcacc tcactgccac caacctggcg ctgagtgccc tgaacctggc agagtgtgca  20700
ggggatgccg tgtctgtggc gacgctggcc gagatctatg tggcggctgc attgagagtg  20760
aagaccagtc tcccacgggc cttgcatttt ctgacagtga gtgggttggg gggctggggg  20820
cttatccctg cagctctctc cagaggctcc ctgggtaaga gctacacggg atgtggcagt  20880
ggttaccagg gggactccag gccaagctgg gactcggccc ggggtctggc cccaggctgt  20940
gtccactgtg acagcccagt accctcccct acagcgcttc ttcctgagca gtgcccgcca  21000
ggcctgcctg gcacagagtg gctcagtgcc tcctgccatg cagtggctct gccaccccgt  21060
```

-continued

```
gggccaccgt ttcttcgtgg atggggactg gtccgtgctc agtaccccat gggagagcct  21120
gtacagcttg gccgggaacc caggtgctct cttacccctt ccctgtcccc tctcctgtcc  21180
ctcatcctca ttcctgtcct gtcccttgtc gcctgaatct ctggctgtct ctggccaccc  21240
cagtccttct ccctgccatg ggttgttgct gtgggggttg caggaaggga aaggcctggg  21300
tgcctctcgt tcccattggg gctttcagaa gcacatgcag ggattgatgg gcagatggct  21360
aattggagaa gtgaccccag gcagtgccgc tgtggagtaa ggaagcggag ccaacaatgg  21420
catcttctca agtcggtttt cctttggaag cagtgtaggg caggcctcag tgttgtctcc  21480
tggccaaggc tggtgctggt gatagttatg tccacccgct ttcccctgtc cttggcaggg  21540
gctgcaccca ggggcatgcc ggcacttccc agtggcccta ggtgtggccc cagcccaccc  21600
aggaaaaagc ccttagcttg gagaggaggg tggggccctg ctccccaccc cactcacctc  21660
ctcctctcca cagtggaccc cctggcccag gtgactcagc tattccggga acatctctta  21720
gagcgagcac tgaactgtgt gacccagccc aaccccagcc ctgggtcagc tgatggggac  21780
aagtaagtgt cgttgtgccc tcctccaggc aaggcccctc cggcgggatt ctgagaatag  21840
ctctggcctc aaccctgtgg agagagccca gagctgggct accgtgcgtg ccatgcacgc  21900
ttcattcctc tctgagtttc ctctccccac cagcctgtgg gaggagacag tggcactttg  21960
cagagccagg ggccaggctg tactctggag ggcaggtggg gagcaccctc ctaggacccc  22020
tgccatctgt tccgacagcc agctctctcc ttccacaggg aattctcgga tgccctcggg  22080
tacctgcagc tgctgaacag ctgttctgat gctgcggggg ctcctgccta cagcttctcc  22140
atcagttcca gcatggccac caccaccggt gagtccccgg cccctgtcct ggctcccttc  22200
tcagctcccc cgtgcagcgt gactgagggt tcaggggacc ctccctcttc tgcaggcgta  22260
gacccggtgg ccaagtggtg ggcctctctg acagctgtgg tgatccactg gctgcggcgg  22320
gatgaggagg cggctgagcg gctgtgcccg ctggtggagc acctgccccg ggtgctgcag  22380
gagtctgagt gagtgcacgg caggttcctc ctgcctggtc ccgggctcag ccttcctcat  22440
cccctgggca ctgtgcctca ctcagccttt gttctgtgca ggaggagtca ccaccttttt  22500
tcctcaggga actcgagcca gggaagtggg gggcactcag ccagggcttg tggactggtc  22560
tgactggcac tcttctgccc tggtcccaac aggagacccc tgcccagggc agctctgcac  22620
tccttcaagg ctgcccgggc cctgctgggc tgtgccaagg cagagtctgg tccagccagc  22680
ctgaccatct gtgagaaggc cagtgggtac ctgcaggaca gcctggctac cacaccagcc  22740
agcagctcca ttgacaaggt gaggggtggg gtcaggggcc tggcagggct gggggattca  22800
gctttccatt ccctggttcc tctccccagc ccccaggggc tgcagaagac catggggtta  22860
gcccaagcag cacaggatag ggggtccagc agaccctgct ttttggctaa ggcttctgtc  22920
cagaggagag gggttgcccc tatctggcct cagtttcccc atccctggga ggaggggggt  22980
ggatggtgtg gtaggatccc tttggaggcc ctgcatcagg agggctggac agctgctccc  23040
gggccggtgg cgggtgtggg ggccgagaga ggcgggcggc cccgcggtgc attgctgttg  23100
cattgcacgt gtgtgaggcg ggtgcagtgc ctcggcagtg cagcccggag ccggcccctg  23160
gcaccacggg cccccatcct gcccctccca gagctggagc cctggtgacc cctgccctgc  23220
ctgccacccc caggccgtgc agctgttcct gtgtgacctg cttcttgtgg tgcgcaccag  23280
cctgtggcgg cagcagcagc cccggccccc ggccccagca gcccagggca ccagcagcag  23340
gccccaggct tccgcccttg agctgcgtgg cttccaacgg gacctgagca gcctgaggcg  23400
```

-continued

```
gctggcacag agcttccggc ccgccatgcg gagggtgagt gcccgatggc cctgtcctca  23460
agacggggag tcaggcagtg gtggagatgg agagccctga gcctccactc tcctggcccc  23520
caggtgttcc tacatgaggc cacggcccgg ctgatggcgg gggccagccc cacacggaca  23580
caccagctcc tcgaccgcag tctgaggcgg cgggcaggcc ccggtggcaa aggaggtgag  23640
ggggcagctg ctgaccaggg atgtgctgtc tgctcagcag ggaagggcgc acatgggatg  23700
tgataccaag ggaggctgtg tgtgtgtcag acgggacaga caggcctggc gcagtggctc  23760
acacctagca ctttgggagg ctcagttggg aggacagctt gagcccagga gttggaggcc  23820
gcagtgagcc tgagtgacag ggagagtccc tgtctcaaaa aaaaaaaaag accaagcatc  23880
ttcttgatgg ttacctgatg acaattcctt tcacaaggaa tcagtggggt gactgtcatt  23940
tgtgggatac atgactgcac gtgcgtgact cagtctgtgg actttgtgtg tgggctgaga  24000
ctagggtggg gagaggggaa cccgccaggc ccccgccagg tacctgtgtg ccaggtacag  24060
gcggctggtg ccgtggcttg tgtgtgggca gggctcccgc gggggcgtgg ccagcttgag  24120
acccatccct gacacatcct cgtgtgcgca ggcgcggtgg cggagctgga gccgcggccc  24180
acgcggcggg agcacgcgga ggccttgctg ctggcctcct gctacctgcc ccccggcttc  24240
ctgtcggcgc ccgggcagcg cgtgggcatg ctggctgagg cggcgcgcac actcgagaag  24300
cttggcgatc gccggctgct gcacgactgt cagcagatgc tcatgcgcct gggcggtggg  24360
accactgtca cttccagcta gaccccgtgt ccccggcctc agcacccctg tctctagcca  24420
ctttggtccc gtgcagcttc tgtcctgcgt cgaagctttg aaggccgaag gcagtgcaag  24480
agactctggc ctccacagtt cgacctgcgg ctgctgtgtg ccttcgcggt ggaaggcccg  24540
aggggcgcga tcttgaccct aagaccggcg gccatgatgg tgctgacctc tggtggccga  24600
tcggggcact gcaggggccg agccattttg gggggccccc ctccttgctc tgcaggcacc  24660
ttagtggctt ttttcctcct gtgtacaggg aagagagggg tacatttccc tgtgctgacg  24720
gaagccaact tggctttccc ggactgcaag cagggctctg ccccagaggc ctctctctcc  24780
gtcgtgggag agagacgtgt acatagtgta ggtcagcgtg cttagcctcc tgacctgagg  24840
ctcctgtgct actttgcctt ttgcaaactt tattttcata gattgagaag ttttgtacag  24900
agaattaaaa atgaaattat ttataatctg                                    24930
```

<210> SEQ ID NO 2
<211> LENGTH: 24930
<212> TYPE: DNA
<213> ORGANISM: homo sapien

<400> SEQUENCE: 2

```
gcggccgggg gaacccagtt tccgaggaac ttttcgccgg cgccgggccg cctctgaggc    60
cagggcagga cacgaacgcg cggagcggcg gcggcgactg agagccgggg ccgcggcggc   120
gctccctagg aagggccgta cgaggcggcg ggcccggcgg gcctcccgga ggaggcggct   180
gcgccatgga cgagccaccc ttcagcgagg cggctttgga gcaggcgctg ggcgagccgt   240
gcgatctgga cgcggcgctg ctgaccgaca tcgaaggtgc gtcagggcgg gcagggcttg   300
aagctgcgcc gggtggcgcg agtagggggc gcgcaggtgt ctccctggcc tttgtctccc   360
ccacgggcgc cagctccgtg ctgtgctcgc gcgggacttc ccggtgtctc tgagctcggt   420
gtcccgagcc tcaccgagcc tccctggttc ccgcgctagc gtctcgggcc gcgcgcttgt   480
gggtgagggc tcctgggccg ggccggggtc ccttggcggc tccgggccgg gacacgtgcg   540
cctctacgcg tcccaggccg ggtgccgccc gaccggtgac tctccagccc tgtgatggcc   600
```

-continued

```
acggctgaag ctggggaccc aggcgtcgcc gaagctccgc cccagcccca gccgtgacgt    660
aattgcgagg ttactcacgg tcattccctc cggcccgaga gttcagctcg gcgtcggagc    720
tcttgcgcat gcgcatgggc gctgcctcgc gcccttcccc cgcctcgtgt cgggttctcc    780
cggtctgcga cgggcacagc ctccgcactc attcactgac atccaccgaa tgccaggccc    840
cgtcttaggc accgagggtt tacagacaga cctgggtacc ccctctttta gggaacacaa    900
aaatctcccg ggaaaccaaa cgggtattta gttgtacctt gggtggagcg aggctggggg    960
agggcaggga tgtggctact ttgggtagag cggtcaggga cttctaagct gagacctgag   1020
ggtcaccccc aggaccagca aggaaagatg ttttccaggc cacggcaagg gaagggcaaa   1080
ggcctcgagg cagggcctaa gtgtgaggag ttagaggctt gcaaaggagt gaggtcaggg   1140
aggaggagga cgcaaaccga cttggtcggc cagggaaagg gcggagcaga acagtggcac   1200
cggcttccat ctttggagca tcaccctggc tgtgatgaga aggggtttgg ggccaatggt   1260
ggcaccaagt gccaattagg aggcccgttg cttccatttt gtagatagag caaacggaag   1320
cccctagcaa attgcctgca tggtttctgt gcaggagttt tagcagcact agctaagttg   1380
cacttggttg atgaggaaac tgaggccaag gtcgcaggaa caagatgcct agactcacag   1440
cctgaatgga catgtccatg gaacccgtgg ccaccctggg gttggcaaaa cagatatatc   1500
tatgccacca ccactcctgc cctactgcag ccttgcagat gagcccagct ggttgccagc   1560
cccagaagct tcccagccct ccctccttcc ccctggggct gggctagggg aggaccccag   1620
aggagaggcc ctgattgtga ggcttttcca aaacagcctc ccctatccct ggcacgaggg   1680
gttgtccttc actgccctct ggagtgatga accctgaaat cccaagccct agggagatct   1740
gggcctgact caactaccag ttccacatca ctgggcccag tgagtgtagt cccaagaggc   1800
aacgtgacca agccaggagg acatgcgctt tggggtcaga acttgaacct ggacactcct   1860
cacttccttt gtcatcctgc tcaagccctc tcaccctcta aaccttagtt tccacctcca   1920
gaaaaatgat gcaaaccctc ccttcatggg caagttggac aacagaaccc gttctgggcc   1980
acaggtctga tacagacctt tgtttgtttg tttgtttgtt ttctgcagtg gcgcaatttt   2040
ggctcactgc aagctcctcc tcctgggttc acgccattct cctgccttag tctcccaagt   2100
agctgggact acaggcgcca gccaccacgc ctggctaatt ttttgtattt ttagtagaga   2160
cggggtttca ctgtgctagc caggatggtc tcgatctcct gaccttgtga tccgcccgcc   2220
tcagcctccc aaagtgctgg gattacaggt gtgagccacc gctcccagcc cagacctttc   2280
ttactgacag aatctggtct gggccagagg tctgatacag acctttctta ctgactcatg   2340
gataaaaaca ttgtctctcc agaaccaaag gccaggcatg ggcagccatg tggcccaagg   2400
tctagtctat gagagagtgg gggcagtccc agccccttga agactggggg cagccccttc   2460
tcactaggca gggctcagct ttacccactt cagtagagga tttttcagtt tttattcaaa   2520
cttcctgttt ttcttcccaa ttacacacat ctttttttcat tgtagaaaac ttagaaaatg   2580
caagtgagca aaaagaagaa aataaaatct ttagacctgg ggtggtggct cacacctata   2640
atcccagcac ttgggaggtc gaagcaagag gatgacttgt gtccaggagt ttgagaccag   2700
cctgggcaac atgacaaaat cctgtctcta caaaaataaa aaattagctg ggtgtgggtg   2760
acatgtgcct gtagtctcag ctactctgga ggctgaagtg ggaggattgc ttgagcctgg   2820
acttagaggc tgcagtgagc tataaccatg ccgttgcact cagcctggat gacagagtga   2880
gattctgttt caaaaaaaac tttaaaccta ccacccagag ataagccctg ctaattatgt   2940
```

-continued

```
gaaagagctt ttcttctctc tctctctctc tctctgtgtg tttatatgtg tttggggatg 3000
ggtgcacact cttcataaac ttttttttt ttgagacagg gtctcgctct tttgcccatg 3060
ctgtagtcca gtggcatgat ctcagctcac tgcaaactct gcctctcagg ttcaagagat 3120
tctccagctc ccaagtagct gggattacag tcatgcaccg ccacgcctgg ttaaattttg 3180
tatttttagt agagatggcc atgttggcca ggctggtctc gaactcctga gctcaggtga 3240
tctgcccacc tcagcctctc aaaagtgctg ggattacagg gcatgaacca ccatgcccgg 3300
ccttcatcaa tttttaaaa acgactttat tgaggtatac tttatgtatc acaaaattta 3360
cccattttta gtatatcatt caatgatttt tagttaactt tttgagttgt gtgacaatta 3420
ctagctgtcg aacattttta tcacacagtg agatccctta tacttcttta gtcagttcct 3480
gttcctgctc ccagccccgg gcagctgtgg atctgtatgt gtgtgtgtat atatatatat 3540
atatatatat attttttttt tttttttttt ttttttttt ttgagacgga gtcttgctct 3600
gtcgcccagg ctggagtgca gtggtgcgat cttggctcac tgcaagctcc gcctcccagg 3660
ttcaaacagt tctgcctcag cctcccgagt agctgggatt acaggcacct gccaccacgc 3720
ccggctaatt tttttgtatt tttagtagag atggggtttc accatgttag ccaggatggt 3780
ctcgatctcc tgaccttgtg atctgcccac ctcggcctcc caacgttctg gaattacagg 3840
cgtgagccac cgcgcccggc tggatctgta tttttataaa ttaaaatagg gtccattggt 3900
tcacagctga ttggaatctg cttggttcca tgtcaacagc cagacgacag taaggtttcc 3960
tcttattacc cacctgattc cctgtcgatg gacacctagg ttgtttttatc tttataaact 4020
gctgcagtgg acactgaggc cggttttttt ctttgttttt ttttttttgt ttgtttgttt 4080
ttgagacaga gtcttgctct gtcacccagg ctggagtgca gtggcgcgat ctcggctcac 4140
tgcaaactcc gcctcccggg ttcacaccat tctcctgcct cagcctcccg agtagcttgg 4200
gactataggt gcgtgccacc atgcctggct aattttttgt atttttagta gagacggggt 4260
ttcaccgtgt tagccaggat ggtctcgatc tcctgacctc atgatctgcc cgcctcggcc 4320
tcccaaagtg ctgggattac aggcgtgagc cactgtgcct ggccactgag gccagtcttt 4380
gcccggatcc tcactgtgtt cctaggatga ggttctggga ggggaattgc tggtcagagg 4440
tcgagcctgc ttttgaagct tcttctacca ggagtggagc tgagcaggtt tgataaggtc 4500
tgaagatttg ggggtggaaa tgccaggtcc cttgagagac atgagggata agaggggggcc 4560
aggctggcct tgagtgccag agtgcagagc tgggctagat gtgaggacag tcgggggtca 4620
gagcaggggc acaccgagct tcagttccct ctggctgctt ggatggagga tcgtaatgtg 4680
aacagaaaac actaattgag tacttactgt gtttcagaca gtgtgttgat aatcccactt 4740
aatcccctga caaccccaag taggtagaca tatgatgaag atgacggcct tgaggaccag 4800
agaggttaag tgatttgcct gagatcacac agccagatga tggcaaagcc agaattcaaa 4860
cccaggctgt gggctccaga gcctagctct taagctctta agcactgggc tcctaagaat 4920
ggggatgagg ggttgaggga ggctcctcca caggggctac tctgggggcc tggaagtggg 4980
tcacagaggg gtcagaggct atgtggctac ctccccatcc cagtccagag cagtgtttga 5040
gtcattagac tgggaaccag ccctggtgag ccagccaagg gccttgggcc ccatccggtc 5100
ctgctgcctg ccacagccaa actcttgtca tgtgaatgga tttggggatg gagctgcctc 5160
catgagtcct tgcatctgtg ggtgaaggca ctgccctggc tatagtgtcc ctgggtttga 5220
gtcctgcatc tgcaccaaga cctcaggtga gcctgtctcc ttctgggcct cagagtacct 5280
tgcagctgtc gggggaggat ggatcaggag atggccctgt acctgtgttg gggattattg 5340
```

```
ttaagcccgt ggcagtcttc acctccctgc tgaggattaa tttatccaat tttgcacaag   5400
cttatgagtg cagaagaggc agacggaaac agagttctgg ccaagagcct ggaacagggc   5460
ctcggggtct ctttcctatg cctggacccc gtcatgtctg ctctttgtct gtcggacccc   5520
agatgtctgc caagccccgt cagaggctgc ttcccagaaa gcccttctgg gtgtcacctt   5580
gccccgagca gtgcgttctc agagttctcc cgccctgatg tccctcccag catgcccagc   5640
ccagccacaa cagggccttg cttctagtca tgtgtctggc tgtttgctgg gtccaggcca   5700
gccctggtag ggcacaatgg gggcccgctc tgccacccca tacctctccc caggatatct   5760
catgccccag ttctctccct agttccacca agcactggca ctccttagaa aacacagctc   5820
tagactagtt actgccctag cttacagcac agaactcccc tggtctccaa ccattcatgg   5880
ctccctagtg ctccaagata aagttccctt gtctcagccg ggttgggagt taccttctgc   5940
ccaacattca cctagctgga cacaaacatc ctgagtgacc cggtcagctc caggcaggag   6000
tcactgccag cagaggcctg ggatctggac tttgcctgct gacaggtgga gcccaggccg   6060
gccagaggaa gtgcctctga ccttgtctcc tagcagccac gggccatgtg gacatgcctt   6120
ttgaccctgg gcactgacag tgtgtgacag cctgcaccat gtgctccaca ggggcggctg   6180
tgtgtgtcgg gggtgaggtg gggaaagcct taactggctc aggggtgaga ggtcagggag   6240
ccattgagac tggctccagg tgtgggtccc ctgctgggtt ggggcttgtg ggaggtggga   6300
cggggctggg ggtccatccc cctaggggga atttgtggcc taccccgaac cctgtttgag   6360
ctcctttcct aactgactcc ccgtccctgc acctgtctcc cagcaggcct tgcctctgca   6420
tgctgcccct gccaggctct ggggtccctg tgctccctgc agctagaagg ctgggatcag   6480
gggtcttaac aagcagccct actgtatgac cttggacaag tccaagaacc ttcaggttct   6540
taacaatgta aagggagcag tactaaaagc agcttcttgg aattgtgggg atccgatgag   6600
tgaaggctta agcagtgcat ggcacatagt aggccctgaa ccaatgccag ttagtgttat   6660
tattatcacc atttagccag atgcagtggc tcacgcctat aatcttattg actttagagg   6720
ctgaggttgg aggattgctt gagaccagga gttcaagacc agcctgggca acatagcaag   6780
gccctgtttg ttttagagaa aacaaacaaa tcaccattta gagcacctaa ccagtacctg   6840
gcacgcgata ggtttagctc aacaaatgtt agcagcaatt acccaaggag cctgtgctgg   6900
aagtttctag gatgtaccag gctatggttc caagttctga gcatctacca tgtggtggtc   6960
tggagttggt gagagacagg atggggctga ctaggccagt ggggagcacc ccccgccatg   7020
gggaacaagc accctatcct tggcttccat ggaagataat tgatgctggg cacagtggct   7080
cacgcctgta atcccagcac tttgggaggc tgaggcaggg ggatcgcttg agtctgggag   7140
ttcaagacca gcctgggcaa cattgtgaga cccaaactaa aaaaattagc ttggcatggt   7200
ggagtgtgcc tgtcgtccca gctactcagg aggctgaggc taaagctgga ggattgcttg   7260
agcccaggag gttgaggctg cagtgagcca tgatcatacc actacactcc agcctgggca   7320
acatagtgag gccctgtctc aaaacaaaca aacaaaaaga acctgctgag gaagcagtgt   7380
ttctggctgg gggaggacgg gcagagtggc catctggcca cagatggcgg tttctgtgca   7440
aaacacatca aggcagcctt ggaaatgtga gtgaaagcac cttcaaagtt ctggtcacag   7500
ccttgggact aagcaaagcc accaaaagta cataaaagac aatgaccatc acccagtgcc   7560
ggtgatgcta gaaggaaagg gaatacgttg tagggaaggt tgtaaagggc tttatctttt   7620
ccagactgga gcctggcagc tcgaaaacat cttgctgcct tcatatgagc tttaaaacaa   7680
```

-continued

```
gctgcagaga aacaactcaa gagggagaaa tatatatata tatgtgtgtg tgtgtgtatg   7740
tgtgagtgtg tgtgtgtgtg tgtatacata tatatatata tatatatata tatatatttt   7800
ttttttttt taagatggag tctcgttctg tcaccaggct ggagtgcagt ggtacaatct   7860
cggctcactg caacctccgc ctcctgggtt caaatgattc tcctgcgtca gcctcccaag   7920
cagctgggac tataggcaca taccaccacg cccagctaat ttttgtattt ttagtagagg   7980
ctggatttca ccatgttggc caggatggtt ttgatctcct gacctcgtga tctgcctgcc   8040
ttagcctccc aaagtgttgg gattacaggc gtgagccagt ttgtttttag agacggggtc   8100
ttgctctgtc acccaggctg gaataccatg gcacaatcac agctcgctgc aatgttgaac   8160
tcccgggttc aagggatcct cccacctcag cctccagagt aatggagact acaggctcat   8220
gccaccatgc ccagctattt ttaaaacttt gtagagatgg ggccttgcta cattgcccag   8280
gctggtcttg aactcctggg ctcaagtgat ctgcctgcct ttgcctccca aagtgctgtt   8340
attacaggtg tgagcccctg cgcctaacct tagcactgcc attttgactg aaaacaggtg   8400
cccagcagca ggggctactc ccagaattgc cactgcatca ggcccgtggg ttgttttcag   8460
ctgccagtga taagtatgtg ccctgggcca cctctcggac aaggtgtctg aattggtgcc   8520
gaccagcatc acatgtaatt gccatctcgc aggtgctgct gagggtaatt ccgcacacct   8580
gtagctccgg gaagagccta gtggggagga ggaaacgtgg ctctgaggtt tatagggtca   8640
gacggtcagt atgttgggag ctggcatgtg gaggggcaca gacaagggaa gaatgggagg   8700
tggcatcaga gcaagttttg atggaggaat aggaattcac caggtggaaa gggcattcct   8760
ggtggaggga acagcctggc cttcaatagc ttgtggtgtt cagaaagcag gcagggaaag   8820
ggaggcccag ggagacacca gttaggggat gggggtggag gcagacgagg gtggaggaag   8880
ccatggctgg agtctgcacg gcctctgact ggggtccctg ctgtggtcag ccctgtgctg   8940
ggtgaggctg gggtcacagc tggttcaggc cctgacagga ggggccccca gctgaggccc   9000
agcctctaat ttggcagggc aggtggatag gtctgggggg gtggtggtta ggaagcctcc   9060
aggaggaggc agtgccggag ctgagcctta aagagcttcg tgttgtcctc tctgtctttg   9120
cactctgcac acactcactg aactgcgaca aatgaggata gctggtcagg gcagaggcag   9180
gccggagttg gggctcactg ctgtccccca caggctgggg ctgaagggca ggctctgggg   9240
ccgcagaatg gggtttgtgt accagattct tcatatggca gctgtgggac tttgggcacg   9300
aggcctccgt ctgagcctta gtttcctcaa gaggacctgc gcccaggtgc acctggggct   9360
ccagccatgg gtgcgtccca ttccgggaag agctggcaca cacttgtgcc cccggggcag   9420
ccatgagtgc acaaagggca gcctgtgcca ctgctggata cacgaccagc tgagaacacg   9480
aggaccgccg actccagtta ggaggatcaa ggaagtgcct ggtgggagca gaacagcagg   9540
tggggtgcag cccagctccc tggagggatg gtgggcaccc atcctcaccc tgctgcctcc   9600
attagcaggc cgagagggtg tgctctggaa tcccatgagc acctgtgcca catcctcccc   9660
tgtggctgac ccttcttcac agttggtgca gctttgtggt ctgtagtgca gggatcaatt   9720
ggcaaatccc tttcccaccc attccctgga gaattggggt ccttggctca gatgacagac   9780
caacctgagt tggaatccca gctccttggt ggccgtcctg gcctccaccc cctcactgcc   9840
tccgctcctc ctatcctgcc cacgcccact gcagggcctt tgcacacact gtttcttctg   9900
ccctcccttc cggcccactc cctcatatca ttcagtcctc ctttcagatg tcacctccta   9960
agatgggctg ccctgaccac ctcatctata atggccccag tgcctggcac aggattggca  10020
cacagtagat attgtcagag atggatctgg gttctgtgga caaggctgtg ggggcaggtg  10080
```

aagagctccc tcttccagga ggttgtttgg ggttcaaggc cttgtttggg ttgtaggctt 10140
ctgtgctggt cagcgttggg ccctacaagc gcatgccatg aggcctgccc aggatttccc 10200
tcatggcctc acagaataca tcggccagag tcattaaagg gcgcctgcat ctgccttcag 10260
agagaggttt gaaggtagaa ctggggaggg atgccaggtg ggggttcagg tttcctgttg 10320
ggtcctgata gaatcagggc aggagaggaa gaagaagagg gaagaggagg aacccaggct 10380
tggggagggg tggcagggct tcacaagcct ggggaaggtg aactagggag cagttggggc 10440
caccatggcc cagagtctat gcctcctctt ccttcctgtg ttcagagtgt gtgtgggaac 10500
cacaagggcc ttctcagtgt tcatagggaa gcccggttca cccatgggtg ggccgcaatt 10560
tgggtgccac agtgagcccc tagagaccag ctctcccagc ttccaggaca gggactaggg 10620
gaggcaagag aggctcttcc ttaaattgtg cacccaaggt gcctcagctg ccttactcta 10680
gactggcccc gttaactccc cttaaaaaaa aaaaaaaaaa gactcagtcg aatggtaatg 10740
gagctccaac gtgaatactg caagtatcag gcaactcact acctgacttt ccagttctaa 10800
accattctaa ttgctgtaga gagaactaac ctttgttgag actgttgagt gatggatgtt 10860
ttacacactt gctttcccag aattcccacc tctggagatc gtaggtgtgg gagctcagag 10920
ggtggggagt ggactgtccc catcacacag caagggaggg gctaaaggaa gagcagggcc 10980
tggcatgcag ccccagatag cccacttggg tgtgtctctg agggaggctg cagggctggc 11040
tctagagttt cctttttcag tcttaacctg gtgaccagct tccacagaaa ttggcacggt 11100
gactcatgcc tgtaatcgca acacattggg aggccgaggt gggaggatca cctgaggtca 11160
ggagttcgag accagcctgg ccaacgtggt gaaaccctgt ctctactaaa aatacaaaaa 11220
ttacatttca ttacaggtgt ggtggcgcac acctgtaatc ccagctactc aggaggctga 11280
ggcaggagag tcacttgaac ccgggaggta gaggttgcag tgagctgaga tcgtgtcact 11340
gcactccagc ctgggtgaca gagccagact ctgtctcaaa aaaaaaaaaa aaaaaaaaag 11400
aaattggcca gtagatcagc cccaggggag agtgagccag ggtttggcca ggccttgagt 11460
ttcagaggct ggccatggcc agtggcaccc aggcccttcc cccttcctcg gggcatctta 11520
gcttagtctg tgccctctgc ccaagggcca gccctctgtt cccaggtcac accccctcct 11580
cttggaaggc cccccccgcc ccaccccccat cagagtcttt aatgactctg ctgcccctgg 11640
ggctcagaga gcaaccgccc tctcccatcg cgcttcctca gtgggatggg agggggttag 11700
agcaggaaga tgagacaaat aaagacacaa taagaggcag gaatatgtgg taaagccaag 11760
atgggtaagg ggaggggaca ggcttgactg ttcacagtgg ccctggccct gctgtctcag 11820
gctagtatct gcttgttggt ctcaccacat tctaggctca gaaactgggg agcaaagtaa 11880
tgaaagaacc aggctgggag gccatgggga actcatgcct ggagttcagc tctcagtgtg 11940
cttttgggtc aaggacgctt ccctgtctta agtcactcat gtcagagcct ttgccaagag 12000
caatgctgtg ttttgttttg ggggtgaggg aacacccgcg ggctgagggg agggttgggc 12060
catgctagag aggccgtctg ttgtccttga acctcccaaa gctgggaaat aagggcctgg 12120
gctggacggc ggtggcgagg acaggttgcg agagagacat ggctgggttt tcttgcttag 12180
ggtcctgaat agagagcaag gttgaggccg cagggacccc agcccccaat ggactgctga 12240
gtcgctgggt ctgcccaggg ttcaggcacc ctctcaggtt gcagccaact ggggtgtgga 12300
ccaggcagag gcgctggcct gcagtttggg gcagaggcag gctttgctgg tggtctactt 12360
ggctgcaaaa tcaactggcc aggctctgat cactttgtgt gtgtgtgtgt gtgtaacttt 12420

-continued

```
taccttttgac aaaagaggga agacaggccc aggcacctcc tcaaaagaac cctagagcct  12480
gtcacccctt ccttacccat cttctgtcct agggactgca gcccttcctg gcttcccagg  12540
gccctacaat gaatagtggg tcgggactca cttggtgact gctgggttgt gaggccttga  12600
gggggagggg cagacttcac ccatctggca gagggacatc ggtgctggca gtcaggaaac  12660
ccttatttcc aggcctcagt ttcccggaag tgacctgttt tcaggagtgg cctcatccca  12720
gaccatcagc cccgctgtgg tgaggggtgg ccccttcctg gggctgccct agaaggggga  12780
ggtccctgca cccaccgcag ctgccactcg gcagcccttg gccttaatta aacgcttctt  12840
gcgtactaag tgctgcaccc atattatctc ccttctacca ttcgacgcca gggagataat  12900
gactgtcctg ttttctggag gagtaaacgg agggttggag cggttaaggc tcgctcaggg  12960
tgccagcgaa ccagtgattt cgaacacaga gttctggtgt gttgggccag gacttctctg  13020
ctttgaccct ttaacgaagg gggcgggagc tgagggccag tgaccgccag taaccccggc  13080
agacgctggc accgagcggg ttaaaggcgg acgtccgcta gtaaccccaa ccccattcag  13140
cgccgcgggg tgaaactcga gcccccgccg ccgtggggag gtggggcggg ggccggggcc  13200
gggccctagc gaggcggcag cgcggccgct gattggccgc gcgcgctcac cccatgcccg  13260
gcccgcagcc ccgaagggcg gggcggggcg ggacctgcag gcggggcggg gctggggcgg  13320
ggctgggggc ggggcggggc ggggcgggcg cgccgcagcg ctcaacggct tcaaaaatcc  13380
gccgcgcctt gacaggtgaa gtcggcgcgg ggaggggtag ggccaacggc ctggacgccc  13440
caagggcggg cgcagatcgc ggagccatgg attgcacttt cgaaggtatt tttggaggcc  13500
tccccaccag ccctttatac aatgcctccg tctcctgcag gttctcctgg ggtgggcggg  13560
catgcgggct acgcaacttg agcaggaaag agccccttcc cgagggagaa ggtgtgacag  13620
ttaccagctc gctggggaag tggagggcta cctccaacca aattagtgtc ccctgcaact  13680
caagggggaa gggtttgctt agagacccaa aagcagcatc ccgacctaag agggtttgga  13740
gggagagggt ggtcttctct acattctctg cacccgcttt gggacaggac caggaggaag  13800
cagggaggag ggcccgttgt ccctctgcca cagcgtctgc cctattcagc acccctgcct  13860
attgtgggca tcttagactt ttcaggaaga cagtgggagc cctagattgt caaaattgtc  13920
agtttttctt tcaggcctca gtttccccca tctatcgaag aggctcacac ggactggggt  13980
aaagggatgg gaaaccctgc agttgaaagt ccattatgac ttgatgactt gtgacctggg  14040
gggtccacaa accaggagag tttctacttg agaagccagg aagactgggg ctgccacccc  14100
atcctgttct gccaactgct ctaggaaatt cccctcctgc agtagcttcc ctgcctgggt  14160
acctgtcagt aggcaatgtt gggtctccac tcggtgccag ctgcctgcca agcaaagcct  14220
cgggcagccg taccaaaagg ggtttagtct tttctgttgt acagatgagg aaactggggc  14280
cagtgagagg aggctgttgg tccaggctcc acttcaagct ggtggtgggc agggctggga  14340
gctcaggctg gggatcctga gagcactgga ggcccccatg ggtcctgtag agcattctga  14400
cccagtgggt gccaccacga gtgggttaga gggccctggg ctgagccaga taggctgcta  14460
gtcaccagct gggggagagg gcccttggcc aggtggggct gaggtgggag tgtgtcccag  14520
tctgtatgag gaggaaggag tcaggacaga cagcacttgc ttttacagag atgaaatcaa  14580
agccctgagt ggccaggcct gggtcttgag gctacttggc tgcaggcaaa gcctggactt  14640
gagcccagaa ctctacacag agacacactg gttggccatg tggccagcag ctggcttggc  14700
cctaagcctt ggtctgttcc actgagtaat gggttggtga tggcagcctg gctcttggct  14760
tcttagtggg gcaagaaaag gcagagagac aatagatttg ggattttgta gacctgggtt  14820
```

-continued tgaaccccac tgcatgctct tgggctgctt gtggtcctcc ctgagcctca gtgtcttttc 14880
ttgtctccaa gatgaggtga gctaatcttt tgaggtagtc tagggtagtg gccagtggtt 14940
ggggcattgg agtcaaaata gggtctggac tcagttgagt ctctgactct ataagaactt 15000
aggccagtaa gtcacctctc tacagctcag tttcttcacg tgtagaatgg ggccaatgat 15060
cacatcaccc tctcagctgt gggtgaggat taggggtcta gcctggcccc atcaatgtgg 15120
gtagccccac agcgggcctg gcttttggac cagacccacc cttctgacat gggcccccac 15180
ccttagagtc cttctagtgt ggatgaggac cctgctctga tctggggtcc tcttggggga 15240
cttccctgtc tgccattctc tttggggatc ctgcgctgcc ctaggaagag tgggcccagg 15300
ctgcacagtt ggtccttggt cacagaggat cccaccactt cttcagggcc tcaaggcaat 15360
cctgcctctc tctgcacccc tcttcccct gtaaactgag gggaggggaa aatcacccac 15420
tcctcagcag tttctaagtt gctttgtcaa attcagtgcc cagaggatcc tgctgggggt 15480
gcgttttagg atgagaccag gagtggccaa tggtggggtg tggggcccat cgctcctata 15540
tgaagacccc ctctgcccta gactgctcct ccctccccat ccccatctcc atcccaaaga 15600
ctggagctgc tggatctgtg gatggaggcg tgccccccgt ttcacacatt gagaaacagg 15660
ccccaagtgg agccagggaa ggctgcacct gggcctctgg attccttttg ttctgtgtgg 15720
ggttgggggt gatggactgt ggagagggca ggagagctgt ctggaagggt tggtcacctc 15780
atgggcaaat gcttggaagc tggtctgagt ccacggtgca gtgtgtatgt gtgtgtgtgt 15840
gtgtgtgtgt atgtgtgtgg actcagaggt ggatgtcttg tagaatgcat gccccatgaa 15900
gacaggagta aaagtttacc accatccaca tcaagctaca ggacactccc agctccccag 15960
aaagttgctt agttctaggc agggatttcc cttattcaca gccgggagca gtgcctggca 16020
tagtgtgggc actcagcact cagcacatgc tcactggatg agtgaatgaa tgtgagcctg 16080
ctgtttgctg tggactaagg atgtttctag atgtttgggc aaataccgga tggtgggaag 16140
agctcaggct ctgaagtctg cagtcttggg cccgaccctg ggctcagccc cagcctagct 16200
gtggggcaag attgtgagcc ttgtggtgcc caccttgtcc aggtattgtg atgcactcgc 16260
agcagcaggc attgctttag acagcacagg tgctcgcaaa atggctgtat gtccgggaac 16320
accagctcct gtgggtggct ttctgtcctg gtggcattgc ccacacatac agctgtgtgc 16380
caacaagggt tgtgcaaata aggttgtgtt tggatgtgtg tgatgccctg tttgggggtc 16440
agtctctgcc tcactcacgc accctcttct ccttttcaca gacatgcttc agcttatcaa 16500
caaccaagac agtgacttcc ctggcctatt tgacccaccc tatgctggga gtggggcagg 16560
gggcacagac cctgccagcc ccgataccag ctccccaggc agcttgtctc cacctcctgc 16620
cacattgagc tcctctcttg aagccttcct gagcgggccg caggcagcgc cctcacccct 16680
gtcccctccc cagcctgcac ccactccatt gaagatgtac ccgtccatgc ccgctttctc 16740
ccctgggcct ggtatcaagg aagagtcagt gccactgagc atcctgcaga cccccacccc 16800
acagcccctg ccaggggccc tcctgccaca gagcttccca gccccagccc caccgcagtt 16860
cagctccacc cctgtgttag gctaccccag ccctccggga ggcttctcta caggtaaggg 16920
ggatgtgtgg cgggagggga cacccggggt ggggcttcca ggagcacagg aagaagcttc 16980
tgctgtgatg tgagtagagg tctgtgcagg ctttagaaac tggggctcca ctcggctgct 17040
tgagatgccc tgttactagc agtcctggtg tgcttgttgc cggggtaggc gcaacctcgc 17100
actggaggcc tggcttgaag ccagtgcatt tgcatcagag cccaggcagg gactgtccat 17160

-continued

```
aggaagccac atggggcaat gactcatcca aggccagtcg gtgatagaga cctgaagagc  17220
aggttgaaag tgggagaggg aggtctgtgt ctgcagcccc atgctttatt tctgcaggaa  17280
gccctcccgg gaacacccag cagccgctgc ctggcctgcc actggcttcc ccgccagggg  17340
tcccgcccgt ctccttgcac acccaggtcc agagtgtggt cccccagcag ctactgacag  17400
tcacagctgc ccccacggca gcccctgtaa cgaccactgt gacctcgcag atccagcagg  17460
tcccggtgag ggggtctggc caggggttgg ggagggggca gccccagccc agacacacag  17520
cttacagcca agcctctccc accctcaggt cctgctgcag ccccacttca tcaaggcaga  17580
ctcgctgctt ctgacagcca tgaagacaga cggagccact gtgaaggcgg caggtctcag  17640
tcccctggtc tctggcacca ctgtgcagac agggcctttg ccggtgggtg acgtgggcag  17700
ggcataaggg agtggggtct acacacacac acacatgccc acctggtaac atgtgcctgg  17760
ccctgcagac cctggtgagt ggcggaacca tcttggcaac agtcccactg gtcgtagatg  17820
cggagaagct gcctatcaac cggctcgcag ctggcagcaa ggccccggcc tctgcccaga  17880
gccgtggaga gaagcgcaca gcccacaacg ccattgagaa gtgctaccgc tcctccatca  17940
atgacaaaat cattgagctc aaggatctgg tggtgggcac tgaggcaaag gtgtggagag  18000
gcctgcaggg gcacagaccg gggtgtccct aggaaggaac agatcagggg caactggaag  18060
gaagagaggg agtgagactg agcctggaca agcagggaat tggaattcag cctccccagg  18120
cctggccagc ctcgtttatt tagttaaact ggtttgcagg cctcttcaat aaaggtgggg  18180
ctgtgctagg cattggggat gcagcaatga acaagacaga caaaaattgt ccctcaaaga  18240
agagccgacc ttctggtggg ggagatggac agtaggcagg atgaataagt gctcgagacc  18300
accacgtttg gctcgttgca gagaaagcag gaagaggatg gtgagggtcc cctggtggta  18360
gccagggaag gcctccctga gatggcggca ggcacagcag cagctagcca gaccctgctg  18420
tctgcatctt acattctaac cctatgcccg gcctgggagg tgggtgctac taggcgagga  18480
acggttcagg tagaaggaac aagtgcaaag gtcctgaggc agtaatgttg caaagcagct  18540
ccgcaccccc ttgctagggc tctccaaccc cacaaccccc gacctgacag gccacctgtg  18600
cgctcccccct ccctcccaca ccgtgcagct gaataaatct gctgtcttgc gcaaggccat  18660
cgactacatt cgctttctgc aacacagcaa ccagaaactc aagcaggaga acctaagtct  18720
gcgcactgct gtccacaaaa gcagtgagtc ctggctttat tgagctccag tctggcctct  18780
tctctagcct tgctccacct cccggcccca ccccatccct agccccaccc cacccttggt  18840
tctggcccac cctctgccct gcccacctca cccttggctg tagccctgca ttcagctcta  18900
gtcccttggt tacctctggt cctgaaagag acctggtgcc tccctttggc cctaacccag  18960
ccccatcaaa gcgtcctggg ctagctttag gagctacagt agtccctagg cctccaaggg  19020
cctaggctct gatttggggt cacatatcca gcctttactc ctggctctgt tcctttcggc  19080
ccacagaatc tctgaaggat ctggtgtcgg cctgtggcag tggagggaac acagacgtgc  19140
tcatggaggg cgtgaagact gaggtggagg acacactgac cccacccccc tcggatgctg  19200
gctcaccttt ccagagcagc cccttgtccc ttggcagcag gggcagtggc agcggtggca  19260
gtggcagtga ctcggagcct gacagcccag tctttgagga cagcaaggtt gggccctgcc  19320
acggtgcccc cttccccact cccagccata tcctctgagc ctcatgacag ggccgggaag  19380
accctaacag atcctacctc ccatttcata gacagaataa ctgaggcctg gagccacgtg  19440
gggtcccaca gtaaggtggg cagaatcctg accccccccct tcccagcccc atgctctctg  19500
gggtccctcc gattctgccc tcaccaccct gcccaacccc accaggcaaa gccagagcag  19560
```

-continued

```
cggccgtctc tgcacagccg gggcatgctg gaccgctccc gcctggccct gtgcacgctc  19620
gtcttcctct gcctgtcctg caacccccttg gcctccttgc tgggggcccg gggcttccc  19680
agcccctcag ataccaccag cgtctaccat agccctgggc gcaacgtgct gggcaccgag  19740
agcagaggtg ggaccggcca gcctgggcat ctttgggagg gacactcggg gtgagccccc  19800
aggcttgtga acttggggct ctggatttcc tgggagctgt gtccccagct ttccctctgt  19860
ccatagatgg ccctggctgg gcccagtggc tgctgccccc agtggtctgg ctgctcaatg  19920
ggctgttggt gctcgtctcc ttggtgcttc tctttgtcta cggtgagcca gtcacacggc  19980
cccactcagg ccccgccgtg tacttctgga ggcatcgcaa gcaggctgac ctggacctgg  20040
cccgggtaag gggctggccc cggcagagtg ggcagggcag ggaccccagg ctgtgaaggt  20100
gctgggtgtc aacccttgtt cctgctccct gtgcacacca tgaatctgtc ccgtcctccc  20160
tgtgcctagc cacgcatccg cagaccccca ccacccctcc agagcctgct gtggacggct  20220
cttctgagct ttggggcagc tgctctgacc tcacttttct cacctggaaa accctcatcc  20280
acagggagac tttgcccagg ctgcccagca gctgtggctg gccctgcggg cactgggccg  20340
gcccctgccc acctcccacc tggacctggc ttgtagcctc ctctggaacc tcatccgtca  20400
cctgctgcag cgtctctggg tgggccgctg gctggcaggc cgggcagggg gcctgcagca  20460
ggactgtgct ctgcgagtgg atgctagcgc cagcgcccga gacgcagccc tggtctacca  20520
taagctgcac cagctgcaca ccatgggtag gactgagcgt ggggcgggct ccgaggtgct  20580
ccctgctgcc tgtgctccac ccacagcctc atgcctgctt gccttccagg gaagcacaca  20640
ggcgggcacc tcactgccac caacctggcg ctgagtgccc tgaacctggc agagtgtgca  20700
ggggatgccg tgtctgtggc gacgctggcc gagatctatg tggcggctgc attgagagtg  20760
aagaccagtc tcccacgggc cttgcatttt ctgacagtga gtgggttggg gggctggggg  20820
cttatccctg cagctctctc cagaggctcc ctgggtaaga gctacacggg atgtggcagt  20880
ggttaccagg gggactccag gccaagctgg gactcggccc ggggtctggc cccaggctgt  20940
gtccactgtg acagcccagt accctcccct acagcgcttc ttcctgagca gtgcccgcca  21000
ggcctgcctg gcacagagtg gctcagtgcc tcctgccatg cagtggctct gccaccccgt  21060
gggccaccgt ttcttcgtgg atggggactg gtccgtgctc agtaccccat gggagagcct  21120
gtacagcttg gccgggaacc caggtgctct cttacccctt ccctgtcccc tctcctgtcc  21180
ctcatcctca ttcctgtcct gtcccttgtc gcctgaatct ctggctgtct ctggccaccc  21240
cagtccttct ccctgccatg ggttgttgct gtgggggttg caggaaggga aaggcctggg  21300
tgcctctcgt tcccattggg gctttcagaa gcacatgcag ggattgatgg gcagatggct  21360
aattggagaa gtgaccccag gcagtgccgc tgtggagtaa ggaagcggag ccaacaatgg  21420
catcttctca agtcggtttt cctttggaag cagtgtaggg caggcctcag tgttgtctcc  21480
tggccaaggc tggtgctggt gatagttatg tccacccgct ttcccctgtc cttggcaggg  21540
gctgcaccca ggggcatgcc ggcacttccc agtggcccta ggtgtggccc cagcccaccc  21600
aggaaaaagc ccttagcttg gagaggaggg tggggccctg ctccccaccc cactcacctc  21660
ctcctctcca cagtggaccc cctggcccag gtgactcagc tattccggga acatctctta  21720
gagcgagcac tgaactgtgt gacccagccc aaccccagcc ctgggtcagc tgatggggac  21780
aagtaagtgt cgttgtgccc tcctccaggc aaggcccctc cggcgggatt ctgagaatag  21840
ctctggcctc aaccctgtgg agagagccca gagctgggct accgtgcgtg ccatgcacgc  21900
```

-continued

```
ttcattcctc tctgagtttc ctctccccac cagcctgtgg gaggagacag tggcactttg  21960
cagagccagg ggccaggctg tactctggag ggcaggtggg gagcaccctc ctaggacccc  22020
tgccatctgt tccgacagcc agctctctcc ttccacaggg aattctcgga tgccctcggg  22080
tacctgcagc tgctgaacag ctgttctgat gctgcggggg ctcctgccta cagcttctcc  22140
atcagttcca gcatggccac caccaccggt gagtccccgg cccctgtcct ggctcccttc  22200
tcagctcccc cgtgcagcgt gactgagggt tcaggggacc ctccctcttc tgcaggcgta  22260
gacccggtgg ccaagtggtg ggcctctctg acagctgtgg tgatccactg gctgcggcgg  22320
gatgaggagg cggctgagcg gctgtgcccg ctggtggagc acctgccccg ggtgctgcag  22380
gagtctgagt gagtgcacgg caggttcctc ctgcctggtc ccgggctcag ccttcctcat  22440
cccctgggca ctgtgcctca ctcagccttt gttctgtgca ggaggagtca ccaccttttt  22500
tcctcaggga actcgagcca gggaagtggg gggcactcag ccagggcttg tggactggtc  22560
tgactggcac tcttctgccc tggtcccaac aggagacccc tgcccagggc agctctgcac  22620
tccttcaagg ctgcccgggc cctgctgggc tgtgccaagg cagagtctgg tccagccagc  22680
ctgaccatct gtgagaaggc cagtgggtac ctgcaggaca gcctggctac cacaccagcc  22740
agcagctcca ttgacaaggt gaggggtggg gtcaggggcc tggcagggct gggggattca  22800
gctttccatt ccctggttcc tctccccagc ccccaggggc tgcagaagac catggggtta  22860
gcccaagcag cacaggatag ggggtccagc agaccctgct ttttggctaa ggcttctgtc  22920
cagaggagag gggttgcccc tatctggcct cagtttcccc atccctggga ggagggggt  22980
ggatggtgtg gtaggatccc tttggaggcc ctgcatcagg agggctggac agctgctccc  23040
gggccggtgg cgggtgtggg ggccgagaga ggcgggcggc cccgcggtgc attgctgttg  23100
cattgcacgt gtgtgaggcg ggtgcagtgc ctcggcagtg cagcccggag ccggcccctg  23160
gcaccacggg cccccatcct gcccctccca gagctggagc cctggtgacc cctgccctgc  23220
ctgccacccc caggccgtgc agctgttcct gtgtgacctg cttcttgtgg tgcgcaccag  23280
cctgtggcgg cagcagcagc ccccggcccc ggccccagca gcccagggca ccagcagcag  23340
gccccaggct tccgcccttg agctgcgtgg cttccaacgg gacctgagca gcctgaggcg  23400
gctggcacag agcttccggc ccgccatgcg gagggtgagt gcccgatggc cctgtcctca  23460
agacggggag tcaggcagtg gtggagatgg agagccctga gcctccactc tcctggcccc  23520
caggtgttcc tacatgaggc cacggcccgg ctgatggcgg gggccagccc cacacggaca  23580
caccagctcc tcgaccgcag tctgaggcgg cgggcaggcc ccggtggcaa ggaggtgag  23640
ggggcagctg ctgaccaggg atgtgctgtc tgctcagcag ggaagggcgc acatgggatg  23700
tgataccaag ggaggctgtg tgtgtgtcag acgggacaga caggcctggc gcagtggctc  23760
acacctagca ctttgggagg ctcagttggg aggacagctt gagcccagga gttggaggcc  23820
gcagtgagcc tgagtgacag ggagagtccc tgtctcaaaa aaaaaaaaag accaagcatc  23880
ttcttgatgg ttacctgatg acaattcctt tcacaaggaa tcagtggggt gactgtcatt  23940
tgtgggatac atgactgcac gtgcgtgact cagtctgtgg actttgtgtg tgggctgaga  24000
ctagggtggg gagaggggaa cccgccaggc ccccgccagg tacctgtgtg ccaggtacag  24060
gcggctggtg ccgtggcttg tgtgtgggca gggctcccgc gggggcgtgg ccagcttgag  24120
acccatccct gacacatcct cgtgtgcgca ggcgcggtgg cggagctgga gccgcggccc  24180
acgcggcggg agcacgcgga ggccttgctg ctggcctcct gctacctgcc ccccggcttc  24240
ctgtcggcgc ccgggcagcg cgtgggcatg ctggctgagg cggcgcgcac actcgagaag  24300
```

-continued cttggcgatc gccggctgct gcacgactgt cagcagatgc tcatgcgcct gggcggtggg 24360
accactgtca cttccagcta gaccccgtgt ccccggcctc agcacccctg tctctagcca 24420
ctttggtccc gtgcagcttc tgtcctgcgt cgaagctttg aaggccgaag gcagtgcaag 24480
agactctggc ctccacagtt cgacctgcgg ctgctgtgtg ccttcgcggt ggaaggcccg 24540
aggggcgcga tcttgaccct aagaccggcg gccatgatgg tgctgacctc tggtggccga 24600
tcggggcact gcaggggccg agccattttg gggggccccc ctccttgctc tgcaggcacc 24660
ttagtggctt ttttcctcct gtgtacaggg aagagagggg tacatttccc tgtgctgacg 24720
gaagccaact tggctttccc ggactgcaag cagggctctg ccccagaggc ctctctctcc 24780
gtcgtgggag agagacgtgt acatagtgta ggtcagcgtg cttagcctcc tgacctgagg 24840
ctcctgtgct actttgcctt ttgcaaactt tattttcata gattgagaag ttttgtacag 24900
agaattaaaa atgaaattat ttataatctg 24930

<210> SEQ ID NO 3
<211> LENGTH: 4178
<212> TYPE: DNA
<213> ORGANISM: homo sapien

<400> SEQUENCE: 3
gcggccgggg gaacccaguu uccgaggaac uuuucgccgg cgccgggccg ccucugaggc 60
cagggcagga cacgaacgcg cggagcggcg gcggcgacug agagccgggg ccgcggcggc 120
gcucccuagg aagggccgua cgaggcggcg ggcccggcgg gccucccgga ggaggcggcu 180
gcgccaugga cgagccaccc uucagcgagg cggcuuugga gcaggcgcug ggcgagccgu 240
gcgaucugga cgcggcgcug cugaccgaca ucgaagacau gcuucagcuu aucaacaacc 300
aagacaguga cuucccuggc cuauuugacc cacccuaugc ugggaguggg gcagggggca 360
cagacccugc cagccccgau accagcuccc caggcagcuu gucuccaccu ccugccacau 420
ugagcuccuc ucuugaagcc uuccugagcg ggccgcaggc agcgcccuca ccccugucccc 480 cuccccagcc ugcacccacu ccauugaaga uguacccguc caugcccgcu uucuccccug 540
ggccugguau caaggaagag ucagugccac ugagcauccu gcagaccccc accccacagc 600
cccugccagg ggcccuccug ccacagagcu ucccagcccc agccccaccg caguucagcu 660
ccaccccugu guuaggcuac ccccagcccuc cgggaggcuu cucuacagga agcccucccg 720
ggaacaccca gcagccgcug ccuggccugc cacuggcuuc ccgccagggg gucccgcccg 780
ucuccuugca cacccagguc cagagugugg ucccccagca gcuacugaca gucacagcug 840
cccccacggc agccccugua acgaccacug ugaccucgca gauccagcag gucccggucc 900
ugcugcagcc ccacuucauc aaggcagacu cgcugcuucu gacagccaug aagacagacg 960
gagccacugu gaaggcggca ggucucaguc cccuggucuc uggcaccacu gugcagacag 1020
ggccuuugcc gacccuggug aguggcggaa ccaucuuggc aacaguccca cuggucguag 1080
augcggagaa gcugccuauc aaccggcucg cagcuggcag caaggccccg gccucugccc 1140
agagccgugg agagaagcgc acagcccaca acgccauuga gaagcgcuac cgcuccucca 1200
ucaaugacaa aaucauugag cucaaggauc ugguggugggg cacugaggca aagcugaaua 1260
aaucugcugu cuugcgcaag gccaucgacu acauucgcuu ucugcaacac agcaaccaga 1320
aacucaagca ggagaaccua agucugcgca cugcugucca caaaagcaaa ucucugaagg 1380 aucuggugucc ggccugugc aguggaggga acacagacgu gcucauggag ggcgugaaga 1440

-continued

```
cugaggugga ggacacacug accccacccc ccucggaugc uggcucaccu uuccagagca   1500
gccccuuguc ccuuggcagc aggggcagug gcagcggugg caguggcagu gacucggagc   1560
cugacagccc agucuuugag gacagcaagg caaagccaga gcagcggccg ucucugcaca   1620
gccggggcau gcuggaccgc ucccgccugg cccugugcac gcucgucuuc cucugccugu   1680
ccugcaaccc cuuggccucc uugcuggggg cccgggggcu ucccagcccc ucagauacca   1740
ccagcgucua ccauagcccu gggcgcaacg ugcugggcac cgagagcaga gauggcccug   1800
gcugggccca guggcugcug cccccagugg ucuggcugcu caaugggcug uuggugcucg   1860
ucuccuuggu gcuucucuuu gucuacggug agccagucac acggccccac ucaggccccg   1920
ccguguacuu cuggaggcau cgcaagcagg cugaccugga ccuggcccgg ggagacuuug   1980
cccaggcugc ccagcagcug uggcuggccc ugcgggcacu gggccggccc cugcccaccu   2040
cccaccugga ccuggcuugu agccuccucu ggaaccucau ccgucaccug cugcagcguc   2100
ucugggugggg ccgcuggcug gcaggccggg caggggggccu gcagcaggac ugugcucugc   2160
gaguggaugc uagcgccagc gcccgagacg cagcccuggu cuaccauaag cugcaccagc   2220
ugcacaccau ggggaagcac acaggcgggc accucacugc caccaaccug gcgcugagug   2280
cccugaaccu ggcagagugu gcaggggaug ccgugucugu ggcgacgcug gccgagaucu   2340
auguggcggc ugcauugaga gugaagacca gucucccacg ggccuugcau uuucugacac   2400
gcuucuuccu gagcagugcc cgccaggccu gccuggcaca gaguggcuca gugccuccug   2460
ccaugcagug gcucugccac cccgugggcc accguuucuu cguggauggg gacugguccg   2520
ugcucaguac cccaugggag agccuguaca gcuuggccgg gaacccagug gacccccugg   2580
cccaggugac ucagcuauuc cgggaacauc ucuuagagcg agcacugaac ugugugaccc   2640
agcccaaccc cagcccuggg ucagcugaug gggacaagga auucucggau gcccucgggu   2700
accugcagcu gcugaacagc uguucugaug cugcgggggc uccugccuac agcuucucca   2760
ucaguuccag cauggccacc accaccggcg uagacccggu ggccaagugg ugggccucuc   2820
ugacagcugu ggugauccac uggcugcggc gggaugagga ggcggcugag cggcugugcc   2880
cgcuggugga gcaccugccc cgggugcugc aggagucuga gagaccccug cccagggcag   2940
cucugcacuc cuucaaggcu gcccgggccc ugcugggcug ugccaaggca gagucugguc   3000
cagccagccu gaccaucugu gagaaggcca gugggguaccu gcaggacagc cuggcuacca   3060
caccagccag cagcuccauu gacaaggccg ugcagcuguu ccugugugac cugcuucuug   3120
uggugcgcac cagccugugg cggcagcagc agcccccggc cccggcccca gcagcccagg   3180
gcaccagcag caggccccag gcuuccgccc uugagcugcg uggcuuccaa cgggaccuga   3240
gcagccugag gcggcuggca cagagcuucc ggcccgccau gcggagggug uuccuacaug   3300
aggccacggc ccggcugaug gcgggggcca gccccacacg gacacaccag cuccucgacc   3360
gcagucugag gcggcgggca ggccccggug gcaaaggagg cgcggguggcg gagcuggagc   3420
cgcggcccac gcggcgggag cacgcggagg ccuugcugcu ggccuccugc uaccugcccc   3480
ccggcuuccu gucggcgccc gggcagcgcg ugggcaugcu ggcugaggcg gcgcgcacac   3540
ucgagaagcu uggcgaucgc cggcugcugc acgacuguca gcagaugcuc augcgccugg   3600
gcggugggac cacugucacu uccagcuaga ccccgugucc ccggccucag caccccuguc   3660
ucuagccacu uuggucccgu gcagcuucug uccugcgucg aagcuuugaa ggccgaaggc   3720
agugcaagag acucuggccu ccacaguucg accugcggcu gcugugugcc uucgcggugg   3780
aaggcccgag gggcgcgauc uugacccuaa gaccggcggc caugauggug cugaccucug   3840
```

```
guggccgauc ggggcacugc aggggccgag ccauuuuggg gggccccccu ccuugcucug   3900

caggcaccuu aguggcuuuu uuccuccugu guacagggaa gagaggggua cauuucccug   3960

ugcugacgga agccaacuug gcuuucccgg acugcaagca gggcucugcc ccagaggccu   4020

cucucuccgu cgugggagag agacguguac auaguguagg ucagcgugcu uagccuccug   4080

accugaggcu ccugugcuac uuugccuuuu gcaaacuuua uuuucauaga uugagaaguu   4140

uuguacagag aauuaaaaau gaaauuauuu auaaucug                           4178


<210> SEQ ID NO 4
<211> LENGTH: 4253
<212> TYPE: DNA
<213> ORGANISM: homo sapien

<400> SEQUENCE: 4

caguuuccga ggaacuuuuc gccggcgccg ggccgccucu gaggccaggg caggacacga     60

acgcgcggag cggcggcggc gacugagagc cggggccgcg gcggcgcucc cuaggaaggg    120

ccguacgagg cggcgggccc ggcgggccuc ccggaggagg cggcugcgcc auggacgagc    180

cacccuucag cgaggcggcu uuggagcagg cgcugggcga gccgugcgau cuggacgcgg    240

cgcugcugac cgacaucgaa ggugaagucg gcgcggggag ggguagggcc aacggccugg    300

acgccccaag ggcgggcgca gaucgcggag ccauggauug cacuuucgaa gacaugcuuc    360

agcuuaucaa caaccaagac agugacuucc cuggccuauu ugacccaccc uaugcuggga    420

guggggcagg gggcacagac ccugccagcc ccgauaccag cuccccaggc agcuugucuc    480

caccuccugc cacauugagc uccucucuug aagccuuccu gagcgggccg caggcagcgc    540

ccucaccccu guccccuccc cagccugcac ccacuccauu gaagauguac ccguccaugc    600

ccgcuuucuc cccugggccu gguaucaagg aagagucagu gccacugagc auccugcaga    660

cccccacccc acagccccug ccaggggccc uccugccaca gagcuuccca gccccagccc    720

caccgcaguu cagcuccacc ccuguguuag gcuaccccag cccuccggga ggcuucucua    780

caggaagccc ucccgggaac acccagcagc cgcugccugg ccugccacug gcuuccccgc    840

caggggaccc gcccgucucc uugcacaccc agguccagag uguggucccc cagcagcuac    900

ugacagucac agcugccccc acggcagccc cuguaacgac cacugugacc ucgcagaucc    960

agcaggaccc gguccugcug cagccccacu ucaucaaggc agacucgcug cuucugacag   1020

ccaugaagac agacggagcc acugugaagg cggcaggucu caguccccug gucucuggca   1080

ccacugugca gacagggccu uugccgaccc uggugagugg cggaaccauc uuggcaacag   1140

ucccacuggu cguagaugcg gagaagcugc cuaucaaccg gcucgcagcu ggcagcaagg   1200

ccccggccuc ugcccagagc cguggagaga agcgcacagc ccacaacgcc auugagaagc   1260

gcuaccgcuc cuccaucaau gacaaaauca uugagcucaa ggaucuggug gugggcacug   1320

aggcaaagcu gaauaaaucu gcugucuugc gcaaggccau cgacuacauu cgcuuucugc   1380

aacacagcaa ccagaaacuc aagcaggaga accuaagucu gcgcacugcu guccacaaaa   1440

gcaaaucucu gaaggaucug gugucggccu guggcagugg agggaacaca gacgugcuca   1500

uggagggcgu gaagacugag guggaggaca cacugacccc acccccucg gaugcuggcu   1560

caccuuucca gagcagcccc uuguccuug gcagcagggg caguggcagc gguggcagug   1620

gcagugacuc ggagccugac agcccagucu uugaggacag caaggcaaag ccagagcagc   1680

ggccgucucu gcacagccgg ggcaugcugg accgcucccg ccuggcccug ugcacgcucg   1740
```

-continued

```
ucuuccucug ccuguccugc aacccccuugg ccuccuugcu gggggcccgg gggcuuccca   1800
gccccucaga uaccaccagc gucuaccaua gcccugggcg caacgugcug ggcaccgaga   1860
gcagagaugg cccuggcugg gcccaguggc ugcugccccc aguggucugg cugcucaaug   1920
ggcuguuggu gcucgucucc uuggugcuuc ucuuugucua cggugagcca gucacacggc   1980
cccacucagg ccccgccgug uacuucugga ggcaucgcaa gcaggcugac cuggaccugg   2040
cccggggaga cuuugcccag gcugcccagc agcuguggcu ggcccugcgg gcacugggcc   2100
ggccccugcc caccucccac cuggaccugg cuuguagccu ccucuggaac cucauccguc   2160
accugcugca gcgucucugg gugggccgcu ggcuggcagg ccgggcaggg ggccugcagc   2220
aggacugugc ucugcgagug gaugcuagcg ccagcgcccg agacgcagcc cuggucuacc   2280
auaagcugca ccagcugcac accaugggga agcacacagg cgggcaccuc acugccacca   2340
accuggcgcu gagugcccug aaccuggcag agugugcagg ggaugccgug ucuguggcga   2400
cgcuggccga gaucuaugug gcggcugcau ugagagugaa gaccagucuc ccacgggccu   2460
ugcauuuucu gacacgcuuc uuccugagca gugcccgcca ggccugccug gcacagagug   2520
gcucagugcc uccugccaug caguggcucu gccaccccgu gggccaccgu uucuucgugg   2580
auggggacug guccgugcuc aguaccccau gggagagccu guacagcuug gccgggaacc   2640
caguggaccc ccuggcccag gugacucagc uauuccggga acaucucuua gagcgagcac   2700
ugaacugugu gacccagccc aaccccagcc cugggucagc ugaugggac aaggaauucu   2760
cggaugcccu cggguaccug cagcugcuga acagcuguuc ugaugcugcg ggggcuccug   2820
ccuacagcuu cuccaucagu uccagcaugg ccaccaccac cggcguagac ccgguggcca   2880
aguggugggc cucucugaca gcugugguga uccacuggcu gcggcgggau gaggaggcgg   2940
cugagcggcu gugcccgcug guggagcacc ugccccgggu gcugcaggag ucugagagac   3000
cccugcccag ggcagcucug cacuccuuca aggcugcccg ggcccugcug ggcugugcca   3060
aggcagaguc ugguccagcc agccugacca ucugugagaa ggccagugg uaccugcagg   3120
acagccuggc uaccacacca gccagcagcu ccauugacaa ggccgugcag cuguuccugu   3180
gugaccugcu ucuuguggug cgcaccagcc uguggcggca gcagcagccc ccggccccgg   3240
ccccagcagc ccagggcacc agcagcaggc cccaggcuuc cgcccuugag cugcguggcu   3300
uccaacggga ccugagcagc cugaggcggc uggcacagag cuuccggccc gccaugcgga   3360
gggguguucc uacaugaggcc acggcccggc ugauggcggg ggccagcccc acacggacac   3420
accagcuccu cgaccgcagu cugaggcggc gggcaggccc cgguggcaaa ggaggcgcgg   3480
uggcggagcu ggagccgcgg cccacgcggc gggagcacgc ggaggccuug cugcuggccu   3540
ccugcuaccu gccccccggc uuccugucgg cgcccgggca gcgcgugggc augcuggcug   3600
aggcggcgcg cacacucgag aagcuuggcg aucgccggcu gcugcacgac ugucagcaga   3660
ugcucaugcg ccugggcggu gggaccacug ucacuuccag cuagaccccg uguccccggc   3720
cucagcaccc cugucucuag ccacuuuggu cccgugcagc uucuguccug cgucgaagcu   3780
uugaaggccg aaggcagugc aagagacucu ggccuccaca guucgaccug cggcugcugu   3840
gugccuucgc gguggaaggc ccgaggggcg cgaucuugac ccuaagaccg gcggccauga   3900
uggugcugac cucugguggc cgaucggggc acugcagggg ccgagccauu uugggggggcc   3960
ccccuccuug cucugcaggc accuuagugg cuuuuuuccu ccuguguaca gggaagagag   4020
ggguacauuu cccugugcug acggaagcca acuuggcuuu cccggacugc aagcagggcu   4080
cugccccaga ggccucucuc uccgucgugg gagagagacg uguacauagu guaggucagc   4140
```

gugcuuagcc uccugaccug aggcuccugu gcuacuuugc cuuuugcaaa cuuuauuuuc 4200
auagauugag aaguuuugua cagagaauua aaaaugaaau uauuuauaau cug 4253

<210> SEQ ID NO 5
<211> LENGTH: 4056
<212> TYPE: DNA
<213> ORGANISM: homo sapien

<400> SEQUENCE: 5
gcggggcggg cgcgccgcag cgcucaacgg cuucaaaaau ccgccgcgcc uugacaggug 60
aagucggcgc ggggaggggu agggccaacg gccuggacgc cccaagggcg ggcgcagauc 120
gcggagccau ggauugcacu uucgaagaca ugcuucagcu uaucaacaac caagacagug 180
acuucccugg ccuauuugac ccacccuaug cugggagugg ggcagggggc acagacccug 240
ccagccccga uaccagcucc ccaggcagcu ugucuccacc uccugccaca uugagcuccu 300
cucuugaagc cuuccugagc gggccgcagg cagcgcccuc accccugucc ccuccccagc 360
cugcacccac uccauugaag auguacccgu ccaugcccgc uuucuccccu gggccuggua 420
ucaaggaaga gucagugcca cugagcaucc ugcagacccc caccccacag ccccugccag 480
gggcccuccu gccacagagc uucccagccc cagccccacc gcaguucagc uccaccccug 540
uguuaggcua ccccagcccu ccgggaggcu ucucuacagg aagcccuccc gggaacaccc 600
agcagccgcu gccuggccug ccacuggcuu ccccgccagg ggucccgccc gucuccuugc 660
acacccaggu ccagagugug gucccccagc agcuacugac agucacagcu gcccccacgg 720
cagccccugu aacgaccacu gugaccucgc agauccagca ggucccgguc cugcugcagc 780
cccacuucau caaggcagac ucgcugcuuc ugacagccau gaagacagac ggagccacug 840
ugaaggcggc aggucucagu ccccuggucu cuggcaccac ugugcagaca gggccuuugc 900
cgacccuggu gaguggcgga accaucuugg caacaguccc acuggucgua gaugcggaga 960
agcugccuau caaccggcuc gcagcuggca gcaaggcccc ggccucugcc cagagccgug 1020
gagagaagcg cacagcccac aacgccauug agaagcgcua ccgcuccucc aucaaugaca 1080
aaaucauuga gcucaaggau cugguggugg gcacugaggc aaagcugaau aaaucugcug 1140
ucuugcgcaa ggccaucgac uacauucgcu uucugcaaca cagcaaccag aaacucaagc 1200
aggagaaccu aagucugcgc acugcugucc acaaaagcaa aucucugaag gaucuggugu 1260
cggccugugg caguggaggg aacacagacg ugcucaugga gggcgugaag acugaggugg 1320
aggacacacu gaccccaccc cccucggaug cuggcucacc uuuccagagc agccccuugu 1380
cccuuggcag caggggcagu ggcagcggug gcaguggcag ugacucggag ccugacagcc 1440
cagucuuuga ggacagcaag gcaaagccag agcagcggcc gucucugcac agccggggca 1500
ugcuggaccg cucccgccug gcccugugca cgcucgucuu ccucugccug uccugcaacc 1560
ccuuggccuc cuugcugggg gcccgggggc uucccagccc cucagauacc accagcgucu 1620
accauagccc ugggcgcaac gugcugggca ccgagagcag agauggcccu ggcugggccc 1680
aguggcugcu gcccccagug gucuggcugc ucaaugggcu guuggugcuc gucuccuugg 1740
ugcuucucuu ugucuacggu gagccaguca cacggcccca cucaggcccc gccguguacu 1800
ucuggaggca ucgcaagcag gcugaccugg accuggcccg gggagacuuu gcccaggcug 1860
cccagcagcu guggcuggcc cugcgggcac ugggccggcc ccugcccacc ucccaccugg 1920
accuggcuug uagccuccuc uggaaccuca uccgucaccu gcugcagcgu cucugggugg 1980

-continued

```
gccgcuggcu ggcaggccgg gcagggggcc ugcagcagga cugugcucug cgaguggaug   2040

cuagcgccag cgcccgagac gcagcccugg ucuaccauaa gcugcaccag cugcacacca   2100

uggggaagca cacaggcggg caccucacug ccaccaaccu ggcgcugagu gcccugaacc   2160

uggcagagug ugcaggggau gccgugucug uggcgacgcu ggccgagauc uauguggcgg   2220

cugcauugag agugaagacc agucucccac gggccuugca uuuucugaca cgcuucuucc   2280

ugagcagugc ccgccaggcc ugccuggcac agaguggcuc agugccuccu gccaugcagu   2340

ggcucugcca ccccguggge caccguuucu ucguggaugg ggacuggucc gugcucagua   2400

ccccauggga gagccuguac agcuuggccg ggaacccagu ggacccccug gcccagguga   2460

cucagcuauu ccgggaacau cucuuagagc gagcacugaa cugugugacc cagcccaacc   2520

ccagcccugg gucagcugau ggggacaagg aauucucgga ugcccucggg uaccugcagc   2580

ugcugaacag cuguucugau gcugcggggg cuccugccua cagcuucucc aucaguucca   2640

gcauggccac caccaccggc guagacccgg uggccaagug gugggccucu cugacagcug   2700

uggugaucca cuggcugcgg cgggaugagg aggcggcuga gcggcugugc ccgcuggugg   2760

agcaccugcc ccgggugcug caggagucug agagaccccu gcccagggca gcucugcacu   2820

ccuucaaggc ugcccgggcc cugcugggcu gugccaaggc agagucuggu ccagccagcc   2880

ugaccaucug ugagaaggcc aguggguacc ugcaggacag ccuggcuacc acaccagcca   2940

gcagcuccau ugacaaggcc gugcagcugu uccugugugu ccugcuucuu guggugcgca   3000

ccagccugug gcggcagcag cagcccccgg ccccggcccc agcagcccag ggcaccagca   3060

gcaggcccca ggcuuccgcc cuugagcugc guggcuucca acgggaccug agcagccuga   3120

ggcggcuggc acagagcuuc cggcccgcca ugcggagggu guuccuacau gaggccacgg   3180

cccggcugau ggcgggggcc agccccacac ggacacacca gcuccucgac cgcagucuga   3240

ggcggcgggc aggccccggu ggcaaaggag gcgcgguggc ggagcuggag ccgcggccca   3300

cgcggcggga gcacgcggag gccuugcugc uggccuccug cuaccugccc cccggcuucc   3360

ugucggcgcc cgggcagcgc gugggcaugc uggcugaggc ggcgcgcaca cucgagaagc   3420

uuggcgaucg ccggcugcug cacgacuguc agcagaugcu caugcgccug ggcgguggga   3480

ccacugucac uuccagcuag accccguguc cccggccuca gcaccccugu cucuagccac   3540

uuuggucccg ugcagcuucu guccugcguc gaagcuuuga aggccgaagg cagugcaaga   3600

gacucuggcc uccacaguuc gaccugcggc ugcugugugc cuucgcggug gaaggcccga   3660

ggggcgcgau cuugacccua agaccggcgg ccaugauggu gcugaccucu gguggccgau   3720

cggggcacug caggggccga gccauuuugg ggggcccccc uccuugcucu gcaggcaccu   3780

uaguggcuuu uuuccuccug uguacaggga agagaggggu acauuucccu gugcugacgg   3840

aagccaacuu ggcuuucccg gacugcaagc agggcucugc cccagaggcc ucucucuccg   3900

ucguggggaga gagacgugua cauaguguag gucagcgugc uuagccuccu gaccugaggc   3960

uccugugcua cuuugccuuu ugcaaacuuu auuuucauag auugagaagu uuuguacaga   4020

gaauuaaaaa ugaaauuauu uauaaucugg aaaaaa                              4056
```

<210> SEQ ID NO 6
<211> LENGTH: 4178
<212> TYPE: DNA
<213> ORGANISM: homo sapien

<400> SEQUENCE: 6

```
gcggccgggg gaacccaguu uccgaggaac uuuucgccgg cgccgggccg ccucugaggc     60
```

-continued

```
cagggcagga cacgaacgcg cggagcggcg gcggcgacug agagccgggg ccgcggcggc    120
gcucccuagg aagggccgua cgaggcggcg ggcccggcgg gccucccgga ggaggcggcu    180
gcgccaugga cgagccaccc uucagcgagg cggcuuugga gcaggcgcug ggcgagccgu    240
gcgaucugga cgcggcgcug cugaccgaca ucgaagacau gcuucagcuu aucaacaacc    300
aagacaguga cuucccuggc cuauuugacc cacccuaugc ugggaguggg gcagggggca    360
cagacccugc cagccccgau accagcuccc caggcagcuu gucuccaccu ccugccacau    420
ugagcuccuc ucuugaagcc uuccugagcg ggccgcaggc agcgcccuca ccccuguccc    480
cuccccagcc ugcacccacu ccauugaaga uguacccguc caugcccgcu uucuccccug    540
ggccugguau caaggaagag ucagugccac ugagcauccu gcagaccccc accccacagc    600
cccugccagg ggcccuccug ccacagagcu ucccagcccc agccccaccg caguucagcu    660
ccaccccugu guuaggcuac ccccagcccuc cgggaggcuu cucuacagga agcccucccg   720
ggaacaccca gcagccgcug ccuggccugc cacuggcuuc ccgcccaggg gucccgcccg    780
ucuccuugca cacccagguc cagagugugg ucccccagca gcuacugaca gucacagcug    840
cccccacggc agccccugua acgaccacug ugaccucgca gauccagcag gucccggucc    900
ugcugcagcc ccacuucauc aaggcagacu cgcugcuucu gacagccaug aagacagacg    960
gagccacugu gaaggcggca ggucucaguc cccuggucuc uggcaccacu gugcagacag   1020
ggccuuugcc gacccuggug aguggcggaa ccaucuuggc aacaguccca cuggucguag   1080
augcggagaa gcugccuauc aaccggcucg cagcuggcag caaggccccg gccucugccc   1140
agagccgugg agagaagcgc acagcccaca acgccauuga gaagugcuac cgcuccucca   1200
ucaaugacaa aaucauugag cucaaggauc ugguggggg cacugaggca aagcugaaua   1260
aaucugcugu cuugcgcaag gccaucgacu acauucgcuu ucugcaacac agcaaccaga   1320
aacucaagca ggagaaccua agucugcgca cugcugucca caaaagcaaa ucucugaagg   1380
aucuggugucc ggccuguggc aguggaggga acacagacgu gcucauggag ggcgugaaga  1440
cugaggugga ggacacacug accccacccc ccucggaugc uggcucaccu uuccagagca   1500
gccccuuguc ccuuggcagc aggggcagug gcagcggugg caguggcagu gacucggagc   1560
cugacagccc agucuuugag gacagcaagg caaagccaga gcagcggccg ucucugcaca   1620
gccggggcau gcuggaccgc ucccgccugg cccugugcac gcucgucuuc cucugccugu   1680
ccugcaaccc cuuggccucc uugcuggggg cccgggggcu ucccagcccc ucagauacca   1740
ccagcgucua ccauagcccu gggcgcaacg ugcugggcac cgagagcaga gauggcccug   1800
gcugggccca guggcugcug cccccagugg ucuggcugcu caaugggcug uuggugcucg   1860
ucuccuuggu gcuucucuuu gucuacggug agccagucac acggccccac ucaggccccg   1920
ccguguacuu cuggaggcau cgcaagcagg cugaccugga ccuggcccgg ggagacuuug   1980
cccaggcugc ccagcagcug uggcuggccc ugcgggcacu gggccggccc cugcccaccu   2040
cccaccugga ccuggcuugu agccuccucu ggaaccucau ccgucaccug cugcagcguc   2100
ucugggugggg ccgcuggcug gcaggccggg cagggggccu gcagcaggac ugugcucugc  2160
gaguggaugc uagcgccagc gccccgagacg cagcccuggu cuaccauaag cugcaccagc  2220
ugcacaccau ggggaagcac acaggcgggc accucacugc caccaaccug gcgcugagug   2280
cccugaaccu ggcagagugu gcaggggaug ccgugucugu ggcgacgcug gccgagaucu   2340
auguggcggc ugcauugaga gugaagacca gucucccacg ggccuugcau uuucugacac   2400
```

gcuucuuccu gagcagugcc cgccaggccu gccuggcaca gaguggcuca gugccuccug 2460
ccaugcagug gcucugccac cccgugggcc accguuucuu cguggauggg gacuggucccg 2520 ugcucaguac cccaugggag agccuguaca gcuuggccgg gaacccagug gacccccugg 2580
cccaggugac ucagcuauuc cgggaacauc ucuuagagcg agcacugaac ugugugaccc 2640
agcccaaccc cagcccuggg ucagcugaug gggacaagga auucucggau gcccucgggu 2700
accugcagcu gcugaacagc uguucugaug cugcgggggc uccugccuac agcuucucca 2760
ucaguuccag cauggccacc accaccggcg uagacccggu ggccaagugg ugggccucuc 2820
ugacagcugu ggugauccac uggcugcggc gggaugagga ggcggcugag cggcugugcc 2880
cgcuggugga gcaccugccc cgggugcugc aggagucuga gagaccccug cccagggcag 2940
cucugcacuc cuucaaggcu gcccgggccc ugcugggcug ugccaaggca gagucugguc 3000
cagccagccu gaccaucugu gagaaggcca gugggguaccu gcaggacagc cuggcuacca 3060
caccagccag cagcuccauu gacaaggccg ugcagcuguu ccugugugac cugcuucuug 3120
uggugcgcac cagccugugg cggcagcagc agcccccggc cccggcccca gcagcccagg 3180
gcaccagcag caggccccag gcuuccgccc uugagcugcg uggcuuccaa cgggaccuga 3240
gcagccugag gcggcuggca cagagcuucc ggcccgccau gcggagggug uuccuacaug 3300
aggccacggc ccggcugaug gcgggggcca gccccacacg gacacaccag cuccucgacc 3360
gcagucugag gcggcgggca ggccccggug gcaaaggagg cgcgguggcg gagcuggagc 3420
cgcggcccac gcggcgggag cacgcggagg ccuugcugcu ggccuccugc uaccugcccc 3480
ccggcuuccu gucggcgccc gggcagcgcg ugggcaugcu ggcugaggcg gcgcgcacac 3540
ucgagaagcu uggcgaucgc cggcugcugc acgacuguca gcagaugcuc augcgccugg 3600
gcggugggac cacugucacu uccagcuaga ccccgugucc ccggccucag caccccuguc 3660
ucuagccacu uuggucccgu gcagcuucug uccugcgucg aagcuuugaa ggccgaaggc 3720
agugcaagag acucuggccu ccacaguucg accugcggcu gcugugugcc uucgcggugg 3780
aaggcccgag gggcgcgauc uugacccuaa gaccggcggc caugauggug cugaccucug 3840
guggccgauc ggggcacugc aggggccgag ccauuuuggg gggccccccu ccuugcucug 3900
caggcaccuu aguggcuuuu uuccuccugu guacagggaa gagaggggua cauuucccug 3960
ugcugacgga agccaacuug gcuuucccgg acugcaagca gggcucugcc ccagaggccu 4020
cucucuccgu cgugggagag agacguguac auaguguagg ucagcgugcu uagccuccug 4080
accugaggcu ccugugcuac uuugccuuuu gcaaacuuua uuuucauaga uugagaaguu 4140
uuguacagag aauuaaaaau gaaauuauuu auaaucug 4178

<210> SEQ ID NO 7
<211> LENGTH: 4253
<212> TYPE: DNA
<213> ORGANISM: homo sapien

<400> SEQUENCE: 7
caguuuccga ggaacuuuuc gccggcgccg ggccgccucu gaggccaggg caggacacga 60
acgcgcggag cggcggcggc gacugagagc cggggccgcg gcggcgcucc cuaggaaggg 120
ccguacgagg cggcgggccc ggcgggccuc ccggaggagg cggcugcgcc auggacgagc 180
cacccuucag cgaggcggcu uuggagcagg cgcugggcga gccgugcgau cuggacgcgg 240
cgcugcugac cgacaucgaa ggugaagucg gcgcggggag ggguagggcc aacggccugg 300
acgccccaag ggcgggcgca gaucgcggag ccauggauug cacuuucgaa gacaugcuuc 360

```
agcuuaucaa caaccaagac agugacuucc cuggccuauu ugacccaccc uaugcuggga    420
guggggcagg gggcacagac ccugccagcc ccgauaccag cuccccaggc agcuugucuc    480
caccuccugc cacauugagc uccucucuug aagccuuccu gagcgggccg caggcagcgc    540
ccucaccccu guccccuccc cagccugcac ccacuccauu gaagauguac ccguccaugc    600
ccgcuuucuc cccugggccu gguaucaagg aagagucagu gccacugagc auccugcaga    660
cccccacccc acagccccug ccaggggccc uccugccaca gagcuuccca gccccagccc    720
caccgcaguu cagcuccacc ccuguguuag gcuaccccag cccuccggga ggcuucucua    780
caggaagccc ucccgggaac acccagcagc cgcugccugg ccugccacug gcuuccccgc    840
caggggaccc gcccgucucc uugcacaccc agguccagag ugugguuccc cagcagcuac    900
ugacagucac agcugccccc acggcagccc cuguaacgac cacugugacc ucgcagaucc    960
agcaggaccc gguccugcug cagccccacu ucaucaaggc agacucgcug cuucugacag   1020
ccaugaagac agacggagcc acugugaagg cggcaggucu caguccccug gucucuggca   1080
ccacugugca gacagggccu uugccgaccc uggugagugg cggaaccauc uuggcaacag   1140
ucccacuggu cguagaugcg gagaagcugc cuaucaaccg gcucgcagcu ggcagcaagg   1200
ccccggccuc ugcccagagc cguggagaga agcgcacagc ccacaacgcc auugagaagu   1260
gcuaccgcuc cuccaucaau gacaaaauca uugagcucaa ggaucuggug gugggcacug   1320
aggcaaagcu gaauaaaucu gcugucuugc gcaaggccau cgacuacauu cgcuuucugc   1380
aacacagcaa ccagaaacuc aagcaggaga accuaagucu gcgcacugcu guccacaaaa   1440
gcaaaucucu gaaggaucug gugucggccu guggcagugg agggaacaca gacgugcuca   1500
uggagggcgu gaagacugag guggaggaca cacugacccc acccccucg gaugcuggcu   1560
caccuuucca gagcagcccc uugucccuug gcagcagggg caguggcagc gguggcagug   1620
gcagugacuc ggagccugac agcccagucu uugaggacag caaggcaaag ccagagcagc   1680
ggccgucucu gcacagccgg ggcaugcugg accgcucccg ccuggcccug ugcacgcucg   1740
ucuuccucug ccuguccugc aaccccuugg ccuccuugcu gggggcccgg gggcuuccca   1800
gccccucaga uaccaccagc gucuaccaua gcccugggcg caacgugcug ggcaccgaga   1860
gcagagaugg cccuggcugg gcccaguggc ugcugccccc aguggucugg cugcucaaug   1920
ggcuguuggu gcucgucucc uuggugcuuc ucuuugucua cggugagcca gucacacggc   1980
cccacucagg ccccgccgug uacuucugga ggcaucgcaa gcaggcugac cuggaccugg   2040
cccggggaga cuuugcccag gcugcccagc agcuguggcu ggcccugcgg gcacugggcc   2100
ggccccugcc caccucccac cuggaccugg cuuguagccu ccucuggaac cucauccguc   2160
accugcugca gcgucucugg gugggccgcu ggcuggcagg ccgggcaggg ggccugcagc   2220
aggacugugc ucugcgagug gaugcuagcg ccagcgcccg agacgcagcc cuggucuacc   2280
auaagcugca ccagcugcac accaugggga agcacacagg cgggcaccuc acugccacca   2340
accuggcgcu gagugcccug aaccuggcag agugugcagg ggaugccgug ucuguggcga   2400
cgcuggccga gaucuaugug gcggcugcau ugagagugaa gaccagucuc ccacgggccu   2460
ugcauuuucu gacacgcuuc uuccugagca gugcccgcca ggccugccug gcacagagug   2520
gcucagugcc uccugccaug caguggcucu gccaccccgu gggccaccgu uucuucgugg   2580
auggggacug guccgugcuc aguaccccau gggagagccu guacagcuug gccgggaacc   2640
caguggaccc ccuggcccag gugacucagc uauuccggga acaucucuua gagcgagcac   2700
```

ugaacugugu gacccagccc aaccccagcc cugggucagc ugauggggac aaggaauucu 2760
cggaugcccu cggguaccug cagcugcuga acagcuguuc ugaugcugcg gggcuccug 2820 ccuacagcuu cuccaucagu uccagcaugg ccaccaccac cggcguagac ccgguggcca 2880 agugguggc cucucugaca gcugugguga uccacuggcu gcggcgggau gaggaggcgg 2940
cugagcggcu gugcccgcug guggagcacc ugccccgggu gcugcaggag ucugagagac 3000
cccugcccag ggcagcucug cacuccuuca aggcugcccg ggcccugcug ggcugugcca 3060
aggcagaguc ugguccagcc agccugacca ucugugagaa ggccaguggg uaccugcagg 3120
acagccuggc uaccacacca gccagcagcu ccauugacaa ggccgugcag cuguuccugu 3180
gugaccugcu ucuugguggug cgcaccagcc uguggcggca gcagcagccc ccggccccgg 3240
ccccagcagc ccagggcacc agcagcaggc cccaggcuuc cgcccuugag cugcguggcu 3300
uccaacggga ccugagcagc cugaggcggc uggcacagag cuuccggccc gccaugcgga 3360
ggguguuccu acaugaggcc acggcccggc ugauggcggg ggccagcccc acacggacac 3420
accagcuccu cgaccgcagu cugaggcggc gggcaggccc cgguggcaaa ggaggcgcgg 3480
uggcggagcu ggagccgcgg cccacgcggc gggagcacgc ggaggccuug cugcuggccu 3540
ccugcuaccu gcccccggc uuccugucgg cgcccgggca gcgcgugggc augcuggcug 3600
aggcggcgcg cacacucgag aagcuuggcg aucgccggcu gcugcacgac ugucagcaga 3660
ugcucaugcg ccugggcggu gggaccacug ucacuuccag cuagaccccg uguccccggc 3720
cucagcaccc cugucucuag ccacuuuggu cccgugcagc uucuguccug cgucgaagcu 3780
uugaaggccg aaggcagugc aagagacucu ggccuccaca guucgaccug cggcugcugu 3840
gugccuucgc gguggaaggc ccgaggggcg cgaucuugac ccuaagaccg gcggccauga 3900
uggugcugac cucugguggc cgaucggggc acugcagggg ccgagccauu uuggggggcc 3960
ccccuccuug cucugcaggc accuuagugg cuuuuuuccu ccuguguaca gggaagagag 4020
ggguacauuu cccugugcug acggaagcca acuuggcuuu cccggacugc aagcagggcu 4080
cugccccaga ggccucucuc uccgucgugg gagagagacg uguacauagu guaggucagc 4140
gugcuuagcc uccugaccug aggcuccugu gcuacuuugc cuuuugcaaa cuuuauuuuc 4200
auagauugag aaguuuugua cagagaauua aaaaugaaau uauuuauaau cug 4253

<210> SEQ ID NO 8
<211> LENGTH: 4056
<212> TYPE: DNA
<213> ORGANISM: homo sapien

<400> SEQUENCE: 8
gcggggcggg cgcgccgcag cgcucaacgg cuucaaaaau ccgccgcgcc uugacaggug 60
aagucggcgc ggggaggggu agggccaacg gccuggacgc cccaagggcg ggcgcagauc 120
gcggagccau ggauugcacu uucgaagaca ugcuucagcu uaucaacaac caagacagug 180
acuucccugg ccuauuugac ccacccuaug cugggagugg ggcagggggc acagacccug 240
ccagccccga uaccagcucc ccaggcagcu ugucuccacc uccugccaca uugagcuccu 300
cucuugaagc cuuccugagc gggccgcagg cagcgcccuc accccugucc ccuccccagc 360
cugcacccac uccauugaag auguacccgu ccaugcccgc uuucuccccu gggccuggua 420
ucaaggaaga gucagugcca cugagcaucc ugcagacccc caccccacag ccccugccag 480
gggcccuccu gccacagagc uucccagccc cagccccacc gcaguucagc uccaccccug 540
uguuaggcua ccccagcccu ccgggaggcu ucucuacagg aagcccuccc gggaacaccc 600

```
agcagccgcu gccuggccug ccacuggcuu ccccgccagg ggucccgccc gucuccuugc    660
acacccaggu ccagagugug guccccccagc agcuacugac agucacagcu gcccccacgg   720
cagccccugu aacgaccacu gugaccucgc agauccagca ggucccgguc cugcugcagc    780
cccacuucau caaggcagac ucgcugcuuc ugacagccau gaagacagac ggagccacug    840
ugaaggcggc aggucucagu ccccuggucu cuggcaccac ugugcagaca gggccuuugc    900
cgacccuggu gaguggcgga accaucuugg caacaguccc acuggucgua gaugcggaga    960
agcugccuau caaccggcuc gcagcuggca gcaaggcccc ggccucugcc cagagccgug   1020
gagagaagcg cacagcccac aacgccauug agaagugcua ccgcuccucc aucaaugaca   1080
aaaucauuga gcucaaggau cugguggugg gcacugaggc aaagcugaau aaaucugcug   1140
ucuugcgcaa ggccaucgac uacauucgcu uucugcaaca cagcaaccag aaacucaagc   1200
aggagaaccu aagucugcgc acugcugucc acaaaagcaa aucucugaag gaucuggugu   1260
cggccugugg caguggaggg aacacagacg ugcucaugga gggcgugaag acugaggugg   1320
aggacacacu gaccccaccc cccucggaug cuggcucacc uuuccagagc agccccuugu   1380
cccuuggcag caggggcagu ggcagcggug gcaguggcag ugacucggag ccugacagcc   1440
cagucuuuga ggacagcaag gcaaagccag agcagcggcc gucucugcac agccggggca   1500
ugcuggaccg cucccgccug gcccugugca cgcucgucuu ccucugccug uccugcaacc   1560
ccuuggccuc cuugcugggg gcccgggggc uucccagccc cucagauacc accagcgucu   1620
accauagccc ugggcgcaac gugcugggca ccgagagcag agauggcccu ggcugggccc   1680
aguggcugcu gcccccagug gucuggcugc ucaaugggcu guuggugcuc gucuccuugg   1740
ugcuucucuu ugucuacggu gagccaguca cacggcccca cucaggcccc gccguguacu   1800
ucuggaggca ucgcaagcag gcugaccugg accuggcccg gggagacuuu gcccaggcug   1860
cccagcagcu guggcuggcc cugcgggcac ugggccggcc ccugcccacc ucccaccugg   1920
accuggcuug uagccuccuc uggaaccuca uccgucaccu gcugcagcgu cucugggugg   1980
gccgcuggcu ggcaggccgg gcagggggcc ugcagcagga cugugcucug cgaguggaug   2040
cuagcgccag cgcccgagac gcagcccugg ucuaccauaa gcugcaccag cugcacacca   2100
uggggaagca cacaggcggg caccucacug ccaccaaccu ggcgcugagu gcccugaacc   2160
uggcagagug ugcaggggau gccgugucug uggcgacgcu ggccgagauc uauguggcgg   2220
cugcauugag agugaagacc agucucccac gggccuugca uuuucugaca cgcuucuucc   2280
ugagcagugc ccgccaggcc ugccuggcac agaguggcuc agugccuccu gccaugcagu   2340
ggcucugcca ccccgugggc caccguuucu ucguggaugg ggacuggucc gugcucagua   2400
ccccauggga gagccuguac agcuuggccg ggaacccagu ggaccccccug gcccaggguga  2460
cucagcuauu ccgggaacau cucuuagagc gagcacugaa cugugugacc cagcccaacc   2520
ccagcccugg gucagcugau ggggacaagg aauucucgga ugcccucggg uaccugcagc   2580
ugcugaacag cuguucugau gcugcggggg cuccugccua cagcuucucc aucaguucca   2640
gcauggccac caccaccggc guagacccgg uggccaagug gugggccucu cugacagcug   2700
uggugaucca cuggcugcgg cgggaugagg aggcggcuga gcggcugugc ccgcuggugg   2760
agcaccugcc ccgggugcug caggagucug agagaccccu gcccagggca gcucugcacu   2820
ccuucaaggc ugcccgggcc cugcugggcu gugccaaggc agagucuggu ccagccagcc   2880
ugaccaucug ugagaaggcc agugggguacc ugcaggacag ccuggcuacc acaccagcca   2940
```

-continued gcagcuccau ugacaaggcc gugcagcugu uccuguguga ccugcuucuu guggugcgca 3000
ccagccugug gcggcagcag cagcccccgg ccccggcccc agcagcccag ggcaccagca 3060
gcaggcccca ggcuuccgcc cuugagcugc guggcuucca acgggaccug agcagccuga 3120
ggcggcuggc acagagcuuc cggcccgcca ugcggagggu guuccuacau gaggccacgg 3180
cccggcugau ggcgggggcc agccccacac ggacacacca gcuccucgac cgcagucuga 3240
ggcggcgggc aggccccggu ggcaaaggag gcgcgguggc ggagcuggag ccgcggccca 3300
cgcggcggga gcacgcggag gccuugcugc uggccuccug cuaccugccc cccggcuucc 3360
ugucggcgcc cgggcagcgc gugggcaugc uggcugaggc ggcgcgcaca cucgagaagc 3420
uuggcgaucg ccggcugcug cacgacuguc agcagaugcu caugcgccug ggcgguggga 3480
ccacugucac uuccagcuag accccguguc cccggccuca gcaccccugu cucuagccac 3540
uuuggucccg ugcagcuucu guccugcguc gaagcuuuga aggccgaagg cagugcaaga 3600
gacucuggcc uccacaguuc gaccugcggc ugcugugugc cuucgcggug gaaggcccga 3660
ggggcgcgau cuugacccua agaccggcgg ccaugauggu gcugaccucu gguggccgau 3720
cggggcacug caggggccga gccauuuugg ggggcccccc uccuugcucu gcaggcaccu 3780
uaguggcuuu uuuccuccug uguacaggga agagaggggu acauuucccu gugcugacgg 3840
aagccaacuu ggcuuucccg gacugcaagc agggcucugc cccagaggcc ucucucuccg 3900
ucgugggaga gagacgugua cauaguguag gucagcgugc uuagccuccu gaccugaggc 3960
uccugugcua cuuugccuuu ugcaaacuuu auuuucauag auugagaagu uuuguacaga 4020
gaauuaaaaa ugaaauuauu uauaaucugg aaaaaa 4056

<210> SEQ ID NO 9
<211> LENGTH: 4178
<212> TYPE: DNA
<213> ORGANISM: homo sapien

<400> SEQUENCE: 9
gcggccgggg gaacccagtt tccgaggaac ttttcgccgg cgccgggccg cctctgaggc 60
cagggcagga cacgaacgcg cggagcggcg gcggcgactg agagccgggg ccgcggcggc 120
gctccctagg aagggccgta cgaggcggcg ggcccggcgg gcctcccgga ggaggcggct 180
gcgccatgga cgagccaccc ttcagcgagg cggctttgga gcaggcgctg ggcgagccgt 240
gcgatctgga cgcggcgctg ctgaccgaca tcgaagacat gcttcagctt atcaacaacc 300
aagacagtga cttccctggc ctatttgacc caccctatgc tgggagtggg gcagggggca 360
cagaccctgc cagccccgat accagctccc caggcagctt gtctccacct cctgccacat 420
tgagctcctc tcttgaagcc ttcctgagcg ggccgcaggc agcgccctca cccctgtccc 480
ctccccagcc tgcacccact ccattgaaga tgtacccgtc catgcccgct ttctcccctg 540
ggcctggtat caaggaagag tcagtgccac tgagcatcct gcagaccccc accccacagc 600
ccctgccagg ggccctcctg ccacagagct tcccagcccc agccccaccg cagttcagct 660
ccacccctgt gttaggctac cccagccctc cgggaggctt ctctacagga agccctcccg 720
ggaacaccca gcagccgctg cctggcctgc cactggcttc cccgccaggg gtcccgcccg 780
tctccttgca cacccaggtc cagagtgtgg tcccccagca gctactgaca gtcacagctg 840
cccccacggc agcccctgta acgaccactg tgacctcgca gatccagcag gtcccggtcc 900
tgctgcagcc ccacttcatc aaggcagact cgctgcttct gacagccatg aagacagacg 960
gagccactgt gaaggcggca ggtctcagtc ccctggtctc tggcaccact gtgcagacag 1020

```
ggcctttgcc gaccctggtg agtggcggaa ccatcttggc aacagtccca ctggtcgtag   1080
atgcggagaa gctgcctatc aaccggctcg cagctggcag caaggccccg gcctctgccc   1140
agagccgtgg agagaagcgc acagcccaca acgccattga gaagcgctac cgctcctcca   1200
tcaatgacaa aatcattgag ctcaaggatc tggtggtggg cactgaggca aagctgaata   1260
aatctgctgt cttgcgcaag gccatcgact acattcgctt tctgcaacac agcaaccaga   1320
aactcaagca ggagaaccta agtctgcgca ctgctgtcca caaaagcaaa tctctgaagg   1380
atctggtgtc ggcctgtggc agtggaggga acacagacgt gctcatggag ggcgtgaaga   1440
ctgaggtgga ggacacactg accccacccc cctcggatgc tggctcacct ttccagagca   1500
gccccttgtc ccttggcagc aggggcagtg gcagcggtgg cagtggcagt gactcggagc   1560
ctgacagccc agtctttgag gacagcaagg caaagccaga gcagcggccg tctctgcaca   1620
gccggggcat gctggaccgc tcccgcctgg ccctgtgcac gctcgtcttc ctctgcctgt   1680
cctgcaaccc cttggcctcc ttgctggggg cccgggggct tcccagcccc tcagatacca   1740
ccagcgtcta ccatagccct gggcgcaacg tgctgggcac cgagagcaga gatggccctg   1800
gctgggccca gtggctgctg cccccagtgg tctggctgct caatgggctg ttggtgctcg   1860
tctccttggt gcttctcttt gtctacggtg agccagtcac acggccccac tcaggccccg   1920
ccgtgtactt ctggaggcat cgcaagcagg ctgacctgga cctggcccgg ggagactttg   1980
cccaggctgc ccagcagctg tggctggccc tgcgggcact gggccggccc ctgcccacct   2040
cccacctgga cctggcttgt agcctcctct ggaacctcat ccgtcacctg ctgcagcgtc   2100
tctgggtggg ccgctggctg gcaggccggg caggggggcct gcagcaggac tgtgctctgc   2160
gagtggatgc tagcgccagc gcccgagacg cagccctggt ctaccataag ctgcaccagc   2220
tgcacaccat ggggaagcac acaggcgggc acctcactgc caccaacctg gcgctgagtg   2280
ccctgaacct ggcagagtgt gcaggggatg ccgtgtctgt ggcgacgctg gccgagatct   2340
atgtggcggc tgcattgaga gtgaagacca gtctcccacg ggccttgcat tttctgacac   2400
gcttcttcct gagcagtgcc cgccaggcct gcctggcaca gagtggctca gtgcctcctg   2460
ccatgcagtg gctctgccac cccgtgggcc accgtttctt cgtggatggg gactggtccg   2520
tgctcagtac cccatgggag agcctgtaca gcttggccgg gaacccagtg gacccccctgg   2580
cccaggtgac tcagctattc cgggaacatc tcttagagcg agcactgaac tgtgtgaccc   2640
agcccaaccc cagccctggg tcagctgatg gggacaagga attctcggat gccctcgggt   2700
acctgcagct gctgaacagc tgttctgatg ctgcgggggc tcctgcctac agcttctcca   2760
tcagttccag catggccacc accaccggcg tagacccggt ggccaagtgg tgggcctctc   2820
tgacagctgt ggtgatccac tggctgcggc gggatgagga ggcggctgag cggctgtgcc   2880
cgctggtgga gcacctgccc cgggtgctgc aggagtctga gagacccctg cccagggcag   2940
ctctgcactc cttcaaggct gcccgggccc tgctgggctg tgccaaggca gagtctggtc   3000
cagccagcct gaccatctgt gagaaggcca gtgggtacct gcaggacagc ctggctacca   3060
caccagccag cagctccatt gacaaggccg tgcagctgtt cctgtgtgac ctgcttcttg   3120
tggtgcgcac cagcctgtgg cggcagcagc agcccccggc cccggcccca gcagcccagg   3180
gcaccagcag caggccccag gcttccgccc ttgagctgcg tggcttccaa cgggacctga   3240
gcagcctgag gcggctggca cagagcttcc ggcccgccat gcggagggtg ttcctacatg   3300
aggccacggc ccggctgatg gcgggggcca gccccacacg gacacaccag ctcctcgacc   3360
```

gcagtctgag gcggcgggca ggccccggtg gcaaaggagg cgcggtggcg gagctggagc 3420
cgcggcccac gcggcgggag cacgcggagg ccttgctgct ggcctcctgc tacctgcccc 3480
ccggcttcct gtcggcgccc gggcagcgcg tgggcatgct ggctgaggcg gcgcgcacac 3540
tcgagaagct tggcgatcgc cggctgctgc acgactgtca gcagatgctc atgcgcctgg 3600
gcggtgggac cactgtcact tccagctaga ccccgtgtcc ccggcctcag cacccctgtc 3660
tctagccact ttggtcccgt gcagcttctg tcctgcgtcg aagctttgaa ggccgaaggc 3720
agtgcaagag actctggcct ccacagttcg acctgcggct gctgtgtgcc ttcgcggtgg 3780
aaggcccgag gggcgcgatc ttgaccctaa gaccggcggc catgatggtg ctgacctctg 3840
gtggccgatc ggggcactgc aggggccgag ccattttggg gggcccccct ccttgctctg 3900
caggcacctt agtggctttt ttcctcctgt gtacagggaa gagaggggta catttccctg 3960
tgctgacgga agccaacttg gctttcccgg actgcaagca gggctctgcc ccagaggcct 4020
ctctctccgt cgtgggagag agacgtgtac atagtgtagg tcagcgtgct tagcctcctg 4080
acctgaggct cctgtgctac tttgcctttt gcaaacttta ttttcataga ttgagaagtt 4140
ttgtacagag aattaaaaat gaaattattt ataatctg 4178

<210> SEQ ID NO 10
<211> LENGTH: 4253
<212> TYPE: DNA
<213> ORGANISM: homo sapien

<400> SEQUENCE: 10
cagtttccga ggaacttttc gccggcgccg ggccgcctct gaggccaggg caggacacga 60
acgcgcggag cggcggcggc gactgagagc cggggccgcg gcggcgctcc ctaggaaggg 120
ccgtacgagg cggcgggccc ggcgggcctc ccggaggagg cggctgcgcc atggacgagc 180 caccccttcag cgaggcggct ttggagcagg cgctgggcga gccgtgcgat ctggacgcgg 240
cgctgctgac cgacatcgaa ggtgaagtcg gcgcggggag gggtagggcc aacggcctgg 300
acgccccaag ggcgggcgca gatcgcggag ccatggattg cactttcgaa gacatgcttc 360
agcttatcaa caaccaagac agtgacttcc ctggcctatt tgacccaccc tatgctggga 420
gtggggcagg gggcacagac cctgccagcc ccgataccag ctccccaggc agcttgtctc 480
cacctcctgc cacattgagc tcctctcttg aagccttcct gagcgggccg caggcagcgc 540
cctcacccct gtcccctccc cagcctgcac ccactccatt gaagatgtac ccgtccatgc 600
ccgctttctc ccctgggcct ggtatcaagg aagagtcagt gccactgagc atcctgcaga 660
cccccacccc acagcccctg ccagggggccc tcctgccaca gagcttccca gccccagccc 720
caccgcagtt cagctccacc cctgtgttag gctaccccag ccctccggga ggcttctcta 780
caggaagccc tcccgggaac acccagcagc cgctgcctgg cctgccactg gcttccccgc 840
caggggtccc gcccgtctcc ttgcacaccc aggtccagag tgtggtcccc cagcagctac 900
tgacagtcac agctgccccc acggcagccc ctgtaacgac cactgtgacc tcgcagatcc 960
agcaggtccc ggtcctgctg cagccccact tcatcaaggc agactcgctg cttctgacag 1020
ccatgaagac agacggagcc actgtgaagg cggcaggtct cagtcccctg gtctctggca 1080
ccactgtgca gacagggcct ttgccgaccc tggtgagtgg cggaaccatc ttggcaacag 1140
tcccactggt cgtagatgcg gagaagctgc ctatcaaccg gctcgcagct ggcagcaagg 1200
ccccggcctc tgcccagagc cgtggagaga agcgcacagc ccacaacgcc attgagaagc 1260
gctaccgctc ctccatcaat gacaaaatca ttgagctcaa ggatctggtg gtgggcactg 1320

-continued

```
aggcaaagct gaataaatct gctgtcttgc gcaaggccat cgactacatt cgctttctgc   1380
aacacagcaa ccagaaactc aagcaggaga acctaagtct gcgcactgct gtccacaaaa   1440
gcaaatctct gaaggatctg gtgtcggcct gtggcagtgg agggaacaca gacgtgctca   1500
tggagggcgt gaagactgag gtggaggaca cactgacccc acccccctcg gatgctggct   1560
cacctttcca gagcagcccc ttgtcccttg gcagcagggg cagtggcagc ggtggcagtg   1620
gcagtgactc ggagcctgac agcccagtct ttgaggacag caaggcaaag ccagagcagc   1680
ggccgtctct gcacagccgg ggcatgctgg accgctcccg cctggccctg tgcacgctcg   1740
tcttcctctg cctgtcctgc aacccccttgg cctccttgct gggggcccgg gggcttccca   1800
gcccctcaga taccaccagc gtctaccata gccctgggcg caacgtgctg ggcaccgaga   1860
gcagagatgg ccctggctgg gcccagtggc tgctgccccc agtggtctgg ctgctcaatg   1920
ggctgttggt gctcgtctcc ttggtgcttc tctttgtcta cggtgagcca gtcacacggc   1980
cccactcagg ccccgccgtg tacttctgga ggcatcgcaa gcaggctgac ctggacctgg   2040
cccggggaga ctttgcccag gctgcccagc agctgtggct ggccctgcgg gcactgggcc   2100
ggcccctgcc cacctcccac ctggacctgg cttgtagcct cctctggaac ctcatccgtc   2160
acctgctgca gcgtctctgg gtgggccgct ggctggcagg ccgggcaggg ggcctgcagc   2220
aggactgtgc tctgcgagtg gatgctagcg ccagcgcccg agacgcagcc ctggtctacc   2280
ataagctgca ccagctgcac accatgggga agcacacagg cgggcacctc actgccacca   2340
acctggcgct gagtgccctg aacctggcag agtgtgcagg ggatgccgtg tctgtggcga   2400
cgctggccga gatctatgtg gcggctgcat tgagagtgaa gaccagtctc ccacgggcct   2460
tgcattttct gacacgcttc ttcctgagca gtgcccgcca ggcctgcctg gcacagagtg   2520
gctcagtgcc tcctgccatg cagtggctct gccaccccgt gggccaccgt ttcttcgtgg   2580
atggggactg gtccgtgctc agtaccccat gggagagcct gtacagcttg gccgggaacc   2640
cagtggaccc cctggcccag gtgactcagc tattccggga acatctctta gagcgagcac   2700
tgaactgtgt gacccagccc aaccccagcc ctgggtcagc tgatggggac aaggaattct   2760
cggatgccct cgggtacctg cagctgctga acagctgttc tgatgctgcg ggggctcctg   2820
cctacagctt ctccatcagt tccagcatgg ccaccaccac cggcgtagac ccggtggcca   2880
agtggtgggc ctctctgaca gctgtggtga tccactggct gcggcgggat gaggaggcgg   2940
ctgagcggct gtgcccgctg gtggagcacc tgccccgggt gctgcaggag tctgagagac   3000
ccctgcccag ggcagctctg cactccttca aggctgcccg ggccctgctg ggctgtgcca   3060
aggcagagtc tggtccagcc agcctgacca tctgtgagaa ggccagtggg tacctgcagg   3120
acagcctggc taccacacca gccagcagct ccattgacaa ggccgtgcag ctgttcctgt   3180
gtgacctgct tcttgtggtg cgcaccagcc tgtggcggca gcagcagccc ccggccccgg   3240
ccccagcagc ccagggcacc agcagcaggc cccaggcttc cgcccttgag ctgcgtggct   3300
tccaacggga cctgagcagc ctgaggcggc tggcacagag cttccggccc gccatgcgga   3360
gggtgttcct acatgaggcc acggcccggc tgatggcggg ggccagcccc acacggacac   3420
accagctcct cgaccgcagt ctgaggcggc gggcaggccc cggtggcaaa ggaggcgcgg   3480
tggcggagct ggagccgcgg cccacgcggc gggagcacgc ggaggccttg ctgctggcct   3540
cctgctacct gcccccggc ttcctgtcgg cgcccgggca gcgcgtgggc atgctggctg   3600
aggcggcgcg cacactcgag aagcttggcg atcgccggct gctgcacgac tgtcagcaga   3660
```

-continued

```
tgctcatgcg cctgggcggt gggaccactg tcacttccag ctagaccccg tgtccccggc   3720

ctcagcaccc ctgtctctag ccactttggt cccgtgcagc ttctgtcctg cgtcgaagct   3780

ttgaaggccg aaggcagtgc aagagactct ggcctccaca gttcgacctg cggctgctgt   3840

gtgccttcgc ggtggaaggc ccgaggggcg cgatcttgac cctaagaccg gcggccatga   3900

tggtgctgac ctctggtggc cgatcggggc actgcagggg ccgagccatt ttgggggggcc  3960

cccctccttg ctctgcaggc accttagtgg ctttttttcct cctgtgtaca gggaagagag  4020

gggtacattt ccctgtgctg acggaagcca acttggcttt cccggactgc aagcagggct   4080

ctgccccaga ggcctctctc tccgtcgtgg gagagagacg tgtacatagt gtaggtcagc   4140

gtgcttagcc tcctgacctg aggctcctgt gctactttgc cttttgcaaa ctttattttc   4200

atagattgag aagttttgta cagagaatta aaaatgaaat tatttataat ctg          4253
```

```
<210> SEQ ID NO 11
<211> LENGTH: 4056
<212> TYPE: DNA
<213> ORGANISM: homo sapien

<400> SEQUENCE: 11

gcggggcggg cgcgccgcag cgctcaacgg cttcaaaaat ccgccgcgcc ttgacaggtg     60

aagtcggcgc ggggaggggt agggccaacg gcctggacgc cccaagggcg ggcgcagatc    120

gcggagccat ggattgcact ttcgaagaca tgcttcagct tatcaacaac caagacagtg    180

acttccctgg cctatttgac ccaccctatg ctgggagtgg ggcagggggc acagaccctg    240

ccagccccga taccagctcc ccaggcagct tgtctccacc tcctgccaca ttgagctcct    300

ctcttgaagc cttcctgagc gggccgcagg cagcgccctc acccctgtcc cctccccagc    360

ctgcacccac tccattgaag atgtacccgt ccatgcccgc tttctcccct gggcctggta    420

tcaaggaaga gtcagtgcca ctgagcatcc tgcagacccc caccccacag cccctgccag    480

gggccctcct gccacagagc ttcccagccc cagccccacc gcagttcagc tccacccctg    540

tgttaggcta ccccagccct ccgggaggct tctctacagg aagccctccc gggaacaccc    600

agcagccgct gcctggcctg ccactggctt ccccgccagg ggtcccgccc gtctccttgc    660

acacccaggt ccagagtgtg gtcccccagc agctactgac agtcacagct gcccccacgg    720

cagcccctgt aacgaccact gtgacctcgc agatccagca ggtcccggtc ctgctgcagc    780

cccacttcat caaggcagac tcgctgcttc tgacagccat gaagacagac ggagccactg    840

tgaaggcggc aggtctcagt cccctggtct ctggcaccac tgtgcagaca gggcctttgc    900

cgaccctggt gagtggcgga accatcttgg caacagtccc actggtcgta gatgcggaga    960

agctgcctat caaccggctc gcagctggca gcaaggcccc ggcctctgcc cagagccgtg   1020

gagagaagcg cacagcccac aacgccattg agaagcgcta ccgctcctcc atcaatgaca   1080

aaatcattga gctcaaggat ctggtggtgg gcactgaggc aaagctgaat aaatctgctg   1140

tcttgcgcaa ggccatcgac tacattcgct ttctgcaaca cagcaaccag aaactcaagc   1200

aggagaacct aagtctgcgc actgctgtcc acaaaagcaa atctctgaag gatctggtgt   1260

cggcctgtgg cagtggaggg aacacagacg tgctcatgga gggcgtgaag actgaggtgg   1320

aggacacact gaccccaccc ccctcggatg ctggctcacc tttccagagc agccccttgt   1380

cccttggcag caggggcagt ggcagcggtg gcagtggcag tgactcggag cctgacagcc   1440

cagtctttga ggacagcaag gcaaagccag agcagcggcc gtctctgcac agccggggca   1500

tgctggaccg ctcccgcctg gccctgtgca cgctcgtctt cctctgcctg tcctgcaacc   1560
```

-continued

```
ccttggcctc cttgctgggg gcccgggggc ttcccagccc ctcagatacc accagcgtct   1620
accatagccc tgggcgcaac gtgctgggca ccgagagcag agatggccct ggctgggccc   1680
agtggctgct gcccccagtg gtctggctgc tcaatgggct gttggtgctc gtctccttgg   1740
tgcttctctt tgtctacggt gagccagtca cacggcccca ctcaggcccc gccgtgtact   1800
tctggaggca tcgcaagcag gctgacctgg acctggcccg gggagacttt gcccaggctg   1860
cccagcagct gtggctggcc ctgcgggcac tgggccggcc cctgcccacc tcccacctgg   1920
acctggcttg tagcctcctc tggaacctca tccgtcacct gctgcagcgt ctctgggtgg   1980
gccgctggct ggcaggccgg gcagggggcc tgcagcagga ctgtgctctg cgagtggatg   2040
ctagcgccag cgcccgagac gcagccctgg tctaccataa gctgcaccag ctgcacacca   2100
tggggaagca cacaggcggg cacctcactg ccaccaacct ggcgctgagt gccctgaacc   2160
tggcagagtg tgcaggggat gccgtgtctg tggcgacgct ggccgagatc tatgtggcgg   2220
ctgcattgag agtgaagacc agtctcccac gggccttgca ttttctgaca cgcttcttcc   2280
tgagcagtgc ccgccaggcc tgcctggcac agagtggctc agtgcctcct gccatgcagt   2340
ggctctgcca ccccgtgggc caccgtttct tcgtggatgg ggactggtcc gtgctcagta   2400
ccccatggga gagcctgtac agcttggccg ggaacccagt ggacccccctg gcccaggtga   2460
ctcagctatt ccgggaacat ctcttagagc gagcactgaa ctgtgtgacc cagcccaacc   2520
ccagccctgg gtcagctgat ggggacaagg aattctcgga tgccctcggg tacctgcagc   2580
tgctgaacag ctgttctgat gctgcggggg ctcctgccta cagcttctcc atcagttcca   2640
gcatggccac caccaccggc gtagacccgg tggccaagtg gtgggcctct ctgacagctg   2700
tggtgatcca ctggctgcgg cgggatgagg aggcggctga gcggctgtgc ccgctggtgg   2760
agcacctgcc ccgggtgctg caggagtctg agagacccct gcccagggca gctctgcact   2820
ccttcaaggc tgcccgggcc ctgctgggct gtgccaaggc agagtctggt ccagccagcc   2880
tgaccatctg tgagaaggcc agtgggtacc tgcaggacag cctggctacc acaccagcca   2940
gcagctccat tgacaaggcc gtgcagctgt tcctgtgtga cctgcttctt gtggtgcgca   3000
ccagcctgtg gcggcagcag cagcccccgg ccccggcccc agcagcccag ggcaccagca   3060
gcaggcccca ggcttccgcc cttgagctgc gtggcttcca acgggacctg agcagcctga   3120
ggcggctggc acagagcttc cggcccgcca tgcggagggt gttcctacat gaggccacgg   3180
cccggctgat ggcgggggcc agccccacac ggacacacca gctcctcgac cgcagtctga   3240
ggcggcgggc aggccccggt ggcaaaggag gcgcggtggc ggagctggag ccgcggccca   3300
cgcggcggga gcacgcggag gccttgctgc tggcctcctg ctacctgccc cccggcttcc   3360
tgtcggcgcc cgggcagcgc gtgggcatgc tggctgaggc ggcgcgcaca ctcgagaagc   3420
ttggcgatcg ccggctgctg cacgactgtc agcagatgct catgcgcctg ggcggtggga   3480
ccactgtcac ttccagctag accccgtgtc cccggcctca gcacccctgt ctctagccac   3540
tttggtcccg tgcagcttct gtcctgcgtc gaagctttga aggccgaagg cagtgcaaga   3600
gactctggcc tccacagttc gacctgcggc tgctgtgtgc cttcgcggtg gaaggcccga   3660
ggggcgcgat cttgacccta agaccggcgg ccatgatggt gctgacctct ggtggccgat   3720
cggggcactg caggggccga gccattttgg ggggcccccc tccttgctct gcaggcacct   3780
tagtggcttt tttcctcctg tgtacaggga agagaggggt acatttccct gtgctgacgg   3840
aagccaactt ggctttcccg gactgcaagc agggctctgc cccagaggcc tctctctccg   3900
```

-continued

```
tcgtgggaga gagacgtgta catagtgtag gtcagcgtgc ttagcctcct gacctgaggc   3960

tcctgtgcta ctttgccttt tgcaaacttt attttcatag attgagaagt tttgtacaga   4020

gaattaaaaa tgaaattatt tataatctgg aaaaaa                             4056


<210> SEQ ID NO 12
<211> LENGTH: 4178
<212> TYPE: DNA
<213> ORGANISM: homo sapien

<400> SEQUENCE: 12

gcggccgggg gaacccagtt tccgaggaac ttttcgccgg cgccgggccg cctctgaggc     60

cagggcagga cacgaacgcg cggagcggcg gcggcgactg agagccgggg ccgcggcggc    120

gctccctagg aagggccgta cgaggcggcg ggcccggcgg gcctcccgga ggaggcggct    180

gcgccatgga cgagccaccc ttcagcgagg cggctttgga gcaggcgctg ggcgagccgt    240

gcgatctgga cgcggcgctg ctgaccgaca tcgaagacat gcttcagctt atcaacaacc    300

aagacagtga cttccctggc ctatttgacc caccctatgc tgggagtggg gcagggggca    360

cagaccctgc cagccccgat accagctccc caggcagctt gtctccacct cctgccacat    420

tgagctcctc tcttgaagcc ttcctgagcg ggccgcaggc agcgccctca cccctgtccc    480

ctccccagcc tgcacccact ccattgaaga tgtacccgtc catgcccgct ttctcccctg    540

ggcctggtat caaggaagag tcagtgccac tgagcatcct gcagaccccc accccacagc    600

ccctgccagg ggccctcctg ccacagagct tcccagcccc agccccaccg cagttcagct    660

ccacccctgt gttaggctac cccagccctc cgggaggctt ctctacagga agccctcccg    720

ggaacaccca gcagccgctg cctggcctgc cactggcttc cccgccaggg gtcccgcccg    780

tctccttgca cacccaggtc cagagtgtgg tcccccagca gctactgaca gtcacagctg    840

cccccacggc agcccctgta acgaccactg tgacctcgca gatccagcag gtcccggtcc    900

tgctgcagcc ccacttcatc aaggcagact cgctgcttct gacagccatg aagacagacg    960

gagccactgt gaaggcggca ggtctcagtc ccctggtctc tggcaccact gtgcagacag   1020

ggcctttgcc gaccctggtg agtggcggaa ccatcttggc aacagtccca ctggtcgtag   1080

atgcggagaa gctgcctatc aaccggctcg cagctggcag caaggccccg gcctctgccc   1140

agagccgtgg agagaagcgc acagcccaca acgccattga gaagtgctac cgctcctcca   1200

tcaatgacaa aatcattgag ctcaaggatc tggtggtggg cactgaggca aagctgaata   1260

aatctgctgt cttgcgcaag gccatcgact acattcgctt tctgcaacac agcaaccaga   1320

aactcaagca ggagaaccta agtctgcgca ctgctgtcca caaaagcaaa tctctgaagg   1380

atctggtgtc ggcctgtggc agtggaggga acacagacgt gctcatggag ggcgtgaaga   1440

ctgaggtgga ggacacactg accccacccc cctcggatgc tggctcacct ttccagagca   1500

gccccttgtc ccttggcagc aggggcagtg gcagcggtgg cagtggcagt gactcggagc   1560

ctgacagccc agtctttgag gacagcaagg caaagccaga gcagcggccg tctctgcaca   1620

gccggggcat gctggaccgc tcccgcctgg ccctgtgcac gctcgtcttc ctctgcctgt   1680

cctgcaaccc cttggcctcc ttgctggggg cccgggggct tcccagcccc tcagatacca   1740

ccagcgtcta ccatagccct gggcgcaacg tgctgggcac cgagagcaga gatggccctg   1800

gctgggccca gtggctgctg cccccagtgg tctggctgct caatgggctg ttggtgctcg   1860

tctccttggt gcttctcttt gtctacggtg agccagtcac acggccccac tcaggccccg   1920

ccgtgtactt ctggaggcat cgcaagcagg ctgacctgga cctggcccgg ggagactttg   1980
```

-continued

```
cccaggctgc ccagcagctg tggctggccc tgcgggcact gggccggccc ctgcccacct   2040
cccacctgga cctggcttgt agcctcctct ggaacctcat ccgtcacctg ctgcagcgtc   2100
tctgggtggg ccgctggctg gcaggccggg caggggggcct gcagcaggac tgtgctctgc   2160
gagtggatgc tagcgccagc gcccgagacg cagccctggt ctaccataag ctgcaccagc   2220
tgcacaccat ggggaagcac acaggcgggc acctcactgc caccaacctg gcgctgagtg   2280
ccctgaacct ggcagagtgt gcaggggatg ccgtgtctgt ggcgacgctg gccgagatct   2340
atgtggcggc tgcattgaga gtgaagacca gtctcccacg ggccttgcat tttctgacac   2400
gcttcttcct gagcagtgcc cgccaggcct gcctggcaca gagtggctca gtgcctcctg   2460
ccatgcagtg gctctgccac cccgtgggcc accgtttctt cgtggatggg gactggtccg   2520
tgctcagtac cccatgggag agcctgtaca gcttggccgg gaacccagtg gaccccctgg   2580
cccaggtgac tcagctattc cgggaacatc tcttagagcg agcactgaac tgtgtgaccc   2640
agcccaaccc cagccctggg tcagctgatg gggacaagga attctcggat gccctcgggt   2700
acctgcagct gctgaacagc tgttctgatg ctgcgggggc tcctgcctac agcttctcca   2760
tcagttccag catggccacc accaccggcg tagacccggt ggccaagtgg tgggcctctc   2820
tgacagctgt ggtgatccac tggctgcggc gggatgagga ggcggctgag cggctgtgcc   2880
cgctggtgga gcacctgccc cgggtgctgc aggagtctga gagacccctg cccagggcag   2940
ctctgcactc cttcaaggct gcccgggccc tgctgggctg tgccaaggca gagtctggtc   3000
cagccagcct gaccatctgt gagaaggcca gtgggtacct gcaggacagc ctggctacca   3060
caccagccag cagctccatt gacaaggccg tgcagctgtt cctgtgtgac ctgcttcttg   3120
tggtgcgcac cagcctgtgg cggcagcagc agcccccggc cccggcccca gcagcccagg   3180
gcaccagcag caggccccag gcttccgccc ttgagctgcg tggcttccaa cgggacctga   3240
gcagcctgag gcggctggca cagagcttcc ggcccgccat gcggagggtg ttcctacatg   3300
aggccacggc ccggctgatg gcgggggcca gccccacacg gacacaccag ctcctcgacc   3360
gcagtctgag gcggcgggca ggccccggtg gcaaaggagg cgcggtggcg gagctggagc   3420
cgcggcccac gcggcgggag cacgcggagg ccttgctgct ggcctcctgc tacctgcccc   3480
ccggcttcct gtcggcgccc gggcagcgcg tgggcatgct ggctgaggcg gcgcgcacac   3540
tcgagaagct tggcgatcgc cggctgctgc acgactgtca gcagatgctc atgcgcctgg   3600
gcggtgggac cactgtcact tccagctaga ccccgtgtcc ccggcctcag cacccctgtc   3660
tctagccact ttggtcccgt gcagcttctg tcctgcgtcg aagctttgaa ggccgaaggc   3720
agtgcaagag actctggcct ccacagttcg acctgcggct gctgtgtgcc ttcgcggtgg   3780
aaggcccgag ggcgcgatc ttgaccctaa gaccggcggc catgatggtg ctgacctctg   3840
gtggccgatc ggggcactgc aggggccgag ccattttggg gggcccccct ccttgctctg   3900
caggcacctt agtggctttt ttcctcctgt gtacagggaa gagaggggta catttccctg   3960
tgctgacgga agccaacttg gctttcccgg actgcaagca gggctctgcc ccagaggcct   4020
ctctctccgt cgtgggagag agacgtgtac atagtgtagg tcagcgtgct tagcctcctg   4080
acctgaggct cctgtgctac tttgcctttt gcaaacttta ttttcataga ttgagaagtt   4140
ttgtacagag aattaaaaat gaaattattt ataatctg                           4178
```

<210> SEQ ID NO 13
<211> LENGTH: 4253
<212> TYPE: DNA

-continued

<213> ORGANISM: homo sapien

<400> SEQUENCE: 13
cagtttccga ggaacttttc gccggcgccg ggccgcctct gaggccaggg caggacacga 60
acgcgcggag cggcggcggc gactgagagc cggggccgcg gcggcgctcc ctaggaaggg 120
ccgtacgagg cggcgggccc ggcgggcctc ccggaggagg cggctgcgcc atggacgagc 180
caccccttcag cgaggcggct ttggagcagg cgctgggcga gccgtgcgat ctggacgcgg 240
cgctgctgac cgacatcgaa ggtgaagtcg gcgcggggag gggtagggcc aacggcctgg 300
acgccccaag ggcgggcgca gatcgcggag ccatggattg cactttcgaa gacatgcttc 360
agcttatcaa caaccaagac agtgacttcc ctggcctatt tgacccaccc tatgctggga 420
gtggggcagg gggcacagac cctgccagcc ccgataccag ctccccaggc agcttgtctc 480
cacctcctgc cacattgagc tcctctcttg aagccttcct gagcgggccg caggcagcgc 540
cctcacccct gtcccctccc cagcctgcac ccactccatt gaagatgtac ccgtccatgc 600
ccgctttctc ccctgggcct ggtatcaagg aagagtcagt gccactgagc atcctgcaga 660
cccccacccc acagcccctg ccaggggccc tcctgccaca gagcttccca gccccagccc 720
caccgcagtt cagctccacc cctgtgttag gctaccccag ccctccggga ggcttctcta 780
caggaagccc tcccgggaac acccagcagc cgctgcctgg cctgccactg gcttccccgc 840
caggggtccc gcccgtctcc ttgcacaccc aggtccagag tgtggtcccc cagcagctac 900
tgacagtcac agctgccccc acggcagccc ctgtaacgac cactgtgacc tcgcagatcc 960
agcaggtccc ggtcctgctg cagccccact tcatcaaggc agactcgctg cttctgacag 1020
ccatgaagac agacggagcc actgtgaagg cggcaggtct cagtcccctg gtctctggca 1080
ccactgtgca gacagggcct ttgccgaccc tggtgagtgg cggaaccatc ttggcaacag 1140
tcccactggt cgtagatgcg gagaagctgc ctatcaaccg gctcgcagct ggcagcaagg 1200
ccccggcctc tgcccagagc cgtggagaga agcgcacagc ccacaacgcc attgagaagt 1260
gctaccgctc ctccatcaat gacaaaatca ttgagctcaa ggatctggtg gtgggcactg 1320
aggcaaagct gaataaatct gctgtcttgc gcaaggccat cgactacatt cgctttctgc 1380
aacacagcaa ccagaaactc aagcaggaga acctaagtct gcgcactgct gtccacaaaa 1440
gcaaatctct gaaggatctg gtgtcggcct gtggcagtgg agggaacaca gacgtgctca 1500
tggagggcgt gaagactgag gtggaggaca cactgacccc acccccctcg gatgctggct 1560
cacctttcca gagcagcccc ttgtcccttg gcagcagggg cagtggcagc ggtggcagtg 1620
gcagtgactc ggagcctgac agcccagtct ttgaggacag caaggcaaag ccagagcagc 1680
ggccgtctct gcacagccgg ggcatgctgg accgctcccg cctggccctg tgcacgctcg 1740
tcttcctctg cctgtcctgc aacccccttgg cctccttgct gggggcccgg gggcttccca 1800
gcccctcaga taccaccagc gtctaccata gccctgggcg caacgtgctg ggcaccgaga 1860
gcagagatgg ccctggctgg gcccagtggc tgctgccccc agtggtctgg ctgctcaatg 1920
ggctgttggt gctcgtctcc ttggtgcttc tctttgtcta cggtgagcca gtcacacggc 1980
cccactcagg ccccgccgtg tacttctgga ggcatcgcaa gcaggctgac ctggacctgg 2040
cccggggaga ctttgcccag gctgcccagc agctgtggct ggccctgcgg gcactgggcc 2100
ggcccctgcc cacctcccac ctggacctgg cttgtagcct cctctggaac ctcatccgtc 2160
acctgctgca gcgtctctgg gtgggccgct ggctggcagg ccgggcaggg ggcctgcagc 2220
aggactgtgc tctgcgagtg gatgctagcg ccagcgcccg agacgcagcc ctggtctacc 2280
ataagctgca ccagctgcac accatgggga agcacacagg cgggcacctc actgccacca 2340
acctggcgct gagtgccctg aacctggcag agtgtgcagg ggatgccgtg tctgtggcga 2400
cgctggccga gatctatgtg gcggctgcat tgagagtgaa gaccagtctc ccacgggcct 2460
tgcattttct gacacgcttc ttcctgagca gtgcccgcca ggcctgcctg gcacagagtg 2520
gctcagtgcc tcctgccatg cagtggctct gccaccccgt gggccaccgt ttcttcgtgg 2580
atggggactg gtccgtgctc agtaccccat gggagagcct gtacagcttg gccgggaacc 2640
cagtggaccc cctggcccag gtgactcagc tattccggga acatctctta gagcgagcac 2700
tgaactgtgt gacccagccc aaccccagcc ctgggtcagc tgatggggac aaggaattct 2760
cggatgccct cgggtacctg cagctgctga acagctgttc tgatgctgcg ggggctcctg 2820
cctacagctt ctccatcagt tccagcatgg ccaccaccac cggcgtagac ccggtggcca 2880
agtggtgggc ctctctgaca gctgtggtga tccactggct gcggcgggat gaggaggcgg 2940
ctgagcggct gtgcccgctg gtggagcacc tgccccgggt gctgcaggag tctgagagac 3000
ccctgcccag ggcagctctg cactccttca aggctgcccg ggccctgctg ggctgtgcca 3060
aggcagagtc tggtccagcc agcctgacca tctgtgagaa ggccagtggg tacctgcagg 3120
acagcctggc taccacacca gccagcagct ccattgacaa ggccgtgcag ctgttcctgt 3180
gtgacctgct tcttgtggtg cgcaccagcc tgtggcggca gcagcagccc ccggccccgg 3240
ccccagcagc ccagggcacc agcagcaggc cccaggcttc cgcccttgag ctgcgtggct 3300
tccaacggga cctgagcagc ctgaggcggc tggcacagag cttccggccc gccatgcgga 3360
gggtgttcct acatgaggcc acggcccggc tgatggcggg ggccagcccc acacggacac 3420
accagctcct cgaccgcagt ctgaggcggc gggcaggccc cggtggcaaa ggaggcgcgg 3480
tggcggagct ggagccgcgg cccacgcggc gggagcacgc ggaggccttg ctgctggcct 3540
cctgctacct gccccccggc ttcctgtcgg cgcccgggca gcgcgtgggc atgctggctg 3600
aggcggcgcg cacactcgag aagcttggcg atcgccggct gctgcacgac tgtcagcaga 3660
tgctcatgcg cctgggcggt gggaccactg tcacttccag ctagaccccg tgtccccggc 3720
ctcagcaccc ctgtctctag ccactttggt cccgtgcagc ttctgtcctg cgtcgaagct 3780
ttgaaggccg aaggcagtgc aagagactct ggcctccaca gttcgacctg cggctgctgt 3840
gtgccttcgc ggtggaaggc ccgaggggcg cgatcttgac cctaagaccg gcggccatga 3900
tggtgctgac ctctggtggc cgatcggggc actgcagggg ccgagccatt ttgggggggcc 3960 cccctccttg ctctgcaggc accttagtgg ctttttttcct cctgtgtaca gggaagagag 4020
gggtacattt ccctgtgctg acggaagcca acttggcttt cccggactgc aagcagggct 4080
ctgccccaga ggcctctctc tccgtcgtgg gagagagacg tgtacatagt gtaggtcagc 4140
gtgcttagcc tcctgacctg aggctcctgt gctactttgc cttttgcaaa ctttattttc 4200
atagattgag aagttttgta cagagaatta aaaatgaaat tatttataat ctg 4253

<210> SEQ ID NO 14
<211> LENGTH: 4056
<212> TYPE: DNA
<213> ORGANISM: homo sapien

<400> SEQUENCE: 14
gcggggcggg cgcgccgcag cgctcaacgg cttcaaaaat ccgccgcgcc ttgacaggtg 60
aagtcggcgc ggggaggggt agggccaacg gcctggacgc cccaagggcg ggcgcagatc 120

-continued

```
gcggagccat ggattgcact ttcgaagaca tgcttcagct tatcaacaac caagacagtg    180
acttccctgg cctatttgac ccaccctatg ctgggagtgg ggcagggggc acagaccctg    240
ccagccccga taccagctcc ccaggcagct tgtctccacc tcctgccaca ttgagctcct    300
ctcttgaagc cttcctgagc gggccgcagg cagcgccctc acccctgtcc cctccccagc    360
ctgcacccac tccattgaag atgtacccgt ccatgcccgc tttctcccct gggcctggta    420
tcaaggaaga gtcagtgcca ctgagcatcc tgcagacccc caccccacag cccctgccag    480
gggccctcct gccacagagc ttcccagccc cagccccacc gcagttcagc tccacccctg    540
tgttaggcta ccccagccct ccgggaggct tctctacagg aagccctccc gggaacaccc    600
agcagccgct gcctggcctg ccactggctt ccccgccagg ggtcccgccc gtctccttgc    660
acacccaggt ccagagtgtg gtcccccagc agctactgac agtcacagct gcccccacgg    720
cagcccctgt aacgaccact gtgacctcgc agatccagca ggtcccggtc ctgctgcagc    780
cccacttcat caaggcagac tcgctgcttc tgacagccat gaagacagac ggagccactg    840
tgaaggcggc aggtctcagt cccctggtct ctggcaccac tgtgcagaca gggcctttgc    900
cgaccctggt gagtggcgga accatcttgg caacagtccc actggtcgta gatgcggaga    960
agctgcctat caaccggctc gcagctggca gcaaggcccc ggcctctgcc cagagccgtg   1020
gagagaagcg cacagcccac aacgccattg agaagtgcta ccgctcctcc atcaatgaca   1080
aaatcattga gctcaaggat ctggtggtgg gcactgaggc aaagctgaat aaatctgctg   1140
tcttgcgcaa ggccatcgac tacattcgct ttctgcaaca cagcaaccag aaactcaagc   1200
aggagaacct aagtctgcgc actgctgtcc acaaaagcaa atctctgaag gatctggtgt   1260
cggcctgtgg cagtggaggg aacacagacg tgctcatgga gggcgtgaag actgaggtgg   1320
aggacacact gaccccaccc ccctcggatg ctggctcacc tttccagagc agccccttgt   1380
cccttggcag caggggcagt ggcagcggtg gcagtggcag tgactcggag cctgacagcc   1440
cagtctttga ggacagcaag gcaaagccag agcagcggcc gtctctgcac agccggggca   1500
tgctggaccg ctcccgcctg gccctgtgca cgctcgtctt cctctgcctg tcctgcaacc   1560
ccttggcctc cttgctgggg gcccgggggc ttcccagccc ctcagatacc accagcgtct   1620
accatagccc tgggcgcaac gtgctgggca ccgagagcag agatggccct ggctgggccc   1680
agtggctgct gcccccagtg gtctggctgc tcaatgggct gttggtgctc gtctccttgg   1740
tgcttctctt tgtctacggt gagccagtca cacggcccca ctcaggcccc gccgtgtact   1800
tctggaggca tcgcaagcag gctgacctgg acctggcccg gggagacttt gcccaggctg   1860
cccagcagct gtggctggcc ctgcgggcac tgggccggcc cctgcccacc tcccacctgg   1920
acctggcttg tagcctcctc tggaacctca tccgtcacct gctgcagcgt ctctgggtgg   1980
gccgctggct ggcaggccgg gcagggggcc tgcagcagga ctgtgctctg cgagtggatg   2040
ctagcgccag cgcccgagac gcagccctgg tctaccataa gctgcaccag ctgcacacca   2100
tggggaagca cacaggcggg cacctcactg ccaccaacct ggcgctgagt gccctgaacc   2160
tggcagagtg tgcaggggat gccgtgtctg tggcgacgct ggccgagatc tatgtggcgg   2220
ctgcattgag agtgaagacc agtctcccac gggccttgca ttttctgaca cgcttcttcc   2280
tgagcagtgc ccgccaggcc tgcctggcac agagtggctc agtgcctcct gccatgcagt   2340
ggctctgcca ccccgtgggc caccgtttct tcgtggatgg ggactggtcc gtgctcagta   2400
ccccatggga gagcctgtac agcttggccg ggaacccagt ggacccccctg gcccaggtga   2460
ctcagctatt ccgggaacat ctcttagagc gagcactgaa ctgtgtgacc cagcccaacc   2520
```

```
ccagccctgg gtcagctgat ggggacaagg aattctcgga tgccctcggg tacctgcagc   2580

tgctgaacag ctgttctgat gctgcggggg ctcctgccta cagcttctcc atcagttcca   2640

gcatggccac caccaccggc gtagacccgg tggccaagtg gtgggcctct ctgacagctg   2700

tggtgatcca ctggctgcgg cgggatgagg aggcggctga gcggctgtgc ccgctggtgg   2760

agcacctgcc ccgggtgctg caggagtctg agagacccct gcccagggca gctctgcact   2820

ccttcaaggc tgcccgggcc ctgctgggct gtgccaaggc agagtctggt ccagccagcc   2880

tgaccatctg tgagaaggcc agtgggtacc tgcaggacag cctggctacc acaccagcca   2940

gcagctccat tgacaaggcc gtgcagctgt tcctgtgtga cctgcttctt gtggtgcgca   3000

ccagcctgtg gcggcagcag cagcccccgg ccccggcccc agcagcccag ggcaccagca   3060

gcaggcccca ggcttccgcc cttgagctgc gtggcttcca acgggacctg agcagcctga   3120

ggcggctggc acagagcttc cggcccgcca tgcggagggt gttcctacat gaggccacgg   3180

cccggctgat ggcgggggcc agccccacac ggacacacca gctcctcgac cgcagtctga   3240

ggcggcgggc aggccccggt ggcaaaggag gcgcggtggc ggagctggag ccgcggccca   3300

cgcggcggga gcacgcggag gccttgctgc tggcctcctg ctacctgccc cccggcttcc   3360

tgtcggcgcc cgggcagcgc gtgggcatgc tggctgaggc ggcgcgcaca ctcgagaagc   3420

ttggcgatcg ccggctgctg cacgactgtc agcagatgct catgcgcctg ggcggtggga   3480

ccactgtcac ttccagctag accccgtgtc cccggcctca gcacccctgt ctctagccac   3540

tttggtcccg tgcagcttct gtcctgcgtc gaagctttga aggccgaagg cagtgcaaga   3600

gactctggcc tccacagttc gacctgcggc tgctgtgtgc cttcgcggtg gaaggcccga   3660

ggggcgcgat cttgacccta agaccggcgg ccatgatggt gctgacctct ggtggccgat   3720

cggggcactg caggggccga gccattttgg ggggcccccc tccttgctct gcaggcacct   3780

tagtggcttt tttcctcctg tgtacaggga agagaggggt acatttccct gtgctgacgg   3840

aagccaactt ggctttcccg gactgcaagc agggctctgc cccagaggcc tctctctccg   3900

tcgtgggaga gagacgtgta catagtgtag gtcagcgtgc ttagcctcct gacctgaggc   3960

tcctgtgcta ctttgccttt tgcaaacttt attttcatag attgagaagt tttgtacaga   4020

gaattaaaaa tgaaattatt tataatctgg aaaaaa                             4056
```

<210> SEQ ID NO 15
<211> LENGTH: 1147
<212> TYPE: PRT
<213> ORGANISM: homo sapien

<400> SEQUENCE: 15

```
Met Asp Glu Pro Pro Phe Ser Glu Ala Ala Leu Glu Gln Ala Leu Gly
1               5                   10                  15

Glu Pro Cys Asp Leu Asp Ala Ala Leu Leu Thr Asp Ile Glu Asp Met
            20                  25                  30

Leu Gln Leu Ile Asn Asn Gln Asp Ser Asp Phe Pro Gly Leu Phe Asp
        35                  40                  45

Pro Pro Tyr Ala Gly Ser Gly Ala Gly Gly Thr Asp Pro Ala Ser Pro
    50                  55                  60

Asp Thr Ser Ser Pro Gly Ser Leu Ser Pro Pro Pro Ala Thr Leu Ser
65                  70                  75                  80

Ser Ser Leu Glu Ala Phe Leu Ser Gly Pro Gln Ala Ala Pro Ser Pro
                85                  90                  95
```

-continued

```
Leu Ser Pro Pro Gln Pro Ala Pro Thr Pro Leu Lys Met Tyr Pro Ser
            100                 105                 110

Met Pro Ala Phe Ser Pro Gly Pro Gly Ile Lys Glu Glu Ser Val Pro
        115                 120                 125

Leu Ser Ile Leu Gln Thr Pro Thr Pro Gln Pro Leu Pro Gly Ala Leu
    130                 135                 140

Leu Pro Gln Ser Phe Pro Ala Pro Ala Pro Pro Gln Phe Ser Ser Thr
145                 150                 155                 160

Pro Val Leu Gly Tyr Pro Ser Pro Pro Gly Gly Phe Ser Thr Gly Ser
                165                 170                 175

Pro Pro Gly Asn Thr Gln Gln Pro Leu Pro Gly Leu Pro Leu Ala Ser
            180                 185                 190

Pro Pro Gly Val Pro Pro Val Ser Leu His Thr Gln Val Gln Ser Val
        195                 200                 205

Val Pro Gln Gln Leu Leu Thr Val Thr Ala Ala Pro Thr Ala Ala Pro
    210                 215                 220

Val Thr Thr Thr Val Thr Ser Gln Ile Gln Gln Val Pro Val Leu Leu
225                 230                 235                 240

Gln Pro His Phe Ile Lys Ala Asp Ser Leu Leu Leu Thr Ala Met Lys
                245                 250                 255

Thr Asp Gly Ala Thr Val Lys Ala Ala Gly Leu Ser Pro Leu Val Ser
            260                 265                 270

Gly Thr Thr Val Gln Thr Gly Pro Leu Pro Thr Leu Val Ser Gly Gly
        275                 280                 285

Thr Ile Leu Ala Thr Val Pro Leu Val Val Asp Ala Glu Lys Leu Pro
    290                 295                 300

Ile Asn Arg Leu Ala Ala Gly Ser Lys Ala Pro Ala Ser Ala Gln Ser
305                 310                 315                 320

Arg Gly Glu Lys Arg Thr Ala His Asn Ala Ile Glu Lys Arg Tyr Arg
                325                 330                 335

Ser Ser Ile Asn Asp Lys Ile Ile Glu Leu Lys Asp Leu Val Val Gly
            340                 345                 350

Thr Glu Ala Lys Leu Asn Lys Ser Ala Val Leu Arg Lys Ala Ile Asp
        355                 360                 365

Tyr Ile Arg Phe Leu Gln His Ser Asn Gln Lys Leu Lys Gln Glu Asn
    370                 375                 380

Leu Ser Leu Arg Thr Ala Val His Lys Ser Lys Ser Leu Lys Asp Leu
385                 390                 395                 400

Val Ser Ala Cys Gly Ser Gly Gly Asn Thr Asp Val Leu Met Glu Gly
                405                 410                 415

Val Lys Thr Glu Val Glu Asp Thr Leu Thr Pro Pro Pro Ser Asp Ala
            420                 425                 430

Gly Ser Pro Phe Gln Ser Ser Pro Leu Ser Leu Gly Ser Arg Gly Ser
        435                 440                 445

Gly Ser Gly Gly Ser Gly Ser Asp Ser Glu Pro Asp Ser Pro Val Phe
    450                 455                 460

Glu Asp Ser Lys Ala Lys Pro Glu Gln Arg Pro Ser Leu His Ser Arg
465                 470                 475                 480

Gly Met Leu Asp Arg Ser Arg Leu Ala Leu Cys Thr Leu Val Phe Leu
                485                 490                 495

Cys Leu Ser Cys Asn Pro Leu Ala Ser Leu Leu Gly Ala Arg Gly Leu
            500                 505                 510

Pro Ser Pro Ser Asp Thr Thr Ser Val Tyr His Ser Pro Gly Arg Asn
```

-continued

```
        515                 520                 525

Val Leu Gly Thr Glu Ser Arg Asp Gly Pro Gly Trp Ala Gln Trp Leu
    530                 535                 540

Leu Pro Pro Val Val Trp Leu Leu Asn Gly Leu Leu Val Leu Val Ser
545                 550                 555                 560

Leu Val Leu Leu Phe Val Tyr Gly Glu Pro Val Thr Arg Pro His Ser
                565                 570                 575

Gly Pro Ala Val Tyr Phe Trp Arg His Arg Lys Gln Ala Asp Leu Asp
            580                 585                 590

Leu Ala Arg Gly Asp Phe Ala Gln Ala Ala Gln Gln Leu Trp Leu Ala
        595                 600                 605

Leu Arg Ala Leu Gly Arg Pro Leu Pro Thr Ser His Leu Asp Leu Ala
    610                 615                 620

Cys Ser Leu Leu Trp Asn Leu Ile Arg His Leu Leu Gln Arg Leu Trp
625                 630                 635                 640

Val Gly Arg Trp Leu Ala Gly Arg Ala Gly Gly Leu Gln Gln Asp Cys
                645                 650                 655

Ala Leu Arg Val Asp Ala Ser Ala Ser Ala Arg Asp Ala Ala Leu Val
            660                 665                 670

Tyr His Lys Leu His Gln Leu His Thr Met Gly Lys His Thr Gly Gly
        675                 680                 685

His Leu Thr Ala Thr Asn Leu Ala Leu Ser Ala Leu Asn Leu Ala Glu
    690                 695                 700

Cys Ala Gly Asp Ala Val Ser Val Ala Thr Leu Ala Glu Ile Tyr Val
705                 710                 715                 720

Ala Ala Ala Leu Arg Val Lys Thr Ser Leu Pro Arg Ala Leu His Phe
                725                 730                 735

Leu Thr Arg Phe Phe Leu Ser Ser Ala Arg Gln Ala Cys Leu Ala Gln
            740                 745                 750

Ser Gly Ser Val Pro Pro Ala Met Gln Trp Leu Cys His Pro Val Gly
        755                 760                 765

His Arg Phe Phe Val Asp Gly Asp Trp Ser Val Leu Ser Thr Pro Trp
    770                 775                 780

Glu Ser Leu Tyr Ser Leu Ala Gly Asn Pro Val Asp Pro Leu Ala Gln
785                 790                 795                 800

Val Thr Gln Leu Phe Arg Glu His Leu Leu Glu Arg Ala Leu Asn Cys
                805                 810                 815

Val Thr Gln Pro Asn Pro Ser Pro Gly Ser Ala Asp Gly Asp Lys Glu
            820                 825                 830

Phe Ser Asp Ala Leu Gly Tyr Leu Gln Leu Leu Asn Ser Cys Ser Asp
        835                 840                 845

Ala Ala Gly Ala Pro Ala Tyr Ser Phe Ser Ile Ser Ser Ser Met Ala
    850                 855                 860

Thr Thr Thr Gly Val Asp Pro Val Ala Lys Trp Trp Ala Ser Leu Thr
865                 870                 875                 880

Ala Val Val Ile His Trp Leu Arg Arg Asp Glu Glu Ala Ala Glu Arg
                885                 890                 895

Leu Cys Pro Leu Val Glu His Leu Pro Arg Val Leu Gln Glu Ser Glu
            900                 905                 910

Arg Pro Leu Pro Arg Ala Ala Leu His Ser Phe Lys Ala Ala Arg Ala
        915                 920                 925

Leu Leu Gly Cys Ala Lys Ala Glu Ser Gly Pro Ala Ser Leu Thr Ile
    930                 935                 940
```

Cys Glu Lys Ala Ser Gly Tyr Leu Gln Asp Ser Leu Ala Thr Thr Pro
945 950 955 960

Ala Ser Ser Ser Ile Asp Lys Ala Val Gln Leu Phe Leu Cys Asp Leu
965 970 975

Leu Leu Val Val Arg Thr Ser Leu Trp Arg Gln Gln Gln Pro Pro Ala
980 985 990

Pro Ala Pro Ala Ala Gln Gly Thr Ser Ser Arg Pro Gln Ala Ser Ala
995 1000 1005

Leu Glu Leu Arg Gly Phe Gln Arg Asp Leu Ser Ser Leu Arg Arg
1010 1015 1020

Leu Ala Gln Ser Phe Arg Pro Ala Met Arg Arg Val Phe Leu His
1025 1030 1035

Glu Ala Thr Ala Arg Leu Met Ala Gly Ala Ser Pro Thr Arg Thr
1040 1045 1050

His Gln Leu Leu Asp Arg Ser Leu Arg Arg Arg Ala Gly Pro Gly
1055 1060 1065

Gly Lys Gly Gly Ala Val Ala Glu Leu Glu Pro Arg Pro Thr Arg
1070 1075 1080

Arg Glu His Ala Glu Ala Leu Leu Leu Ala Ser Cys Tyr Leu Pro
1085 1090 1095

Pro Gly Phe Leu Ser Ala Pro Gly Gln Arg Val Gly Met Leu Ala
1100 1105 1110

Glu Ala Ala Arg Thr Leu Glu Lys Leu Gly Asp Arg Arg Leu Leu
1115 1120 1125

His Asp Cys Gln Gln Met Leu Met Arg Leu Gly Gly Gly Thr Thr
1130 1135 1140

Val Thr Ser Ser
1145

<210> SEQ ID NO 16
<211> LENGTH: 1177
<212> TYPE: PRT
<213> ORGANISM: homo sapien

<400> SEQUENCE: 16

Met Asp Glu Pro Pro Phe Ser Glu Ala Ala Leu Glu Gln Ala Leu Gly
1 5 10 15

Glu Pro Cys Asp Leu Asp Ala Ala Leu Leu Thr Asp Ile Glu Gly Glu
20 25 30

Val Gly Ala Gly Arg Gly Arg Ala Asn Gly Leu Asp Ala Pro Arg Ala
35 40 45

Gly Ala Asp Arg Gly Ala Met Asp Cys Thr Phe Glu Asp Met Leu Gln
50 55 60

Leu Ile Asn Asn Gln Asp Ser Asp Phe Pro Gly Leu Phe Asp Pro Pro
65 70 75 80

Tyr Ala Gly Ser Gly Ala Gly Gly Thr Asp Pro Ala Ser Pro Asp Thr
85 90 95

Ser Ser Pro Gly Ser Leu Ser Pro Pro Pro Ala Thr Leu Ser Ser Ser
100 105 110

Leu Glu Ala Phe Leu Ser Gly Pro Gln Ala Ala Pro Ser Pro Leu Ser
115 120 125

Pro Pro Gln Pro Ala Pro Thr Pro Leu Lys Met Tyr Pro Ser Met Pro
130 135 140

Ala Phe Ser Pro Gly Pro Gly Ile Lys Glu Glu Ser Val Pro Leu Ser

```
145                 150                 155                 160

Ile Leu Gln Thr Pro Thr Pro Gln Pro Leu Pro Gly Ala Leu Leu Pro
                165                 170                 175

Gln Ser Phe Pro Ala Pro Ala Pro Pro Gln Phe Ser Ser Thr Pro Val
            180                 185                 190

Leu Gly Tyr Pro Ser Pro Pro Gly Gly Phe Ser Thr Gly Ser Pro Pro
        195                 200                 205

Gly Asn Thr Gln Gln Pro Leu Pro Gly Leu Pro Leu Ala Ser Pro Pro
    210                 215                 220

Gly Val Pro Pro Val Ser Leu His Thr Gln Val Gln Ser Val Val Pro
225                 230                 235                 240

Gln Gln Leu Leu Thr Val Thr Ala Ala Pro Thr Ala Ala Pro Val Thr
                245                 250                 255

Thr Thr Val Thr Ser Gln Ile Gln Gln Val Pro Val Leu Leu Gln Pro
            260                 265                 270

His Phe Ile Lys Ala Asp Ser Leu Leu Leu Thr Ala Met Lys Thr Asp
        275                 280                 285

Gly Ala Thr Val Lys Ala Ala Gly Leu Ser Pro Leu Val Ser Gly Thr
    290                 295                 300

Thr Val Gln Thr Gly Pro Leu Pro Thr Leu Val Ser Gly Gly Thr Ile
305                 310                 315                 320

Leu Ala Thr Val Pro Leu Val Val Asp Ala Glu Lys Leu Pro Ile Asn
                325                 330                 335

Arg Leu Ala Ala Gly Ser Lys Ala Pro Ala Ser Ala Gln Ser Arg Gly
            340                 345                 350

Glu Lys Arg Thr Ala His Asn Ala Ile Glu Lys Arg Tyr Arg Ser Ser
        355                 360                 365

Ile Asn Asp Lys Ile Ile Glu Leu Lys Asp Leu Val Val Gly Thr Glu
    370                 375                 380

Ala Lys Leu Asn Lys Ser Ala Val Leu Arg Lys Ala Ile Asp Tyr Ile
385                 390                 395                 400

Arg Phe Leu Gln His Ser Asn Gln Lys Leu Lys Gln Glu Asn Leu Ser
                405                 410                 415

Leu Arg Thr Ala Val His Lys Ser Lys Ser Leu Lys Asp Leu Val Ser
            420                 425                 430

Ala Cys Gly Ser Gly Gly Asn Thr Asp Val Leu Met Glu Gly Val Lys
        435                 440                 445

Thr Glu Val Glu Asp Thr Leu Thr Pro Pro Pro Ser Asp Ala Gly Ser
    450                 455                 460

Pro Phe Gln Ser Ser Pro Leu Ser Leu Gly Ser Arg Gly Ser Gly Ser
465                 470                 475                 480

Gly Gly Ser Gly Ser Asp Ser Glu Pro Asp Ser Pro Val Phe Glu Asp
                485                 490                 495

Ser Lys Ala Lys Pro Glu Gln Arg Pro Ser Leu His Ser Arg Gly Met
            500                 505                 510

Leu Asp Arg Ser Arg Leu Ala Leu Cys Thr Leu Val Phe Leu Cys Leu
        515                 520                 525

Ser Cys Asn Pro Leu Ala Ser Leu Leu Gly Ala Arg Gly Leu Pro Ser
    530                 535                 540

Pro Ser Asp Thr Thr Ser Val Tyr His Ser Pro Gly Arg Asn Val Leu
545                 550                 555                 560

Gly Thr Glu Ser Arg Asp Gly Pro Gly Trp Ala Gln Trp Leu Leu Pro
                565                 570                 575
```

-continued

```
Pro Val Val Trp Leu Leu Asn Gly Leu Leu Val Leu Val Ser Leu Val
            580                 585                 590

Leu Leu Phe Val Tyr Gly Glu Pro Val Thr Arg Pro His Ser Gly Pro
        595                 600                 605

Ala Val Tyr Phe Trp Arg His Arg Lys Gln Ala Asp Leu Asp Leu Ala
    610                 615                 620

Arg Gly Asp Phe Ala Gln Ala Ala Gln Gln Leu Trp Leu Ala Leu Arg
625                 630                 635                 640

Ala Leu Gly Arg Pro Leu Pro Thr Ser His Leu Asp Leu Ala Cys Ser
                645                 650                 655

Leu Leu Trp Asn Leu Ile Arg His Leu Leu Gln Arg Leu Trp Val Gly
            660                 665                 670

Arg Trp Leu Ala Gly Arg Ala Gly Gly Leu Gln Gln Asp Cys Ala Leu
        675                 680                 685

Arg Val Asp Ala Ser Ala Ser Ala Arg Asp Ala Ala Leu Val Tyr His
    690                 695                 700

Lys Leu His Gln Leu His Thr Met Gly Lys His Thr Gly Gly His Leu
705                 710                 715                 720

Thr Ala Thr Asn Leu Ala Leu Ser Ala Leu Asn Leu Ala Glu Cys Ala
                725                 730                 735

Gly Asp Ala Val Ser Val Ala Thr Leu Ala Glu Ile Tyr Val Ala Ala
            740                 745                 750

Ala Leu Arg Val Lys Thr Ser Leu Pro Arg Ala Leu His Phe Leu Thr
        755                 760                 765

Arg Phe Phe Leu Ser Ser Ala Arg Gln Ala Cys Leu Ala Gln Ser Gly
    770                 775                 780

Ser Val Pro Pro Ala Met Gln Trp Leu Cys His Pro Val Gly His Arg
785                 790                 795                 800

Phe Phe Val Asp Gly Asp Trp Ser Val Leu Ser Thr Pro Trp Glu Ser
                805                 810                 815

Leu Tyr Ser Leu Ala Gly Asn Pro Val Asp Pro Leu Ala Gln Val Thr
            820                 825                 830

Gln Leu Phe Arg Glu His Leu Leu Glu Arg Ala Leu Asn Cys Val Thr
        835                 840                 845

Gln Pro Asn Pro Ser Pro Gly Ser Ala Asp Gly Asp Lys Glu Phe Ser
    850                 855                 860

Asp Ala Leu Gly Tyr Leu Gln Leu Leu Asn Ser Cys Ser Asp Ala Ala
865                 870                 875                 880

Gly Ala Pro Ala Tyr Ser Phe Ser Ile Ser Ser Ser Met Ala Thr Thr
                885                 890                 895

Thr Gly Val Asp Pro Val Ala Lys Trp Trp Ala Ser Leu Thr Ala Val
            900                 905                 910

Val Ile His Trp Leu Arg Arg Asp Glu Glu Ala Ala Glu Arg Leu Cys
        915                 920                 925

Pro Leu Val Glu His Leu Pro Arg Val Leu Gln Glu Ser Glu Arg Pro
    930                 935                 940

Leu Pro Arg Ala Ala Leu His Ser Phe Lys Ala Ala Arg Ala Leu Leu
945                 950                 955                 960

Gly Cys Ala Lys Ala Glu Ser Gly Pro Ala Ser Leu Thr Ile Cys Glu
                965                 970                 975

Lys Ala Ser Gly Tyr Leu Gln Asp Ser Leu Ala Thr Thr Pro Ala Ser
            980                 985                 990
```

-continued

```
Ser Ser Ile Asp Lys Ala Val Gln  Leu Phe Leu Cys Asp  Leu Leu Leu
        995                 1000                 1005

Val Val  Arg Thr Ser Leu Trp  Arg Gln Gln Gln Pro  Pro Ala Pro
    1010                 1015                 1020

Ala Pro  Ala Ala Gln Gly Thr  Ser Ser Arg Pro Gln  Ala Ser Ala
    1025                 1030                 1035

Leu Glu  Leu Arg Gly Phe Gln  Arg Asp Leu Ser Ser  Leu Arg Arg
    1040                 1045                 1050

Leu Ala  Gln Ser Phe Arg Pro  Ala Met Arg Arg Val  Phe Leu His
    1055                 1060                 1065

Glu Ala  Thr Ala Arg Leu Met  Ala Gly Ala Ser Pro  Thr Arg Thr
    1070                 1075                 1080

His Gln  Leu Leu Asp Arg Ser  Leu Arg Arg Arg Ala  Gly Pro Gly
    1085                 1090                 1095

Gly Lys  Gly Gly Ala Val Ala  Glu Leu Glu Pro Arg  Pro Thr Arg
    1100                 1105                 1110

Arg Glu  His Ala Glu Ala Leu  Leu Leu Ala Ser Cys  Tyr Leu Pro
    1115                 1120                 1125

Pro Gly  Phe Leu Ser Ala Pro  Gly Gln Arg Val Gly  Met Leu Ala
    1130                 1135                 1140

Glu Ala  Ala Arg Thr Leu Glu  Lys Leu Gly Asp Arg  Arg Leu Leu
    1145                 1150                 1155

His Asp  Cys Gln Gln Met Leu  Met Arg Leu Gly Gly  Gly Thr Thr
    1160                 1165                 1170

Val Thr  Ser Ser
    1175


<210> SEQ ID NO 17
<211> LENGTH: 1123
<212> TYPE: PRT
<213> ORGANISM: homo sapien

<400> SEQUENCE: 17

Met Asp Cys Thr Phe Glu Asp Met Leu Gln Leu Ile Asn Asn Gln Asp
1               5                   10                  15

Ser Asp Phe Pro Gly Leu Phe Asp Pro Pro Tyr Ala Gly Ser Gly Ala
            20                  25                  30

Gly Gly Thr Asp Pro Ala Ser Pro Asp Thr Ser Ser Pro Gly Ser Leu
        35                  40                  45

Ser Pro Pro Pro Ala Thr Leu Ser Ser Ser Leu Glu Ala Phe Leu Ser
    50                  55                  60

Gly Pro Gln Ala Ala Pro Ser Pro Leu Ser Pro Pro Gln Pro Ala Pro
65                  70                  75                  80

Thr Pro Leu Lys Met Tyr Pro Ser Met Pro Ala Phe Ser Pro Gly Pro
                85                  90                  95

Gly Ile Lys Glu Glu Ser Val Pro Leu Ser Ile Leu Gln Thr Pro Thr
            100                 105                 110

Pro Gln Pro Leu Pro Gly Ala Leu Leu Pro Gln Ser Phe Pro Ala Pro
        115                 120                 125

Ala Pro Pro Gln Phe Ser Ser Thr Pro Val Leu Gly Tyr Pro Ser Pro
    130                 135                 140

Pro Gly Gly Phe Ser Thr Gly Ser Pro Pro Gly Asn Thr Gln Gln Pro
145                 150                 155                 160

Leu Pro Gly Leu Pro Leu Ala Ser Pro Pro Gly Val Pro Pro Val Ser
                165                 170                 175
```

```
Leu His Thr Gln Val Gln Ser Val Val Pro Gln Gln Leu Leu Thr Val
            180                 185                 190

Thr Ala Ala Pro Thr Ala Ala Pro Val Thr Thr Thr Val Thr Ser Gln
        195                 200                 205

Ile Gln Gln Val Pro Val Leu Leu Gln Pro His Phe Ile Lys Ala Asp
    210                 215                 220

Ser Leu Leu Leu Thr Ala Met Lys Thr Asp Gly Ala Thr Val Lys Ala
225                 230                 235                 240

Ala Gly Leu Ser Pro Leu Val Ser Gly Thr Thr Val Gln Thr Gly Pro
                245                 250                 255

Leu Pro Thr Leu Val Ser Gly Gly Thr Ile Leu Ala Thr Val Pro Leu
            260                 265                 270

Val Val Asp Ala Glu Lys Leu Pro Ile Asn Arg Leu Ala Ala Gly Ser
        275                 280                 285

Lys Ala Pro Ala Ser Ala Gln Ser Arg Gly Glu Lys Arg Thr Ala His
    290                 295                 300

Asn Ala Ile Glu Lys Arg Tyr Arg Ser Ser Ile Asn Asp Lys Ile Ile
305                 310                 315                 320

Glu Leu Lys Asp Leu Val Val Gly Thr Glu Ala Lys Leu Asn Lys Ser
                325                 330                 335

Ala Val Leu Arg Lys Ala Ile Asp Tyr Ile Arg Phe Leu Gln His Ser
            340                 345                 350

Asn Gln Lys Leu Lys Gln Glu Asn Leu Ser Leu Arg Thr Ala Val His
        355                 360                 365

Lys Ser Lys Ser Leu Lys Asp Leu Val Ser Ala Cys Gly Ser Gly Gly
    370                 375                 380

Asn Thr Asp Val Leu Met Glu Gly Val Lys Thr Glu Val Glu Asp Thr
385                 390                 395                 400

Leu Thr Pro Pro Pro Ser Asp Ala Gly Ser Pro Phe Gln Ser Ser Pro
                405                 410                 415

Leu Ser Leu Gly Ser Arg Gly Ser Gly Ser Gly Gly Ser Gly Ser Asp
            420                 425                 430

Ser Glu Pro Asp Ser Pro Val Phe Glu Asp Ser Lys Ala Lys Pro Glu
        435                 440                 445

Gln Arg Pro Ser Leu His Ser Arg Gly Met Leu Asp Arg Ser Arg Leu
    450                 455                 460

Ala Leu Cys Thr Leu Val Phe Leu Cys Leu Ser Cys Asn Pro Leu Ala
465                 470                 475                 480

Ser Leu Leu Gly Ala Arg Gly Leu Pro Ser Pro Ser Asp Thr Thr Ser
                485                 490                 495

Val Tyr His Ser Pro Gly Arg Asn Val Leu Gly Thr Glu Ser Arg Asp
            500                 505                 510

Gly Pro Gly Trp Ala Gln Trp Leu Leu Pro Pro Val Val Trp Leu Leu
        515                 520                 525

Asn Gly Leu Leu Val Leu Val Ser Leu Val Leu Leu Phe Val Tyr Gly
    530                 535                 540

Glu Pro Val Thr Arg Pro His Ser Gly Pro Ala Val Tyr Phe Trp Arg
545                 550                 555                 560

His Arg Lys Gln Ala Asp Leu Asp Leu Ala Arg Gly Asp Phe Ala Gln
                565                 570                 575

Ala Ala Gln Gln Leu Trp Leu Ala Leu Arg Ala Leu Gly Arg Pro Leu
            580                 585                 590
```

-continued

```
Pro Thr Ser His Leu Asp Leu Ala Cys Ser Leu Leu Trp Asn Leu Ile
        595                 600                 605

Arg His Leu Leu Gln Arg Leu Trp Val Gly Arg Trp Leu Ala Gly Arg
    610                 615                 620

Ala Gly Gly Leu Gln Gln Asp Cys Ala Leu Arg Val Asp Ala Ser Ala
625                 630                 635                 640

Ser Ala Arg Asp Ala Ala Leu Val Tyr His Lys Leu His Gln Leu His
                645                 650                 655

Thr Met Gly Lys His Thr Gly Gly His Leu Thr Ala Thr Asn Leu Ala
            660                 665                 670

Leu Ser Ala Leu Asn Leu Ala Glu Cys Ala Gly Asp Ala Val Ser Val
        675                 680                 685

Ala Thr Leu Ala Glu Ile Tyr Val Ala Ala Ala Leu Arg Val Lys Thr
    690                 695                 700

Ser Leu Pro Arg Ala Leu His Phe Leu Thr Arg Phe Phe Leu Ser Ser
705                 710                 715                 720

Ala Arg Gln Ala Cys Leu Ala Gln Ser Gly Ser Val Pro Pro Ala Met
                725                 730                 735

Gln Trp Leu Cys His Pro Val Gly His Arg Phe Phe Val Asp Gly Asp
            740                 745                 750

Trp Ser Val Leu Ser Thr Pro Trp Glu Ser Leu Tyr Ser Leu Ala Gly
        755                 760                 765

Asn Pro Val Asp Pro Leu Ala Gln Val Thr Gln Leu Phe Arg Glu His
    770                 775                 780

Leu Leu Glu Arg Ala Leu Asn Cys Val Thr Gln Pro Asn Pro Ser Pro
785                 790                 795                 800

Gly Ser Ala Asp Gly Asp Lys Glu Phe Ser Asp Ala Leu Gly Tyr Leu
                805                 810                 815

Gln Leu Leu Asn Ser Cys Ser Asp Ala Ala Gly Ala Pro Ala Tyr Ser
            820                 825                 830

Phe Ser Ile Ser Ser Ser Met Ala Thr Thr Thr Gly Val Asp Pro Val
        835                 840                 845

Ala Lys Trp Trp Ala Ser Leu Thr Ala Val Val Ile His Trp Leu Arg
    850                 855                 860

Arg Asp Glu Glu Ala Ala Glu Arg Leu Cys Pro Leu Val Glu His Leu
865                 870                 875                 880

Pro Arg Val Leu Gln Glu Ser Glu Arg Pro Leu Pro Arg Ala Ala Leu
                885                 890                 895

His Ser Phe Lys Ala Ala Arg Ala Leu Leu Gly Cys Ala Lys Ala Glu
            900                 905                 910

Ser Gly Pro Ala Ser Leu Thr Ile Cys Glu Lys Ala Ser Gly Tyr Leu
        915                 920                 925

Gln Asp Ser Leu Ala Thr Thr Pro Ala Ser Ser Ser Ile Asp Lys Ala
    930                 935                 940

Val Gln Leu Phe Leu Cys Asp Leu Leu Leu Val Val Arg Thr Ser Leu
945                 950                 955                 960

Trp Arg Gln Gln Gln Pro Pro Ala Pro Ala Pro Ala Ala Gln Gly Thr
                965                 970                 975

Ser Ser Arg Pro Gln Ala Ser Ala Leu Glu Leu Arg Gly Phe Gln Arg
            980                 985                 990

Asp Leu Ser Ser Leu Arg Arg Leu  Ala Gln Ser Phe Arg  Pro Ala Met
        995                 1000                 1005

Arg Arg  Val Phe Leu His Glu  Ala Thr Ala Arg Leu  Met Ala Gly
```

```
    1010                1015                1020

Ala Ser  Pro Thr Arg Thr His  Gln Leu Leu Asp Arg  Ser Leu Arg
    1025                1030                1035

Arg Arg  Ala Gly Pro Gly Gly  Lys Gly Gly Ala Val  Ala Glu Leu
    1040                1045                1050

Glu Pro  Arg Pro Thr Arg Arg  Glu His Ala Glu Ala  Leu Leu Leu
    1055                1060                1065

Ala Ser  Cys Tyr Leu Pro Pro  Gly Phe Leu Ser Ala  Pro Gly Gln
    1070                1075                1080

Arg Val  Gly Met Leu Ala Glu  Ala Ala Arg Thr Leu  Glu Lys Leu
    1085                1090                1095

Gly Asp  Arg Arg Leu Leu His  Asp Cys Gln Gln Met  Leu Met Arg
    1100                1105                1110

Leu Gly  Gly Gly Thr Thr Val  Thr Ser Ser
    1115                1120


<210> SEQ ID NO 18
<211> LENGTH: 1147
<212> TYPE: PRT
<213> ORGANISM: homo sapien

<400> SEQUENCE: 18

Met Asp Glu Pro Pro Phe Ser Glu Ala Ala Leu Glu Gln Ala Leu Gly
1               5                   10                  15

Glu Pro Cys Asp Leu Asp Ala Ala Leu Leu Thr Asp Ile Glu Asp Met
            20                  25                  30

Leu Gln Leu Ile Asn Asn Gln Asp Ser Asp Phe Pro Gly Leu Phe Asp
        35                  40                  45

Pro Pro Tyr Ala Gly Ser Gly Ala Gly Gly Thr Asp Pro Ala Ser Pro
    50                  55                  60

Asp Thr Ser Ser Pro Gly Ser Leu Ser Pro Pro Pro Ala Thr Leu Ser
65                  70                  75                  80

Ser Ser Leu Glu Ala Phe Leu Ser Gly Pro Gln Ala Ala Pro Ser Pro
                85                  90                  95

Leu Ser Pro Pro Gln Pro Ala Pro Thr Pro Leu Lys Met Tyr Pro Ser
            100                 105                 110

Met Pro Ala Phe Ser Pro Gly Pro Gly Ile Lys Glu Glu Ser Val Pro
        115                 120                 125

Leu Ser Ile Leu Gln Thr Pro Thr Pro Gln Pro Leu Pro Gly Ala Leu
    130                 135                 140

Leu Pro Gln Ser Phe Pro Ala Pro Ala Pro Pro Gln Phe Ser Ser Thr
145                 150                 155                 160

Pro Val Leu Gly Tyr Pro Ser Pro Pro Gly Gly Phe Ser Thr Gly Ser
                165                 170                 175

Pro Pro Gly Asn Thr Gln Gln Pro Leu Pro Gly Leu Pro Leu Ala Ser
            180                 185                 190

Pro Pro Gly Val Pro Pro Val Ser Leu His Thr Gln Val Gln Ser Val
        195                 200                 205

Val Pro Gln Gln Leu Leu Thr Val Thr Ala Ala Pro Thr Ala Ala Pro
    210                 215                 220

Val Thr Thr Thr Val Thr Ser Gln Ile Gln Gln Val Pro Val Leu Leu
225                 230                 235                 240

Gln Pro His Phe Ile Lys Ala Asp Ser Leu Leu Leu Thr Ala Met Lys
                245                 250                 255
```

-continued

```
Thr Asp Gly Ala Thr Val Lys Ala Ala Gly Leu Ser Pro Leu Val Ser
            260                 265                 270

Gly Thr Thr Val Gln Thr Gly Pro Leu Pro Thr Leu Val Ser Gly Gly
        275                 280                 285

Thr Ile Leu Ala Thr Val Pro Leu Val Val Asp Ala Glu Lys Leu Pro
    290                 295                 300

Ile Asn Arg Leu Ala Ala Gly Ser Lys Ala Pro Ala Ser Ala Gln Ser
305                 310                 315                 320

Arg Gly Glu Lys Arg Thr Ala His Asn Ala Ile Glu Lys Cys Tyr Arg
                325                 330                 335

Ser Ser Ile Asn Asp Lys Ile Ile Glu Leu Lys Asp Leu Val Val Gly
            340                 345                 350

Thr Glu Ala Lys Leu Asn Lys Ser Ala Val Leu Arg Lys Ala Ile Asp
        355                 360                 365

Tyr Ile Arg Phe Leu Gln His Ser Asn Gln Lys Leu Lys Gln Glu Asn
    370                 375                 380

Leu Ser Leu Arg Thr Ala Val His Lys Ser Lys Ser Leu Lys Asp Leu
385                 390                 395                 400

Val Ser Ala Cys Gly Ser Gly Gly Asn Thr Asp Val Leu Met Glu Gly
                405                 410                 415

Val Lys Thr Glu Val Glu Asp Thr Leu Thr Pro Pro Pro Ser Asp Ala
            420                 425                 430

Gly Ser Pro Phe Gln Ser Ser Pro Leu Ser Leu Gly Ser Arg Gly Ser
        435                 440                 445

Gly Ser Gly Gly Ser Gly Ser Asp Ser Glu Pro Asp Ser Pro Val Phe
    450                 455                 460

Glu Asp Ser Lys Ala Lys Pro Glu Gln Arg Pro Ser Leu His Ser Arg
465                 470                 475                 480

Gly Met Leu Asp Arg Ser Arg Leu Ala Leu Cys Thr Leu Val Phe Leu
                485                 490                 495

Cys Leu Ser Cys Asn Pro Leu Ala Ser Leu Leu Gly Ala Arg Gly Leu
            500                 505                 510

Pro Ser Pro Ser Asp Thr Thr Ser Val Tyr His Ser Pro Gly Arg Asn
        515                 520                 525

Val Leu Gly Thr Glu Ser Arg Asp Gly Pro Gly Trp Ala Gln Trp Leu
    530                 535                 540

Leu Pro Pro Val Val Trp Leu Leu Asn Gly Leu Leu Val Leu Val Ser
545                 550                 555                 560

Leu Val Leu Leu Phe Val Tyr Gly Glu Pro Val Thr Arg Pro His Ser
                565                 570                 575

Gly Pro Ala Val Tyr Phe Trp Arg His Arg Lys Gln Ala Asp Leu Asp
            580                 585                 590

Leu Ala Arg Gly Asp Phe Ala Gln Ala Ala Gln Gln Leu Trp Leu Ala
        595                 600                 605

Leu Arg Ala Leu Gly Arg Pro Leu Pro Thr Ser His Leu Asp Leu Ala
    610                 615                 620

Cys Ser Leu Leu Trp Asn Leu Ile Arg His Leu Leu Gln Arg Leu Trp
625                 630                 635                 640

Val Gly Arg Trp Leu Ala Gly Arg Ala Gly Gly Leu Gln Gln Asp Cys
                645                 650                 655

Ala Leu Arg Val Asp Ala Ser Ala Ser Ala Arg Asp Ala Ala Leu Val
            660                 665                 670

Tyr His Lys Leu His Gln Leu His Thr Met Gly Lys His Thr Gly Gly
```

-continued

```
        675                 680                 685

His Leu Thr Ala Thr Asn Leu Ala Leu Ser Ala Leu Asn Leu Ala Glu
    690                 695                 700

Cys Ala Gly Asp Ala Val Ser Val Ala Thr Leu Ala Glu Ile Tyr Val
705                 710                 715                 720

Ala Ala Ala Leu Arg Val Lys Thr Ser Leu Pro Arg Ala Leu His Phe
                725                 730                 735

Leu Thr Arg Phe Phe Leu Ser Ser Ala Arg Gln Ala Cys Leu Ala Gln
            740                 745                 750

Ser Gly Ser Val Pro Pro Ala Met Gln Trp Leu Cys His Pro Val Gly
        755                 760                 765

His Arg Phe Phe Val Asp Gly Asp Trp Ser Val Leu Ser Thr Pro Trp
    770                 775                 780

Glu Ser Leu Tyr Ser Leu Ala Gly Asn Pro Val Asp Pro Leu Ala Gln
785                 790                 795                 800

Val Thr Gln Leu Phe Arg Glu His Leu Leu Glu Arg Ala Leu Asn Cys
                805                 810                 815

Val Thr Gln Pro Asn Pro Ser Pro Gly Ser Ala Asp Gly Asp Lys Glu
            820                 825                 830

Phe Ser Asp Ala Leu Gly Tyr Leu Gln Leu Leu Asn Ser Cys Ser Asp
        835                 840                 845

Ala Ala Gly Ala Pro Ala Tyr Ser Phe Ser Ile Ser Ser Ser Met Ala
    850                 855                 860

Thr Thr Thr Gly Val Asp Pro Val Ala Lys Trp Trp Ala Ser Leu Thr
865                 870                 875                 880

Ala Val Val Ile His Trp Leu Arg Arg Asp Glu Glu Ala Ala Glu Arg
                885                 890                 895

Leu Cys Pro Leu Val Glu His Leu Pro Arg Val Leu Gln Glu Ser Glu
            900                 905                 910

Arg Pro Leu Pro Arg Ala Ala Leu His Ser Phe Lys Ala Ala Arg Ala
        915                 920                 925

Leu Leu Gly Cys Ala Lys Ala Glu Ser Gly Pro Ala Ser Leu Thr Ile
    930                 935                 940

Cys Glu Lys Ala Ser Gly Tyr Leu Gln Asp Ser Leu Ala Thr Thr Pro
945                 950                 955                 960

Ala Ser Ser Ser Ile Asp Lys Ala Val Gln Leu Phe Leu Cys Asp Leu
                965                 970                 975

Leu Leu Val Val Arg Thr Ser Leu Trp Arg Gln Gln Gln Pro Pro Ala
            980                 985                 990

Pro Ala Pro Ala Ala Gln Gly Thr  Ser Ser Arg Pro Gln  Ala Ser Ala
        995                 1000                1005

Leu Glu  Leu Arg Gly Phe Gln  Arg Asp Leu Ser Ser  Leu Arg Arg
    1010                 1015                 1020

Leu Ala  Gln Ser Phe Arg Pro  Ala Met Arg Arg Val  Phe Leu His
    1025                 1030                 1035

Glu Ala  Thr Ala Arg Leu Met  Ala Gly Ala Ser Pro  Thr Arg Thr
    1040                 1045                 1050

His Gln  Leu Leu Asp Arg Ser  Leu Arg Arg Arg Ala  Gly Pro Gly
    1055                 1060                 1065

Gly Lys  Gly Gly Ala Val Ala  Glu Leu Glu Pro Arg  Pro Thr Arg
    1070                 1075                 1080

Arg Glu  His Ala Glu Ala Leu  Leu Leu Ala Ser Cys  Tyr Leu Pro
    1085                 1090                 1095
```

```
Pro Gly  Phe Leu Ser Ala Pro  Gly Gln Arg Val Gly  Met Leu Ala
    1100                 1105                 1110

Glu Ala  Ala Arg Thr Leu Glu  Lys Leu Gly Asp Arg  Arg Leu Leu
    1115                 1120                 1125

His Asp  Cys Gln Gln Met Leu  Met Arg Leu Gly Gly  Gly Thr Thr
    1130                 1135                 1140

Val Thr  Ser Ser
    1145


<210> SEQ ID NO 19
<211> LENGTH: 1177
<212> TYPE: PRT
<213> ORGANISM: homo sapien

<400> SEQUENCE: 19

Met Asp Glu Pro Pro Phe Ser Glu Ala Ala Leu Glu Gln Ala Leu Gly
1               5                   10                  15

Glu Pro Cys Asp Leu Asp Ala Ala Leu Leu Thr Asp Ile Glu Gly Glu
            20                  25                  30

Val Gly Ala Gly Arg Gly Arg Ala Asn Gly Leu Asp Ala Pro Arg Ala
        35                  40                  45

Gly Ala Asp Arg Gly Ala Met Asp Cys Thr Phe Glu Asp Met Leu Gln
    50                  55                  60

Leu Ile Asn Asn Gln Asp Ser Asp Phe Pro Gly Leu Phe Asp Pro Pro
65                  70                  75                  80

Tyr Ala Gly Ser Gly Ala Gly Gly Thr Asp Pro Ala Ser Pro Asp Thr
                85                  90                  95

Ser Ser Pro Gly Ser Leu Ser Pro Pro Pro Ala Thr Leu Ser Ser Ser
            100                 105                 110

Leu Glu Ala Phe Leu Ser Gly Pro Gln Ala Ala Pro Ser Pro Leu Ser
        115                 120                 125

Pro Pro Gln Pro Ala Pro Thr Pro Leu Lys Met Tyr Pro Ser Met Pro
    130                 135                 140

Ala Phe Ser Pro Gly Pro Gly Ile Lys Glu Glu Ser Val Pro Leu Ser
145                 150                 155                 160

Ile Leu Gln Thr Pro Thr Pro Gln Pro Leu Pro Gly Ala Leu Leu Pro
                165                 170                 175

Gln Ser Phe Pro Ala Pro Ala Pro Pro Gln Phe Ser Ser Thr Pro Val
            180                 185                 190

Leu Gly Tyr Pro Ser Pro Pro Gly Gly Phe Ser Thr Gly Ser Pro Pro
        195                 200                 205

Gly Asn Thr Gln Gln Pro Leu Pro Gly Leu Pro Leu Ala Ser Pro Pro
    210                 215                 220

Gly Val Pro Pro Val Ser Leu His Thr Gln Val Gln Ser Val Val Pro
225                 230                 235                 240

Gln Gln Leu Leu Thr Val Thr Ala Ala Pro Thr Ala Ala Pro Val Thr
                245                 250                 255

Thr Thr Val Thr Ser Gln Ile Gln Gln Val Pro Val Leu Leu Gln Pro
            260                 265                 270

His Phe Ile Lys Ala Asp Ser Leu Leu Leu Thr Ala Met Lys Thr Asp
        275                 280                 285

Gly Ala Thr Val Lys Ala Ala Gly Leu Ser Pro Leu Val Ser Gly Thr
    290                 295                 300

Thr Val Gln Thr Gly Pro Leu Pro Thr Leu Val Ser Gly Gly Thr Ile
```

-continued

```
305                 310                 315                 320

Leu Ala Thr Val Pro Leu Val Val Asp Ala Glu Lys Leu Pro Ile Asn
                325                 330                 335

Arg Leu Ala Ala Gly Ser Lys Ala Pro Ala Ser Ala Gln Ser Arg Gly
            340                 345                 350

Glu Lys Arg Thr Ala His Asn Ala Ile Glu Lys Cys Tyr Arg Ser Ser
        355                 360                 365

Ile Asn Asp Lys Ile Ile Glu Leu Lys Asp Leu Val Val Gly Thr Glu
    370                 375                 380

Ala Lys Leu Asn Lys Ser Ala Val Leu Arg Lys Ala Ile Asp Tyr Ile
385                 390                 395                 400

Arg Phe Leu Gln His Ser Asn Gln Lys Leu Lys Gln Glu Asn Leu Ser
                405                 410                 415

Leu Arg Thr Ala Val His Lys Ser Lys Ser Leu Lys Asp Leu Val Ser
            420                 425                 430

Ala Cys Gly Ser Gly Gly Asn Thr Asp Val Leu Met Glu Gly Val Lys
        435                 440                 445

Thr Glu Val Glu Asp Thr Leu Thr Pro Pro Pro Ser Asp Ala Gly Ser
    450                 455                 460

Pro Phe Gln Ser Ser Pro Leu Ser Leu Gly Ser Arg Gly Ser Gly Ser
465                 470                 475                 480

Gly Gly Ser Gly Ser Asp Ser Glu Pro Asp Ser Pro Val Phe Glu Asp
                485                 490                 495

Ser Lys Ala Lys Pro Glu Gln Arg Pro Ser Leu His Ser Arg Gly Met
            500                 505                 510

Leu Asp Arg Ser Arg Leu Ala Leu Cys Thr Leu Val Phe Leu Cys Leu
        515                 520                 525

Ser Cys Asn Pro Leu Ala Ser Leu Leu Gly Ala Arg Gly Leu Pro Ser
    530                 535                 540

Pro Ser Asp Thr Thr Ser Val Tyr His Ser Pro Gly Arg Asn Val Leu
545                 550                 555                 560

Gly Thr Glu Ser Arg Asp Gly Pro Gly Trp Ala Gln Trp Leu Leu Pro
                565                 570                 575

Pro Val Val Trp Leu Leu Asn Gly Leu Leu Val Leu Val Ser Leu Val
            580                 585                 590

Leu Leu Phe Val Tyr Gly Glu Pro Val Thr Arg Pro His Ser Gly Pro
        595                 600                 605

Ala Val Tyr Phe Trp Arg His Arg Lys Gln Ala Asp Leu Asp Leu Ala
    610                 615                 620

Arg Gly Asp Phe Ala Gln Ala Ala Gln Gln Leu Trp Leu Ala Leu Arg
625                 630                 635                 640

Ala Leu Gly Arg Pro Leu Pro Thr Ser His Leu Asp Leu Ala Cys Ser
                645                 650                 655

Leu Leu Trp Asn Leu Ile Arg His Leu Leu Gln Arg Leu Trp Val Gly
            660                 665                 670

Arg Trp Leu Ala Gly Arg Ala Gly Gly Leu Gln Gln Asp Cys Ala Leu
        675                 680                 685

Arg Val Asp Ala Ser Ala Ser Ala Arg Asp Ala Ala Leu Val Tyr His
    690                 695                 700

Lys Leu His Gln Leu His Thr Met Gly Lys His Thr Gly Gly His Leu
705                 710                 715                 720

Thr Ala Thr Asn Leu Ala Leu Ser Ala Leu Asn Leu Ala Glu Cys Ala
                725                 730                 735
```

```
Gly Asp Ala Val Ser Val Ala Thr Leu Ala Glu Ile Tyr Val Ala Ala
            740                 745                 750

Ala Leu Arg Val Lys Thr Ser Leu Pro Arg Ala Leu His Phe Leu Thr
        755                 760                 765

Arg Phe Phe Leu Ser Ser Ala Arg Gln Ala Cys Leu Ala Gln Ser Gly
    770                 775                 780

Ser Val Pro Pro Ala Met Gln Trp Leu Cys His Pro Val Gly His Arg
785                 790                 795                 800

Phe Phe Val Asp Gly Asp Trp Ser Val Leu Ser Thr Pro Trp Glu Ser
                805                 810                 815

Leu Tyr Ser Leu Ala Gly Asn Pro Val Asp Pro Leu Ala Gln Val Thr
            820                 825                 830

Gln Leu Phe Arg Glu His Leu Leu Glu Arg Ala Leu Asn Cys Val Thr
        835                 840                 845

Gln Pro Asn Pro Ser Pro Gly Ser Ala Asp Gly Asp Lys Glu Phe Ser
    850                 855                 860

Asp Ala Leu Gly Tyr Leu Gln Leu Leu Asn Ser Cys Ser Asp Ala Ala
865                 870                 875                 880

Gly Ala Pro Ala Tyr Ser Phe Ser Ile Ser Ser Ser Met Ala Thr Thr
                885                 890                 895

Thr Gly Val Asp Pro Val Ala Lys Trp Trp Ala Ser Leu Thr Ala Val
            900                 905                 910

Val Ile His Trp Leu Arg Arg Asp Glu Glu Ala Ala Glu Arg Leu Cys
        915                 920                 925

Pro Leu Val Glu His Leu Pro Arg Val Leu Gln Glu Ser Glu Arg Pro
    930                 935                 940

Leu Pro Arg Ala Ala Leu His Ser Phe Lys Ala Ala Arg Ala Leu Leu
945                 950                 955                 960

Gly Cys Ala Lys Ala Glu Ser Gly Pro Ala Ser Leu Thr Ile Cys Glu
                965                 970                 975

Lys Ala Ser Gly Tyr Leu Gln Asp Ser Leu Ala Thr Thr Pro Ala Ser
            980                 985                 990

Ser Ser Ile Asp Lys Ala Val Gln  Leu Phe Leu Cys Asp  Leu Leu Leu
        995                 1000                 1005

Val Val  Arg Thr Ser Leu Trp  Arg Gln Gln Gln Pro  Pro Ala Pro
    1010                 1015                 1020

Ala Pro  Ala Ala Gln Gly Thr  Ser Ser Arg Pro Gln  Ala Ser Ala
    1025                 1030                 1035

Leu Glu  Leu Arg Gly Phe Gln  Arg Asp Leu Ser Ser  Leu Arg Arg
    1040                 1045                 1050

Leu Ala  Gln Ser Phe Arg Pro  Ala Met Arg Arg Val  Phe Leu His
    1055                 1060                 1065

Glu Ala  Thr Ala Arg Leu Met  Ala Gly Ala Ser Pro  Thr Arg Thr
    1070                 1075                 1080

His Gln  Leu Leu Asp Arg Ser  Leu Arg Arg Arg Ala  Gly Pro Gly
    1085                 1090                 1095

Gly Lys  Gly Gly Ala Val Ala  Glu Leu Glu Pro Arg  Pro Thr Arg
    1100                 1105                 1110

Arg Glu  His Ala Glu Ala Leu  Leu Leu Ala Ser Cys  Tyr Leu Pro
    1115                 1120                 1125

Pro Gly  Phe Leu Ser Ala Pro  Gly Gln Arg Val Gly  Met Leu Ala
    1130                 1135                 1140
```

```
Glu Ala  Ala Arg Thr Leu Glu  Lys Leu Gly Asp Arg  Arg Leu Leu
    1145                 1150                 1155

His Asp  Cys Gln Gln Met Leu  Met Arg Leu Gly Gly  Gly Thr Thr
    1160                 1165                 1170

Val Thr  Ser Ser
    1175
```

<210> SEQ ID NO 20
<211> LENGTH: 1123
<212> TYPE: PRT
<213> ORGANISM: homo sapien

<400> SEQUENCE: 20

```
Met Asp Cys Thr Phe Glu Asp Met Leu Gln Leu Ile Asn Asn Gln Asp
1               5                   10                  15

Ser Asp Phe Pro Gly Leu Phe Asp Pro Pro Tyr Ala Gly Ser Gly Ala
            20                  25                  30

Gly Gly Thr Asp Pro Ala Ser Pro Asp Thr Ser Ser Pro Gly Ser Leu
        35                  40                  45

Ser Pro Pro Pro Ala Thr Leu Ser Ser Ser Leu Glu Ala Phe Leu Ser
    50                  55                  60

Gly Pro Gln Ala Ala Pro Ser Pro Leu Ser Pro Pro Gln Pro Ala Pro
65                  70                  75                  80

Thr Pro Leu Lys Met Tyr Pro Ser Met Pro Ala Phe Ser Pro Gly Pro
                85                  90                  95

Gly Ile Lys Glu Glu Ser Val Pro Leu Ser Ile Leu Gln Thr Pro Thr
            100                 105                 110

Pro Gln Pro Leu Pro Gly Ala Leu Leu Pro Gln Ser Phe Pro Ala Pro
        115                 120                 125

Ala Pro Pro Gln Phe Ser Ser Thr Pro Val Leu Gly Tyr Pro Ser Pro
    130                 135                 140

Pro Gly Gly Phe Ser Thr Gly Ser Pro Pro Gly Asn Thr Gln Gln Pro
145                 150                 155                 160

Leu Pro Gly Leu Pro Leu Ala Ser Pro Pro Gly Val Pro Pro Val Ser
                165                 170                 175

Leu His Thr Gln Val Gln Ser Val Val Pro Gln Gln Leu Leu Thr Val
            180                 185                 190

Thr Ala Ala Pro Thr Ala Ala Pro Val Thr Thr Thr Val Thr Ser Gln
        195                 200                 205

Ile Gln Gln Val Pro Val Leu Leu Gln Pro His Phe Ile Lys Ala Asp
    210                 215                 220

Ser Leu Leu Leu Thr Ala Met Lys Thr Asp Gly Ala Thr Val Lys Ala
225                 230                 235                 240

Ala Gly Leu Ser Pro Leu Val Ser Gly Thr Thr Val Gln Thr Gly Pro
                245                 250                 255

Leu Pro Thr Leu Val Ser Gly Gly Thr Ile Leu Ala Thr Val Pro Leu
            260                 265                 270

Val Val Asp Ala Glu Lys Leu Pro Ile Asn Arg Leu Ala Ala Gly Ser
        275                 280                 285

Lys Ala Pro Ala Ser Ala Gln Ser Arg Gly Glu Lys Arg Thr Ala His
    290                 295                 300

Asn Ala Ile Glu Lys Cys Tyr Arg Ser Ser Ile Asn Asp Lys Ile Ile
305                 310                 315                 320

Glu Leu Lys Asp Leu Val Val Gly Thr Glu Ala Lys Leu Asn Lys Ser
                325                 330                 335
```

```
Ala Val Leu Arg Lys Ala Ile Asp Tyr Ile Arg Phe Leu Gln His Ser
            340                 345                 350

Asn Gln Lys Leu Lys Gln Glu Asn Leu Ser Leu Arg Thr Ala Val His
        355                 360                 365

Lys Ser Lys Ser Leu Lys Asp Leu Val Ser Ala Cys Gly Ser Gly Gly
    370                 375                 380

Asn Thr Asp Val Leu Met Glu Gly Val Lys Thr Glu Val Glu Asp Thr
385                 390                 395                 400

Leu Thr Pro Pro Pro Ser Asp Ala Gly Ser Pro Phe Gln Ser Ser Pro
                405                 410                 415

Leu Ser Leu Gly Ser Arg Gly Ser Gly Ser Gly Gly Ser Gly Ser Asp
            420                 425                 430

Ser Glu Pro Asp Ser Pro Val Phe Glu Asp Ser Lys Ala Lys Pro Glu
        435                 440                 445

Gln Arg Pro Ser Leu His Ser Arg Gly Met Leu Asp Arg Ser Arg Leu
    450                 455                 460

Ala Leu Cys Thr Leu Val Phe Leu Cys Leu Ser Cys Asn Pro Leu Ala
465                 470                 475                 480

Ser Leu Leu Gly Ala Arg Gly Leu Pro Ser Pro Ser Asp Thr Thr Ser
                485                 490                 495

Val Tyr His Ser Pro Gly Arg Asn Val Leu Gly Thr Glu Ser Arg Asp
            500                 505                 510

Gly Pro Gly Trp Ala Gln Trp Leu Leu Pro Pro Val Val Trp Leu Leu
        515                 520                 525

Asn Gly Leu Leu Val Leu Val Ser Leu Val Leu Leu Phe Val Tyr Gly
    530                 535                 540

Glu Pro Val Thr Arg Pro His Ser Gly Pro Ala Val Tyr Phe Trp Arg
545                 550                 555                 560

His Arg Lys Gln Ala Asp Leu Asp Leu Ala Arg Gly Asp Phe Ala Gln
                565                 570                 575

Ala Ala Gln Gln Leu Trp Leu Ala Leu Arg Ala Leu Gly Arg Pro Leu
            580                 585                 590

Pro Thr Ser His Leu Asp Leu Ala Cys Ser Leu Leu Trp Asn Leu Ile
        595                 600                 605

Arg His Leu Leu Gln Arg Leu Trp Val Gly Arg Trp Leu Ala Gly Arg
    610                 615                 620

Ala Gly Gly Leu Gln Gln Asp Cys Ala Leu Arg Val Asp Ala Ser Ala
625                 630                 635                 640

Ser Ala Arg Asp Ala Ala Leu Val Tyr His Lys Leu His Gln Leu His
                645                 650                 655

Thr Met Gly Lys His Thr Gly Gly His Leu Thr Ala Thr Asn Leu Ala
            660                 665                 670

Leu Ser Ala Leu Asn Leu Ala Glu Cys Ala Gly Asp Ala Val Ser Val
        675                 680                 685

Ala Thr Leu Ala Glu Ile Tyr Val Ala Ala Ala Leu Arg Val Lys Thr
    690                 695                 700

Ser Leu Pro Arg Ala Leu His Phe Leu Thr Arg Phe Phe Leu Ser Ser
705                 710                 715                 720

Ala Arg Gln Ala Cys Leu Ala Gln Ser Gly Ser Val Pro Pro Ala Met
                725                 730                 735

Gln Trp Leu Cys His Pro Val Gly His Arg Phe Phe Val Asp Gly Asp
            740                 745                 750
```

```
Trp Ser Val Leu Ser Thr Pro Trp Glu Ser Leu Tyr Ser Leu Ala Gly
        755                 760                 765

Asn Pro Val Asp Pro Leu Ala Gln Val Thr Gln Leu Phe Arg Glu His
    770                 775                 780

Leu Leu Glu Arg Ala Leu Asn Cys Val Thr Gln Pro Asn Pro Ser Pro
785                 790                 795                 800

Gly Ser Ala Asp Gly Asp Lys Glu Phe Ser Asp Ala Leu Gly Tyr Leu
                805                 810                 815

Gln Leu Leu Asn Ser Cys Ser Asp Ala Ala Gly Ala Pro Ala Tyr Ser
            820                 825                 830

Phe Ser Ile Ser Ser Ser Met Ala Thr Thr Thr Gly Val Asp Pro Val
        835                 840                 845

Ala Lys Trp Trp Ala Ser Leu Thr Ala Val Val Ile His Trp Leu Arg
    850                 855                 860

Arg Asp Glu Glu Ala Ala Glu Arg Leu Cys Pro Leu Val Glu His Leu
865                 870                 875                 880

Pro Arg Val Leu Gln Glu Ser Glu Arg Pro Leu Pro Arg Ala Ala Leu
                885                 890                 895

His Ser Phe Lys Ala Ala Arg Ala Leu Leu Gly Cys Ala Lys Ala Glu
            900                 905                 910

Ser Gly Pro Ala Ser Leu Thr Ile Cys Glu Lys Ala Ser Gly Tyr Leu
        915                 920                 925

Gln Asp Ser Leu Ala Thr Thr Pro Ala Ser Ser Ser Ile Asp Lys Ala
    930                 935                 940

Val Gln Leu Phe Leu Cys Asp Leu Leu Leu Val Val Arg Thr Ser Leu
945                 950                 955                 960

Trp Arg Gln Gln Gln Pro Pro Ala Pro Ala Pro Ala Ala Gln Gly Thr
                965                 970                 975

Ser Ser Arg Pro Gln Ala Ser Ala Leu Glu Leu Arg Gly Phe Gln Arg
            980                 985                 990

Asp Leu Ser Ser Leu Arg Arg Leu  Ala Gln Ser Phe Arg  Pro Ala Met
        995                 1000                 1005

Arg Arg  Val Phe Leu His Glu  Ala Thr Ala Arg Leu  Met Ala Gly
    1010                 1015                 1020

Ala Ser  Pro Thr Arg Thr His  Gln Leu Leu Asp Arg  Ser Leu Arg
    1025                 1030                 1035

Arg Arg  Ala Gly Pro Gly Gly  Lys Gly Gly Ala Val  Ala Glu Leu
    1040                 1045                 1050

Glu Pro  Arg Pro Thr Arg Arg  Glu His Ala Glu Ala  Leu Leu Leu
    1055                 1060                 1065

Ala Ser  Cys Tyr Leu Pro Pro  Gly Phe Leu Ser Ala  Pro Gly Gln
    1070                 1075                 1080

Arg Val  Gly Met Leu Ala Glu  Ala Ala Arg Thr Leu  Glu Lys Leu
    1085                 1090                 1095

Gly Asp  Arg Arg Leu Leu His  Asp Cys Gln Gln Met  Leu Met Arg
    1100                 1105                 1110

Leu Gly  Gly Gly Thr Thr Val  Thr Ser Ser
    1115                 1120
```

<210> SEQ ID NO 21
<211> LENGTH: 23
<212> TYPE: DNA
<213> ORGANISM: artificial sequence
<220> FEATURE:
<223> OTHER INFORMATION: Guide RNA Recognition Sequence Near SREBF1

Variation

<400> SEQUENCE: 21
tctccgcatc tacgaccagt ggg 23

<210> SEQ ID NO 22
<211> LENGTH: 23
<212> TYPE: DNA
<213> ORGANISM: artificial sequence
<220> FEATURE:
<223> OTHER INFORMATION: Guide RNA Recognition Sequence Near SREBF1
Variation

<400> SEQUENCE: 22
ccagctgcga gccggttgat agg 23

<210> SEQ ID NO 23
<211> LENGTH: 23
<212> TYPE: DNA
<213> ORGANISM: artificial sequence
<220> FEATURE:
<223> OTHER INFORMATION: Guide RNA Recognition Sequence Near SREBF1
Variation

<400> SEQUENCE: 23
ttctccgcat ctacgaccag tgg 23

<210> SEQ ID NO 24
<211> LENGTH: 23
<212> TYPE: DNA
<213> ORGANISM: artificial sequence
<220> FEATURE:
<223> OTHER INFORMATION: Guide RNA Recognition Sequence Near SREBF1
Variation

<400> SEQUENCE: 24
agtcccactg gtcgtagatg cgg 23

<210> SEQ ID NO 25
<211> LENGTH: 23
<212> TYPE: DNA
<213> ORGANISM: artificial sequence
<220> FEATURE:
<223> OTHER INFORMATION: Guide RNA Recognition Sequence Near SREBF1
Variation

<400> SEQUENCE: 25
cctatcaacc ggctcgcagc tgg 23

<210> SEQ ID NO 26
<211> LENGTH: 23
<212> TYPE: DNA
<213> ORGANISM: artificial sequence
<220> FEATURE:
<223> OTHER INFORMATION: Guide RNA Recognition Sequence Near SREBF1
Variation

<400> SEQUENCE: 26
cggagaagct gcctatcaac cgg 23

<210> SEQ ID NO 27
<211> LENGTH: 23
<212> TYPE: DNA
<213> ORGANISM: artificial sequence
<220> FEATURE:
<223> OTHER INFORMATION: Guide RNA Recognition Sequence Near SREBF1
Variation

<400> SEQUENCE: 27
tgcgcttctc tccacggctc tgg 23

<210> SEQ ID NO 28
<211> LENGTH: 23
<212> TYPE: DNA
<213> ORGANISM: artificial sequence
<220> FEATURE:
<223> OTHER INFORMATION: Guide RNA Recognition Sequence Near SREBF1 Variation

<400> SEQUENCE: 28
gcgcttctct ccacggctct ggg 23

<210> SEQ ID NO 29
<211> LENGTH: 23
<212> TYPE: DNA
<213> ORGANISM: artificial sequence
<220> FEATURE:
<223> OTHER INFORMATION: Guide RNA Recognition Sequence Near SREBF1 Variation

<400> SEQUENCE: 29
aatcattgag ctcaaggatc tgg 23

<210> SEQ ID NO 30
<211> LENGTH: 23
<212> TYPE: DNA
<213> ORGANISM: artificial sequence
<220> FEATURE:
<223> OTHER INFORMATION: Guide RNA Recognition Sequence Near SREBF1 Variation

<400> SEQUENCE: 30
ccttgctgcc agctgcgagc cgg 23

<210> SEQ ID NO 31
<211> LENGTH: 23
<212> TYPE: DNA
<213> ORGANISM: artificial sequence
<220> FEATURE:
<223> OTHER INFORMATION: Guide RNA Recognition Sequence Near SREBF1 Variation

<400> SEQUENCE: 31
agaccggggt gtccctagga agg 23

<210> SEQ ID NO 32
<211> LENGTH: 23
<212> TYPE: DNA
<213> ORGANISM: artificial sequence
<220> FEATURE:
<223> OTHER INFORMATION: Guide RNA Recognition Sequence Near SREBF1 Variation

<400> SEQUENCE: 32
gttccttcct agggacaccc cgg 23

<210> SEQ ID NO 33
<211> LENGTH: 23
<212> TYPE: DNA
<213> ORGANISM: artificial sequence
<220> FEATURE:
<223> OTHER INFORMATION: Guide RNA Recognition Sequence Near SREBF1 Variation

<400> SEQUENCE: 33
gcacagaccg gggtgtccct agg 23

<210> SEQ ID NO 34
<211> LENGTH: 23
<212> TYPE: DNA
<213> ORGANISM: artificial sequence
<220> FEATURE:
<223> OTHER INFORMATION: Guide RNA Recognition Sequence Near SREBF1
Variation

<400> SEQUENCE: 34
gagctcaagg atctggtggt ggg 23

<210> SEQ ID NO 35
<211> LENGTH: 23
<212> TYPE: DNA
<213> ORGANISM: artificial sequence
<220> FEATURE:
<223> OTHER INFORMATION: Guide RNA Recognition Sequence Near SREBF1
Variation

<400> SEQUENCE: 35
tccctaggaa ggaacagatc agg 23

<210> SEQ ID NO 36
<211> LENGTH: 23
<212> TYPE: DNA
<213> ORGANISM: artificial sequence
<220> FEATURE:
<223> OTHER INFORMATION: Guide RNA Recognition Sequence Near SREBF1
Variation

<400> SEQUENCE: 36
tgagctcaag gatctggtgg tgg 23

<210> SEQ ID NO 37
<211> LENGTH: 23
<212> TYPE: DNA
<213> ORGANISM: artificial sequence
<220> FEATURE:
<223> OTHER INFORMATION: Guide RNA Recognition Sequence Near SREBF1
Variation

<400> SEQUENCE: 37
accccggtct gtgcccctgc agg 23

<210> SEQ ID NO 38
<211> LENGTH: 23
<212> TYPE: DNA
<213> ORGANISM: artificial sequence
<220> FEATURE:
<223> OTHER INFORMATION: Guide RNA Recognition Sequence Near SREBF1
Variation

<400> SEQUENCE: 38
gcctgcaggg gcacagaccg ggg 23

<210> SEQ ID NO 39
<211> LENGTH: 23
<212> TYPE: DNA
<213> ORGANISM: artificial sequence
<220> FEATURE:
<223> OTHER INFORMATION: Guide RNA Recognition Sequence Near SREBF1
Variation

<400> SEQUENCE: 39

-continued

```
cattgagctc aaggatctgg tgg                                              23


<210> SEQ ID NO 40
<211> LENGTH: 23
<212> TYPE: DNA
<213> ORGANISM: artificial sequence
<220> FEATURE:
<223> OTHER INFORMATION: Guide RNA Recognition Sequence Near SREBF1
      Variation

<400> SEQUENCE: 40

ccggctcgca gctggcagca agg                                              23


<210> SEQ ID NO 41
<211> LENGTH: 23
<212> TYPE: DNA
<213> ORGANISM: artificial sequence
<220> FEATURE:
<223> OTHER INFORMATION: Guide RNA Recognition Sequence Near SREBF1
      Variation

<400> SEQUENCE: 41

ggagcggtag cacttctcaa tgg                                              23
```

TREATMENT OF INCREASED LIPID LEVELS WITH STEROL REGULATORY ELEMENT BINDING TRANSCRIPTION FACTOR 1 (SREBF1) INHIBITORS

REFERENCE TO SEQUENCE LISTING

This application includes a Sequence Listing submitted electronically as a text file named 18923802001SEQ, created on Mar. 7, 2020, with a size of 191 kilobytes. The Sequence Listing is incorporated herein by reference.

FIELD

The present disclosure relates generally to the treatment of subjects having increased lipid levels with Sterol Regulatory Element Binding Transcription Factor 1 (SREBF1) inhibitors, methods of identifying subjects having an increased risk of developing increased lipid levels, methods of detecting SREBF1 variant nucleic acid molecules and variant polypeptides, and SREBF1 variant nucleic acid molecules and SREBF1 variant polypeptides.

BACKGROUND

Lipid metabolism disorders are a well-known complication of obesity. Lipid metabolism disorders are often characterised by hyperinsulinaemia, elevated apolipoprotein B levels, high triglycerides concentration, high low-density lipoproteins (LDL) cholesterol concentration, and low high-density lipoproteins (HDL) cholesterol concentration.

Sterol Regulatory Element Binding Proteins (SREBPs) are transcriptional factors that control lipogenesis and lipid uptake. There are two SREBP genes in mammals, SREBP-1 and SREBP-2. The SREBP-1 gene transcribes two isoforms SREBP-1a and SREBP-1c encoded from different promoters, which regulate genes that control fatty acid synthesis. SREBP-2 regulates genes involved in cholesterol synthesis. The roles of SREBP-1 and SREBP-2, however, significantly overlap in the regulation of lipid metabolism. In normal tissues, SREBPs levels and activity are tightly controlled by endogenous sterol levels via negative feedback regulation. SREBPs are located in the endoplasmic reticulum (ER) membrane in association with SREBPs cleavage-activating protein (SCAP) in which they are retained by Insulin-induced gene (Insig) when cellular sterol levels are sufficient. Once sterol levels decrease, SCAP protein dissociates with Insig protein and escorts SREBPs to the Golgi, in which they are sequentially cleaved by site-1 and site-2 proteases (S1P and S2P) thereby releasing the N-terminus, which then enters into the nucleus to transcribe lipogenesis genes and low-density lipoprotein receptor (LDLR).

SUMMARY

The present disclosure also provides methods of treating a subject having increased total cholesterol, the method comprising administering an SREBF1 inhibitor to the subject.

The present disclosure also provides methods of treating a subject having increased low density lipoprotein (LDL), the method comprising administering an SREBF1 inhibitor to the subject.

The present disclosure also provides methods of treating a subject with a therapeutic agent that treats or inhibits an increased lipid level, wherein the subject is suffering from an increased lipid level, the method comprising the steps of determining whether the subject has an SREBF1 variant nucleic acid molecule encoding a human SREBF1 polypeptide by: obtaining or having obtained a biological sample from the subject; and performing or having performed a genotyping assay on the biological sample to determine if the subject has a genotype comprising the SREBF1 variant nucleic acid molecule; and when the subject is SREBF1 reference, then administering or continuing to administer to the subject the therapeutic agent that treats or inhibits the increased lipid level in a standard dosage amount, and administering to the subject an SREBF1 inhibitor; and when the subject is heterozygous for the SREBF1 variant, then administering or continuing to administer to the subject the therapeutic agent that treats or inhibits the increased lipid level in an amount that is the same as or lower than a standard dosage amount, and administering to the subject an SREBF1 inhibitor; wherein the presence of a genotype having the SREBF1 variant nucleic acid molecule encoding the human SREBF1 polypeptide indicates the subject has a reduced risk of developing the increased lipid level; wherein the increased lipid level is increased serum lipid level, increased total cholesterol, or increased LDL; and wherein the SREBF1 variant nucleic acid molecule is: i) a genomic nucleic acid molecule having a nucleotide sequence comprising a thymine at a position corresponding to position 17,922 according to SEQ ID NO:2, or the complement thereof, ii) an mRNA molecule having a nucleotide sequence comprising a uracil at a position corresponding to position 1,185 according to SEQ ID NO:6, or the complement thereof, iii) an mRNA molecule having a nucleotide sequence comprising a uracil at a position corresponding to position 1,260 according to SEQ ID NO:7, or the complement thereof, iv) an mRNA molecule having a nucleotide sequence comprising a uracil at a position corresponding to position 1,056 according to SEQ ID NO:8, or the complement thereof, v) a cDNA molecule produced from an mRNA molecule in the sample, wherein the cDNA molecule has a nucleotide sequence comprising a thymine at a position corresponding to position 1,185 according to SEQ ID NO:12, or the complement thereof, vi) a cDNA molecule produced from an mRNA molecule in the sample, wherein the cDNA molecule has a nucleotide sequence comprising a thymine at a position corresponding to position 1,260 according to SEQ ID NO:13, or the complement thereof, and/or vii) a cDNA molecule produced from an mRNA molecule in the sample, wherein the cDNA molecule has a nucleotide sequence comprising a thymine at a position corresponding to position 1,056 according to SEQ ID NO:14, or the complement thereof.

The present disclosure also provides methods of identifying a human subject having an increased risk for developing an increased lipid level, wherein the method comprises determining or having determined the presence or absence of an SREBF1 variant nucleic acid molecule encoding a human SREBF1 polypeptide in a biological sample obtained from the subject; wherein: when the human subject is SREBF1 reference, then the human subject has an increased risk for developing the increased lipid level; and when the human subject is heterozygous for the SREBF1 variant nucleic acid molecule or homozygous for the variant nucleic acid molecule, then the human subject has a decreased risk for developing the increased lipid level; wherein the SREBF1 variant nucleic acid molecule is: i) a genomic nucleic acid molecule having a nucleotide sequence comprising a thymine at a position corresponding to position 17,922 according to SEQ ID NO:2, or the complement thereof, ii) an mRNA molecule having a nucleotide sequence comprising a uracil at a position corresponding to position 1,185 according to SEQ ID NO:6, or the complement thereof, iii) an mRNA molecule having a nucleotide sequence comprising a uracil at a position corresponding to position 1,260 according to SEQ ID NO:7, or the complement thereof, iv) an mRNA molecule having a nucleotide sequence comprising a uracil at a position corresponding to position 1,056 according to SEQ ID NO:8, or the complement thereof, v) a cDNA molecule produced from an mRNA molecule in the sample, wherein the cDNA molecule has a nucleotide sequence comprising a thymine at a position corresponding to position 1,185 according to SEQ ID NO:12, or the complement thereof, vi) a cDNA molecule produced from an mRNA molecule in the sample, wherein the cDNA molecule has a nucleotide sequence comprising a thymine at a position corresponding to position 1,260 according to SEQ ID NO:13, or the complement thereof, and/or vii) a cDNA molecule produced from an mRNA molecule in the sample, wherein the cDNA molecule has a nucleotide sequence comprising a thymine at a position corresponding to position 1,056 according to SEQ ID NO:14, or the complement thereof.

The present disclosure also provides methods of detecting a human SREBF1 variant nucleic acid molecule in a human subject comprising assaying a sample obtained from the human subject to determine whether a nucleic acid molecule in the sample comprises a nucleotide sequence comprising: i) a thymine at a position corresponding to position 17,922 according to SEQ ID NO:2, or the complement thereof; ii) a uracil at a position corresponding to position 1,185 according to SEQ ID NO:6, or the complement thereof; iii) a uracil at a position corresponding to position 1,260 according to SEQ ID NO:7, or the complement thereof; iv) a uracil at a position corresponding to position 1,056 according to SEQ ID NO:8, or the complement thereof; v) a thymine at a position corresponding to position 1,185 according to SEQ ID NO:12, or the complement thereof; vi) a thymine at a position corresponding to position 1,260 according to SEQ ID NO:13, or the complement thereof; and/or vii) a thymine at a position corresponding to position 1,056 according to SEQ ID NO:14, or the complement thereof.

The present disclosure also provides isolated alteration-specific probes or alteration-specific primers comprising at least about 15 nucleotides, wherein the alteration-specific probe or alteration-specific primer comprises a nucleotide sequence which is complementary to a portion of a nucleotide sequence encoding a human SREBF1 polypeptide, wherein the portion comprises a position corresponding to: i) position 17,922 according to SEQ ID NO:2, or the complement thereof; ii) position 1,185 according to SEQ ID NO:6, or the complement thereof; iii) position 1,260 according to SEQ ID NO:7, or the complement thereof; iv) position 1,056 according to SEQ ID NO:8, or the complement thereof; v) position 1,185 according to SEQ ID NO:12, or the complement thereof; vi) position 1,260 according to SEQ ID NO:13, or the complement thereof; or vii) position 1,056 according to SEQ ID NO:14, or the complement thereof.

The present disclosure also provides isolated nucleic acid molecules comprising a nucleotide sequence encoding a human SREBF1 polypeptide, wherein the polypeptide comprises: i) a cysteine at a position corresponding to position 334 according to SEQ ID NO:18, or the complement thereof; ii) a cysteine at a position corresponding to position 364 according to SEQ ID NO:19, or the complement thereof; or iii) a cysteine at a position corresponding to position 310 according to SEQ ID NO:20, or the complement thereof.

The present disclosure also provides isolated nucleic acid molecules comprising a nucleotide sequence encoding a human SREBF1 polypeptide, wherein the nucleotide sequence comprises a thymine at a position corresponding to position 17,922 according to SEQ ID NO:2, or the complement thereof.

The present disclosure also provides isolated mRNA molecules comprising a nucleotide sequence encoding a human SREBF1 polypeptide, wherein the nucleotide sequence comprises: i) a uracil at a position corresponding to position 1,185 according to SEQ ID NO:6, or the complement thereof; ii) a uracil at a position corresponding to position 1,260 according to SEQ ID NO:7, or the complement thereof; or iii) a uracil at a position corresponding to position 1,056 according to SEQ ID NO:8, or the complement thereof.

The present disclosure also provides cDNA molecules comprising a nucleotide sequence encoding a human SREBF1 polypeptide, wherein the nucleotide sequence comprises: i) a thymine at a position corresponding to position 1,185 according to SEQ ID NO:12, or the complement thereof; ii) a thymine at a position corresponding to position 1,260 according to SEQ ID NO:13, or the complement thereof; or iii) a thymine at a position corresponding to position 1,056 according to SEQ ID NO:14, or the complement thereof.

The present disclosure also provides isolated SREBF1 polypeptides having: i) an amino acid sequence at least about 90% identical to SEQ ID NO:18, wherein the polypeptide comprises a cysteine at a position corresponding to position 334 according to SEQ ID NO:18; ii) an amino acid sequence at least about 90% identical to SEQ ID NO:19, wherein the polypeptide comprises a cysteine at a position corresponding to position 364 according to SEQ ID NO:19; or iii) an amino acid sequence at least about 90% identical to SEQ ID NO:20, wherein the polypeptide comprises a cysteine at a position corresponding to position 310 according to SEQ ID NO:20.

The present disclosure also provides molecular complexes comprising an alteration-specific primer or an alteration-specific probe hybridized to: i) a genomic nucleic acid molecule comprising a nucleotide sequence encoding a human SREBF1 polypeptide, wherein the alteration-specific primer or the alteration-specific probe is hybridized to a thymine at a position corresponding to position 17,922 according to SEQ ID NO:2, or the complement thereof; ii) an mRNA molecule comprising a nucleotide sequence encoding a human SREBF1 polypeptide, wherein the alteration-specific primer or the alteration-specific probe is hybridized to: a uracil at a position corresponding to position 1,185 according to SEQ ID NO:6, or the complement thereof; a uracil at a position corresponding to position 1,260 according to SEQ ID NO:7, or the complement thereof; or a uracil at a position corresponding to position 1,056 according to SEQ ID NO:8, or the complement thereof; or iii) a cDNA molecule comprising a nucleotide sequence encoding a human SREBF1 polypeptide, wherein the alteration-specific primer or the alteration-specific probe is hybridized to: a thymine at a position corresponding to position 1,185 according to SEQ ID NO:12, or the complement thereof; a thymine at a position corresponding to position 1,260 according to SEQ ID NO:13, or the complement thereof; or a thymine at a position corresponding to position 1,056 according to SEQ ID NO:14, or the complement thereof.

BRIEF DESCRIPTION OF THE DRAWINGS

The accompanying figures, which are incorporated in and constitute a part of this specification, illustrate several aspects and together with the description serve to explain the principles of the present disclosure.

The patent or application file contains at least one drawing executed in color. Copies of this patent or patent application publication with color drawing(s) will be provided by the Office upon request and payment of the necessary fee.

DESCRIPTION

Figure 1:
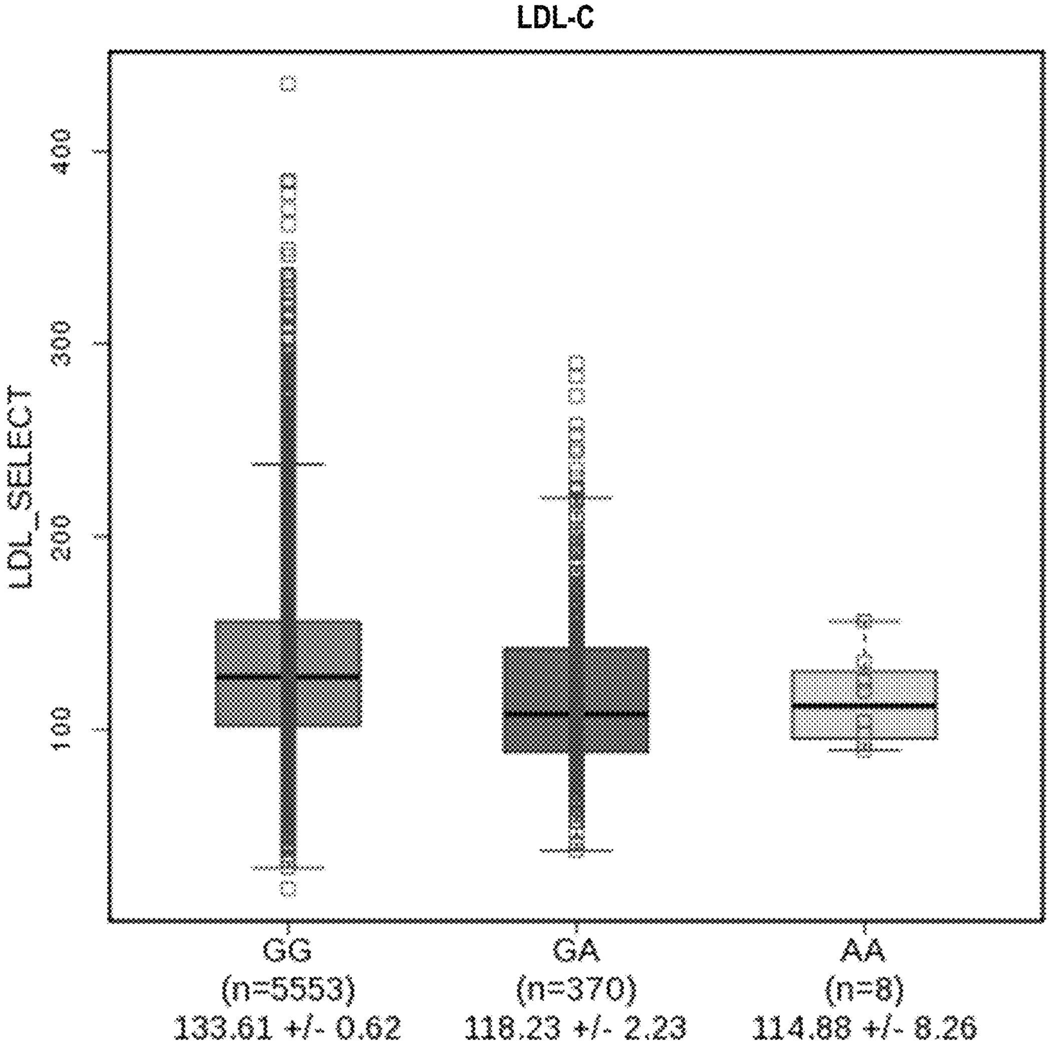
FIG. 1 (Panels A-C) shows an association of an SREBF1 missense variant with decreased low-density lipoprotein-cholesterol (LDL-C) (Panel A), decreased non-HDL cholesterol (Panel B), and decreased total cholesterol (Panel C).
Figure 1:
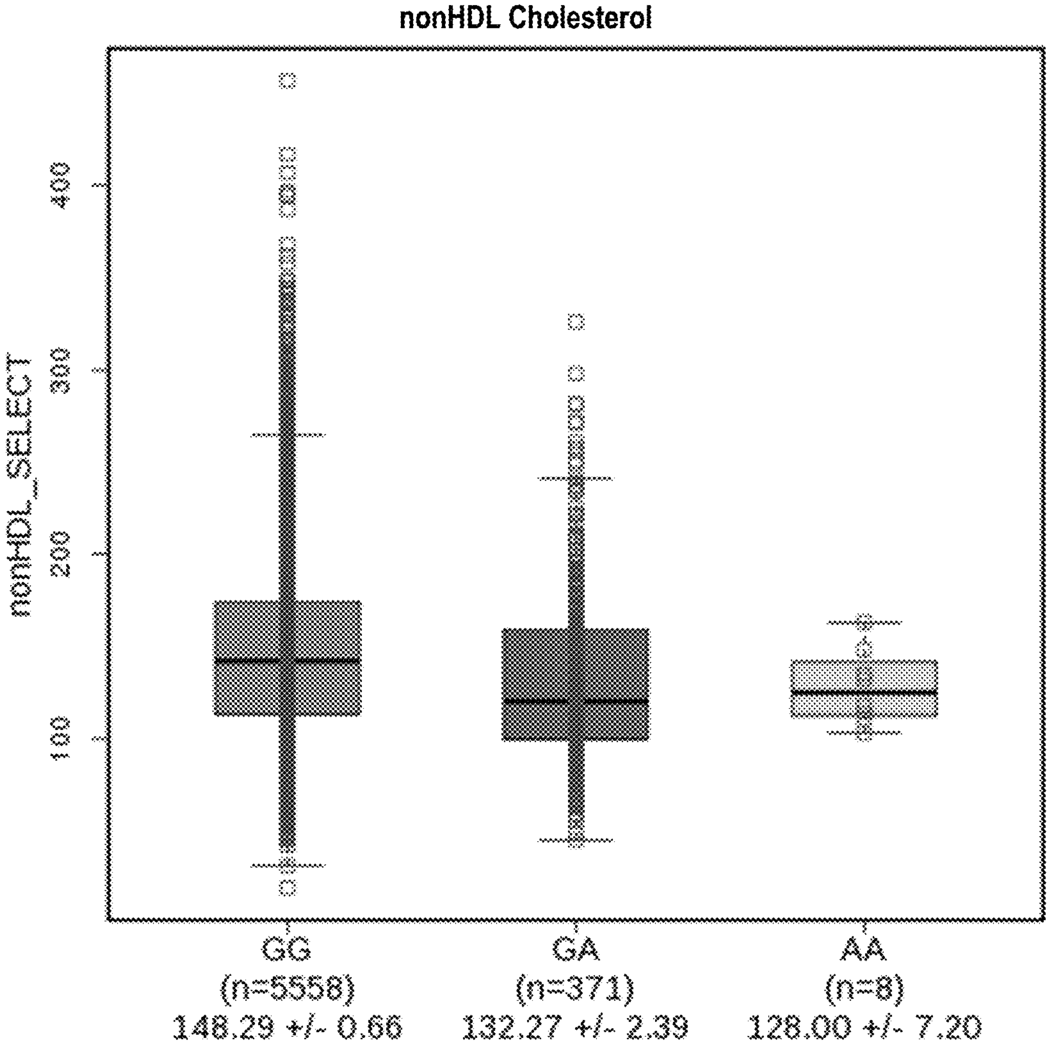
Figure 1:
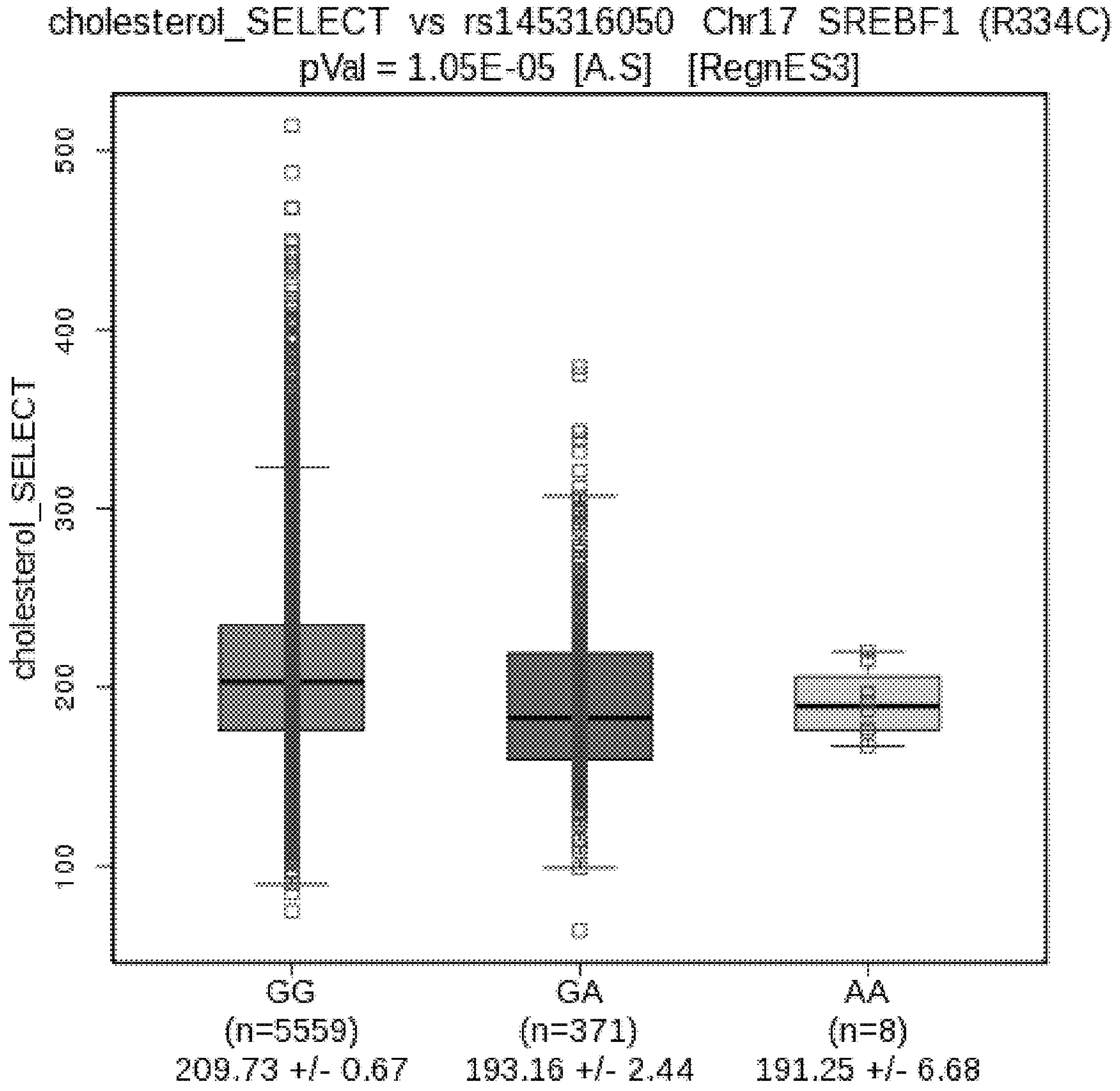

Various terms relating to aspects of the present disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the term "subject" includes any animal, including mammals. Mammals include, but are not limited to, farm animals (such as, for example, horse, cow, pig), companion animals (such as, for example, dog, cat), laboratory animals (such as, for example, mouse, rat, rabbits), and non-human primates. In some embodiments, the subject is a human.

As used herein, a "nucleic acid," a "nucleic acid molecule," a "nucleic acid sequence," a "polynucleotide," or an "oligonucleotide" can comprise a polymeric form of nucleotides of any length, can comprise DNA and/or RNA, and can be single-stranded, double-stranded, or multiple stranded. One strand of a nucleic acid also refers to its complement.

As used herein, the term "comprising" may be replaced with "consisting" or "consisting essentially of" in particular embodiments as desired.

An "isolated" nucleic acid molecule is a polynucleotide that is in a condition other than its native environment, such as apart from blood and animal tissue. In a preferred form, the isolated nucleic acid molecule is substantially free of other polynucleotides, particularly other polypeptides of animal origin. It is preferred to provide the nucleic acid molecule in a highly purified form, i.e., greater than 95% pure, more preferably greater than 99% pure. When used in this context, the term "isolated" does not exclude the presence of the same nucleic acid molecule in alternative physical forms, such as dimers or alternatively phosphorylated or derivatized forms.

It has been observed in accordance with the present disclosure that particular variations in SREBF1 associate with decreased low density lipoprotein (LDL) and decreased total cholesterol. It is believed that no variants of the SREBF1 gene or protein have any known association with decreased low density lipoprotein (LDL) and decreased total cholesterol.

A rare variant in the SREBF1 gene segregating with decreased LDL and decreased total cholesterol has been identified in accordance with the present disclosure. For example, a genetic alteration that changes the cytosine nucleotide of position 17,922 in the human wild type SREBF1 gene (SEQ ID NO:1) to thymine has been observed to indicate that the human having such an alteration may have decreased LDL and decreased total cholesterol. Altogether, the genetic analyses described herein surprisingly indicate that the SREBF1 gene and, in particular, a variant in the SREBF1 gene, associates with decreased LDL and decreased total cholesterol. Therefore, human subjects that are SREBF1 reference that have an increased risk of developing an increased lipid level may be treated such that the increased lipid level is inhibited, the symptoms thereof are reduced, and/or development of symptoms is repressed. Accordingly, the disclosure provides methods of leveraging the identification of such variants in subjects to identify or stratify risk in such subjects of developing increased lipid levels, such that subjects at risk or subjects with active disease may be treated accordingly. Additionally, the present disclosure provides isolated SREBF1 variant genomic nucleic acid molecules, variant mRNA molecule, and variant cDNA molecules. Accordingly, provided herein are SREBF1 variant nucleic acid molecules discovered to be associated with decreased LDL and decreased total cholesterol.

For purposes of the present disclosure, any particular human can be categorized as having one of three SREBF1 genotypes: i) SREBF1 reference; ii) heterozygous for an SREBF1 variant (such as a predicted loss-of-function variant), and iii) homozygous for an SREBF1 variant (such as a predicted loss-of-function variant). A human in the SREBF1 reference category does not have a copy of an SREBF1 variant nucleic acid molecule (such as a predicted loss-of-function variant nucleic acid molecule). A human who is heterozygous for an SREBF1 variant nucleic acid molecule (such as a predicted loss-of-function variant nucleic acid molecule) has a single copy of an SREBF1 variant nucleic acid molecule (such as a predicted loss-of-function variant nucleic acid molecule). A human who is homozygous for an SREBF1 variant nucleic acid molecule (such as a predicted loss-of-function variant nucleic acid molecule) has two copies of an SREBF1 variant nucleic acid molecule (such as a predicted loss-of-function variant nucleic acid molecule). An SREBF1 predicted loss-of-function variant nucleic acid molecule is any SREBF1 nucleic acid molecule (such as, a genomic nucleic acid molecule, an mRNA molecule, or a cDNA molecule) encoding an SREBF1 polypeptide having a partial loss-of-function, a complete loss-of-function, a predicted partial loss-of-function, or a predicted complete loss-of-function. A human who has an SREBF1 polypeptide having a partial loss-of-function (or predicted partial lossof-function) is hypomorphic for SREBF1. The SREBF1 variant nucleic acid molecule can be any nucleic acid molecule encoding SREBF1 Arg334Cys, Arg364Cys, or Arg310Cys. It is believed that the SREBF1 variant nucleic acid molecules described herein encoding SREBF1 Arg334Cys, Arg364Cys, or Arg310Cys are SREBF1 predicted loss-of-function variant nucleic acid molecules. In some embodiments, the SREBF1 variant nucleic acid molecule encodes SREBF1 Arg334Cys. In some embodiments, the SREBF1 variant nucleic acid molecule encodes SREBF1 Arg364Cys. In some embodiments, the SREBF1 variant nucleic acid molecule encodes SREBF1 Arg310Cys.

For human subjects that are genotyped or determined to be SREBF1 reference, such human subjects have an increased risk of developing an increased lipid level, such as increased serum lipid level, increased total cholesterol, and/or increased LDL. For human subjects that are genotyped or determined to be either SREBF1 reference or heterozygous for an SREBF1 variant nucleic acid molecule (such as a predicted loss-of-function variant), such human subjects can be treated with an SREBF1 inhibitor.

The present disclosure provides methods of treating a subject having increased serum lipid level, the methods comprising administering an SREBF1 inhibitor to the subject.

The present disclosure also provides methods of treating a subject having increased total cholesterol, the methods comprising administering an SREBF1 inhibitor to the subject.

The present disclosure also provides methods of treating a subject having increased LDL, the methods comprising administering an SREBF1 inhibitor to the subject.

In any of the embodiments described herein, the increased lipid level is increased serum lipid level, increased total cholesterol, or increased LDL. In some embodiments, the increased lipid level is increased serum lipid level. In some embodiments, the increased lipid level is increased total cholesterol. In some embodiments, the increased lipid level is increased serum cholesterol. In some embodiments, the increased lipid level is increased LDL.

In some embodiments, the SREBF1 inhibitor comprises an antisense molecule. Examples of antisense molecules include, but are not limited to, antisense nucleic acid molecules, small interfering RNAs (siRNAs), and short hairpin RNAs (shRNAs). Such antisense molecules can be designed to target any region of an SREBF1 mRNA. In some embodiments, the antisense RNA, siRNA, or shRNA hybridizes to a sequence within an SREBF1 genomic nucleic acid molecule or mRNA molecule and decreases expression of the SREBF1 polypeptide in a cell in the subject. In some embodiments, the SREBF1 inhibitor comprises an antisense RNA that hybridizes to an SREBF1 genomic nucleic acid molecule or mRNA molecule and decreases expression of the SREBF1 polypeptide in a cell in the subject. In some embodiments, the SREBF1 inhibitor comprises an siRNA that hybridizes to an SREBF1 genomic nucleic acid molecule or mRNA molecule and decreases expression of the SREBF1 polypeptide in a cell in the subject. In some embodiments, the SREBF1 inhibitor comprises an shRNA that hybridizes to an SREBF1 genomic nucleic acid molecule or mRNA molecule and decreases expression of the SREBF1 polypeptide in a cell in the subject.

In some embodiments, the SREBF1 inhibitor comprises a nuclease agent that induces one or more nicks or double-strand breaks at a recognition sequence(s) or a DNA-binding protein that binds to a recognition sequence within an SREBF1 genomic nucleic acid molecule. The recognition sequence can be located within a coding region of an SREBF1 gene, or within regulatory regions that influence the expression of the gene. A recognition sequence of the DNA-binding protein or nuclease agent can be located in an intron, an exon, a promoter, an enhancer, a regulatory region, or any non-protein coding region. The recognition sequence can include or be proximate to the start codon of an SREBF1 gene. For example, the recognition sequence can be located from about 10, 20, 30, 40, 50, 100, 200, 300, 400, 500, or 1,000 nucleotides of the start codon. As another example, two or more nuclease agents can be used, each targeting a nuclease recognition sequence including or proximate to the start codon. As another example, two nuclease agents can be used, one targeting a nuclease recognition sequence including or proximate to the start codon, and one targeting a nuclease recognition sequence including or proximate to the stop codon, wherein cleavage by the nuclease agents can result in deletion of the coding region between the two nuclease recognition sequences. Any nuclease agent that induces a nick or double-strand break into a desired recognition sequence can be used in the methods and compositions disclosed herein. Any DNA-binding protein that binds to a desired recognition sequence can be used in the methods and compositions disclosed herein.

Suitable nuclease agents and DNA-binding proteins for use herein include, but are not limited to, zinc finger protein or zinc finger nuclease (ZFN) pair, Transcription Activator-Like Effector (TALE) protein or Transcription Activator-Like Effector Nuclease (TALEN), or Clustered Regularly Interspersed Short Palindromic Repeats (CRISPR)/CRISPR-associated (Cas) systems. The length of the recognition sequence can vary, and includes, for example, recognition sequences that are about 30-36 bp for a zinc finger protein or ZFN pair (i.e., about 15-18 bp for each ZFN), about 36 bp for a TALE protein or TALEN, and about 20 bp for a CRISPR/Cas guide RNA.

In some embodiments, CRISPR/Cas systems can be used to modify an SREBF1 genomic nucleic acid molecule within a cell. The methods and compositions disclosed herein can employ CRISPR-Cas systems by utilizing CRISPR complexes (comprising a guide RNA (gRNA) complexed with a Cas protein) for site-directed cleavage of SREBF1 nucleic acid molecules.

Cas proteins generally comprise at least one RNA recognition or binding domain that can interact with gRNAs. Cas proteins can also comprise nuclease domains (such as, for example, DNase or RNase domains), DNA binding domains, helicase domains, protein-protein interaction domains, dimerization domains, and other domains. Suitable Cas proteins include, for example, a wild type Cas9 protein and a wild type Cpf1 protein (such as, for example, FnCpf1). A Cas protein can have full cleavage activity to create a double-strand break in an SREBF1 genomic nucleic acid molecule or it can be a nickase that creates a single-strand break in an SREBF1 genomic nucleic acid molecule. Additional examples of Cas proteins include, but are not limited to, Cas1, Cas1B, Cas2, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof. Cas proteins can also be operably linked to heterologous polypeptides as fusion proteins. For example, a Cas protein can be fused to a cleavage domain, an epigenetic modification domain, a transcriptional activation domain, or a transcriptional repressor domain. Cas proteins can be provided in any form. For example, a Cas protein can be provided in the form of a protein, such as a Cas protein complexed with a gRNA. Alternately, a Cas protein can be provided in the form of a nucleic acid molecule encoding the Cas protein, such as an RNA or DNA.

In some embodiments, targeted genetic modifications of SREBF1 genomic nucleic acid molecules can be generated by contacting a cell with a Cas protein and one or more gRNAs that hybridize to one or more gRNA recognition sequences that are located within a target genomic locus in the SREBF1 genomic nucleic acid molecule. For example, a gRNA recognition sequence can be within a region of SEQ ID NO:1. As another example, the gRNA recognition sequence can also include or be proximate to a position corresponding to position 17,922 according to SEQ ID NO:1. For example, the gRNA recognition sequence can be located from about 1000, 500, 400, 300, 200, 100, 50, 45, 40, 35, 30, 25, 20, 15, 10, or 5 nucleotides of a position corresponding to position 17,922 according to SEQ ID NO:1. As yet another example, a gRNA recognition sequence can include or be proximate to the start codon of an SREBF1 genomic nucleic acid molecule or the stop codon of an SREBF1 genomic nucleic acid molecule. For example, the gRNA recognition sequence can be located from about 10, 20, 30, 40, 50, 100, 200, 300, 400, 500, or 1,000 nucleotides of the start codon or the stop codon.

The gRNA recognition sequences that are located within a target genomic locus in an SREBF1 genomic nucleic acid molecule are located near a Protospacer Adjacent Motif (PAM) sequence, which is a 2-6 base pair DNA sequence immediately following the DNA sequence targeted by the Cas9 nuclease. The canonical PAM is the sequence 5'-NGG-3' where "N" is any nucleobase followed by two guanine ("G") nucleobases. gRNAs can transport Cas9 to anywhere in the genome for gene editing, but no editing can occur at any site other than one at which Cas9 recognizes PAM. In addition, 5'-NGA-3' can be a highly efficient non-canonical PAM for human cells. Generally, the PAM is about 2-6 nucleotides downstream of the DNA sequence targeted by the gRNA. The PAM can flank the gRNA recognition sequence. In some embodiments, the gRNA recognition sequence can be flanked on the 3' end by the PAM. In some embodiments, the gRNA recognition sequence can be flanked on the 5' end by the PAM. For example, the cleavage site of Cas proteins can be about 1 to about 10, about 2 to about 5 base pairs, or three base pairs upstream or downstream of the PAM sequence. In some embodiments (such as when Cas9 from *S. pyogenes* or a closely related Cas9 is used), the PAM sequence of the non-complementary strand can be 5'-NGG-3', where N is any DNA nucleotide and is immediately 3' of the gRNA recognition sequence of the non-complementary strand of the target DNA. As such, the PAM sequence of the complementary strand would be 5'-CCN-3', where N is any DNA nucleotide and is immediately 5' of the gRNA recognition sequence of the complementary strand of the target DNA.

A gRNA is an RNA molecule that binds to a Cas protein and targets the Cas protein to a specific location within an SREBF1 genomic nucleic acid molecule. One exemplary gRNA is a gRNA effective to direct a Cas enzyme to bind to or cleave an SREBF1 genomic nucleic acid molecule, wherein the gRNA comprises a DNA-targeting segment that hybridizes to a gRNA recognition sequence within the SREBF1 genomic nucleic acid molecule that includes or is proximate to a position corresponding to position 17,922 according to SEQ ID NO:1. For example, a gRNA can be selected such that it hybridizes to a gRNA recognition sequence that is located from about 5, 10, 15, 20, 25, 30, 35, 40, 45, 50, 100, 200, 300, 400, 500, or 1,000 nucleotides of a position corresponding to position 17,922 according to SEQ ID NO:1. Other exemplary gRNAs comprise a DNA-targeting segment that hybridizes to a gRNA recognition sequence within an SREBF1 genomic nucleic acid molecule that is within a region of SEQ ID NO:1. Other exemplary gRNAs comprise a DNA-targeting segment that hybridizes to a gRNA recognition sequence within an SREBF1 genomic nucleic acid molecule that includes or is proximate to the start codon or the stop codon. For example, a gRNA can be selected such that it hybridizes to a gRNA recognition sequence that is located from about 5, 10, 15, 20, 25, 30, 35, 40, 45, 50, 100, 200, 300, 400, 500, or 1,000 nucleotides of the start codon or located from about 5, 10, 15, 20, 25, 30, 35, 40, 45, 50, 100, 200, 300, 400, 500, or 1,000 nucleotides of the start codon or stop codon. The design and synthesis of gRNAs are described in, for example, Mali et al., Science, 2013, 339, 823-826; Jinek et al., Science, 2012, 337, 816-821; Hwang et al., Nat. Biotechnol., 2013, 31, 227-229; Jiang et al., Nat. Biotechnol., 2013, 31, 233-239; and Cong et al., Science, 2013, 339, 819-823. Suitable gRNAs can comprise from about 17 to about 23 nucleotides, from about 18 to about 22 nucleotides, or from about 19 to about 21 nucleotides. In some embodiments, the gRNAs can comprise 20 nucleotides.

Examples of suitable gRNA recognition sequences located within the human wild type SREBF1 gene are set forth in SEQ ID NOS: 21-41.

Guide RNA Recognition Sequences Near SREBF1 Variation

| Strand | Sequence | SEQ ID NO: |
|---|---|---|
| - | TCTCCGCATCTACGACCAGTGGG | 21 |
| - | CCAGCTGCGAGCCGGTTGATAGG | 22 |
| - | TTCTCCGCATCTACGACCAGTGG | 23 |
| + | AGTCCCACTGGTCGTAGATGCGG | 24 |
| + | CCTATCAACCGGCTCGCAGCTGG | 25 |
| + | CGGAGAAGCTGCCTATCAACCGG | 26 |
| - | TGCGCTTCTCTCCACGGCTCTGG | 27 |
| - | GCGCTTCTCTCCACGGCTCTGGG | 28 |
| + | AATCATTGAGCTCAAGGATCTGG | 29 |
| - | CCTTGCTGCCAGCTGCGAGCCGG | 30 |
| + | AGACCGGGGTGTCCCTAGGAAGG | 31 |
| - | GTTCCTTCCTAGGGACACCCCGG | 32 |
| + | GCACAGACCGGGGTGTCCCTAGG | 33 |
| + | GAGCTCAAGGATCTGGTGGTGGG | 34 |
| + | TCCCTAGGAAGGAACAGATCAGG | 35 |
| + | TGAGCTCAAGGATCTGGTGGTGG | 36 |
| - | ACCCCGGTCTGTGCCCCTGCAGG | 37 |

-continued

| Strand | Sequence | SEQ ID NO: |
|---|---|---|
| + | GCCTGCAGGGGCACAGACCGGGG | 38 |
| + | CATTGAGCTCAAGGATCTGGTGG | 39 |
| + | CCGGCTCGCAGCTGGCAGCAAGG | 40 |
| - | GGAGCGGTAGCACTTCTCAATGG | 41 |

The Cas protein and the gRNA form a complex, and the Cas protein cleaves the target SREBF1 genomic nucleic acid molecule. The Cas protein can cleave the nucleic acid molecule at a site within or outside of the nucleic acid sequence present in the target SREBF1 genomic nucleic acid molecule to which the DNA-targeting segment of a gRNA will bind. For example, formation of a CRISPR complex (comprising a gRNA hybridized to a gRNA recognition sequence and complexed with a Cas protein) can result in cleavage of one or both strands in or near (such as, for example, within 1, 2, 3, 4, 5, 6, 7, 8, 9, 10, 20, 50, or more base pairs from) the nucleic acid sequence present in the SREBF1 genomic nucleic acid molecule to which a DNA-targeting segment of a gRNA will bind.

Such methods can result, for example, in an SREBF1 genomic nucleic acid molecule in which a region of SEQ ID NO:1 is disrupted, the start codon is disrupted, the stop codon is disrupted, or the coding sequence is deleted. Optionally, the cell can be further contacted with one or more additional gRNAs that hybridize to additional gRNA recognition sequences within the target genomic locus in the SREBF1 genomic nucleic acid molecule. By contacting the cell with one or more additional gRNAs (such as, for example, a second gRNA that hybridizes to a second gRNA recognition sequence), cleavage by the Cas protein can create two or more double-strand breaks or two or more single-strand breaks.

In some embodiments, the SREBF1 inhibitor comprises a small molecule. In some embodiments, the SREBF1 inhibitor is Fatostatin A or PF-429242.

In some embodiments, the methods further comprise detecting the presence or absence of an SREBF1 predicted loss-of-function variant nucleic acid molecule encoding a human SREBF1 polypeptide in a biological sample from the subject. In some embodiments, the methods further comprise detecting the presence or absence of an SREBF1 predicted loss-of-function variant polypeptide in a biological sample from the subject. As used throughout the present disclosure an "SREBF1 predicted loss-of-function variant nucleic acid molecule" is any SREBF1 nucleic acid molecule (such as, for example, genomic nucleic acid molecule, mRNA molecule, or cDNA molecule) encoding an SREBF1 polypeptide having a partial loss-of-function, a complete loss-of-function, a predicted partial loss-of-function, or a predicted complete loss-of-function. For example, the SREBF1 predicted loss-of-function variant nucleic acid molecule can be any nucleic acid molecule encoding SREBF1 Arg334Cys, Arg364Cys, or Arg310Cys. In some embodiments, the SREBF1 predicted loss-of-function variant nucleic acid molecule encodes SREBF1 Arg334Cys. In some embodiments, the SREBF1 predicted loss-of-function variant nucleic acid molecule encodes SREBF1 Arg364Cys. In some embodiments, the SREBF1 predicted loss-of-function variant nucleic acid molecule encodes SREBF1 Arg310Cys.

In some embodiments, the SREBF1 predicted loss-of-function variant nucleic acid molecule is: i) a genomic nucleic acid molecule having a nucleotide sequence comprising a thymine at a position corresponding to position 17,922 according to SEQ ID NO:2; ii) an mRNA molecule having a nucleotide sequence comprising a uracil at a position corresponding to position 1,185 according to SEQ ID NO:6; iii) an mRNA molecule having a nucleotide sequence comprising a uracil at a position corresponding to position 1,260 according to SEQ ID NO:7; iv) an mRNA molecule having a nucleotide sequence comprising a uracil at a position corresponding to position 1,056 according to SEQ ID NO:8; v) a cDNA molecule produced from an mRNA molecule, wherein the cDNA molecule has a nucleotide sequence comprising a thymine at a position corresponding to position 1,185 according to SEQ ID NO:12; vi) a cDNA molecule produced from an mRNA molecule, wherein the cDNA molecule has a nucleotide sequence comprising a thymine at a position corresponding to position 1,260 according to SEQ ID NO:13; or vii) a cDNA molecule produced from an mRNA molecule, wherein the cDNA molecule has a nucleotide sequence comprising a thymine at a position corresponding to position 1,056 according to SEQ ID NO:14.

In some embodiments, when the subject is SREBF reference, the subject is also administered a therapeutic agent that treats or inhibits an increased lipid level in a standard dosage amount. In some embodiments, when the subject is heterozygous for an SREBF predicted loss-of-function variant, the subject is also administered a therapeutic agent that treats or inhibits an increased lipid level in a dosage amount that is the same as or lower than the standard dosage amount.

The present disclosure also provides methods of treating a subject with a therapeutic agent that treats or inhibits an increased lipid level, wherein the subject is suffering from an increased lipid level, the method comprising the steps of: determining whether the subject has an SREBF1 predicted loss-of-function variant nucleic acid molecule encoding a human SREBF1 polypeptide by: obtaining or having obtained a biological sample from the subject; and performing or having performed a genotyping assay on the biological sample to determine if the subject has a genotype comprising the SREBF1 predicted loss-of-function variant nucleic acid molecule; and when the subject is SREBF1 reference, then: i) administering or continuing to administer to the subject the therapeutic agent that treats or inhibits the increased lipid level in a standard dosage amount, and administering to the subject an SREBF1 inhibitor; and when the subject is heterozygous for an SREBF1 predicted loss-of-function variant, then: i) administering or continuing to administer to the subject the therapeutic agent that treats or inhibits the increased lipid level in an amount that is the same as or lower than a standard dosage amount, and administering to the subject an SREBF1 inhibitor; wherein the presence of a genotype having the SREBF1 predicted loss-of-function variant nucleic acid molecule encoding the human SREBF1 polypeptide indicates the subject has a reduced risk of developing the increased lipid level. In some embodiments, the subject is SREBF1 reference. In some embodiments, the subject is heterozygous for an SREBF1 predicted loss-of-function variant.

The SREBF1 predicted loss-of-function variant nucleic acid molecule can be any SREBF1 nucleic acid molecule (such as, for example, genomic nucleic acid molecule, mRNA molecule, or cDNA molecule) encoding an SREBF1 polypeptide having a partial loss-of-function, a complete loss-of-function, a predicted partial loss-of-function, or a predicted complete loss-of-function. For example, the SREBF1 predicted loss-of-function variant nucleic acid molecule can be any nucleic acid molecule encoding SREBF1 Arg334Cys, Arg364Cys, or Arg310Cys.

In some embodiments, the SREBF1 predicted loss-of-function variant nucleic acid molecule is: i) a genomic nucleic acid molecule having a nucleotide sequence comprising a thymine at a position corresponding to position 17,922 according to SEQ ID NO:2; ii) an mRNA molecule having a nucleotide sequence comprising a uracil at a position corresponding to position 1,185 according to SEQ ID NO:6; iii) an mRNA molecule having a nucleotide sequence comprising a uracil at a position corresponding to position 1,260 according to SEQ ID NO:7; iv) an mRNA molecule having a nucleotide sequence comprising a uracil at a position corresponding to position 1,056 according to SEQ ID NO:8; v) a cDNA molecule produced from an mRNA molecule, wherein the cDNA molecule has a nucleotide sequence comprising a thymine at a position corresponding to position 1,185 according to SEQ ID NO:12; vi) a cDNA molecule produced from an mRNA molecule, wherein the cDNA molecule has a nucleotide sequence comprising a thymine at a position corresponding to position 1,260 according to SEQ ID NO:13; and/or vii) a cDNA molecule produced from an mRNA molecule, wherein the cDNA molecule has a nucleotide sequence comprising a thymine at a position corresponding to position 1,056 according to SEQ ID NO:14.

Detecting the presence or absence of an SREBF1 predicted loss-of-function variant nucleic acid molecule (such as, for example, a nucleic acid molecule encoding SREBF1 Arg334Cys, Arg364Cys, or Arg310Cys) in a biological sample from a subject and/or determining whether a subject has an SREBF1 predicted loss-of-function variant nucleic acid molecule (such as, for example, a nucleic acid molecule encoding SREBF1 Arg334Cys, Arg364Cys, or Arg310Cys) can be carried out by any of the methods described herein. In some embodiments, these methods can be carried out in vitro. In some embodiments, these methods can be carried out in situ. In some embodiments, these methods can be carried out in vivo.

In some embodiments, the detection step, detecting step, or genotyping assay comprises sequencing at least a portion of the nucleotide sequence of the SREBF1 genomic nucleic acid molecule, the SREBF1 mRNA molecule, or the SREBF1 cDNA molecule in the biological sample, wherein the sequenced portion comprises variation(s) that cause a loss-of-function or are predicted to cause a loss-of-function. For example, in some embodiments, the detection step, detecting step, or genotyping assay comprises sequencing at least a portion of: i) the nucleotide sequence of the genomic nucleic acid molecule encoding the SREBF1 polypeptide, wherein the sequenced portion comprises a position corresponding to position 17,922 according to SEQ ID NO:2, or the complement thereof; ii) the nucleotide sequence of the mRNA molecule encoding the SREBF1 polypeptide, wherein the sequenced portion comprises a position corresponding to position 1,185 according to SEQ ID NO:6, or the complement thereof; iii) the nucleotide sequence of the mRNA molecule encoding the SREBF1 polypeptide, wherein the sequenced portion comprises a position corresponding to position 1,260 according to SEQ ID NO:7, or the complement thereof; iv) the nucleotide sequence of the mRNA molecule encoding the SREBF1 polypeptide, wherein the sequenced portion comprises a position corresponding to position 1,056 according to SEQ ID NO:8, or the complement thereof; v) the nucleotide sequence of the cDNA molecule encoding the SREBF1 polypeptide, wherein the sequenced portion comprises a position corresponding to position 1,185 according to SEQ ID NO:12, or the complement thereof; vi) the nucleotide sequence of the cDNA molecule encoding the SREBF1 polypeptide, wherein the sequenced portion comprises a position corresponding to position 1,260 according to SEQ ID NO:13, or the complement thereof; and/or vii) the nucleotide sequence of the cDNA molecule encoding the SREBF1 polypeptide, wherein the sequenced portion comprises a position corresponding to position 1,056 according to SEQ ID NO:14, or the complement thereof. When the sequenced portion of the SREBF1 genomic nucleic acid molecule in the biological sample comprises: a thymine at a position corresponding to position 17,922 according to SEQ ID NO:2; a uracil at a position corresponding to position 1,185 according to SEQ ID NO:6; a uracil at a position corresponding to position 1,260 according to SEQ ID NO:7; a uracil at a position corresponding to position 1,056 according to SEQ ID NO:8; a thymine at a position corresponding to position 1,185 according to SEQ ID NO:12; a thymine at a position corresponding to position 1,260 according to SEQ ID NO:13; or a thymine at a position corresponding to position 1,056 according to SEQ ID NO:14, then the SREBF1 cDNA molecule in the biological sample is an SREBF1 predicted loss-of-function variant cDNA molecule.

In some embodiments, the detection step, detecting step, or genotyping assay comprises: a) contacting the biological sample with a primer hybridizing to: i) a portion of the nucleotide sequence of the SREBF1 genomic nucleic acid molecule that is proximate to a position corresponding to position 17,922 according to SEQ ID NO:2; ii) a portion of the nucleotide sequence of the SREBF1 mRNA molecule that is proximate to a position corresponding to position 1,185 according to SEQ ID NO:6; iii) a portion of the nucleotide sequence of the SREBF1 mRNA molecule that is proximate to a position corresponding to position 1,260 according to SEQ ID NO:7; iv) a portion of the nucleotide sequence of the SREBF1 mRNA molecule that is proximate to a position corresponding to position 1,056 according to SEQ ID NO:8; v) a portion of the nucleotide sequence of the SREBF1 cDNA molecule that is proximate to a position corresponding to position 1,185 according to SEQ ID NO:12; vi) a portion of the nucleotide sequence of the SREBF1 cDNA molecule that is proximate to a position corresponding to position 1,260 according to SEQ ID NO:13; and/or vii) a portion of the nucleotide sequence of the SREBF1 cDNA molecule that is proximate to a position corresponding to position 1,056 according to SEQ ID NO:14; b) extending the primer at least through: i) the position of the nucleotide sequence of the SREBF1 genomic nucleic acid molecule corresponding to position 17,922 according to SEQ ID NO:2; ii) the position of the nucleotide sequence of the SREBF1 mRNA molecule corresponding to position 1,185 according to SEQ ID NO:6; iii) the position of the nucleotide sequence of the SREBF1 mRNA molecule corresponding to position 1,260 according to SEQ ID NO:7; iv) the position of the nucleotide sequence of the SREBF1 mRNA molecule corresponding to position 1,056 according to SEQ ID NO:8; v) the position of the nucleotide sequence of the SREBF1 cDNA molecule corresponding to position 1,185 according to SEQ ID NO:12; vi) the position of the nucleotide sequence of the SREBF1 cDNA molecule corresponding to position 1,260 according to SEQ ID NO:13; and/or vii) the position of the nucleotide sequence of the SREBF1 cDNA molecule corresponding to position 1,056 according to SEQ ID NO:14; and c) determining whether the extension product of the primer comprises: i) a thymine at a position corresponding to position 17,922 according to SEQ ID NO:2; ii) a uracil at a position corresponding to position 1,185 according to SEQ ID NO:6; iii) a uracil at a position corresponding to position 1,260 according to SEQ ID NO:7; iv) a uracil at a position corresponding to position 1,056 according to SEQ ID NO:8; v) a thymine at a position corresponding to position 1,185 according to SEQ ID NO:12; vi) a thymine at a position corresponding to position 1,260 according to SEQ ID NO:13; and/or vii) a thymine at a position corresponding to position 1,056 according to SEQ ID NO:14. In some embodiments, the determining step comprises sequencing the entire nucleic acid molecule.

In some embodiments, the detection step, detecting step, or genotyping assay comprises: a) amplifying at least a portion of the nucleic acid molecule that encodes the human SREBF1 polypeptide, wherein the portion comprises: i) a thymine at a position corresponding to position 17,922 according to SEQ ID NO:2, or the complement thereof; ii) a uracil at a position corresponding to position 1,185 according to SEQ ID NO:6, or the complement thereof; iii) a uracil at a position corresponding to position 1,260 according to SEQ ID NO:7, or the complement thereof; iv) a uracil at a position corresponding to position 1,056 according to SEQ ID NO:8, or the complement thereof; v) a thymine at a position corresponding to position 1,185 according to SEQ ID NO:12, or the complement thereof; vi) a thymine at a position corresponding to position 1,260 according to SEQ ID NO:13, or the complement thereof; and/or vii) a thymine at a position corresponding to position 1,056 according to SEQ ID NO:14, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to: i) the nucleotide sequence of the amplified nucleic acid molecule comprising a thymine at a position corresponding to position 17,922 according to SEQ ID NO:2, or the complement thereof; ii) the nucleotide sequence of the amplified nucleic acid molecule comprising a uracil at a position corresponding to position 1,185 according to SEQ ID NO:6, or the complement thereof; iii) the nucleotide sequence of the amplified nucleic acid molecule comprising a uracil at a position corresponding to position 1,260 according to SEQ ID NO:7, or the complement thereof; iv) the nucleotide sequence of the amplified nucleic acid molecule comprising a uracil at a position corresponding to position 1,056 according to SEQ ID NO:8, or the complement thereof; v) the nucleotide sequence of the amplified nucleic acid molecule comprising a thymine at a position corresponding to position 1,185 according to SEQ ID NO:12, or the complement thereof; vi) the nucleotide sequence of the amplified nucleic acid molecule comprising a thymine at a position corresponding to position 1,260 according to SEQ ID NO:13, or the complement thereof; and/or vii) the nucleotide sequence of the amplified nucleic acid molecule comprising a thymine at a position corresponding to position 1,056 according to SEQ ID NO:14, or the complement thereof; and d) detecting the detectable label. In some embodiments, the nucleic acid molecule is mRNA and the determining step further comprises reverse-transcribing the mRNA into a cDNA prior to the amplifying step.

In some embodiments, the detection step, detecting step, or genotyping assay comprises: contacting the nucleic acid molecule in the biological sample with an alteration-specific probe comprising a detectable label, wherein the alteration-specific probe comprises a nucleotide sequence which hybridizes under stringent conditions to: i) the nucleotide sequence of the amplified nucleic acid molecule comprising a thymine at a position corresponding to position 17,922 according to SEQ ID NO:2, or the complement thereof; ii) the nucleotide sequence of the amplified nucleic acid molecule comprising a uracil at a position corresponding to position 1,185 according to SEQ ID NO:6, or the complement thereof; iii) the nucleotide sequence of the amplified nucleic acid molecule comprising a uracil at a position corresponding to position 1,260 according to SEQ ID NO:7, or the complement thereof; iv) the nucleotide sequence of the amplified nucleic acid molecule comprising a uracil at a position corresponding to position 1,056 according to SEQ ID NO:8, or the complement thereof; v) the nucleotide sequence of the amplified nucleic acid molecule comprising a thymine at a position corresponding to position 1,185 according to SEQ ID NO:12, or the complement thereof; vi) the nucleotide sequence of the amplified nucleic acid molecule comprising a thymine at a position corresponding to position 1,260 according to SEQ ID NO:13, or the complement thereof; and/or vii) the nucleotide sequence of the amplified nucleic acid molecule comprising a thymine at a position corresponding to position 1,056 according to SEQ ID NO:14, or the complement thereof; and detecting the detectable label.

In any of these embodiments, the nucleic acid molecule can be present within a cell obtained from the human subject.

In any of the embodiments described herein, the increased lipid level is increased serum lipid level, increased total cholesterol, or increased LDL. In some embodiments, the increased lipid level is increased serum lipid level. In some embodiments, the increased lipid level is increased total cholesterol. In some embodiments, the increased lipid level is increased serum cholesterol. In some embodiments, the increased lipid level is increased LDL.

In some embodiments, increased lipid levels include hyperlipidemia, such as hypercholesterolemia (elevated cholesterol). Increased lipid levels also include hyperlipoproteinemia, which refers to the presence of elevated lipoproteins (usually LDL).

For human subjects that are genotyped or determined to be either SREBF1 reference or heterozygous for an SREBF1 predicted loss-of-function variant, such human subjects can be treated with an SREBF1 inhibitor, as described herein.

Examples of therapeutic agents that treat or inhibit an increased lipid level include, but are not limited to: a spirocyclic azetidinone derivative, a statin, a PPAR agonist, nicotinic acid, niacin, ezetimibe, a PCSK9 inhibitor, an RXR agonist, a hormone, a sulfonylurea-based drug, a biguanide, an α-glucosidase inhibitor, a GLP-1 agonist, and a PPARα/δ dual agonist, or any combination thereof.

Spirocyclic azetidinone derivatives include, but are not limited to those disclosed in, for example, U.S. Pat. No. RE 37,721; U.S. Pat. Nos. 5,631,356; 5,767,115; 5,846,966; 5,698,548; 5,633,246; 5,656,624; 5,624,920; 5,688,787; and 5,756,470; U.S. Publication No. 2002/0137689; and PCT Publication Nos. WO 02/066464, WO 95/08522, and WO96/19450.

Statins include, but are not limited to, atorvastatin, fluvastatin, lovastatin, pitavastatin, pravastatin, rosuvastatin, cerivastatin, and simvastatin.

PPAR agonists include, but are not limited to, a thiazolidinedione or a fibrate. Thiazolidinediones include, but are not limited to, 5-((4-(2-(methyl-2-pyridinylamino) ethoxy) phenyl)methyl)-2,4-thiazolidinedione, troglitazone, pioglitazone, ciglitazone, WAY-120,744, englitazone, AD 5075, darglitazone, and rosiglitazone. Fibrates include, but are not limited to, gemfibrozil, fenofibrate, clofibrate, and ciprofibrate.

RXR agonists include, but are not limited to, LG 100268, LGD 1069, 9-cis retinoic acid, 2-(1-(3,5,5,8,8-pentamethyl-5,6,7,8-tetrahydro-2-naphthyl)-cyclopropyl)-pyridine-5-carboxylic acid, and 4-((3,5,5,8,8-pentamethyl-5,6,7,8-tetrahydro-2-naphthyl)2-carbonyl)-benzoic acid.

Hormones include, but are not limited to, thyroid hormone, estrogen and insulin. Suitable insulins include, but are not limited, to injectable insulin, transdermal insulin, and inhaled insulin, or any combination thereof. As an alternative to insulin, an insulin derivative, secretagogue, sensitizer or mimetic may be used. Insulin secretagogues include, but are not limited to, forskolin, dibutryl cAMP, and isobutylmethylxanthine (IBMX).

Sulfonylurea-based drugs include, but are not limited to, glisoxepid, glyburide, acetohexamide, chlorpropamide, glibornuride, tolbutamide, tolazamide, glipizide, gliclazide, gliquidone, glyhexamide, phenbutamide, and tolcyclamide.

Biguanides include, but are not limited to, metformin, phenformin and buformin.

α-glucosidase inhibitors include, but are not limited to, acarbose and miglitol.

GLP-1 agonists include, but are not limited to, VICTOZA® and SAXENDA® (liraglutide), BYETTA® and BYDUREON® (exenatide), LYXUMIA® (lixisenatide), TANZEUM® (albiglutide), TRULICITY® (dulaglutide), and OZEMPIC® (semaglutide).

For human subjects that are genotyped or determined to be either SREBF1 reference or heterozygous for an SREBF1 predicted loss-of-function variant, such human subjects can also be treated with any one or more of the SREBF1 predicted loss-of-function polypeptides described herein.

In some embodiments, the dose of the therapeutic agents that treat or inhibit the increased lipid level can be reduced by about 10%, by about 20%, by about 30%, by about 40%, by about 50%, by about 60%, by about 70%, by about 80%, or by about 90% for subjects that are heterozygous for an SREBF1 predicted loss-of-function variant nucleic acid molecule (i.e., a lower than the standard dosage amount) compared to subjects that are SREBF1 reference (who may receive a standard dosage amount). In some embodiments, the dose of the therapeutic agents that treat or inhibit the increased lipid level can be reduced by about 10%, by about 20%, by about 30%, by about 40%, or by about 50%. In addition, the dose of therapeutic agents that treat or inhibit the increased lipid level in subjects that are heterozygous for an SREBF1 predicted loss-of-function variant nucleic acid molecule can be administered less frequently compared to subjects that are SREBF1 reference.

Administration of the therapeutic agents that treat or inhibit the increased lipid level and/or SREBF1 inhibitors can be repeated, for example, after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens a subject can receive therapy for a prolonged period of time such as, for example, 6 months, 1 year, or more.

Administration of the therapeutic agents that treat or inhibit the increased lipid level and/or SREBF1 inhibitors can occur by any suitable route including, but not limited to, parenteral, intravenous, oral, subcutaneous, intra-arterial, intracranial, intrathecal, intraperitoneal, topical, intranasal, or intramuscular. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

The terms "treat", "treating", and "treatment" and "prevent", "preventing", and "prevention" as used herein, refer to eliciting the desired biological response, such as a therapeutic and prophylactic effect, respectively. In some embodiments, a therapeutic effect comprises one or more of a decrease/reduction in an increased lipid level, a decrease/reduction in the severity of an increased lipid level (such as, for example, a reduction or inhibition of development or an increased lipid level), a decrease/reduction in symptoms and increased lipid level-related effects, delaying the onset of symptoms and increased lipid level-related effects, reducing the severity of symptoms of the increased lipid level-related effects, reducing the severity of an acute episode, reducing the number of symptoms and increased lipid level-related effects, reducing the latency of symptoms and increased lipid level-related effects, an amelioration of symptoms and increased lipid level-related effects, reducing secondary symptoms, reducing secondary infections, preventing relapse to an increased lipid level, decreasing the number or frequency of relapse episodes, increasing latency between symptomatic episodes, increasing time to sustained progression, expediting remission, inducing remission, augmenting remission, speeding recovery, or increasing efficacy of or decreasing resistance to alternative therapeutics, and/or an increased survival time of the affected host animal, following administration of the agent or composition comprising the agent. A prophylactic effect may comprise a complete or partial avoidance/inhibition or a delay of increased lipid level development/progression (such as, for example, a complete or partial avoidance/inhibition or a delay), and an increased survival time of the affected host animal, following administration of a therapeutic protocol. Treatment of an increased lipid level encompasses the treatment of subjects already diagnosed as having any form of the increased lipid level at any clinical stage or manifestation, the delay of the onset or evolution or aggravation or deterioration of the symptoms or signs of the increased lipid level, and/or preventing and/or reducing the severity of the increased lipid level.

In some embodiments, the methods comprise detecting the presence or absence of an SREBF1 polypeptide in a biological sample from the subject, wherein the SREBF1 polypeptide comprises: i) a cysteine at a position corresponding to position 334 according to SEQ ID NO:18; ii) a cysteine at a position corresponding to position 364 according to SEQ ID NO:19; or iii) a cysteine at a position corresponding to position 310 according to SEQ ID NO:20; wherein: when the human subject does not have the SREBF1 polypeptide, then the human subject has an increased risk for developing an increased lipid level; and when the human subject has the SREBF1 polypeptide, then the human subject has a decreased risk for developing an increased lipid level.

In some embodiments, the detecting step comprises sequencing at least a portion of the polypeptide that comprises: i) a position corresponding to position 334 according to SEQ ID NO:18; ii) a position corresponding to position 364 according to SEQ ID NO:19; or iii) a position corresponding to position 310 according to SEQ ID NO:20. In some embodiments, the detecting step comprises sequencing the entire polypeptide. In some embodiments, the detecting step comprises an immunoassay for detecting the presence of a polypeptide that comprises: i) a position corresponding to position 334 according to SEQ ID NO:18; ii) a position corresponding to position 364 according to SEQ ID NO:19; or iii) a position corresponding to position 310 according to SEQ ID NO:20.

The present disclosure also provides methods of identifying a human subject having an increased risk for developing an increased lipid level, wherein the method comprises any of the methods described herein for detecting the presence or absence of any of the SREBF1 predicted loss-of-function variant nucleic acid molecules (such as a genomic nucleic acid molecule, mRNA molecule, and/or cDNA molecule) described herein. Determining or having determined in a sample obtained from the subject the presence or absence of the particular nucleic acid molecules can be carried out by any of the methods described herein. When the human subject lacks an SREBF1 predicted loss-of-function variant nucleic acid molecule (i.e., the human subject is genotypically categorized as an SREBF1 reference), then the human subject has an increased risk for developing an increased lipid level. When the human subject has an SREBF1 predicted loss-of-function variant nucleic acid molecule (i.e., the human subject is categorized as heterozygous for an SREBF1 predicted loss-of-function variant or homozygous for an SREBF1 predicted loss-of-function variant), then the human subject has a decreased risk for developing an increased lipid level. Having a single copy of an SREBF1 predicted loss-of-function variant nucleic acid molecule is more protective of a human subject from developing an increased lipid level than having no copies of an SREBF1 predicted loss-of-function variant nucleic acid molecule.

Without intending to be limited to any particular theory or mechanism of action, it is believed that a single copy of an SREBF1 predicted loss-of-function variant nucleic acid molecule (i.e., heterozygous for an SREBF1 predicted loss-of-function variant) is protective of a human subject from developing an increased lipid level, and it is also believed that having two copies of an SREBF1 predicted loss-of-function variant nucleic acid molecule (i.e., homozygous for an SREBF1 predicted loss-of-function variant) may be more protective of a human subject from developing an increased lipid level, relative to a human subject with a single copy. Thus, in some embodiments, a single copy of an SREBF1 predicted loss-of-function variant nucleic acid molecule may not be completely protective, but instead, may be partially or incompletely protective of a human subject from developing an increased lipid level. While not desiring to be bound by any particular theory, there may be additional factors or molecules involved in the development of increased lipid level that are still present in a human subject having a single copy of an SREBF1 predicted loss-of-function variant nucleic acid molecule, thus resulting in less than complete protection from the development of increased lipid level.

The present disclosure also provides methods of identifying a human subject having an increased risk for developing an increased lipid level, wherein the method comprises: detecting the presence or absence of an SREBF1 predicted loss-of-function variant polypeptide in a biological sample from the subject, wherein the SREBF1 predicted loss-of-function variant polypeptide comprises: i) a cysteine at a position corresponding to position 334 according to SEQ ID NO:18; ii) a cysteine at a position corresponding to position 364 according to SEQ ID NO:19; or iii) a cysteine at a position corresponding to position 310 according to SEQ ID NO:20; wherein: when the human subject does not have an SREBF1 predicted loss-of-function variant polypeptide, then the human subject has an increased risk for developing an increased lipid level; and when the human subject has an SREBF1 predicted loss-of-function variant polypeptide, then the human subject has a decreased risk for developing an increased lipid level.

In some embodiments, the determining step comprises sequencing at least a portion of the polypeptide that comprises a position corresponding to position 334 according to SEQ ID NO:18. In some embodiments, the determining step comprises sequencing at least a portion of the polypeptide that comprises a position corresponding to position 364 according to SEQ ID NO:19. In some embodiments, the determining step comprises sequencing at least a portion of the polypeptide that comprises a position corresponding to position 310 according to SEQ ID NO:20. In some embodiments, the determining step comprises sequencing the entire polypeptide. In some embodiments, the determining step comprises an immunoassay.

In some embodiments, the human subject is further treated with a therapeutic agent that treats or inhibits the increased lipid level and/or an SREBF1 inhibitor, as described herein. For example, when the human subject is SREBF1 reference, and therefore has an increased risk for developing an increased lipid level, the human subject is administered a SREBF1 inhibitor. In some embodiments, such a subject is also administered a therapeutic agent that treats or inhibits the increased lipid level. In some embodiments, when the subject is heterozygous for an SREBF1 predicted loss-of-function variant, the subject is administered the therapeutic agent that treats or inhibits the increased lipid level in a dosage amount that is the same as or lower than the standard dosage amount, and is also administered a SREBF1 inhibitor. In some embodiments, the subject is SREBF1 reference. In some embodiments, the subject is heterozygous for an SREBF1 predicted loss-of-function variant.

The present disclosure also provides methods of detecting the presence of an SREBF1 predicted loss-of-function variant genomic nucleic acid molecule, an SREBF1 predicted loss-of-function variant mRNA molecule, and/or an SREBF1 predicted loss-of-function variant cDNA molecule in a biological sample from a subject human. It is understood that gene sequences within a population and mRNA molecules encoded by such genes can vary due to polymorphisms such as single-nucleotide polymorphisms. The sequences provided herein for the SREBF1 variant genomic nucleic acid molecule, SREBF1 variant mRNA molecule, and SREBF1 variant cDNA molecule are only exemplary sequences. Other sequences for the SREBF1 variant genomic nucleic acid molecule, variant mRNA molecule, and variant cDNA molecule are also possible.

The biological sample can be derived from any cell, tissue, or biological fluid from the subject. The sample may comprise any clinically relevant tissue, such as a bone marrow sample, a tumor biopsy, a fine needle aspirate, or a sample of bodily fluid, such as blood, gingival crevicular fluid, plasma, serum, lymph, ascitic fluid, cystic fluid, or urine. In some cases, the sample comprises a buccal swab. The sample used in the methods disclosed herein will vary based on the assay format, nature of the detection method, and the tissues, cells, or extracts that are used as the sample. A biological sample can be processed differently depending on the assay being employed. For example, when detecting any SREBF1 variant nucleic acid molecule, preliminary processing designed to isolate or enrich the sample for the genomic DNA can be employed. A variety of known techniques may be used for this purpose. When detecting the level of any SREBF1 variant mRNA, different techniques can be used enrich the biological sample with mRNA. Various methods to detect the presence or level of a mRNA or the presence of a particular variant genomic DNA locus can be used.

In some embodiments, the methods of detecting a human SREBF1 predicted loss-of-function variant nucleic acid molecule in a human subject comprise assaying a biological sample obtained from the human subject to determine whether an SREBF1 genomic nucleic acid molecule, an SREBF1 mRNA molecule, or an SREBF1 cDNA molecule in the biological sample comprises one or more variations that cause a loss-of-function (partial or complete) or are predicted to cause a loss-of-function (partial or complete). For example, in some embodiments, the methods of detecting a human SREBF1 predicted loss-of-function variant nucleic acid molecule in a human subject comprise assaying a biological sample obtained from the subject to determine whether an SREBF1 nucleic acid molecule in the biological sample comprises a nucleotide sequence comprising: i) a thymine at a position corresponding to position 17,922 according to SEQ ID NO:2, or the complement thereof, ii) a uracil at a position corresponding to position 1,185 according to SEQ ID NO:6, or the complement thereof, iii) a uracil at a position corresponding to position 1,260 according to SEQ ID NO:7, or the complement thereof, iv) a uracil at a position corresponding to position 1,056 according to SEQ ID NO:8, or the complement thereof, v) a thymine at a position corresponding to position 1,185 according to SEQ ID NO:12, or the complement thereof, vi) a thymine at a position corresponding to position 1,260 according to SEQ ID NO:13, or the complement thereof, or vii) a thymine at a position corresponding to position 1,056 according to SEQ ID NO:14, or the complement thereof. In some embodiments, the method is an in vitro method.

In some embodiments, the methods of detecting the presence or absence of an SREBF1 predicted loss-of-function variant nucleic acid molecule (such as, for example, a genomic nucleic acid molecule, an mRNA molecule, and/or a cDNA molecule) in a human subject, comprise: performing an assay on a biological sample obtained from the subject, which assay determines whether a nucleic acid molecule in the biological sample comprises a nucleotide sequence that encodes: i) a thymine at a position corresponding to position 17,922 according to SEQ ID NO:2; ii) a uracil at a position corresponding to position 1,185 according to SEQ ID NO:6; iii) a uracil at a position corresponding to position 1,260 according to SEQ ID NO:7; iv) a uracil at a position corresponding to position 1,056 according to SEQ ID NO:8; v) a thymine at a position corresponding to position 1,185 according to SEQ ID NO:12; vi) a thymine at a position corresponding to position 1,260 according to SEQ ID NO:13; or vii) a thymine at a position corresponding to position 1,056 according to SEQ ID NO:14. In some embodiments, the biological sample comprises a cell or cell lysate. Such methods can further comprise, for example, obtaining a biological sample from the subject comprising an SREBF1 genomic nucleic acid molecule or mRNA molecule, and if mRNA, optionally reverse transcribing the mRNA into cDNA, and performing an assay on the biological sample that determines that a position of the SREBF1 genomic nucleic acid molecule, mRNA, or cDNA encodes: i) a thymine at a position corresponding to position 17,922 according to SEQ ID NO:2; ii) a uracil at a position corresponding to position 1,185 according to SEQ ID NO:6; iii) a uracil at a position corresponding to position 1,260 according to SEQ ID NO:7; iv) a uracil at a position corresponding to position 1,056 according to SEQ ID NO:8; v) a thymine at a position corresponding to position 1,185 according to SEQ ID NO:12; vi) a thymine at a position corresponding to position 1,260 according to SEQ ID NO:13; or vii) a thymine at a position corresponding to position 1,056 according to SEQ ID NO:14. Such assays can comprise, for example determining the identity of these positions of the particular SREBF1 nucleic acid molecule. In some embodiments, the method is an in vitro method.

In some embodiments, the assay comprises sequencing at least a portion of the nucleotide sequence of the SREBF1 genomic nucleic acid molecule, the SREBF1 mRNA molecule, or the SREBF1 cDNA molecule in the biological sample, wherein the sequenced portion comprises one or more variations that cause a loss-of-function (partial or complete). For example, in some embodiments, the assay comprises sequencing at least a portion of: i) the nucleotide sequence of the SREBF1 genomic nucleic acid molecule in the biological sample, wherein the sequenced portion comprises a position corresponding to position 17,922 according to SEQ ID NO:2, or the complement thereof; ii) the nucleotide sequence of an SREBF1 mRNA molecule in the biological sample, wherein the sequenced portion comprises a position corresponding to position 1,185 according to SEQ ID NO:6, or the complement thereof; iii) the nucleotide sequence of an SREBF1 mRNA molecule in the biological sample, wherein the sequenced portion comprises a position corresponding to position 1,260 according to SEQ ID NO:7, or the complement thereof; iv) the nucleotide sequence of an SREBF1 mRNA molecule in the biological sample, wherein the sequenced portion comprises a position corresponding to position 1,056 according to SEQ ID NO:8, or the complement thereof; v) the nucleotide sequence of an SREBF1 cDNA molecule in the biological sample, wherein the sequenced portion comprises a position corresponding to position 1,185 according to SEQ ID NO:12, or the complement thereof; vi) the nucleotide sequence of an SREBF1 cDNA molecule in the biological sample, wherein the sequenced portion comprises a position corresponding to position 1,260 according to SEQ ID NO:13, or the complement thereof; and/or vii) the nucleotide sequence of an SREBF1 cDNA molecule in the biological sample, wherein the sequenced portion comprises a position corresponding to position 1,056 according to SEQ ID NO:14, or the complement thereof. When the sequenced portion of the SREBF1 genomic nucleic acid molecule in the biological sample comprises a thymine at a position corresponding to position 17,922 according to SEQ ID NO:2, then the SREBF1 genomic nucleic acid molecule in the biological sample is an SREBF1 predicted loss-of-function variant genomic nucleic acid molecule. When the sequenced portion of an SREBF1 mRNA molecule in the biological sample comprises a uracil at a position corresponding to position 1,185 according to SEQ ID NO:6, then the SREBF1 mRNA molecule in the biological sample is an SREBF1 predicted loss-of-function variant mRNA molecule. When the sequenced portion of an SREBF1 mRNA molecule in the biological sample comprises a uracil at a position corresponding to position 1,260 according to SEQ ID NO:7, then the SREBF1 mRNA molecule in the biological sample is an SREBF1 predicted loss-of-function variant mRNA molecule. When the sequenced portion of an SREBF1 mRNA molecule in the biological sample comprises a uracil at a position corresponding to position 1,056 according to SEQ ID NO:8, then the SREBF1 mRNA molecule in the biological sample is an SREBF1 predicted loss-of-function variant mRNA molecule. When the sequenced portion of an SREBF1 cDNA molecule in the biological sample comprises a thymine at a position corresponding to position 1,185 according to SEQ ID NO:12, then the SREBF1 cDNA molecule in the biological sample is an SREBF1 predicted loss-of-function variant cDNA molecule. When the sequenced portion of an SREBF1 cDNA molecule in the biological sample comprises a thymine at a position corresponding to position 1,260 according to SEQ ID NO:13, then the SREBF1 cDNA molecule in the biological sample is an SREBF1 predicted loss-of-function variant cDNA molecule. When the sequenced portion of an SREBF1 cDNA molecule in the biological sample comprises a thymine at a position corresponding to position 1,056 according to SEQ ID NO:14, then the SREBF1 cDNA molecule in the biological sample is an SREBF1 predicted loss-of-function variant cDNA molecule.

In some embodiments, the assay comprises: a) contacting the sample with a primer hybridizing to: i) a portion of the nucleotide sequence of SREBF1 genomic nucleic acid molecule that is proximate to a position corresponding to position 17,922 according to SEQ ID NO:2; ii) a portion of the nucleotide sequence of SREBF1 mRNA molecule that is proximate to a position corresponding to position 1,185 according to SEQ ID NO:6; iii) a portion of the nucleotide sequence of SREBF1 mRNA molecule that is proximate to a position corresponding to position 1,260 according to SEQ ID NO:7; iv) a portion of the nucleotide sequence of SREBF1 mRNA molecule that is proximate to a position corresponding to position 1,056 according to SEQ ID NO:8; v) a portion of the nucleotide sequence of SREBF1 cDNA molecule that is proximate to a position corresponding to position 1,185 according to SEQ ID NO:12; vi) a portion of the nucleotide sequence of SREBF1 cDNA molecule that is proximate to a position corresponding to position 1,260 according to SEQ ID NO:13; or vii) a portion of the nucleotide sequence of SREBF1 cDNA molecule that is proximate to a position corresponding to position 1,056 according to SEQ ID NO:14; b) extending the primer at least through: i) the position of the nucleotide sequence of SREBF1 genomic nucleic acid molecule corresponding to position 17,922 according to SEQ ID NO:2; ii) the position of the nucleotide sequence of SREBF1 mRNA molecule corresponding to position 1,185 according to SEQ ID NO:6; iii) the position of the nucleotide sequence of SREBF1 mRNA molecule corresponding to position 1,260 according to SEQ ID NO:7; iv) the position of the nucleotide sequence of SREBF1 mRNA molecule corresponding to position 1,056 according to SEQ ID NO:8; v) the position of the nucleotide sequence of SREBF1 cDNA molecule corresponding to position 1,185 according to SEQ ID NO:12; vi) the position of the nucleotide sequence of SREBF1 cDNA molecule corresponding to position 1,260 according to SEQ ID NO:13; or vii) the position of the nucleotide sequence of SREBF1 cDNA molecule corresponding to position 1,056 according to SEQ ID NO:14; and c) determining whether the extension product of the primer comprises: i) a thymine at a position corresponding to position 17,922 according to SEQ ID NO:2; ii) a uracil at a position corresponding to position 1,185 according to SEQ ID NO:6; iii) a uracil at a position corresponding to position 1,260 according to SEQ ID NO:7; iv) a uracil at a position corresponding to position 1,056 according to SEQ ID NO:8; v) a thymine at a position corresponding to position 1,185 according to SEQ ID NO:12; vi) a thymine at a position corresponding to position 1,260 according to SEQ ID NO:13; vii) a thymine at a position corresponding to position 1,056 according to SEQ ID NO:14. In some embodiments, the assay comprises sequencing the entire nucleic acid molecule. In some embodiments, only SREBF1 genomic nucleic acid molecule is analyzed. In some embodiments, only SREBF1 mRNA is analyzed. In some embodiments, only SREBF1 cDNA obtained from SREBF1 mRNA is analyzed.

In some embodiments, the assay comprises: a) amplifying at least a portion of the nucleic acid molecule that encodes the human SREBF1 polypeptide, wherein the portion comprises: i) a thymine at a position corresponding to position 17,922 according to SEQ ID NO:2, or the complement thereof; ii) a uracil at a position corresponding to position 1,185 according to SEQ ID NO:6, or the complement thereof; iii) a uracil at a position corresponding to position 1,260 according to SEQ ID NO:7, or the complement thereof; iv) a uracil at a position corresponding to position 1,056 according to SEQ ID NO:8, or the complement thereof; v) a thymine at a position corresponding to position 1,185 according to SEQ ID NO:12, or the complement thereof; v) a thymine at a position corresponding to position 1,260 according to SEQ ID NO:13, or the complement thereof; v) a thymine at a position corresponding to position 1,056 according to SEQ ID NO:14, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to: i) the nucleic acid sequence of the amplified nucleic acid molecule comprising a thymine at a position corresponding to position 17,922 according to SEQ ID NO:2, or the complement thereof; ii) the nucleic acid sequence of the amplified nucleic acid molecule comprising a uracil at a position corresponding to position 1,185 according to SEQ ID NO:6, or the complement thereof; iii) the nucleic acid sequence of the amplified nucleic acid molecule comprising a uracil at a position corresponding to position 1,260 according to SEQ ID NO:7, or the complement thereof; iv) the nucleic acid sequence of the amplified nucleic acid molecule comprising a uracil at a position corresponding to position 1,056 according to SEQ ID NO:8, or the complement thereof; v) the nucleic acid sequence of the amplified nucleic acid molecule comprising a thymine at a position corresponding to position 1,185 according to SEQ ID NO:12, or the complement thereof; vi) the nucleic acid sequence of the amplified nucleic acid molecule comprising a thymine at a position corresponding to position 1,260 according to SEQ ID NO:13, or the complement thereof; vii) the nucleic acid sequence of the amplified nucleic acid molecule comprising a thymine at a position corresponding to position 1,056 according to SEQ ID NO:14, or the complement thereof; and d) detecting the detectable label. In some embodiments, the nucleic acid molecule is mRNA and the determining step further comprises reverse-transcribing the mRNA into a cDNA prior to the amplifying step.

In some embodiments, the assay comprises: contacting the nucleic acid molecule in the biological sample with an alteration-specific probe comprising a detectable label, wherein the alteration-specific probe comprises a nucleotide sequence which hybridizes under stringent conditions to: i) the nucleotide sequence of the amplified nucleic acid molecule comprising a thymine at a position corresponding to position 17,922 according to SEQ ID NO:2, or the complement thereof; ii) the nucleotide sequence of the amplified nucleic acid molecule comprising a uracil at a position corresponding to position 1,185 according to SEQ ID NO:6, or the complement thereof; iii) the nucleotide sequence of the amplified nucleic acid molecule comprising a uracil at a position corresponding to position 1,260 according to SEQ ID NO:7, or the complement thereof; iv) the nucleotide sequence of the amplified nucleic acid molecule comprising a uracil at a position corresponding to position 1,056 according to SEQ ID NO:8, or the complement thereof; v) the nucleotide sequence of the amplified nucleic acid molecule comprising a thymine at a position corresponding to position 1,185 according to SEQ ID NO:12, or the complement thereof; vi) the nucleotide sequence of the amplified nucleic acid molecule comprising a thymine at a position corresponding to position 1,260 according to SEQ ID NO:13, or the complement thereof; vii) the nucleotide sequence of the amplified nucleic acid molecule comprising a thymine at a position corresponding to position 1,056 according to SEQ ID NO:14, or the complement thereof; and detecting the detectable label. Alteration-specific polymerase chain reaction techniques can be used to detect mutations such as SNPs in a nucleic acid sequence. Alteration-specific primers can be used because the DNA polymerase will not extend when a mismatch with the template is present.

In some embodiments, the nucleic acid molecule in the sample is mRNA and the mRNA is reverse-transcribed into a cDNA prior to the amplifying step. In some embodiments, the nucleic acid molecule is present within a cell obtained from the human subject.

The SREBF1 predicted loss-of-function variant nucleic acid molecule can be any SREBF1 nucleic acid molecule (such as, for example, genomic nucleic acid molecule, mRNA molecule, or cDNA molecule) encoding an SREBF1 polypeptide having a partial loss-of-function, a complete loss-of-function, a predicted partial loss-of-function, or a predicted complete loss-of-function. For example, the SREBF1 predicted loss-of-function variant nucleic acid molecule can be any nucleic acid molecule encoding SREBF1 Arg334Cys, Arg364Cys, or Arg310Cys.

In some embodiments, the assay comprises contacting the biological sample with a primer or probe, such as an alteration-specific primer or alteration-specific probe, that specifically hybridizes to an SREBF1 variant genomic sequence, variant mRNA sequence, or variant cDNA sequence and not the corresponding SREBF1 reference sequence under stringent conditions, and determining whether hybridization has occurred.

In some embodiments, the assay comprises RNA sequencing (RNA-Seq). In some embodiments, the assays also comprise reverse transcribing mRNA into cDNA, such as by the reverse transcriptase polymerase chain reaction (RT-PCR).

In some embodiments, the methods utilize probes and primers of sufficient nucleotide length to bind to the target nucleotide sequence and specifically detect and/or identify a polynucleotide comprising an SREBF1 variant genomic nucleic acid molecule, variant mRNA molecule, or variant cDNA molecule. The hybridization conditions or reaction conditions can be determined by the operator to achieve this result. This nucleotide length may be any length that is sufficient for use in a detection method of choice, including any assay described or exemplified herein. Such probes and primers can hybridize specifically to a target nucleotide sequence under high stringency hybridization conditions. Probes and primers may have complete nucleotide sequence identity of contiguous nucleotides within the target nucleotide sequence, although probes differing from the target nucleotide sequence and that retain the ability to specifically detect and/or identify a target nucleotide sequence may be designed by conventional methods. Accordingly, probes and primers can share about 80%, about 85%, about 90%, about 91%, about 92%, about 93%, about 94%, about 95%, about 96%, about 97%, about 98%, about 99%, or 100% sequence identity or complementarity to the nucleotide sequence of the target nucleic acid molecule.

In some embodiments, to determine whether the SREBF1 nucleic acid molecule (genomic nucleic acid molecule, mRNA molecule, or cDNA molecule), or complement thereof, within a biological sample comprises a nucleotide sequence encoding a thymine at a position corresponding to position 17,922 according to SEQ ID NO:2, a uracil at a position corresponding to position 1,185 according to SEQ ID NO:6, a uracil at a position corresponding to position 1,260 according to SEQ ID NO:7, a uracil at a position corresponding to position 1,056 according to SEQ ID NO:8, a thymine at a position corresponding to position 1,185 according to SEQ ID NO:12, a thymine at a position corresponding to position 1,260 according to SEQ ID NO:13, or a thymine at a position corresponding to position 1,056 according to SEQ ID NO:14, the biological sample may be subjected to an amplification method using a primer pair that includes a first primer derived from the 5' flanking sequence adjacent to a thymine at a position corresponding to position 17,922 according to SEQ ID NO:2, a uracil at a position corresponding to position 1,185 according to SEQ ID NO:6, a uracil at a position corresponding to position 1,260 according to SEQ ID NO:7, a uracil at a position corresponding to position 1,056 according to SEQ ID NO:8, a thymine at a position corresponding to position 1,185 according to SEQ ID NO:12, a thymine at a position corresponding to position 1,260 according to SEQ ID NO:13, or a thymine at a position corresponding to position 1,056 according to SEQ ID NO:14, and a second primer derived from the 3' flanking sequence adjacent to a thymine at a position corresponding to position 17,922 according to SEQ ID NO:2, a uracil at a position corresponding to position 1,185 according to SEQ ID NO:6, a uracil at a position corresponding to position 1,260 according to SEQ ID NO:7, a uracil at a position corresponding to position 1,056 according to SEQ ID NO:8, a thymine at a position corresponding to position 1,185 according to SEQ ID NO:12, a thymine at a position corresponding to position 1,260 according to SEQ ID NO:13, or a thymine at a position corresponding to position 1,056 according to SEQ ID NO:14, to produce an amplicon that is indicative of the presence of the SNP at positions encoding a thymine at a position corresponding to position 17,922 according to SEQ ID NO:2, a uracil at a position corresponding to position 1,185 according to SEQ ID NO:6, a uracil at a position corresponding to position 1,260 according to SEQ ID NO:7, a uracil at a position corresponding to position 1,056 according to SEQ ID NO:8, a thymine at a position corresponding to position 1,185 according to SEQ ID NO:12, a thymine at a position corresponding to position 1,260 according to SEQ ID NO:13, or a thymine at a position corresponding to position 1,056 according to SEQ ID NO:14. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions encoding a thymine at a position corresponding to position 17,922 according to SEQ ID NO:2, a uracil at a position corresponding to position 1,185 according to SEQ ID NO:6, a uracil at a position corresponding to position 1,260 according to SEQ ID NO:7, a uracil at a position corresponding to position 1,056 according to SEQ ID NO:8, a thymine at a position corresponding to position 1,185 according to SEQ ID NO:12, a thymine at a position corresponding to position 1,260 according to SEQ ID NO:13, or a thymine at a position corresponding to position 1,056 according to SEQ ID NO:14, and at least 1, 2, 3, 4, 5, 6, 7, 8, 9, 10, or more nucleotides on each side of positions encoding a thymine at a position corresponding to position 17,922 according to SEQ ID NO:2, a uracil at a position corresponding to position 1,185 according to SEQ ID NO:6, a uracil at a position corresponding to position 1,260 according to SEQ ID NO:7, a uracil at a position corresponding to position 1,056 according to SEQ ID NO:8, a thymine at a position corresponding to position 1,185 according to SEQ ID NO:12, a thymine at a position corresponding to position 1,260 according to SEQ ID NO:13, or a thymine at a position corresponding to position 1,056 according to SEQ ID NO:14. Similar amplicons can be generated from the mRNA and/or cDNA sequences. PCR primer pairs can be derived from a known sequence, for example, by using computer programs intended for that purpose, such as the PCR primer analysis tool in Vector NTI version 10 (Informax Inc., Bethesda Md.); PrimerSelect (DNASTAR Inc., Madison, Wis.); and Primer3 (Version 0.4.0.COPYRGT., 1991, Whitehead Institute for Biomedical Research, Cambridge, Mass.). Additionally, the sequence can be visually scanned and primers manually identified using known guidelines.

A variety of techniques including, for example, nucleic acid sequencing, nucleic acid hybridization, and nucleic acid amplification can be used. Illustrative examples of nucleic acid sequencing techniques include, but are not limited to, chain terminator (Sanger) sequencing and dye terminator sequencing.

Other methods involve nucleic acid hybridization methods other than sequencing, including using labeled primers or probes directed against purified DNA, amplified DNA, and fixed cell preparations (fluorescence in situ hybridization (FISH)). In some methods, a target nucleic acid molecule may be amplified prior to or simultaneous with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

In hybridization techniques, stringent conditions can be employed such that a probe or primer will specifically hybridize to its target. In some embodiments, a polynucleotide primer or probe under stringent conditions will hybridize to its target sequence to a detectably greater degree than to other non-target sequences, such as, at least 2-fold, at least 3-fold, at least 4-fold, or more over background, including over 10-fold over background. In some embodiments, a polynucleotide primer or probe under stringent conditions will hybridize to its target nucleotide sequence to a detectably greater degree than to other nucleotide sequences by at least 2-fold. In some embodiments, a polynucleotide primer or probe under stringent conditions will hybridize to its target nucleotide sequence to a detectably greater degree than to other nucleotide sequences by at least 3-fold. In some embodiments, a polynucleotide primer or probe under stringent conditions will hybridize to its target nucleotide sequence to a detectably greater degree than to other nucleotide sequences by at least 4-fold. In some embodiments, a polynucleotide primer or probe under stringent conditions will hybridize to its target nucleotide sequence to a detectably greater degree than to other nucleotide sequences by over 10-fold over background. Stringent conditions are sequence-dependent and will be different in different circumstances.

Appropriate stringency conditions which promote DNA hybridization, for example, 6× sodium chloride/sodium citrate (SSC) at about 45° C., followed by a wash of 2×SSC at 50° C., are known or can be found in *Current Protocols in Molecular Biology*, John Wiley & Sons, N.Y. (1989), 6.3.1-6.3.6. Typically, stringent conditions for hybridization and detection will be those in which the salt concentration is less than about 1.5 M $Na^+$ ion, typically about 0.01 to 1.0 M $Na^+$ ion concentration (or other salts) at pH 7.0 to 8.3 and the temperature is at least about 30° C. for short probes (such as, for example, 10 to 50 nucleotides) and at least about 60° C. for longer probes (such as, for example, greater than 50 nucleotides). Stringent conditions may also be achieved with the addition of destabilizing agents such as formamide. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

The present disclosure also provides methods of detecting the presence of a human SREBF1 predicted loss-of-function variant polypeptide comprising performing an assay on a sample obtained from a human subject to determine whether an SREBF1 polypeptide in the subject contains one or more variations that causes the polypeptide to have a loss-of-function (partial or complete). In some embodiments, the methods detect the presence of a human SREBF1 predicted loss-of-function variant polypeptide, such as, for example, the SREBF1 Arg334Cys variant polypeptide, and comprise performing an assay on a sample obtained from a human subject to determine whether an SREBF1 polypeptide in the sample comprises a cysteine at a position corresponding to position 334 according to SEQ ID NO:18. In some embodiments, the detecting step comprises sequencing at least a portion of the polypeptide that comprises a position corresponding to position 334 according to SEQ ID NO:15 or SEQ ID NO:18. In some embodiments, the detecting step comprises sequencing the entire polypeptide. In some embodiments, the detecting step comprises an immunoassay for detecting the presence of a polypeptide that comprises a position corresponding to position 334 according to SEQ ID NO:15 or SEQ ID NO:18.

In some embodiments, the methods detect the presence of a human SREBF1 predicted loss-of-function variant polypeptide, such as, for example, the SREBF1 Arg364Cys variant polypeptide, and comprise performing an assay on a sample obtained from a human subject to determine whether an SREBF1 polypeptide in the sample comprises a cysteine at a position corresponding to position 364 according to SEQ ID NO:19. In some embodiments, the detecting step comprises sequencing at least a portion of the polypeptide that comprises a position corresponding to position 364 according to SEQ ID NO:16 or SEQ ID NO:19. In some embodiments, the detecting step comprises sequencing the entire polypeptide. In some embodiments, the detecting step comprises an immunoassay for detecting the presence of a polypeptide that comprises a position corresponding to position 364 according to SEQ ID NO:16 or SEQ ID NO:19.

In some embodiments, the methods detect the presence of a human SREBF1 predicted loss-of-function variant polypeptide, such as, for example, the SREBF1 Arg310Cys variant polypeptide, and comprise performing an assay on a sample obtained from a human subject to determine whether an SREBF1 polypeptide in the sample comprises a cysteine at a position corresponding to position 310 according to SEQ ID NO:20. In some embodiments, the detecting step comprises sequencing at least a portion of the polypeptide that comprises a position corresponding to position 310 according to SEQ ID NO:17 or SEQ ID NO:20. In some embodiments, the detecting step comprises sequencing the entire polypeptide. In some embodiments, the detecting step comprises an immunoassay for detecting the presence of a polypeptide that comprises a position corresponding to position 310 according to SEQ ID NO:17 or SEQ ID NO:20.

The present disclosure also provides isolated nucleic acid molecules that hybridize to SREBF1 predicted loss-of-function variant genomic nucleic acid molecules (such as SEQ ID NO:2), SREBF1 predicted loss-of-function variant mRNA molecules (such as SEQ ID NO:6, SEQ ID NO:7, and SEQ ID NO:8), and/or SREBF1 predicted loss-of-function variant cDNA molecules (such as SEQ ID NO:12, SEQ ID NO:13, and SEQ ID NO:14). In some embodiments, the isolated nucleic acid molecules hybridize to the portion of the SREBF1 nucleic acid molecule that includes a position corresponding to position 17,922 according to SEQ ID NO:2, and include a position corresponding to position 1,185 according to SEQ ID NO:6 or SEQ ID NO:12, include a position corresponding to position 1,260 according to SEQ ID NO:7 or SEQ ID NO:13, or include a position corresponding to position 1,056 according to SEQ ID NO:8 or SEQ ID NO:14.

In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 200, at least about 300, at least about 400, at least about 500, at least about 600, at least about 700, at least about 800, at least about 900, at least about 1000, at least about 2000, at least about 3000, at least about 4000, at least about 5000, at least about 6000, at least about 7000, at least about 8000, at least about 9000, at least about 10000, at least about 11000, at least about 12000, at least about 13000, at least about 14000, at least about 15000, at least about 16000, at least about 17000, at least about 18000, at least about 19000, or at least about 20000 nucleotides. In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, or at least about 25 nucleotides. In preferred embodiments, the isolated nucleic acid molecules comprise or consist of at least about 18 nucleotides. In some embodiments, the isolated nucleic acid molecules comprise or consists of at least about 15 nucleotides. In some embodiments, the isolated nucleic acid molecules comprise or consist of from about 10 to about 35, from about 10 to about 30, from about 10 to about 25, from about 12 to about 30, from about 12 to about 28, from about 12 to about 24, from about 15 to about 30, from about 15 to about 25, from about 18 to about 30, from about 18 to about 25, from about 18 to about 24, or from about 18 to about 22 nucleotides. In preferred embodiments, the isolated nucleic acid molecules comprise or consist of from about 18 to about 30 nucleotides. In some embodiments, the isolated nucleic acid molecules comprise or consist of at least about 15 nucleotides to at least about 35 nucleotides.

In some embodiments, such isolated nucleic acid molecules hybridize to SREBF1 predicted loss-of-function variant genomic nucleic acid molecules (such as SEQ ID NO:2), SREBF1 predicted loss-of-function variant mRNA molecules (such as SEQ ID NO:6, SEQ ID NO:7, and SEQ ID NO:8), and/or SREBF1 predicted loss-of-function variant cDNA molecules (such as SEQ ID NO:12, SEQ ID NO:13, and SEQ ID NO:14) under stringent conditions. Such nucleic acid molecules can be used, for example, as probes, primers, alteration-specific probes, or alteration-specific primers as described or exemplified herein, and include, without limitation primers, probes, antisense RNAs, shRNAs, and siRNAs, each of which is described in more detail elsewhere herein, and can be used in any of the methods described herein.

In some embodiments, the isolated nucleic acid molecules hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to SREBF1 predicted loss-of-function variant genomic nucleic acid molecules (such as SEQ ID NO:2), SREBF1 predicted loss-of-function variant mRNA molecules (such as SEQ ID NO:6, SEQ ID NO:7, and SEQ ID NO:8), and/or SREBF1 predicted loss-of-function variant cDNA molecules (such as SEQ ID NO:12, SEQ ID NO:13, and SEQ ID NO:14). In some embodiments, the isolated nucleic acid molecules comprise or consist of from about 15 to about 100 nucleotides, or from about 15 to about 35 nucleotides. In some embodiments, the isolated nucleic acid molecules comprise or consist of from about 15 to about 100 nucleotides. In some embodiments, the isolated nucleic acid molecules comprise or consist of from about 15 to about 35 nucleotides.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a human SREBF1 polypeptide, wherein the portion comprises a position corresponding to: position 17,922 according to SEQ ID NO:2, or the complement thereof; position 1,185 according to SEQ ID NO:6, or the complement thereof; position 1,260 according to SEQ ID NO:7, or the complement thereof; position 1,056 according to SEQ ID NO:8, or the complement thereof; position 1,185 according to SEQ ID NO:12, or the complement thereof;

position 1,260 according to SEQ ID NO:13, or the complement thereof; or position 1,056 according to SEQ ID NO:14, or the complement thereof.

In some embodiments, the alteration-specific probe or alteration-specific primer comprises a nucleotide sequence which is complementary to a portion of a nucleotide sequence comprising a position corresponding to position 17,922 according to SEQ ID NO:2, or the complement thereof. In some embodiments, the alteration-specific probe or alteration-specific primer comprises a nucleotide sequence which is complementary to a portion of a nucleotide sequence comprising positions corresponding to positions 17,922 to 17,924 according to SEQ ID NO:2, or the complement thereof.

In some embodiments, the alteration-specific probe or alteration-specific primer comprises a nucleotide sequence which is complementary to a portion of a nucleotide sequence comprising a position corresponding to position 1,185 according to SEQ ID NO:6, or the complement thereof. In some embodiments, the alteration-specific probe or alteration-specific primer comprises a nucleotide sequence which is complementary to a portion of a nucleotide sequence comprising positions corresponding to positions 1,185 to 1,187 according to SEQ ID NO:6, or the complement thereof.

In some embodiments, the alteration-specific probe or alteration-specific primer comprises a nucleotide sequence which is complementary to a portion of a nucleotide sequence comprising a position corresponding to position 1,260 according to SEQ ID NO:7, or the complement thereof. In some embodiments, the alteration-specific probe or alteration-specific primer comprises a nucleotide sequence which is complementary to a portion of a nucleotide sequence comprising positions corresponding to positions 1,260 to 1,262 according to SEQ ID NO:7, or the complement thereof.

In some embodiments, the alteration-specific probe or alteration-specific primer comprises a nucleotide sequence which is complementary to a portion of a nucleotide sequence comprising a position corresponding to position 1,056 according to SEQ ID NO:8, or the complement thereof. In some embodiments, the alteration-specific probe or alteration-specific primer comprises a nucleotide sequence which is complementary to a portion of a nucleotide sequence comprising positions corresponding to positions 1,056 to 1,058 according to SEQ ID NO:8, or the complement thereof.

In some embodiments, the alteration-specific probe or alteration-specific primer comprises a nucleotide sequence which is complementary to a portion of a nucleotide sequence comprising a position corresponding to position 1,185 according to SEQ ID NO:12, or the complement thereof. In some embodiments, the alteration-specific probe or alteration-specific primer comprises a nucleotide sequence which is complementary to a portion of a nucleotide sequence comprising positions corresponding to positions 1,185 to 1,187 according to SEQ ID NO:12, or the complement thereof.

In some embodiments, the alteration-specific probe or alteration-specific primer comprises a nucleotide sequence which is complementary to a portion of a nucleotide sequence comprising a position corresponding to position 1,260 according to SEQ ID NO:13, or the complement thereof. In some embodiments, the alteration-specific probe or alteration-specific primer comprises a nucleotide sequence which is complementary to a portion of a nucleotide sequence comprising positions corresponding to positions 1,260 to 1,262 according to SEQ ID NO:13, or the complement thereof.

In some embodiments, the alteration-specific probe or alteration-specific primer comprises a nucleotide sequence which is complementary to a portion of a nucleotide sequence comprising a position corresponding to position 1,056 according to SEQ ID NO:14, or the complement thereof. In some embodiments, the alteration-specific probe or alteration-specific primer comprises a nucleotide sequence which is complementary to a portion of a nucleotide sequence comprising positions corresponding to positions 1,056 to 1,058 according to SEQ ID NO:14, or the complement thereof.

In some embodiments, the alteration-specific probes and alteration-specific primers comprise DNA. In some embodiments, the alteration-specific probes and alteration-specific primers comprise RNA.

In some embodiments, the probes and primers described herein (including alteration-specific probes and alteration-specific primers) have a nucleotide sequence that specifically hybridizes to any of the nucleic acid molecules disclosed herein, or the complement thereof. In some embodiments, the probes and primers specifically hybridize to any of the nucleic acid molecules disclosed herein under stringent conditions.

In some embodiments, the primers, including alteration-specific primers, can be used in second generation sequencing or high throughput sequencing. In some instances, the primers, including alteration-specific primers, can be modified. In particular, the primers can comprise various modifications that are used at different steps of, for example, Massive Parallel Signature Sequencing (MPSS), Polony sequencing, and 454 Pyrosequencing. Modified primers can be used at several steps of the process, including biotinylated primers in the cloning step and fluorescently labeled primers used at the bead loading step and detection step. Polony sequencing is generally performed using a paired-end tags library wherein each molecule of DNA template is about 135 bp in length. Biotinylated primers are used at the bead loading step and emulsion PCR. Fluorescently labeled degenerate nonamer oligonucleotides are used at the detection step. An adaptor can contain a 5'-biotin tag for immobilization of the DNA library onto streptavidin-coated beads.

The probes and primers described herein can be used to detect the C17,922T variation within the SREBF1 variant genomic nucleic acid molecule (such as SEQ ID NO:2), the C1,185U variation within the SREBF1 variant mRNA molecule (such as SEQ ID NO:6), the C1,260U variation within the SREBF1 variant mRNA molecule (such as SEQ ID NO:7), the C1,056U variation within the SREBF1 variant mRNA molecule (such as SEQ ID NO:8), the C1,185T variation within the SREBF1 variant cDNA molecule (such as SEQ ID NO:12), the C1,260T variation within the SREBF1 variant cDNA molecule (such as SEQ ID NO:13), or the C1,056T variation within the SREBF1 variant cDNA molecule (such as SEQ ID NO:14). For example, the primers can be used to amplify SREBF1 variant genomic nucleic acid molecules or a fragment thereof comprising the C17,922T variation. The primers can also be used to amplify SREBF1 variant mRNA or a fragment thereof comprising the C1,185U variation, C1,260U variation, and/or C1,056U variation. The primers can also be used to amplify SREBF1 variant cDNA or a fragment thereof comprising the C1,185T variation, C1,260T variation, and/or C1,056T variation.

The present disclosure also provides pairs of primers comprising any of the primers described above. If one of the primers' 3'-ends hybridizes to a cytosine at position 17,922 (rather than thymine) in a particular SREBF1 nucleic acid molecule, then the presence of the amplified fragment would indicate the presence of an SREBF1 reference genomic nucleic acid molecule. Conversely, if one of the primers' 3'-ends hybridizes to a thymine at position 17,922 (rather than cytosine) in a particular SREBF1 nucleic acid molecule, then the presence of the amplified fragment would indicate the presence of the SREBF1 variant genomic nucleic acid molecule. In some embodiments, the nucleotide of the primer complementary to the thymine at a position corresponding to position 17,922 in SEQ ID NO:2 can be at the 3' end of the primer.

If one of the primers' 3'-ends hybridizes to a cytosine at position 1,185 (rather than uracil) in a particular SREBF1 mRNA molecule, then the presence of the amplified fragment would indicate the presence of an SREBF1 reference mRNA molecule. Conversely, if one of the primers' 3'-ends hybridizes to a uracil at position 1,185 (rather than cytosine) in a particular SREBF1 mRNA molecule, then the presence of the amplified fragment would indicate the presence of the SREBF1 variant mRNA molecule. In some embodiments, the nucleotide of the primer complementary to the uracil at a position corresponding to position 1,185 in SEQ ID NO:6 can be at the 3' end of the primer. In addition, if one of the primers' 3'-ends hybridizes to a cytosine at position 1,260 (rather than uracil) in a particular SREBF1 mRNA molecule, then the presence of the amplified fragment would indicate the presence of an SREBF1 reference mRNA molecule. Conversely, if one of the primers' 3'-ends hybridizes to a uracil at position 1,260 (rather than cytosine) in a particular SREBF1 mRNA molecule, then the presence of the amplified fragment would indicate the presence of the SREBF1 variant mRNA molecule. In some embodiments, the nucleotide of the primer complementary to the uracil at a position corresponding to position 1,260 in SEQ ID NO:7 can be at the 3' end of the primer. In addition, if one of the primers' 3'-ends hybridizes to a cytosine at position 1,056 (rather than uracil) in a particular SREBF1 mRNA molecule, then the presence of the amplified fragment would indicate the presence of an SREBF1 reference mRNA molecule. Conversely, if one of the primers' 3'-ends hybridizes to a uracil at position 1,056 (rather than cytosine) in a particular SREBF1 mRNA molecule, then the presence of the amplified fragment would indicate the presence of the SREBF1 variant mRNA molecule. In some embodiments, the nucleotide of the primer complementary to the uracil at a position corresponding to position 1,056 in SEQ ID NO:8 can be at the 3' end of the primer.

If one of the primers' 3'-ends hybridizes to a cytosine at position 1,185 (rather than thymine) in a particular SREBF1 cDNA molecule, then the presence of the amplified fragment would indicate the presence of an SREBF1 reference cDNA molecule. Conversely, if one of the primers' 3'-ends hybridizes to a thymine at position 1,185 (rather than cytsone) in a particular SREBF1 cDNA molecule, then the presence of the amplified fragment would indicate the presence of the SREBF1 variant cDNA molecule. In some embodiments, the nucleotide of the primer complementary to the thymine at a position corresponding to position 1,185 in SEQ ID NO:12 can be at the 3' end of the primer. In addition, if one of the primers' 3'-ends hybridizes to a cytosine at position 1,260 (rather than thymine) in a particular SREBF1 cDNA molecule, then the presence of the amplified fragment would indicate the presence of an SREBF1 reference cDNA molecule. Conversely, if one of the primers' 3'-ends hybridizes to a thymine at position 1,260 (rather than cytsone) in a particular SREBF1 cDNA molecule, then the presence of the amplified fragment would indicate the presence of the SREBF1 variant cDNA molecule. In some embodiments, the nucleotide of the primer complementary to the thymine at a position corresponding to position 1,260 in SEQ ID NO:13 can be at the 3' end of the primer. In addition, if one of the primers' 3'-ends hybridizes to a cytosine at position 1,056 (rather than thymine) in a particular SREBF1 cDNA molecule, then the presence of the amplified fragment would indicate the presence of an SREBF1 reference cDNA molecule. Conversely, if one of the primers' 3'-ends hybridizes to a thymine at position 1,056 (rather than cytsone) in a particular SREBF1 cDNA molecule, then the presence of the amplified fragment would indicate the presence of the SREBF1 variant cDNA molecule. In some embodiments, the nucleotide of the primer complementary to the thymine at a position corresponding to position 1,056 in SEQ ID NO:14 can be at the 3' end of the primer.

In some embodiments, the probes or primers comprise a nucleotide sequence which hybridizes to a portion of an SREBF1 genomic nucleic acid molecule, wherein the portion comprises a thymine at a position corresponding to position 17,922 according to SEQ ID NO:2, or which hybridizes to the complement of this nucleic acid molecule. In some embodiments, the probes or primers comprise a nucleotide sequence which hybridizes to an SREBF1 genomic nucleic acid molecule comprising SEQ ID NO:2 at a portion comprising a thymine at a position corresponding to position 17,922 according to SEQ ID NO:2, or which hybridizes to the complement of this nucleic acid molecule.

In some embodiments, the probes or primers comprise a nucleotide sequence which hybridizes to a portion of an SREBF1 mRNA molecule, wherein the portion comprises a uracil at a position corresponding to position 1,185 according to SEQ ID NO:6, or which hybridizes to the complement of this nucleic acid molecule. In some embodiments, the probes or primers comprise a nucleotide sequence which hybridizes to an SREBF16 mRNA molecule comprising SEQ ID NO:6 at a portion comprising a uracil at a position corresponding to position 1,185 according to SEQ ID NO:6, or which hybridizes to the complement of this nucleic acid molecule.

In some embodiments, the probes or primers comprise a nucleotide sequence which hybridizes to a portion of an SREBF1 mRNA molecule, wherein the portion comprises a uracil at a position corresponding to position 1,260 according to SEQ ID NO:7, or which hybridizes to the complement of this nucleic acid molecule. In some embodiments, the probes or primers comprise a nucleotide sequence which hybridizes to an SREBF16 mRNA molecule comprising SEQ ID NO:7 at a portion comprising a uracil at a position corresponding to position 1,260 according to SEQ ID NO:7, or which hybridizes to the complement of this nucleic acid molecule.

In some embodiments, the probes or primers comprise a nucleotide sequence which hybridizes to a portion of an SREBF1 mRNA molecule, wherein the portion comprises a uracil at a position corresponding to position 1,056 according to SEQ ID NO:8, or which hybridizes to the complement of this nucleic acid molecule. In some embodiments, the probes or primers comprise a nucleotide sequence which hybridizes to an SREBF16 mRNA molecule comprising SEQ ID NO:8 at a portion comprising a uracil at a position corresponding to position 1,056 according to SEQ ID NO:8, or which hybridizes to the complement of this nucleic acid molecule.

In some embodiments, the probes or primers comprise a nucleotide sequence which hybridizes to a portion of an SREBF1 cDNA molecule, wherein the portion comprises a thymine at a position corresponding to position 1,185 according to SEQ ID NO:12, or which hybridizes to the complement of this nucleic acid molecule. In some embodiments, the probes or primers comprise a nucleotide sequence which hybridizes to an SREBF1 cDNA molecule comprising SEQ ID NO:12 at a portion comprising a thymine at a position corresponding to position 1,185 according to SEQ ID NO:12, or which hybridizes to the complement of this nucleic acid molecule.

In some embodiments, the probes or primers comprise a nucleotide sequence which hybridizes to a portion of an SREBF1 cDNA molecule, wherein the portion comprises a thymine at a position corresponding to position 1,260 according to SEQ ID NO:13, or which hybridizes to the complement of this nucleic acid molecule. In some embodiments, the probes or primers comprise a nucleotide sequence which hybridizes to an SREBF1 cDNA molecule comprising SEQ ID NO:13 at a portion comprising a thymine at a position corresponding to position 1,260 according to SEQ ID NO:13, or which hybridizes to the complement of this nucleic acid molecule.

In some embodiments, the probes or primers comprise a nucleotide sequence which hybridizes to a portion of an SREBF1 cDNA molecule, wherein the portion comprises a thymine at a position corresponding to position 1,056 according to SEQ ID NO:14, or which hybridizes to the complement of this nucleic acid molecule. In some embodiments, the probes or primers comprise a nucleotide sequence which hybridizes to an SREBF1 cDNA molecule comprising SEQ ID NO:14 at a portion comprising a thymine at a position corresponding to position 1,056 according to SEQ ID NO:14, or which hybridizes to the complement of this nucleic acid molecule.

In the context of the disclosure "specifically hybridizes" means that the probe or primer (such as, for example, the alteration-specific probe or alteration-specific primer) does not hybridize to a nucleic acid sequence encoding an SREBF1 reference genomic nucleic acid molecule, an SREBF1 reference mRNA molecule, and/or an SREBF1 reference cDNA molecule.

In some embodiments, the probes (such as, for example, an alteration-specific probe) comprise a label. In some embodiments, the label is a fluorescent label, a radiolabel, or biotin.

The present disclosure also provides supports comprising a substrate to which any one or more of the probes disclosed herein is attached. Solid supports are solid-state substrates or supports with which molecules, such as any of the probes disclosed herein, can be associated. A form of solid support is an array. Another form of solid support is an array detector. An array detector is a solid support to which multiple different probes have been coupled in an array, grid, or other organized pattern. A form for a solid-state substrate is a microtiter dish, such as a standard 96-well type. In some embodiments, a multiwell glass slide can be employed that normally contains one array per well.

The present disclosure also provides molecular complexes comprising or consisting of any of the SREBF1 nucleic acid molecules (genomic nucleic acid molecules, mRNA molecules, or cDNA molecules), or complement thereof, described herein and any of the alteration-specific primers or alteration-specific probes described herein. In some embodiments, the SREBF1 nucleic acid molecules (genomic nucleic acid molecules, mRNA molecules, or cDNA molecules), or complement thereof, in the molecular complexes are single-stranded. In some embodiments, the SREBF1 nucleic acid molecule is any of the genomic nucleic acid molecules described herein. In some embodiments, the SREBF1 nucleic acid molecule is any of the mRNA molecules described herein. In some embodiments, the SREBF1 nucleic acid molecule is any of the cDNA molecules described herein. In some embodiments, the molecular complex comprises or consists of any of the SREBF1 nucleic acid molecules (genomic nucleic acid molecules, mRNA molecules, or cDNA molecules), or complement thereof, described herein and any of the alteration-specific primers described herein. In some embodiments, the molecular complex comprises or consists of any of the SREBF1 nucleic acid molecules (genomic nucleic acid molecules, mRNA molecules, or cDNA molecules), or complement thereof, described herein and any of the alteration-specific probes described herein.

In some embodiments, the molecular complex comprises or consists of an alteration-specific primer or an alteration-specific probe hybridized to a genomic nucleic acid molecule comprising a nucleotide sequence encoding a human SREBF1 polypeptide, wherein the alteration-specific primer or the alteration-specific probe is hybridized to: a thymine at a position corresponding to position 17,922 according to SEQ ID NO:2, or the complement thereof. In some embodiments, the molecular complex comprises or consists of an alteration-specific primer or an alteration-specific probe that is hybridized to: a TGC codon at positions corresponding to positions 17,922 to 17,924 according to SEQ ID NO:2. In some embodiments, the molecular complex comprises or consists of a genomic nucleic acid molecule that comprises SEQ ID NO:2.

In some embodiments, the molecular complex comprises or consists of an alteration-specific primer or an alteration-specific probe hybridized to an mRNA molecule comprising a nucleotide sequence encoding a human SREBF1 polypeptide, wherein the alteration-specific primer or the alteration-specific probe is hybridized to: uracil at a position corresponding to position 1,185 according to SEQ ID NO:6, or the complement thereof; a uracil at a position corresponding to position 1,260 according to SEQ ID NO:7, or the complement thereof; or a uracil at a position corresponding to position 1,056 according to SEQ ID NO:8, or the complement thereof. In some embodiments, the molecular complex comprises or consists of an alteration-specific primer or an alteration-specific probe that is hybridized to: a UGC codon at positions corresponding to positions 1,185 to 1,187 according to SEQ ID NO:6, a UGC codon at positions corresponding to positions 1,260 to 1,262 according to SEQ ID NO:6, or a UGC codon at positions corresponding to positions 1,056 to 1,058 according to SEQ ID NO:8. In some embodiments, the molecular complex comprises or consists of an mRNA molecule that comprises SEQ ID NO:6, SEQ ID NO:7, or SEQ ID NO:8.

In some embodiments, the molecular complex comprises or consists of an alteration-specific primer or an alteration-specific probe hybridized to a cDNA molecule comprising a nucleotide sequence encoding a human SREBF1 polypeptide, wherein the alteration-specific primer or the alteration-specific probe is hybridized to: a thymine at a position corresponding to position 1,185 according to SEQ ID NO:12, or the complement thereof; a thymine at a position corresponding to position 1,260 according to SEQ ID NO:13, or the complement thereof; or a thymine at a position corresponding to position 1,056 according to SEQ ID NO:14, or the complement thereof. In some embodiments, the molecular complex comprises or consists of an alteration-specific primer or an alteration-specific probe that is hybridized to: a TGC codon at positions corresponding to positions 1,185 to 1,187 according to SEQ ID NO:12, a TGC codon at positions corresponding to positions 1,260 to 1,262 according to SEQ ID NO:13, or a TGC codon at positions corresponding to positions 1,056 to 1,058 according to SEQ ID NO:14. In some embodiments, the molecular complex comprises or consists of a cDNA molecule that comprises SEQ ID NO:12, SEQ ID NO:13, or SEQ ID NO:14.

In some embodiments, the molecular complex comprises an alteration-specific probe or an alteration-specific primer comprising a label. In some embodiments, the label is a fluorescent label, a radiolabel, or biotin. In some embodiments, the molecular complex further comprises a non-human polymerase.

The present disclosure also provides isolated nucleic acid molecules comprising a nucleotide sequence encoding a human SREBF1 polypeptide, wherein the polypeptide comprises a cysteine at a position corresponding to: position 334 according to SEQ ID NO:18, or the complement thereof; position 364 according to SEQ ID NO:19, or the complement thereof; or position 310 according to SEQ ID NO:20, or the complement thereof.

In some embodiments, the isolated nucleic acid molecule encodes an SREBF1 polypeptide having an amino acid sequence that has at least about 90%, at least about 91%, at least about 92%, at least about 93%, at least about 94%, at least about 95%, at least about 96%, at least about 97%, at least about 98%, or at least about 99% sequence identity to: SEQ ID NO:18, and comprises a cysteine at a position corresponding to position 334 according to SEQ ID NO:18; SEQ ID NO:19, and comprises a cysteine at a position corresponding to position 364 according to SEQ ID NO:19; or SEQ ID NO:20, and comprises a cysteine at a position corresponding to position 310 according to SEQ ID NO:20.

In some embodiments, the nucleic acid molecule encodes an SREBF1 polypeptide comprising SEQ ID NO:18, SEQ ID NO:19, or SEQ ID NO:20. In some embodiments, the nucleic acid molecule encodes an SREBF1 polypeptide consisting of SEQ ID NO:18, SEQ ID NO:19, or SEQ ID NO:20.

The nucleotide sequence of an SREBF1 reference genomic nucleic acid molecule is set forth in SEQ ID NO:1. Referring to SEQ ID NO:1, position 17,922 of the SREBF1 reference genomic nucleic acid molecule is a cytosine. A variant genomic nucleic acid molecule of SREBF1 exists, wherein the cytosine at position 17,922 is replaced with thymine. The nucleotide sequence of this SREBF1 predicted loss-of-function variant genomic nucleic acid molecule is set forth in SEQ ID NO:2.

The present disclosure provides isolated genomic nucleic acid molecules comprising or consisting of a nucleotide sequence encoding a human SREBF1 polypeptide, wherein the nucleotide sequence comprises a thymine at a position corresponding to position 17,922 (C17,922T) according to SEQ ID NO:2, or the complement thereof. In some embodiments, the isolated genomic nucleic acid molecules comprise a nucleotide sequence encoding a human SREBF1 polypeptide, wherein the nucleotide sequence comprises a TGC codon at positions corresponding to positions 17,922 to 17,924 according to SEQ ID NO:2.

In some embodiments, the isolated genomic nucleic acid molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:2, and comprises a thymine at a position corresponding to position 17,922 according to SEQ ID NO:2, or the complement thereof. Herein, if reference is made to percent sequence identity, the higher percentages of sequence identity are preferred over the lower ones.

In some embodiments, the isolated genomic nucleic acid molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:2, and comprises a TGC codon at positions corresponding to positions 17,922 to 17,924 according to SEQ ID NO:2, or the complement thereof. Herein, if reference is made to percent sequence identity, the higher percentages of sequence identity are preferred over the lower ones.

In some embodiments, the isolated genomic nucleic acid molecules comprise SEQ ID NO:2. In some embodiments, the isolated genomic nucleic acid molecules consist of SEQ ID NO:2.

In some embodiments, the isolated genomic nucleic acid molecules comprise less than the entire genomic DNA sequence. In some embodiments, the isolated genomic nucleic acid molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 2000, at least about 3000, at least about 4000, at least about 5000, at least about 6000, at least about 7000, at least about 8000, at least about 9000, at least about 10000, at least about 11000, at least about 12000, at least about 13000, at least about 14000, at least about 15000, at least about 16000, at least about 17000, or at least about 18000 contiguous nucleotides of SEQ ID NO:2. In some embodiments, the isolated genomic nucleic acid molecules comprise or consist of at least about 1000 to at least about 2000 contiguous nucleotides of SEQ ID NO:2. In some embodiments, these isolated genomic nucleic acid molecules comprise the thymine at a position corresponding to position 17,922 according to SEQ ID NO:2.

The nucleotide sequences of three SREBF1 reference mRNA molecules are set forth in SEQ ID NO:3, SEQ ID NO:4, and SEQ ID NO:5. Referring to SEQ ID NO:3, position 1,185 of the SREBF1 reference mRNA molecule is a cytosine. Referring to SEQ ID NO:4, position 1,260 of the SREBF1 reference mRNA molecule is a cytosine. Referring to SEQ ID NO:5, position 1,056 of the SREBF1 reference mRNA molecule is a cytosine. Three variant mRNA molecules of SREBF1 exist, wherein the cytosine is replaced with thymine. Referring to SEQ ID NO:6, position 1,185 of the variant SREBF1 mRNA molecule is a thymine. Referring to SEQ ID NO:7, position 1,260 of the variant SREBF1 mRNA molecule is a thymine. Referring to SEQ ID NO:8, position 1,056 of the variant SREBF1 mRNA molecule is a thymine.

The present disclosure provides isolated mRNA molecules comprising or consisting of a nucleotide sequence encoding a human SREBF1 polypeptide, wherein the nucleotide sequence comprises: a uracil at a position corresponding to position 1,185 according to SEQ ID NO:6, or the complement thereof; a uracil at a position corresponding to position 1,260 according to SEQ ID NO:7, or the complement thereof; or a uracil at a position corresponding to position 1,056 according to SEQ ID NO:8, or the complement thereof.

In some embodiments, the isolated mRNA molecules comprise or consist of a nucleotide sequence encoding a human SREBF1 polypeptide, wherein the nucleotide sequence comprises: a UGC codon at positions corresponding to positions 1,185 to 1,187 according to SEQ ID NO:6; a UGC codon at positions corresponding to positions 1,260 to 1,262 according to SEQ ID NO:7; or a UGC codon at positions corresponding to positions 1,056 to 1,058 according to SEQ ID NO:8.

In some embodiments, the isolated mRNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to: SEQ ID NO:6, and comprise a uracil at a position corresponding to position 1,185 according to SEQ ID NO:6, or the complement thereof; SEQ ID NO:7, and comprise a uracil at a position corresponding to position 1,260 according to SEQ ID NO:7, or the complement thereof; SEQ ID NO:8, and comprise a uracil at a position corresponding to position 1,056 according to SEQ ID NO:8, or the complement thereof. Herein, if reference is made to percent sequence identity, the higher percentages of sequence identity are preferred over the lower ones.

In some embodiments, the isolated mRNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to: SEQ ID NO:6, and comprise a UGC codon at positions corresponding to positions 1,185 to 1,187 according to SEQ ID NO:6, or the complement thereof; SEQ ID NO:7, and comprise a UGC codon at positions corresponding to positions 1,260 to 1,262 according to SEQ ID NO:7, or the complement thereof; or SEQ ID NO:8, and comprise a UGC codon at positions corresponding to positions 1,056 to 1,058 according to SEQ ID NO:8, or the complement thereof. Herein, if reference is made to percent sequence identity, the higher percentages of sequence identity are preferred over the lower ones.

In some embodiments, the isolated mRNA molecules comprise SEQ ID NO:6, SEQ ID NO:7, or SEQ ID NO:8. In some embodiments, the isolated mRNA molecules consist of SEQ ID NO:6, SEQ ID NO:7, or SEQ ID NO:8. In some embodiments, the isolated mRNA molecules consist of SEQ ID NO:6.

The nucleotide sequences of three SREBF1 reference cDNA molecules are set forth in SEQ ID NO:9, SEQ ID NO:10, and SEQ ID NO:11. Referring to SEQ ID NO:9, position 1,185 of the SREBF1 reference cDNA molecule is a cytosine. Referring to SEQ ID NO:10, position 1,260 of the SREBF1 reference cDNA molecule is a cytosine. Referring to SEQ ID NO:11, position 1,056 of the SREBF1 reference cDNA molecule is a cytosine. Three variant cDNA molecules of SREBF1 exist, wherein the cytosine is replaced with thymine. Referring to SEQ ID NO:12, position 1,185 of the variant SREBF1 cDNA molecule is a thymine. Referring to SEQ ID NO:13, position 1,260 of the variant SREBF1 cDNA molecule is a thymine. Referring to SEQ ID NO:14, position 1,056 of the variant SREBF1 cDNA molecule is a thymine.

The present disclosure provides isolated cDNA molecules comprising or consisting of a nucleotide sequence encoding a human SREBF1 polypeptide, wherein the nucleotide sequence comprises: a thymine at a position corresponding to position 1,185 according to SEQ ID NO:12, or the complement thereof; a thymine at a position corresponding to position 1,260 according to SEQ ID NO:13, or the complement thereof; or a thymine at a position corresponding to position 1,056 according to SEQ ID NO:14, or the complement thereof.

In some embodiments, the isolated cDNA molecule comprises or consists of a nucleotide sequence encoding a human SREBF1 polypeptide, wherein the nucleotide sequence comprises: a TGC codon at positions corresponding to positions 1,185 to 1,187 according to SEQ ID NO:12; a TGC codon at positions corresponding to positions 1,260 to 1,262 according to SEQ ID NO:13; or a TGC codon at positions corresponding to positions 1,056 to 1,058 according to SEQ ID NO:14.

In some embodiments, the isolated cDNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to: SEQ ID NO:12, and comprise a thymine at a position corresponding to position 1,185 according to SEQ ID NO:12, or the complement thereof; SEQ ID NO:13, and comprise a thymine at a position corresponding to position 1,260 according to SEQ ID NO:13, or the complement thereof; or SEQ ID NO:14, and comprise a thymine at a position corresponding to position 1,056 according to SEQ ID NO:14, or the complement thereof. Herein, if reference is made to percent sequence identity, the higher percentages of sequence identity are preferred over the lower ones.

In some embodiments, the isolated cDNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to: SEQ ID NO:12, and comprise a TGC codon at positions corresponding to positions 1,185 to 1,187 according to SEQ ID NO:12, or the complement thereof; SEQ ID NO:13, and comprise a TGC codon at positions corresponding to positions 1,260 to 1,262 according to SEQ ID NO:13, or the complement thereof; or SEQ ID NO:14, and comprise a TGC codon at positions corresponding to positions 1,056 to 1,058 according to SEQ ID NO:14, or the complement thereof. Herein, if reference is made to percent sequence identity, the higher percentages of sequence identity are preferred over the lower ones.

In some embodiments, the isolated cDNA molecules comprise SEQ ID NO:12, SEQ ID NO:13, or SEQ ID NO:14. In some embodiments, the isolated cDNA molecules consist of SEQ ID NO:12, SEQ ID NO:13, or SEQ ID NO:14.

In some embodiments, the isolated mRNA molecules or cDNA molecules comprise less than the entire mRNA or cDNA sequence. In some embodiments, the isolated cDNA molecules comprise or consist of at least about 5, at least about 8, at least about 10, at least about 12, at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 1100, at least about 1200, at least about 1300, at least about 1400, at least about 1500, at least about 1600, at least about 1700, at least about 1800, at least about 1900, at least about 2000, at least about 2100, at least about 2200, at least about 2300, at least about 2400, at least about 2500, at least about 2600, at least about 2700, at least about 2800, at least about 2900, at least about 3000, at least about 3100, at least about 3200, or at least about 3300 contiguous nucleotides of SEQ ID NO:6, SEQ ID NO:7, or SEQ ID NO:8 (for mRNA) or SEQ ID NO:12, SEQ ID NO:13, or SEQ ID NO:14 (for cDNA).

The genomic nucleic acid molecules, mRNA molecule, and cDNA molecules can be from any organism. For example, the genomic nucleic acid molecules, mRNA molceules, and cDNA molecules can be human or an ortholog from another organism, such as a non-human mammal, a rodent, a mouse, or a rat. It is understood that genomic nucleic acid molecules, mRNA molceules, and cDNA sequences within a population can vary due to polymorphisms such as single-nucleotide polymorphisms. The examples provided herein are only exemplary sequences. Other sequences are also possible.

Also provided herein are functional polynucleotides that can interact with the disclosed nucleic acid molecules. Functional polynucleotides are nucleic acid molecules that have a specific function, such as binding a target molecule or catalyzing a specific reaction. Examples of functional polynucleotides include, but are not limited to, antisense molecules, aptamers, ribozymes, triplex forming molecules, and external guide sequences. The functional polynucleotides can act as effectors, inhibitors, modulators, and stimulators of a specific activity possessed by a target molecule, or the functional polynucleotides can possess a de novo activity independent of any other molecules.

The isolated nucleic acid molecules disclosed herein can comprise RNA, DNA, or both RNA and DNA. The isolated nucleic acid molecules can also be linked or fused to a heterologous label. Such labels include, for example, chemiluminescents, metals, tags, enzymes, radiolabels, pigments, dyes, chromogens, spin labels, and fluorescent labels. Labels also include, for example, particles, fluorophores, haptens, enzymes and their calorimetric, fluorogenic and chemiluminescent substrates and other labels.

The disclosed nucleic acid molecules can comprise, for example, nucleotides or non-natural or modified nucleotides, such as nucleotide analogs or nucleotide substitutes. Such nucleotides include a nucleotide that contains a modified base, modified sugar, or modified phosphate group, or that incorporates a non-natural moiety in its structure.

The present disclosure also provides vectors comprising any one or more of the nucleic acid molecules disclosed herein. In some embodiments, the vectors comprise any one or more of the nucleic acid molecules disclosed herein and a heterologous nucleic acid. The vectors can be viral or nonviral vectors capable of transporting a nucleic acid molecule. In some embodiments, the vector is a plasmid or cosmid.

Percent identity (or percent complementarity) between particular stretches of nucleotide sequences within nucleic acid molecules or amino acid sequences within polypeptides can be determined routinely using BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). Herein, if reference is made to percent sequence identity, the higher percentages of sequence identity are preferred over the lower ones.

The present disclosure also provides compositions comprising any one or more of the isolated nucleic acid molecules, genomic nucleic acid molecules, mRNA molecules, and/or cDNA molecules disclosed herein. In some embodiments, the composition is a pharmaceutical composition. In some embodiments, the compositions comprise a carrier and/or excipient.

The amino acid sequences of three SREBF1 reference polypeptides are set forth in SEQ ID NO:15, SEQ ID NO:16, and SEQ ID NO:17. Referring to SEQ ID NO:15, position 334 of the SREBF1 reference polypeptide is an arginine. Referring to SEQ ID NO:16, position 364 of the SREBF1 reference polypeptide is an arginine. Referring to SEQ ID NO:17, position 310 of the SREBF1 reference polypeptide is an arginine. Three variant SREBF1 polypeptides exist, wherein the arginine is replaced with cysteine. Referring to SEQ ID NO:18, position 334 of the variant SREBF1 polypeptide is a cysteine. Referring to SEQ ID NO:19, position 364 of the variant SREBF1 polypeptide is a cysteine. Referring to SEQ ID NO:20, position 310 of the variant SREBF1 polypeptide is a cysteine.

The present disclosure also provides isolated human SREBF1 polypeptides having an amino acid sequence at least about 90%, at least about 91%, at least about 92%, at least about 93%, at least about 94%, at least about 95%, at least about 96%, at least about 97%, at least about 98%, or at least about 99% identical to: SEQ ID NO:18, wherein the polypeptide comprises a cysteine at a position corresponding to position 334 according to SEQ ID NO:18; SEQ ID NO:19, wherein the polypeptide comprises a cysteine at a position corresponding to position 364 according to SEQ ID NO:19; or SEQ ID NO:20, wherein the polypeptide comprises a cysteine at a position corresponding to position 310 according to SEQ ID NO:20. Herein, if reference is made to percent sequence identity, the higher percentages of sequence identity are preferred over the lower ones.

In some embodiments, the amino acid sequence of the isolated human SREBF1 polypeptide comprises SEQ ID NO:18, SEQ ID NO:19, or SEQ ID NO:20. In some embodiments, the amino acid sequence of the isolated human SREBF1 polypeptide consists of SEQ ID NO:18, SEQ ID NO:19, or SEQ ID NO:20.

In some embodiments, the isolated polypeptides comprise or consist of an amino acid sequence at least about 90%, at least about 91%, at least about 92%, at least about 93%, at least about 94%, at least about 95%, at least about 96%, at least about 97%, at least about 98%, at least about 99%, or 100% identical to at least about 8, at least about 10, at least about 15, at least about 20, at least about 25, at least about 30, at least about 35, at least about 40, at least about 45, at least about 50, at least about 60, at least about 70, at least about 80, at least about 90, at least about 100, at least about 150, at least about 200, at least about 250, at least about 300, at least about 350, at least about 400, at least about 450, at least about 500, at least about 550, at least about 600 at least about 650, at least about 700, at least about 750, at least about 800, at least about 850, at least about 900, at least about 950, at least about 1000, at least about 1050, or at least about 1100 contiguous amino acids of SEQ ID NO:18, SEQ ID NO:19, or SEQ ID NO:20. In some embodiments, the isolated polypeptides also comprise: a cysteine at a position corresponding to position 334 of SEQ ID NO:18; a cysteine at a position corresponding to position 364 of SEQ ID NO:19; or a cysteine at a position corresponding to position 310 of SEQ ID NO:20.

The isolated polypeptides disclosed herein can comprise an amino acid sequence of a naturally occurring SREBF1 polypeptide, or can comprise a non-naturally occurring sequence. In some embodiments, the naturally occurring sequence can differ from the non-naturally occurring sequence due to conservative amino acid substitutions.

In some embodiments, the isolated polypeptides comprise non-natural or modified amino acids or peptide analogs. For example, there are numerous D-amino acids or amino acids which have a different functional substituent than the naturally occurring amino acids.

The SREBF1 reference polypeptides can be used, for example, to screen for compounds that act as antagonists, which can be used to treat subjects who are either SREBF1 reference or heterozygous for an SREBF1 predicted loss-of-function nucleic acid molecule. The variant SREBF1 polypeptides (such as the SREBF1 predicted loss-of-function polypeptides described herein) can be used, for example, to screen for compounds that act as agonists, which can be used to treat subjects who are either SREBF1 reference or heterozygous for an SREBF1 predicted loss-of-function nucleic acid molecule.

The present disclosure also provides nucleic acid molecules encoding any of the polypeptides disclosed herein. This includes all degenerate sequences related to a specific polypeptide sequence. Thus, while each particular nucleic acid sequence may not be written out herein, each and every sequence is in fact disclosed and described herein through the disclosed polypeptide sequences.

The present disclosure also provides compositions comprising any one or more of the nucleic acid molecules and/or any one or more of the polypeptides disclosed herein. In some embodiments, the compositions comprise a carrier.

The present disclosure also provides methods of producing any of the SREBF1 polypeptides or fragments thereof disclosed herein. Such SREBF1 polypeptides or fragments thereof can be produced by any suitable method.

The present disclosure also provides cells comprising any one or more of the nucleic acid molecules and/or any one or more of the polypeptides disclosed herein. The cells can be in vitro, ex vivo, or in vivo. Nucleic acid molecules can be linked to a promoter and other regulatory sequences so they are expressed to produce an encoded protein.

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequence follows the standard convention of beginning at the amino terminus of the sequence and proceeding forward (i.e., from left to right in each line) to the carboxy terminus.

As used herein, the phrase "corresponding to" or grammatical variations thereof when used in the context of the numbering of a particular nucleotide or nucleotide sequence or position refers to the numbering of a specified reference sequence when the particular nucleotide or nucleotide sequence is compared to the reference sequence. In other words, the residue (such as, for example, nucleotide or amino acid) number or residue (such as, for example, nucleotide or amino acid) position of a particular polymer is designated with respect to the reference sequence rather than by the actual numerical position of the residue within the particular nucleotide or nucleotide sequence. For example, a particular nucleotide sequence can be aligned to a reference sequence by introducing gaps to optimize residue matches between the two sequences. In these cases, although the gaps are present, the numbering of the residue in the particular nucleotide or nucleotide sequence is made with respect to the reference sequence to which it has been aligned.

For example, a nucleic acid molecule comprising a nucleotide sequence encoding a human SREBF1 polypeptide, wherein the nucleotide sequence comprises a thymine at a position corresponding to position 17,922 according to SEQ ID NO:2 means that if the nucleotide sequence of the SREBF1 genomic nucleic acid molecule is aligned to the sequence of SEQ ID NO:2, the SREBF1 sequence has a thymine residue at the position that corresponds to position 17,922 of SEQ ID NO:2. The same applies for mRNA molecules comprising a nucleotide sequence encoding a human SREBF1 polypeptide, wherein the nucleotide sequence comprises: a uracil at a position corresponding to position 1,185 according to SEQ ID NO:6; a uracil at a position corresponding to position 1,260 according to SEQ ID NO:7; or a uracil at a position corresponding to position 1,056 according to SEQ ID NO:8, and cDNA molecules comprising a nucleotide sequence encoding a human SREBF1 polypeptide, wherein the nucleotide sequence comprises: a thymine at a position corresponding to position 1,185 according to SEQ ID NO:12; a thymine at a position corresponding to position 1,260 according to SEQ ID NO:13; or a thymine at a position corresponding to position 1,056 according to SEQ ID NO:14. In other words, these phrases refer to a nucleic acid molecule encoding an SREBF1 polypeptide, wherein the genomic nucleic acid molecule has a nucleotide sequence that comprises a thymine residue that is homologous to the thymine residue at position 17,922 of SEQ ID NO:2 (or wherein the mRNA molecule has a nucleotide sequence that comprises a uracil residue that is: homologous to the uracil residue at position 1,185 of SEQ ID NO:6; homologous to the uracil residue at position 1,260 of SEQ ID NO:7; or homologous to the uracil residue at position 1,056 of SEQ ID NO:8, or wherein the cDNA molecule has a nucleotide sequence that comprises a thymine residue that is: homologous to the thymine residue at position 1,185 of SEQ ID NO:12; homologous to the thymine residue at position 1,260 of SEQ ID NO:13; or homologous to the thymine residue at position 1,056 of SEQ ID NO:14). Herein, such a sequence is also referred to as an "SREBF1 sequence with the C17,922T alteration" or "SREBF1 sequence with the C17,922T variation" referring to genomic nucleic acid molecules (or "SREBF1 sequence with the C1,185U alteration" or "SREBF1 sequence with the C1,185U variation" or "SREBF1 sequence with the C1,260U alteration" or "SREBF1 sequence with the C1,260U variation" or "SREBF1 sequence with the C1,056U alteration" or "SREBF1 sequence with the C1,056U variation" referring to mRNA molecules, and "SREBF1 sequence with the C1,185T alteration" or "SREBF1 sequence with the C1,185T variation" or "SREBF1 sequence with the C1,260T alteration" or "SREBF1 sequence with the C1,260T variation" or "SREBF1 sequence with the C1,056T alteration" or "SREBF1 sequence with the C1,056T variation" referring to cDNA molecules).

As described herein, a position within an SREBF1 genomic nucleic acid molecule that corresponds to position 17,922 according to SEQ ID NO:2 can be identified by performing a sequence alignment between the nucleotide sequence of a particular SREBF1 nucleic acid molecule and the nucleotide sequence of SEQ ID NO:2. A variety of computational algorithms exist that can be used for performing a sequence alignment to identify a nucleotide position that corresponds to, for example, position 17,922 in SEQ ID NO:2. For example, by using the NCBI BLAST algorithm (Altschul et al., Nucleic Acids Res., 1997, 25, 3389-3402) or CLUSTALW software (Sievers and Higgins, Methods Mol. Biol., 2014, 1079, 105-116) sequence alignments may be performed. However, sequences can also be aligned manually.

The present disclosure also provides therapeutic agents that treat or inhibit an increased lipid level for use in the treatment of an increased lipid level (or for use in the preparation of a medicament for treating an increased lipid level) in a human subject, wherein the human subject has: i) a genomic nucleic acid molecule having a nucleotide sequence encoding a human SREBF1 polypeptide, wherein the nucleotide sequence comprises a thymine at a position corresponding to position 17,922 according to SEQ ID NO:2, or the complement thereof; ii) an mRNA molecule having a nucleotide sequence encoding a human SREBF1 polypeptide, wherein the nucleotide sequence comprises a uracil at a position corresponding to position 1,185 according to SEQ ID NO:6, or the complement thereof; iii) an mRNA molecule having a nucleotide sequence encoding a human SREBF1 polypeptide, wherein the nucleotide sequence comprises a uracil at a position corresponding to position 1,260 according to SEQ ID NO:7, or the complement thereof; iv) an mRNA molecule having a nucleotide sequence encoding a human SREBF1 polypeptide, wherein the nucleotide sequence comprises a uracil at a position corresponding to position 1,056 according to SEQ ID NO:8, or the complement thereof; v) a cDNA molecule having a nucleotide sequence encoding a human SREBF1 polypeptide, wherein the nucleotide sequence comprises a thymine at a position corresponding to position 1,185 according to SEQ ID NO:12, or the complement thereof; vi) a cDNA molecule having a nucleotide sequence encoding a human SREBF1 polypeptide, wherein the nucleotide sequence comprises a thymine at a position corresponding to position 1,260 according to SEQ ID NO:13, or the complement thereof; vii) a cDNA molecule having a nucleotide sequence encoding a human SREBF1 polypeptide, wherein the nucleotide sequence comprises a thymine at a position corresponding to position 1,056 according to SEQ ID NO:14, or the complement thereof; viii) an SREBF1 polypeptide comprising a cysteine at a position corresponding to position 334 according to SEQ ID NO:18; ix) an SREBF1 polypeptide comprising a cysteine at a position corresponding to position 364 according to SEQ ID NO:19; and/or x) an SREBF1 polypeptide comprising a cysteine at a position corresponding to position 310 according to SEQ ID NO:20. The therapeutic agents that treat or inhibit an increased lipid level can be any of the therapeutic agents that treat or inhibit an increased lipid level described herein.

The present disclosure also provides SREBF1 inhibitors for use in the treatment of an increased lipid level (or for use in the preparation of a medicament for treating an increased lipid level) in a human subject, wherein the human subject has: i) a genomic nucleic acid molecule having a nucleotide sequence encoding a human SREBF1 polypeptide, wherein the nucleotide sequence comprises a thymine at a position corresponding to position 17,922 according to SEQ ID NO:2, or the complement thereof; ii) an mRNA molecule having a nucleotide sequence encoding a human SREBF1 polypeptide, wherein the nucleotide sequence comprises a uracil at a position corresponding to position 1,185 according to SEQ ID NO:6, or the complement thereof; iii) an mRNA molecule having a nucleotide sequence encoding a human SREBF1 polypeptide, wherein the nucleotide sequence comprises a uracil at a position corresponding to position 1,260 according to SEQ ID NO:7, or the complement thereof; iv) an mRNA molecule having a nucleotide sequence encoding a human SREBF1 polypeptide, wherein the nucleotide sequence comprises a uracil at a position corresponding to position 1,056 according to SEQ ID NO:8, or the complement thereof; v) a cDNA molecule having a nucleotide sequence encoding a human SREBF1 polypeptide, wherein the nucleotide sequence comprises a thymine at a position corresponding to position 1,185 according to SEQ ID NO:12, or the complement thereof; vi) a cDNA molecule having a nucleotide sequence encoding a human SREBF1 polypeptide, wherein the nucleotide sequence comprises a thymine at a position corresponding to position 1,260 according to SEQ ID NO:13, or the complement thereof; vii) a cDNA molecule having a nucleotide sequence encoding a human SREBF1 polypeptide, wherein the nucleotide sequence comprises a thymine at a position corresponding to position 1,056 according to SEQ ID NO:14, or the complement thereof; viii) an SREBF1 polypeptide comprising a cysteine at a position corresponding to position 334 according to SEQ ID NO:18; ix) an SREBF1 polypeptide comprising a cysteine at a position corresponding to position 364 according to SEQ ID NO:19; and/or x) an SREBF1 polypeptide comprising a cysteine at a position corresponding to position 310 according to SEQ ID NO:20. The SREBF1 inhibitors can be any of the SREBF1 inhibitors described herein.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The following examples are provided to describe the embodiments in greater detail. They are intended to illustrate, not to limit, the claimed embodiments. The following examples provide those of ordinary skill in the art with a disclosure and description of how the compounds, compositions, articles, devices and/or methods described herein are made and evaluated, and are intended to be purely exemplary and are not intended to limit the scope of any claims. Efforts have been made to ensure accuracy with respect to numbers (such as, for example, amounts, temperature, etc.), but some errors and deviations may be accounted for. Unless indicated otherwise, parts are parts by weight, temperature is in ° C. or is at ambient temperature, and pressure is at or near atmospheric.

EXAMPLES

Example 1: A Missense Variant in SREBF1 (SREBP) is Significantly Associated with Decreased LDL-C and Total Cholesterol in the Old Order Amish pLoF polymorphisms and missense variants obtained from the Old Order Amish cohort were analyzed. The results (see, Table 1 and FIG. 1) show significant association of SREBF1 variant with decreased LDL-C and total cholesterol. The variant is present at an allele frequency of 0.032 in the Old Order Amish and is drifted about 2900-fold compared to gnomAD.

TABLE 1

Association of SREBF1 Variant with Decreased LDL-C, non-HDL Cholesterol, and Total Cholesterol

| SREBF1 | Trait | P-Value | Effect | P-Value* | Effect* | Ref-Het-Alt |
|---|---|---|---|---|---|---|
| 17:17819081:G:A | LDL-C | 5.85e−6 | −11.31 mg/dL | 1.43e−9 | −12.23 mg/dL | 5554-370-8 |
| p.Arg364Cys, p.Arg334Cys | nonHDL Cholesterol | 2.52e−6 | −12.41 mg/dL | 1.58e−9 | −13.24 mg/dL | 5559-371-8 |
| | Total Cholesterol | 6.26e−6 | −12.34 mg/dL | 1.62e−8 | −13.20 mg/dL | 5559-371-8 |

*The p-value and effect have been adjusted for APOB p.R3527Q genotype, which is more common in the Old Order Amish. All traits are also adjusted for age, $age^2$, sex, and study.

Example 2: SREBF1 Variants Modulate LDLR Promoter Activity

Figure 2:
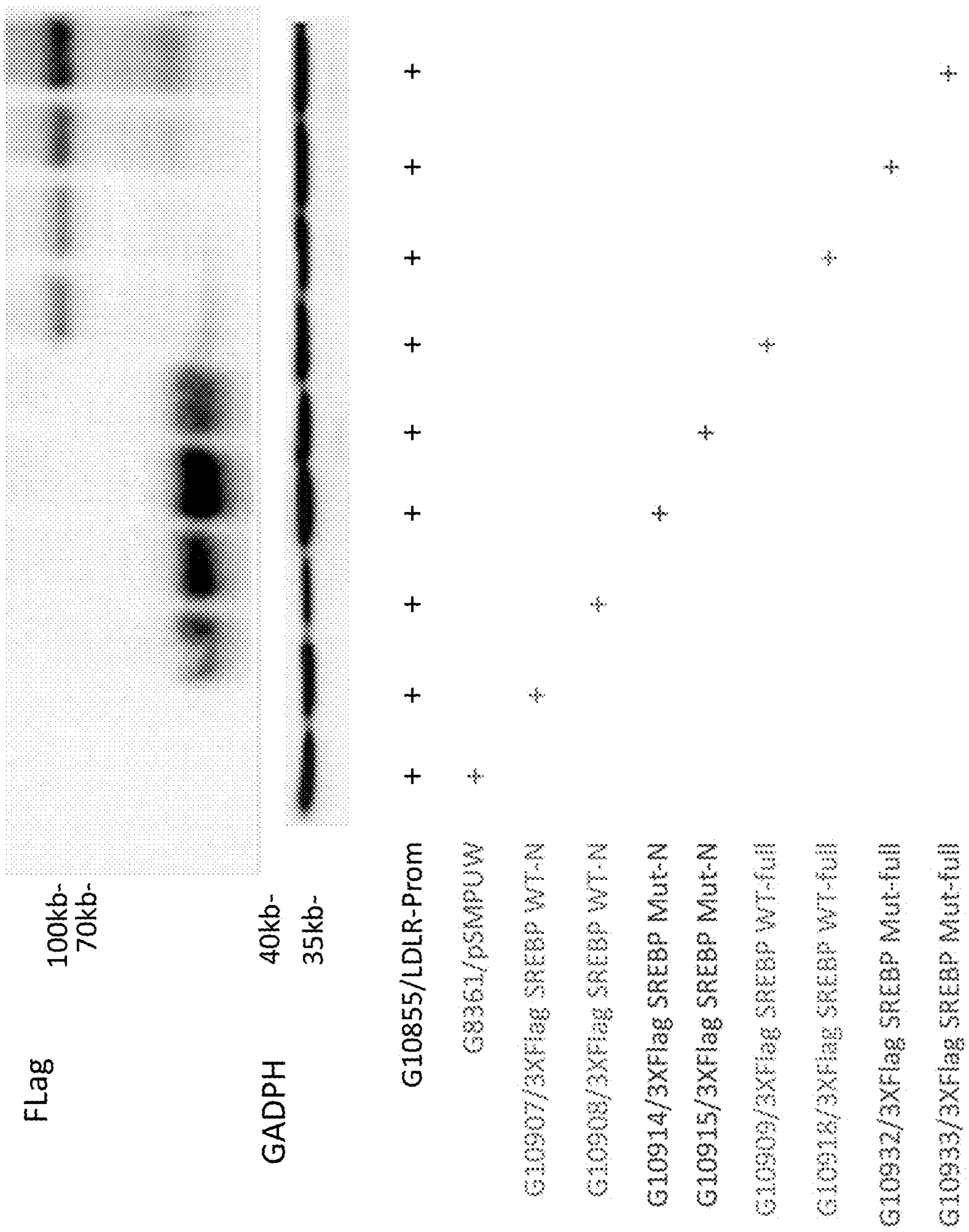
FIG. 2 shows an anti-flag Western blot protein analysis of 3×flag tagged nuclear and full-length SREBP-wt and SREBP-R334C plasmid construct transactivating activities on an LDLR-promoter luciferase reporter.
Figure 3:
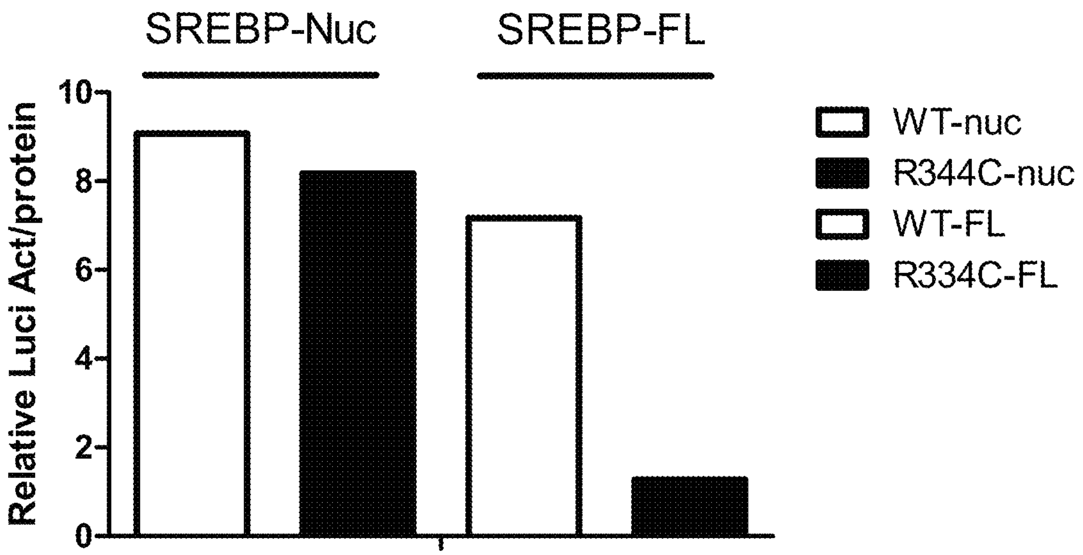
FIG. 3 shows relative activity of luc reporter with SREBP-wt and SREBP-R334C from FIG. 2.

Transient transfections of plasmids containing a pLDLR-luc reporter (G10855) were conducted with 0.4 μg each of SREBF1 WT or Mut SREBF1 (R334C) variant in the nuclear form or full-length form and a control pSMPUW plasmid at constant and titrated dosages in HEK293 cells. The cells were collected 48 hours later for luciferase assay and anti-flag Western blot protein analysis. Luciferase activities were measured as a surrogate of LDLR promoter activity, Western blots (FIG. 2) were performed with anti-flag antibodies to measure flag-tagged SREBP protein expression, and the protein bands were quantified using ImageLab software (FIG. 3).

Figure 4:
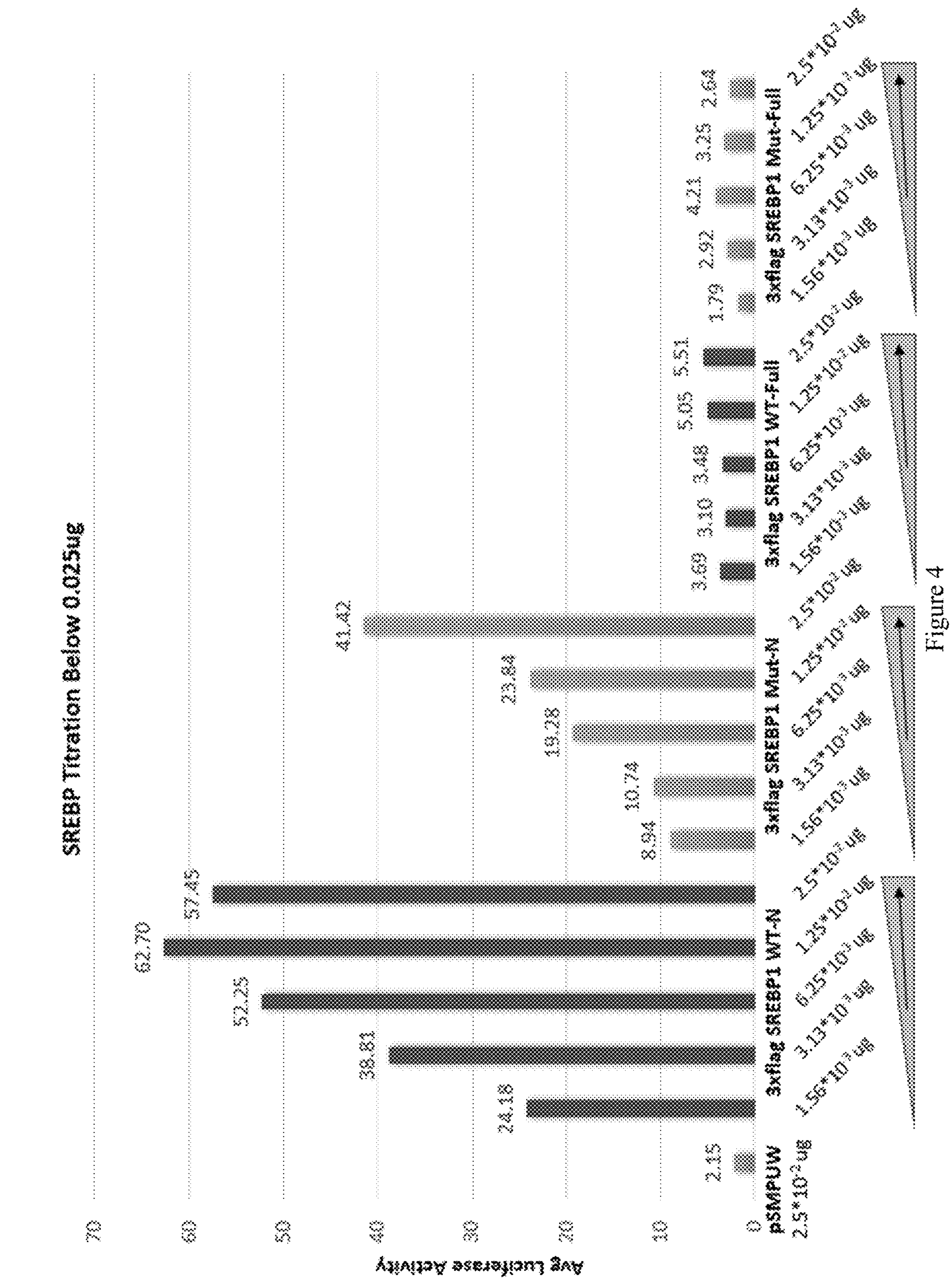
FIG. 4 shows results of an SREBP titration transfection below 0.025 μg.

Results have shown that the full-length and cleaved nuclear and full-length variants of SREBF1 (R334C) have less LDLR promoter trans-activating reporter activity than the wild-type on the LDLR promoter reporter, as indicated by luciferase and ImageLab results (FIG. 4), indicating that the SREBP variant may have less regulatory activities on LDLR and other target genes. The R334C variation falls in the HLH domain of SREBP, which binds to the promoter DNA of target genes.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety and for all purposes.

What is claimed is:

1. A method of treating a subject having increased total cholesterol or increased low density lipoprotein (LDL), the method comprising administering an SREBF1 inhibitor to the subject, and further comprising detecting the presence or absence of an SREBF1 variant nucleic acid molecule encoding a human SREBF1 polypeptide in a biological sample from the subject, wherein the SREBF1 variant nucleic acid molecule comprises:

i) a genomic nucleic acid molecule having a nucleotide sequence comprising a thymine at a position corresponding to position 17,922 according to SEQ ID NO:2, or the complement thereof, ii) an mRNA molecule having a nucleotide sequence comprising a uracil at a position corresponding to position 1,185 according to SEQ ID NO:6, or the complement thereof, iii) an mRNA molecule having a nucleotide sequence comprising a uracil at a position corresponding to position 1,260 according to SEQ ID NO:7, or the complement thereof, iv) an mRNA molecule having a nucleotide sequence comprising a uracil at a position corresponding to position 1,056 according to SEQ ID NO:8, or the complement thereof, v) a cDNA molecule produced from an mRNA molecule in the sample, wherein the cDNA molecule has a nucleotide sequence comprising a thymine at a position corresponding to position 1,185 according to SEQ ID NO:12, or the complement thereof, vi) a cDNA molecule produced from an mRNA molecule in the sample, wherein the cDNA molecule has a nucleotide sequence comprising a thymine at a position corresponding to position 1,260 according to SEQ ID NO:13, or the complement thereof, and/or vii) a cDNA molecule produced from an mRNA molecule in the sample, wherein the cDNA molecule has a nucleotide sequence comprising a thymine at a position corresponding to position 1,056 according to SEQ ID NO:14, or the complement thereof; and when the subject is SREBF1 reference, the subject is also administered a therapeutic agent that treats or inhibits an increased lipid level in a standard dosage amount, and when the subject is heterozygous for the SREBF1 variant nucleic acid molecule, the subject is also administered a therapeutic agent that treats or inhibits an increased lipid level in a dosage amount that is the same as or lower than the standard dosage amount; and wherein the SREBF1 inhibitor comprises an antisense nucleic acid molecule that hybridizes to an SREBF1 mRNA, a small interfering RNA (siRNA) that hybridizes to an SREBF1 mRNA, a short hairpin RNA (shRNA) that hybridizes to an SREBF1 mRNA, Fatostatin A, or PF-429242.

2. A method of treating a subject with a therapeutic agent that treats or inhibits an increased lipid level, wherein the subject is suffering from an increased lipid level, the method comprising the steps of:

determining whether the subject has an SREBF1 variant nucleic acid molecule encoding a human SREBF1 polypeptide by:

obtaining or having obtained a biological sample from the subject; and performing or having performed a genotyping assay on the biological sample to determine if the subject has a genotype comprising the SREBF1 variant nucleic acid molecule; and when the subject is SREBF1 reference, then administering or continuing to administer to the subject the therapeutic agent that treats or inhibits the increased lipid level in a standard dosage amount, and administering to the subject an SREBF1 inhibitor; and when the subject is heterozygous for the SREBF1 variant nucleic acid molecule, then administering or continuing to administer to the subject the therapeutic agent that treats or inhibits the increased lipid level in an amount that is the same as or lower than a standard dosage amount, and administering to the subject an SREBF1 inhibitor;

wherein the presence of a genotype having the SREBF1 variant nucleic acid molecule encoding the human SREBF1 polypeptide indicates the subject has a reduced risk of developing the increased lipid level;

wherein the increased lipid level is increased serum lipid level, increased total cholesterol, or increased LDL;

wherein the SREBF1 variant nucleic acid molecule comprises:

i) a genomic nucleic acid molecule having a nucleotide sequence comprising a thymine at a position corresponding to position 17,922 according to SEQ ID NO:2, or the complement thereof, ii) an mRNA molecule having a nucleotide sequence comprising a uracil at a position corresponding to position 1,185 according to SEQ ID NO:6, or the complement thereof, iii) an mRNA molecule having a nucleotide sequence comprising a uracil at a position corresponding to position 1,260 according to SEQ ID NO:7, or the complement thereof, iv) an mRNA molecule having a nucleotide sequence comprising a uracil at a position corresponding to position 1,056 according to SEQ ID NO:8, or the complement thereof, v) a cDNA molecule produced from an mRNA molecule in the sample, wherein the cDNA molecule has a nucleotide sequence comprising a thymine at a position corresponding to position 1,185 according to SEQ ID NO:12, or the complement thereof, vi) a cDNA molecule produced from an mRNA molecule in the sample, wherein the cDNA molecule has a nucleotide sequence comprising a thymine at a position corresponding to position 1,260 according to SEQ ID NO:13, or the complement thereof, and/or vii) a cDNA molecule produced from an mRNA molecule in the sample, wherein the cDNA molecule has a nucleotide sequence comprising a thymine at a position corresponding to position 1,056 according to SEQ ID NO:14, or the complement thereof; and wherein the SREBF1 inhibitor comprises an antisense nucleic acid molecule that hybridizes to an SREBF1 mRNA, a small interfering RNA (siRNA) that hybridizes to an SREBF1 mRNA, a short hairpin RNA (shRNA) that hybridizes to an SREBF1 mRNA, Fatostatin A, or PF-429242.

3. A method of identifying a human subject having an increased risk for developing an increased lipid level, wherein the method comprises determining or having determined the presence or absence of an SREBF1 variant nucleic acid molecule encoding a human SREBF1 polypeptide in a biological sample obtained from the subject; wherein: when the human subject is SREBF1 reference, then the human subject has an increased risk for developing the increased lipid level; and when the human subject is heterozygous for the SREBF1 variant nucleic acid molecule or homozygous for the SREBF1 variant nucleic acid molecule, then the human subject has a decreased risk for developing the increased lipid level; wherein the SREBF1 variant nucleic acid molecule comprises:

i) a genomic nucleic acid molecule having a nucleotide sequence comprising a thymine at a position corresponding to position 17,922 according to SEQ ID NO:2, or the complement thereof, ii) an mRNA molecule having a nucleotide sequence comprising a uracil at a position corresponding to position 1,185 according to SEQ ID NO:6, or the complement thereof, iii) an mRNA molecule having a nucleotide sequence comprising a uracil at a position corresponding to position 1,260 according to SEQ ID NO:7, or the complement thereof, iv) an mRNA molecule having a nucleotide sequence comprising a uracil at a position corresponding to position 1,056 according to SEQ ID NO:8, or the complement thereof, v) a cDNA molecule produced from an mRNA molecule in the sample, wherein the cDNA molecule has a nucleotide sequence comprising a thymine at a position corresponding to position 1,185 according to SEQ ID NO:12, or the complement thereof, vi) a cDNA molecule produced from an mRNA molecule in the sample, wherein the cDNA molecule has a nucleotide sequence comprising a thymine at a position corresponding to position 1,260 according to SEQ ID NO:13, or the complement thereof, and/or vii) a cDNA molecule produced from an mRNA molecule in the sample, wherein the cDNA molecule has a nucleotide sequence comprising a thymine at a position corresponding to position 1,056 according to SEQ ID NO:14, or the complement thereof.

4. The method according to claim 1, wherein the SREBF1 inhibitor comprises an antisense nucleic acid molecule that hybridizes to an SREBF1 mRNA.

5. The method according to claim 1, wherein the SREBF1 inhibitor comprises an siRNA that hybridizes to an SREBF1 mRNA.

6. The method according to claim 1, wherein the SREBF1 inhibitor comprises an shRNA that hybridizes to an SREBF1 mRNA.

7. The method according to claim 1, wherein the SREBF1 inhibitor comprises Fatostatin A.

8. The method according to claim 1, wherein the SREBF1 inhibitor comprises PF-429242.

9. The method according to claim 2, wherein the SREBF1 inhibitor comprises an antisense nucleic acid molecule that hybridizes to an SREBF1 mRNA.

10. The method according to claim 2, wherein the SREBF1 inhibitor comprises an siRNA that hybridizes to an SREBF1 mRNA.

11. The method according to claim 2, wherein the SREBF1 inhibitor comprises an shRNA that hybridizes to an SREBF1 mRNA.

12. The method according to claim 2, wherein the SREBF1 inhibitor comprises Fatostatin A.

13. The method according to claim 2, wherein the SREBF1 inhibitor comprises PF-429242.

14. The method according to claim 3, wherein the SREBF1 variant nucleic acid molecule comprises a genomic nucleic acid molecule having a nucleotide sequence comprising a thymine at a position corresponding to position 17,922 according to SEQ ID NO:2, or the complement thereof.

15. The method according to claim 3, wherein the SREBF1 variant nucleic acid molecule comprises an mRNA molecule having a nucleotide sequence comprising a uracil at a position corresponding to position 1,185 according to SEQ ID NO:6, or the complement thereof.

16. The method according to claim 3, wherein the SREBF1 variant nucleic acid molecule comprises an mRNA molecule having a nucleotide sequence comprising a uracil at a position corresponding to position 1,260 according to SEQ ID NO:7, or the complement thereof.

17. The method according to claim 3, wherein the SREBF1 variant nucleic acid molecule comprises an mRNA molecule having a nucleotide sequence comprising a uracil at a position corresponding to position 1,056 according to SEQ ID NO:8, or the complement thereof.

18. The method according to claim 3, wherein the SREBF1 variant nucleic acid molecule comprises a cDNA molecule produced from an mRNA molecule in the sample, wherein the cDNA molecule has a nucleotide sequence comprising a thymine at a position corresponding to position 1,185 according to SEQ ID NO:12, or the complement thereof.

19. The method according to claim 3, wherein the SREBF1 variant nucleic acid molecule comprises a cDNA molecule produced from an mRNA molecule in the sample, wherein the cDNA molecule has a nucleotide sequence comprising a thymine at a position corresponding to position 1,260 according to SEQ ID NO:13, or the complement thereof.

20. The method according to claim 3, wherein the SREBF1 variant nucleic acid molecule comprises a cDNA molecule produced from an mRNA molecule in the sample, wherein the cDNA molecule has a nucleotide sequence comprising a thymine at a position corresponding to position 1,056 according to SEQ ID NO:14, or the complement thereof.

* * * * *